United States Patent
O'Riordan et al.

(10) Patent No.: US 11,103,598 B2
(45) Date of Patent: Aug. 31, 2021

(54) GENE THERAPY FOR RETINITIS PIGMENTOSA

(71) Applicant: Genzyme Corporation, Cambridge, MA (US)

(72) Inventors: Catherine O'Riordan, Bridgewater, NJ (US); Matthew Adamowicz, Bridgewater, NJ (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 16/503,091

(22) Filed: Jul. 3, 2019

(65) Prior Publication Data

US 2020/0046851 A1 Feb. 13, 2020

Related U.S. Application Data

(62) Division of application No. 15/127,757, filed as application No. PCT/US2015/021896 on Mar. 20, 2015, now Pat. No. 10,383,953.

(60) Provisional application No. 61/969,027, filed on Mar. 21, 2014.

(51) Int. Cl.
| | | |
|---|---|---|
| *A61K 48/00* | (2006.01) | |
| *A61K 31/7105* | (2006.01) | |
| *C12N 15/86* | (2006.01) | |
| *A61K 9/00* | (2006.01) | |
| *C12N 15/113* | (2010.01) | |
| *A61K 38/17* | (2006.01) | |

(52) U.S. Cl.
CPC ........ *A61K 48/0058* (2013.01); *A61K 9/0019* (2013.01); *A61K 9/0048* (2013.01); *A61K 31/7105* (2013.01); *A61K 38/1709* (2013.01); *C12N 15/113* (2013.01); *C12N 15/86* (2013.01); *C12N 2310/141* (2013.01); *C12N 2320/34* (2013.01); *C12N 2330/51* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 5,262,529 A | 11/1993 | Dryja et al. | |
| 5,985,583 A | 11/1999 | Sealfon | |
| 6,566,118 B1 | 5/2003 | Atkinson et al. | |
| 6,596,535 B1 | 7/2003 | Carter | |
| 6,989,264 B2 | 1/2006 | Atkinson et al. | |
| 6,995,006 B2 | 2/2006 | Atkinson et al. | |
| 7,125,717 B2 | 10/2006 | Carter | |
| 7,765,583 B2 | 7/2010 | Kalonji et al. | |
| 7,785,888 B2 | 8/2010 | Carter | |
| 7,790,154 B2 | 9/2010 | Samulski et al. | |
| 7,846,729 B2 | 12/2010 | Carter | |
| 8,093,054 B2 | 1/2012 | Carter | |
| 8,283,151 B2 | 10/2012 | Schmidt et al. | |
| 8,361,457 B2 | 1/2013 | Samulski et al. | |
| 8,617,876 B2 | 12/2013 | Farrar et al. | |
| 8,741,650 B2 | 6/2014 | Iida et al. | |
| 8,999,380 B2 | 4/2015 | Bancel et al. | |
| 9,512,425 B2 | 12/2016 | Mittal et al. | |
| 10,383,953 B2 | 8/2019 | O'Riordan et al. | |
| 2010/0190841 A1 | 7/2010 | Farrar et al. | |
| 2012/0066783 A1 | 3/2012 | Kay et al. | |
| 2012/0164106 A1 | 6/2012 | Schaffer et al. | |
| 2013/0323226 A1 | 12/2013 | Wilson et al. | |
| 2015/0105317 A1 | 4/2015 | Lin | |
| 2020/0046851 A1* | 2/2020 | O'Riordan | A61K 38/1709 |
| 2020/0325493 A1 | 10/2020 | Muramatsu | |

FOREIGN PATENT DOCUMENTS

| | | |
|---|---|---|
| JP | 2013-517798 A | 5/2013 |
| WO | WO-2003/042397 A2 | 5/2003 |
| WO | WO-2008/125846 A2 | 10/2008 |
| WO | WO-2010/138263 A2 | 12/2010 |
| WO | WO-2011/094198 A1 | 8/2011 |
| WO | 2012057363 A1 | 5/2012 |
| WO | 2013018612 A1 | 2/2013 |
| WO | 2013093870 A1 | 6/2013 |
| WO | WO-2013/176772 A1 | 11/2013 |
| WO | WO-2014/011210 A1 | 1/2014 |
| WO | WO-2015/143418 A2 | 9/2015 |

OTHER PUBLICATIONS

Adamowicz, M. et al. (2012). "Development of a Cellular Model of Rod Opsin Retinitis Pigmentosa," Chapter 73 in *Retinal Degenerative Diseases, Advances in Experimental Medicine and Biology,* M.M. LaVail et al. (eds.), Springer Science+Business Media, LLC 723:573-579.
Bartel, D.P. (Jan. 23, 2004). "MicroRNAs: Genomics, Biogenesis, Mechanism, and Function" *Cell* 116(2):281-297.
Behrman, S. et al. (Mar. 14, 2011). "A CHOP-Regulated MicroRNA Controls Rhodopsin Expression" *J. Cell Biol.* 192(6):919-927.
Bossis, I. et al. (Jun. 2003). "Cloning of an Avian Adeno-Associated Virus (AAAV) and Generation of Recombinant AAAV Particles," *J. Virol.* 77(12):6799-6810.
Clark, K.R. et al. (Apr. 10, 1999). "Highly Purified Recombinant Adeno-Associated Virus Vectors Are Biologically Active and Free of Detectable Helper and Wild-Type Viruses," *Hum. Gene Ther.* 10(6):1031-1039.
Davidson, B.L. et al. (Mar. 28, 2000; e-pub Feb. 25, 2000). "Recombinant Adeno-Associated Virus Type 2, 4, and 5 Vectors: Transduction of Variant Cell Types and Regions in the Mammalian Central Nervous System," *PNAS* 97(7):3428-3432.
Dryja, T.P. et al. (Jan. 25, 1990). "A Point Mutation of the Rhodopsin Gene in One Form of Retinitis Pigmentosa," *Nature* 343:364-366.

(Continued)

*Primary Examiner* — Michael D Burkhart
(74) *Attorney, Agent, or Firm* — Morrison & Foerster LLP

(57) ABSTRACT

Provided herein are methods for treating retinitis pigmentosa using an AAV particles encoding miR-708. In one aspect, viral particles are administered to the eye of a human subject; for example, by subretinal injection. Viral particles comprising AAV5 capsids or mutants thereof are contemplated.

28 Claims, 28 Drawing Sheets

Specification includes a Sequence Listing.

(56) References Cited

OTHER PUBLICATIONS

Dryja, T.P. et al. (Oct. 1995). "Mutations in the Gene Encoding the a Subunit of the Rod cGMP-gated Channel in Autosomal Recessive Retinitis Pigmentosa," *Proc. Natl. Acad. Sci. U.S.A.* 92(22):10177-10181.

Farrar, G.J. et al. (Mar. 1, 2002). "On the Genetics of Retinitis Pigmentosa and on Mutation-Independent Approaches to Therapeutic Intervention", *EMBO J.* 21(5):857-864.

Farrar, G.J. et al. (Sep. 1990). "Autosomal Dominant Retinitis Pigmentosa: Linkage to Rhodopsin and Evidence for Genetic Heterogeneity", *Genomics* 8(1):35-40.

Fisher, K.J. et al. (Jan. 1996). "Transduction with Recombinant Adeno-Associated Virus for Gene Therapy is Limited by Leading-Strand Synthesis", *J. Virol.* 70(1):520-532.

Gao, G-P et al. (May 13, 2003). "Adeno-Associated Viruses Undergo Substantial Evolution in . Primates During Natural Infections," *PNAS* 100(10):6081-6086.

Gao, G-P. et al. (Sep. 3, 2002). "Novel Adeno-Associated Viruses from Rhesus Monkeys as Vectors for Human Gene Therapy," *PNAS* 99(18):11854-11859.

Georgiadis, A. et al. (Apr. 2010, e-pub. Dec. 10, 2009). "AAV-mediated knockdown of Peripherin-2 in vivo using miRNA-based hairpins", 17(4):486-493.

Gray S. J. et al. (Sep. 2011). "Optimizing Promoters for Recombinant Adeno-Associated Virus-Mediated Gene Expression in the Peripheral and Central Nervous System Using Self-Complementary Vectors," *Hum. Gen. Ther.* 22(9):1143-1153.

Greenwald D. L. et al. (Apr. 2013). "Mutation-independent Rescue of a Novel Mouse Model of Retinitis Pigmentosa," *Gene Ther.* 20(4):425-434.

Gregersen, N. et al. (2006, e-pub. May 24, 2006). "Protein Misfolding and Human Disease," *Annu. Rev. Genomics Hum. Genet.* 7:103-124.

Griciuc, A. et al. (Aug. 2011, e-pub May 27, 2011). "ER Stress in Retinal Degeneration: A Target for Rational Therapy?", *Trends Mol Med* 17(8):442-451.

Guo, Z.S. et al. (Sep. 1996). "Evaluation of Promoter Strength for Hepatic Gene Expression In Vivo Following Adenovirus-Mediated Gene Transfer," *Gene Ther.* 3(9):802-810.

Humphries, M.M. et al. (Feb. 15, 1997). "Retinopathy Induced in Mice by Targeted Disruption of the Rhodopsin Gene," *Nat. Genet.* 15(2):216-219.

International Search Report dated Sep. 14, 2015 for PCT Application No. PCT/US2015/021896, filed on Mar. 20, 2015, 7 pages.

Kalloniatis, M. et al. (Mar. 8, 2004). "Retinitis Pigmentosa: Understanding the Clinical Presentation, Mechanisms and Treatment Options," *Clin. Exp. Optom.* 87(2):65-80.

Khani, S.C. et al. (Sep. 2007). "AAV-Mediated Expression Targeting of Rod and Cone Photoreceptors with a Human Rhodopsin Kinase Promoter," *Invest. Ophthalmol. Vis. Sci.* 48(9):3954-3961.

Kim, D.W. et al. (Jul. 16, 1990). "Use of the Human Elongation Factor 1 α Promoter as a Versatile and Efficient Expression System," *Gene* 91(2):217-223.

Kotin, R.M. (Jul. 1994). "Prospects for the Use of Adeno-Associated Virus as a Vector for Human Gene Therapy," Hum. Gene Ther. 5(7):793-801.

Le, Y.Z. et al. (Apr. 18, 2006). "Mouse Opsin Promoter-Directed Cre Recombinase Expression in Transgenic Mice," *Mol. Vis.* 12:389-398.

Lee, E.S. et al. (2007, e-pub Aug. 14, 2007). "The Double-Strand RNA-Dependent Protein Kinase PKR Plays a Significant Role in a Sustained ER Stress-Induced Apoptosis," *FEBS Lett.* 581(22):4325-4332.

Li, T. et al. (Nov. 1996). "Transgenic Mice Carrying the Dominant Rhodopsin Mutation P347S: Evidence for Defective Vectorial Transport of Rhodopsin to the Outer Segments," *Proc. Natl. Acad. Sci.* 93(24):14176-14181.

Mao, H. et al. (Apr. 2012). "Long-Term Rescue of Retinal Structure and Function by Rhodopsin RNA Replacement with a Single Adeno-Associated Viral Vector in P23H RHO Transgenic Mice," *Hum. Gen. Ther.* 23(4):356-366.

McLaughlin, S.K. et al. (Jun. 1988). "Adeno-Associated Virus General Transduction Vectors: Analysis of Proviral Structures," *J. Virol.* 62(6):1963-1973.

McWilliam, P. et al. (Oct. 1989). "Autosomal Dominant Retinitis Pigmentosa (ADRP): Localization of an ADRP Gene to the Long Arm of Chromosome 3," *Genomics* 5(3):619-622.

Niwa, H. et al. (1991). "Efficient Selection for High-Expression Transfectants with a Novel Eukaryotic Vector," *Gene* 108(2):193-200.

Olsson, J.E. et al. (Nov. 1992). "Transgenic Mice with a Rhodopsin Mutation (Pro23His): A Mouse Model of Autosomal Dominant Retinitis Pigmentosa," *Neuron* 9(5):815-830.

Passini, M.A. et al. (Jun. 2003). "Intraventricular Brain Injection of Adeno-Associated Virus Type 1 (AAV1) in Neonatal Mice Results in Complementary Patterns of Neuronal Transduction to AAV2 and Total Long-Term Correction of Storage Lesions in the Brains of β-Glucuronidase-Deficient Mice," *J. Virol.* 77(12):7034-7040.

Pechan, P.et al. (2009, e-pub Jul. 17, 2008). "Novel anti-VEGF Chimeric Molecules Delivered by AAV Vectors for Inhibition of Retinal Neovascularization" *Gene Ther.* 16:10-16.

Quiambao, A.B. et al. (Jul.-Aug. 1997). "A 221-bp Fragment of the Mouse Opsin Promoter Directs Expression Specifically to the Rod Photoreceptors of Transgenic Mice," *Vis. Neurosci.* 14(4):617-625.

Saliba, R.S. et al. (2002). "The Cellular Fate of Mutant Rhodopsin: Quality Control, Degradation and Aggresome Formation," *J. Cell Sci.* 115(14):2907-2918.

Skarnes, W.C. et al. (Jun. 15, 2011). "A Conditional Knockout Resource for the Genome-Wide Study of Mouse Gene Function", *Nature* 474(7351):337-342.

Tam, B.M. et al. (Aug. 2006). "Characterization of Rhodopsin P23H-Induced Retinal Degeneration in a *Xenopus laevis* Model of Retinitis Pigmentosa" *Invest. Ophthalmol. Vis. Sci.* 47(8):3234-3241.

Veldwijk, M.R. et al. (Aug. 2002). "Development and Optimization of a Real-Time Quantitative PCR-Based Method for the Titration of AAV-2 Vector Stocks," *Mol. Ther.* 6(2):272-278.

Wang, Z. et al. (2003). "Rapid and Highly Efficient Transduction by Double-Stranded Adeno-Associated Virus Vectors in Vitro and in Vivo," *Gene Ther* 10:2105-2111.

Written Opinion of the International Search Authority dated Sep. 14, 2015 for PCT Application No. PCT/US2015/021896, filed on Mar. 20, 2015, 10 pages.

Xiao, X. et al. (Mar. 1, 1997). "Gene Transfer by Adeno-Associated Virus Vectors into the Central Nervous System," *Exp. Neurobiol.* 144(1):113-124.

Young, J.E. et al. (Sep. 2003). "A Short, Highly Active Photoreceptor-Specific Enhancer/Promoter Region Upstream of the Human Rhodopsin Kinase Gene," *Invest. Ophthalmol. Vis. Sci.* 44(9):4076-4085.

Zhong, L. et al. (Jun. 3, 2008; e-pub May 29, 2008). "Next Generation of Adeno-Associated Virus 2 Vectors: Point Mutations in Tyrosines Lead to High-Efficiency Transduction at Lower Doses," *Proc Natl Acad Sci* 105(22):7827-7832.

Woltczak, A. (Dec. 2000). "Glossary of Medical Education Terms," Institute of International Medical Education, as retrieved on Mar. 2013 from http://www.iime.org/glossary.htm, 23 pages.

\* cited by examiner

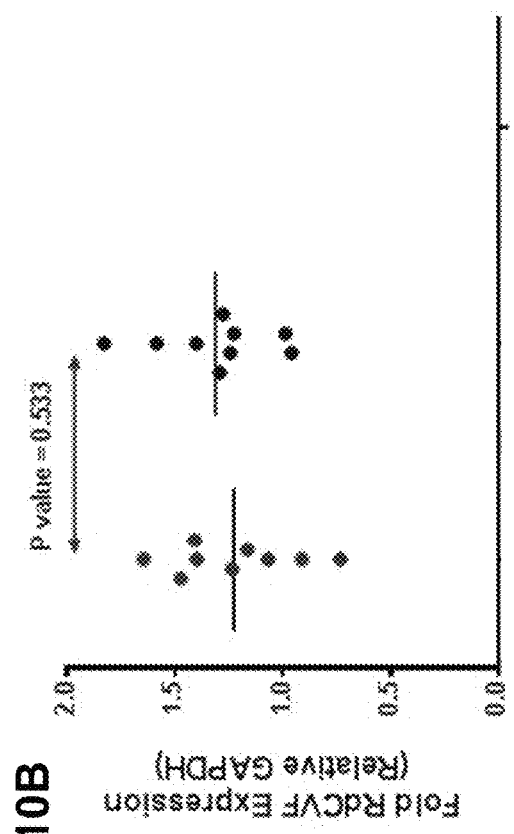
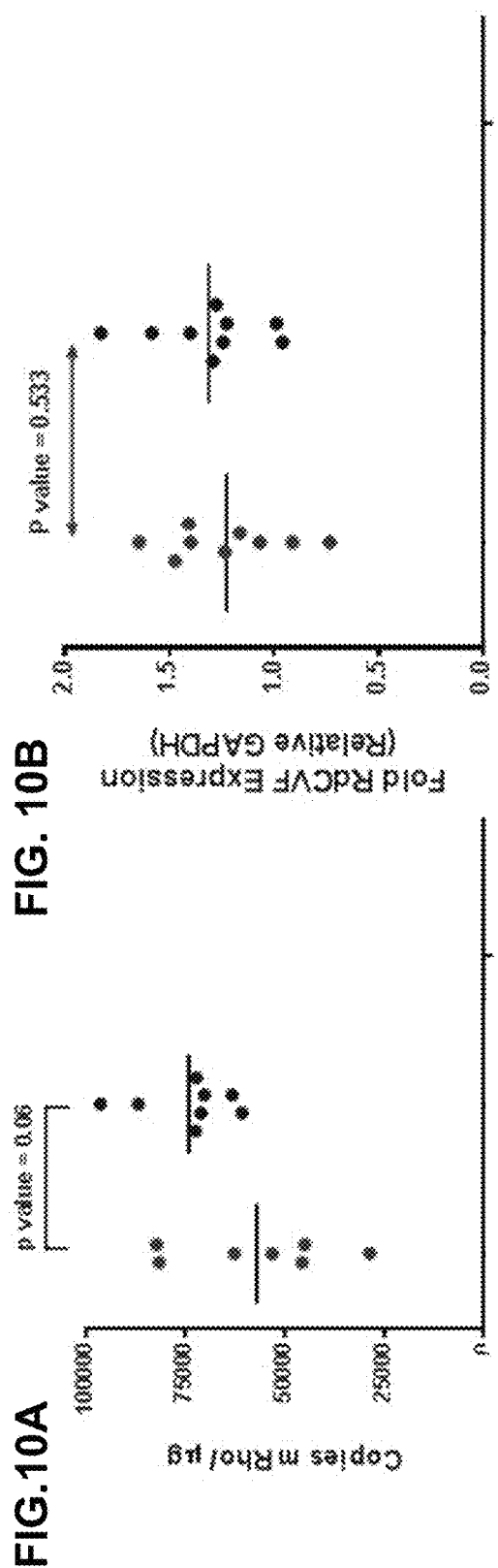
FIG. 10A
FIG. 10B
FIG. 10C

Animal # 45595

Animal # 45596

Animal # 45599

Animal # 45595

Animal # 45596

Animal # 45599 miR-155

Derived from miR-155 miR-708

GENE THERAPY FOR RETINITIS PIGMENTOSA

CROSS REFERENCE TO RELATED APPLICATIONS

This application is a divisional of U.S. patent application Ser. No. 15/127,757, which adopts the international filing date of Mar. 20, 2015, which is a National Phase application under 35 U.S.C. § 371 of International Application No. PCT/US2015/021896, filed Mar. 20, 2015, which claims the priority benefit of U.S. Provisional Application No. 61/969,027, filed Mar. 21, 2014, the disclosure of each of which is incorporated herein by reference in its entirety.

SEQUENCE LISTING

The content of the following submission on ASCII text file is incorporated herein by reference in its entirety: a computer readable form (CRF) of the Sequence Listing (file name: 159792010010SeqList.txt, date recorded: Jun. 28, 2019, size: 61 KB).

FIELD OF THE INVENTION

The present invention relates to AAV vectors and methods of using AAV vectors for treating retinitis pigmentosa.

BRIEF SUMMARY OF THE INVENTION

Retinitis pigmentosa (RP) is the most common cause of inherited retinal degeneration, which is clinically characterized by night blindness and the loss of peripheral vision. Mutations in the rod visual pigment rhodopsin are recognized as the most common cause of autosomal dominant RP (ADRP), and although a number of treatments for rhodopsin RP have been proposed and tested in animal models and clinical studies, the disease remains incurable (Kalloniatis, M., et al. (2004) Clin. Exp. Optom. 87(2):65-80). Much data supports the view that rhodopsin RP is a protein-misfolding disease in which the misfolding or misassembly of a mutant protein alters its cellular fate and induces cell death (Gregersen, N. et al. (2006) Annu. Rev. Genomics Hum. Genet. 7:103-24). Known RP mutations in the rhodopsin gene include missense and short, in-frame deletion mutations, with a single base substitution in codon 23 (P23H) of the rhodopsin gene accounting for ~7% of all cases of dominant Retinitis Pigmentosa in the US (Dryja, T. P., et al. (1995) Proc. Natl. Acad. Sci. U.S.A. 92(22):10177-81). In cultured cells, the P23H mutant protein, unlike wild type (WT) protein, is retained in the ER, leading to induction of the unfolded protein response (UPR), inhibition of the proteasome, and aggregation of the mutant protein into oligomeric, high molecular weight species that form intracellular inclusions (Saliba, R. S., et al. (2002) J. Cell Sci. 115:2907-18). Similarly, P23H rhodopsin mislocalizes and/or aggregates in the rod cells of animal RP models (Olsson, J. E., et al. (1992) Neuron 9(5):815-30), suggesting that cell culture models may be predictive of in vivo models of this disease. What is needed is a means of ameliorating the symptoms of RP.

The invention described herein provides methods for treating retinitis pigmentosa in a mammal, comprising administering to the eye of the mammal a recombinant adeno-associated virus (rAAV) viral particle comprising a vector encoding a miR-708. In some embodiments, the rAAV vector comprising nucleic acid encoding a miR-708 and rhodopsin. In some embodiments, the invention provides methods for treating retinitis pigmentosa comprising administering to the eye of the mammal a first rAAV viral particle comprising a first rAAV vector comprising nucleic acid encoding a miR-708 and a second rAAV viral particle comprising a second rAAV vector comprising nucleic acid encoding a rhodopsin. In other embodiments, the invention provides methods for treating retinitis pigmentosa comprising administering to the eye of the mammal a rAAV viral particle comprising a rAAV vector comprising nucleic acid encoding a miR-708 and rhodopsin. In some embodiments, treating retinitis pigmentosa comprises reducing or preventing symptoms associated with the retinitis pigmentosa. In some embodiments or the invention, methods of treating retinitis pigmentosa include methods of reducing a symptom associated with RP, methods of preventing retinal degeneration, methods for arresting progression of RP, methods for increasing photoreceptor function, and the like. Symptoms and/or pathology of RP include but are not limited to loss of sight, loss of night vision, loss of peripheral visual fields, loss of ERG function; loss of visual acuity and contrast sensitivity; loss of visually guided behavior, reduction in rod photoreceptor function, rod photoreceptor cell death, decreased scotopic vision, reduction in retinal cell changes (loss of photoreceptor structure or function; thinning or thickening of the outer nuclear layer (ONL); thinning or thickening of the outer plexiform layer (OPL); disorganization followed by loss of rod and cone outer segments; shortening of the rod and cone inner segments; retraction of bipolar cell dendrites; thinning or thickening of the inner retinal layers including inner nuclear layer, inner plexiform layer, ganglion cell layer and nerve fiber layer; opsin mislocalization; overexpression of neurofilaments; and the like. In some embodiments, the invention provides methods to prevent deterioration of rod cell function and rod cell death and cone cell function and cone cell death.

In some aspects, the invention provides methods for treating endoplasmic reticulum (ER) stress in a cell comprising administering to the mammal a rAAV viral particle comprising a rAAV vector comprising nucleic acid encoding a miR-708. In some embodiments, the mammal has or is at risk of having RP. In some embodiments, the mammal is a human that has or is at risk of having RP. In some embodiments, the rAAV particle is administered to an eye of the mammal. In some embodiments, the cell is an ocular cell. In further embodiments, the cell is a photoreceptor cell. In yet further embodiments, the cell is a rod photoreceptor cell. In some embodiments, the method comprises reducing one or more cellular markers of ER stress. In further embodiments, the one or more cellular marker of ER stress is spliced XBP-1, CHOP or Grp78. In some embodiments, the rAAV vector comprises nucleic acid encoding a miR-708 and rhodopsin. In other embodiments, the invention provides methods for treating endoplasmic reticulum (ER) stress in a cell comprising administering to the mammal a first rAAV vector comprising nucleic acid encoding a miR-708 and a second rAAV viral particle comprising a second rAAV vector comprising nucleic acid encoding a rhodopsin.

In some embodiments of the invention, the nucleic acid encoding miR-708 is operably linked to a promoter. In some embodiments, the promoter is capable of expressing the miR-708 in photoreceptor cells (e.g., a rod photoreceptor cell). In further embodiments, the promoter comprises a rhodopsin kinase (RK) promoter or an opsin promoter. In other embodiments of the invention, the nucleic acid encoding rhodopsin is operably linked to a promoter. In some embodiments, the promoter is capable of expressing the rhodopsin in photoreceptor cells (e.g., a rod photoreceptor cell). In further embodiments, the promoter comprises a RK promoter or an opsin promoter.

In some embodiments, the invention provides methods to treat RP and/or ER stress comprising administering to a mammal, a rAAV particle comprising a rAAV vector comprising nucleic acid encoding miR-708 and rhodopsin. In some embodiments, the nucleic acid encoding miR-708 and the nucleic acid encoding rhodopsin are operably linked to one RK promoter. In other embodiments, the nucleic acid encoding miR-708 is operably linked to a first RK promoter or a first opsin promoter and the nucleic acid encoding rhodopsin is operably linked to a second RK promoter or a second opsin promoter. In some embodiments, the first and/or second opsin promoter includes an MVM intron (e.g., an intron of SEQ ID NO:23). In some embodiments, the nucleic acid encoding miR-708 is 5' to the nucleic acid encoding rhodopsin. In other embodiments, the nucleic acid encoding miR-708 is 3' to the nucleic acid encoding rhodopsin. In some embodiments, the nucleic acid encoding miR-708 is operably linked to the chicken β-actin (CBA) promoter. In some embodiments, the nucleic acid encoding rhodopsin is operably linked to the chicken β-actin (CBA) promoter. In some embodiments, a sequence derived from a minute virus of mouse (MVM) intron is located 3' to the promoter. In some embodiments, the MMV intron comprises the nucleotide sequence of SEQ ID NO:23. In some embodiments, the promoter further comprises i) a CMV enhancer; ii) a sequence derived from a photoreceptor specific transcription factor; iii) a sequence derived from a rod photoreceptor specific transcription factor; iv) a sequence derived from a neural retinal basic zipper factor; v) a sequence derived from a cone rod homeobox-containing transcription factor sequence; vi) a CMV enhancer and at least one or more of a sequence derived from a photoreceptor specific transcription factor, a sequence derived from a rod photoreceptor specific transcription factor, a sequence derived from a neural retinal basic zipper factor; a sequence derived from a cone rod homeobox-containing transcription factor sequence; vii) a neural retinal basic leucine zipper factor, a CMV enhancer and an Opsin promoter (−500 to +17); viii) a neural retinal basic leucine zipper factor, a CMV enhancer, an Opsin promoter (−500 to +17), and an MVM intron; ix) a CMV enhancer comprising SEQ ID NO:29; x) a neural retinal basic leucine zipper factor sequence comprising SEQ ID NO:30; xi) a sequence derived from a cone rod homeobox-containing transcription factor sequence comprising SEQ ID NO:28; xii) a CMV enhancer comprising SEQ ID NO:29 and at least one or more of a sequence derived from a photoreceptor specific transcription factor, a sequence derived from a rod photoreceptor specific transcription factor, a sequence derived from a neural retinal basic zipper factor comprising SEQ ID NO:30; a sequence derived from a cone rod homeobox-containing transcription factor sequence comprising SEQ ID NO:28; xiii) a neural retinal basic leucine zipper factor comprising SEQ ID NO:30, a CMV enhancer comprising SEQ ID NO:29 and an Opsin promoter (−500 to +17) comprising SEQ ID NO:22; or xiv) a neural retinal basic leucine zipper factor comprising SEQ ID NO:28, a CMV enhancer comprising SEQ ID NO:29, an Opsin promoter (−500 to +17) comprising SEQ ID NO:22, and an MVM intron comprising SEQ ID NO:23. In some embodiments, the nucleic acid encoding miR-708 is embedded in an intron. In some embodiments, the nucleic acid encoding miR-708 comprises an endogenous miR-708 scaffold or a miR-155 scaffold.

In some embodiments, the invention provides methods to treat RP and/or ER stress comprising administering to a mammal, a rAAV particle comprising a rAAV vector comprising nucleic acid encoding miR-708. In some embodiments, the nucleic acid encoding miR-708 comprises the nucleic acid of SEQ ID NO:1. In some embodiments, the nucleic acid encoding miR-708 comprises a nucleic acid having about at least 85%, 90%, 91%, 92%, 93%, 94%, 95%, 96%, 97%, 98%, or 99% identity to SEQ ID NO:1.

In some embodiments, the invention provides methods to treat RP and/or ER stress comprising administering to a mammal, a rAAV particle comprising a rAAV vector comprising nucleic acid encoding rhodopsin. In some embodiments, the rhodopsin is mammalian rhodopsin or functional equivalent thereof. In some embodiments, the rhodopsin is human rhodopsin or functional equivalent thereof. In some embodiments, the rhodopsin lacks the 3' untranslated region (UTR) miR-708 target sequence. In some embodiments, the nucleic acid encoding rhodopsin comprises a substitution, insertion or deletion of nucleic acid in the miR-708 target sequence. In some embodiments, the substitution, insertion or deletion reduces or prevents recognition by miR-708. In some embodiments, the nucleic acid encoding rhodopsin comprises a substitution, insertion or deletion of nucleic acid in the miR-708 target sequence wherein the miR-708 target sequence is SEQ ID NO:19. In some embodiments, expression of the rhodopsin is refractory to suppression by miR-708. In some embodiments, the rhodopsin comprises the amino acid sequence of SEQ ID NO:2. In some embodiments, the rhodopsin comprises an amino acid sequence having about at least t 85%, 90%, 91%, 92%, 93%, 94%, 95%, 96%, 97%, 98%, or 99% identity to SEQ ID NO:2. In some embodiments, the nucleic acid encoding the rhodopsin comprises nucleic acid of SEQ ID NO:3. In some embodiments, the nucleic acid encoding the rhodopsin comprises a nucleic acid having about 85%, 90%, 91%, 92%, 93%, 94%, 95%, 96%, 97%, 98%, or 99% identity to SEQ ID NO:3.

In some embodiments, the invention provides methods to treat RP and/or ER stress comprising administering to a mammal, a rAAV particle comprising a polynucleotide of SEQ ID NO:5, SEQ ID NO:6, SEQ ID NO:7, SEQ ID NO:8 or SEQ ID NO:9. In some embodiments, the AAV viral particle comprises a recombinant viral genome comprises a polynucleotide having about at least t 85%, 90%, 91%, 92%, 93%, 94%, 95%, 96%, 97%, 98%, or 99% identity to SEQ ID NO:5, SEQ ID NO:6 SEQ ID NO:7, SEQ ID NO:8, SEQ ID NO:9, SEQ ID NO:24, SEQ ID NO:25, SEQ ID NO:26, or SEQ ID NO:27.

In some embodiments, the invention provides methods to treat RP and/or ER stress comprising administering to a mammal, a rAAV particle wherein the AAV viral particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the rAAV viral particle comprises an AAV serotype 5 capsid. In some embodiments, the rAAV viral particle comprises an AAV serotype 5 tyrosine mutant capsid.

In some embodiments, the invention provides methods of treating RP and/or ER stress comprising administering to a mammal a first rAAV virus particle comprising nucleic acid encoding miR-708 and a second rAAV virus particle encoding rhodopsin. In some embodiments, the first rAAV particle and/or the second rAAV virus particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the first rAAV viral particle and/or the second rAAV viral particle comprise an AAV serotype 5 capsid. In some embodiments, the first rAAV viral particle and/or the second rAAV viral particle comprise an AAV serotype 5 tyrosine mutant capsid.

In some embodiments, the invention provides methods to treat RP and/or ER stress comprising administering to a mammal, a rAAV particle wherein the AAV vector comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITR. In some embodiments, the invention provides methods of treating RP and/or ER stress comprising administering to a mammal a first rAAV virus particle comprising a first rAAV vector comprising nucleic acid encoding miR-708 and a second rAAV virus particle comprising a second rAAV vector encoding rhodopsin. In some embodiments, the first rAAV vector and/or the second rAAV virus vector comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITR.

In some embodiments of the invention, the rAAV vectors of the method comprise AAV serotype 2 ITRs. In some embodiments, the ITR and the capsid of the rAAV viral particle are derived from the same AAV serotype. In other embodiments, the ITR and the capsid of the rAAV viral particles are derived from different AAV serotypes. In some embodiments, the rAAV viral particle comprises an AAV-5 capsid, and wherein the vector comprises AAV2 ITRs. In some embodiments, the rAAV viral particle comprises an AAV-5 tyrosine mutant capsid, and wherein the vector comprises AAV2 ITRs.

In some embodiments, the invention provides methods to treat RP and/or ER stress in a mammal wherein the rAAV particles are injected into the subretinal space of the retina of the mammal. In some embodiments, the rAAV is administered to more than one location of the subretinal space of the retina of the mammal. In other embodiments, the rAAV particles are injected intravitreally to the mammal. In some embodiments, at least 10-30% of the photoreceptor cells (e.g., rod photoreceptor cells) are transduced by the AAV.

In some embodiments, the invention provides methods to treat RP and/or ER stress in a mammal, wherein the mammal has a mutation in the endogenous rhodopsin gene. In some embodiments, the mutation in the endogenous rhodopsin gene is an autosomal dominant mutation. In some embodiments, the retinitis pigmentosa is autosomal dominant retinitis pigmentosa. In some embodiments, the mammal is a human. In some embodiments, the human has a P23H mutation in the endogenous rhodopsin gene.

In some embodiments, the invention provides methods of treating RP and/or ER stress comprising administering to a mammal a first rAAV virus particle comprising nucleic acid encoding miR-708 and a second rAAV virus particle encoding rhodopsin wherein the first rAAV viral particle encoding the miR-708 and the second rAAV viral particle encoding the rhodopsin are administered to the mammal at the same time. In some embodiments, the first rAAV viral particle encoding the miR-708 and the rAAV viral particle encoding the rhodopsin are administered to the mammal sequentially. In some embodiments, the rAAV viral particle encoding the miR-708 is administered to the mammal first and the rAAV viral particle encoding the rhodopsin is administered to the mammal second. In some embodiments, the rAAV viral particle encoding the rhodopsin is administered to the mammal first and the rAAV viral particle encoding the miR-708 is administered to the mammal second.

In some embodiments of the invention, the rAAV viral particles are in a pharmaceutical composition. In some embodiments, the pharmaceutical composition further comprises a pharmaceutically acceptable carrier. In some embodiments, the invention provides a composition comprising a rAAV particle comprising a rAAV vector comprising nucleic acid encoding miR-708 used in the methods described herein. In some embodiments, the invention provides a rAAV particle comprising a rAAV vector comprising nucleic acid encoding a miR708 for use in treating retitinis pigmentosa or reducing ER stress according to any of the methods described herein. In some embodiments, the invention provides a first rAAV particle comprising a rAAV vector comprising nucleic acid encoding a miR708 and a second rAAV particle comprising a rAAV vector comprising nucleic acid encoding rhodopsin for use in treating retitinis pigmentosa or reducing ER stress according to any of the methods described herein. In some embodiments, the rAAV particle comprises a rAAV vector comprising nucleic acid encoding a miR708 and rhodopsin for use in treating retitinis pigmentosa or reducing ER stress according to any one of the methods described herein.

In some aspects, the invention described herein provides compositions for treating retinitis pigmentosa in a mammal, comprising a recombinant adeno-associated virus (rAAV) viral particle comprising a vector encoding a miR-708. In some embodiments, the rAAV vector comprising nucleic acid encoding a miR-708 further comprises nucleic acid encoding rhodopsin. In some embodiments, the invention provides compositions for treating retinitis pigmentosa comprising a first rAAV viral particle comprising a first rAAV vector comprising nucleic acid encoding a miR-708 and a second rAAV viral particle comprising a second rAAV vector comprising nucleic acid encoding a rhodopsin. In other embodiments, the invention provides compositions for treating retinitis pigmentosa comprising a rAAV viral particle comprising a rAAV vector comprising nucleic acid encoding a miR-708 and rhodopsin.

In some aspects, the invention provides compositions for treating endoplasmic reticulum (ER) stress in a cell comprising a rAAV viral particle comprising a rAAV vector comprising nucleic acid encoding a miR-708. In some aspects, the invention provides compositions for treating endoplasmic reticulum (ER) stress in a cell comprising a rAAV viral particle comprising a rAAV vector comprising nucleic acid encoding a miR-708 and rhodopsin. In some embodiments, the mammal with ER stress has or is at risk of having RP. In some embodiments, the mammal with ER stress is a human who has or is at risk of having RP. In some embodiments, the rAAV particle is administered to an eye of the mammal. In some embodiments, the cell is an ocular cell. In further embodiments, the cell is a photoreceptor cell. In yet further embodiments, the cell is a rod photoreceptor cell. In some embodiments, the composition reduces one or more cellular markers of ER stress. In further embodiments, the one or more cellular marker of ER stress is spliced XBP-1, CHOP or Grp78. In some embodiments, the rAAV vector comprises nucleic acid encoding a miR-708 further comprises nucleic acid encoding rhodopsin. In other embodiments, the invention provides compositions for treating endoplasmic reticulum (ER) stress in a cell comprising a first rAAV vector comprising nucleic acid encoding a miR-708 and a second rAAV viral particle comprising a second rAAV vector comprising nucleic acid encoding a rhodopsin.

In some embodiments of the invention, the nucleic acid encoding miR-708 is operably linked to a promoter. In some embodiments, the promoter is capable of expressing the miR-708 in photoreceptor cells (e.g., rod photoreceptor cells). In further embodiments, the promoter comprises a rhodopsin kinase (RK) promoter or an opsin promoter. In other embodiments of the invention, the nucleic acid encoding rhodopsin is operably linked to a promoter. In some embodiments, the promoter is capable of expressing the rhodopsin in photoreceptor cells (e.g., rod photoreceptor cells). In further embodiments, the promoter comprises a RK promoter or an opsin promoter.

In some embodiments, the invention provides compositions to treat RP and/or ER stress comprising a rAAV particle comprising a rAAV vector comprising nucleic acid encoding miR-708 and rhodopsin. In some embodiments, the nucleic acid encoding miR-708 and the nucleic acid encoding rhodopsin are operably linked to one RK promoter. In other embodiments, the nucleic acid encoding miR-708 is operably linked to a first RK promoter or a first opsin promoter and the nucleic acid encoding rhodopsin is operably linked to a second RK promoter or a second opsin promoter. In some embodiments, the first and/or second opsin promoter includes an MVM intron (e.g., an intron of SEQ ID NO:23). In some embodiments, the nucleic acid encoding miR-708 is 5' to the nucleic acid encoding rhodopsin. In other embodiments, the nucleic acid encoding miR-708 is 3' to the nucleic acid encoding rhodopsin. In some embodiments, the nucleic acid encoding miR-708 is operably linked to the chicken β-actin (CBA) promoter. In some embodiments, the nucleic acid encoding rhodopsin is operably linked to the chicken β-actin (CBA) promoter. In some embodiments, the first and/or second opsin promoter includes an MVM intron (e.g., an intron of SEQ ID NO:23). In some embodiments, the nucleic acid encoding miR-708 is 5' to the nucleic acid encoding rhodopsin. In other embodiments, the nucleic acid encoding miR-708 is 3' to the nucleic acid encoding rhodopsin. In some embodiments, the nucleic acid encoding miR-708 is operably linked to the chicken β-actin (CBA) promoter. In some embodiments, the nucleic acid encoding rhodopsin is operably linked to the chicken β-actin (CBA) promoter. In some embodiments, a sequence derived from a minute virus of mouse (MVM) intron is located 3' to the promoter. In some embodiments, the MMV intron comprises the nucleotide sequence of SEQ ID NO:23. In some embodiments, the promoter further comprises i) a CMV enhancer; ii) a sequence derived from a photoreceptor specific transcription factor; iii) a sequence derived from a rod photoreceptor specific transcription factor; iv) a sequence derived from a neural retinal basic zipper factor; v) a sequence derived from a cone rod homeobox-containing transcription factor sequence; vi) a CMV enhancer and at least one or more of a sequence derived from a photoreceptor specific transcription factor, a sequence derived from a rod photoreceptor specific transcription factor, a sequence derived from a neural retinal basic zipper factor; a sequence derived from a cone rod homeobox-containing transcription factor sequence; vii) a neural retinal basic leucine zipper factor, a CMV enhancer and an Opsin promoter (−500 to +17); viii) a neural retinal basic leucine zipper factor, a CMV enhancer, an Opsin promoter (−500 to +17), and an MVM intron; ix) a CMV enhancer comprising SEQ ID NO:29; x) a neural retinal basic leucine zipper factor sequence comprising SEQ ID NO:30; xi) a sequence derived from a cone rod homeobox-containing transcription factor sequence comprising SEQ ID NO:28; xii) a CMV enhancer comprising SEQ ID NO:29 and at least one or more of a sequence derived from a photoreceptor specific transcription factor, a sequence derived from a rod photoreceptor specific transcription factor, a sequence derived from a neural retinal basic zipper factor comprising SEQ ID NO:30; a sequence derived from a cone rod homeobox-containing transcription factor sequence comprising SEQ ID NO:28; xiii) a neural retinal basic leucine zipper factor comprising SEQ ID NO:30, a CMV enhancer comprising SEQ ID NO:29 and an Opsin promoter (−500 to +17) comprising SEQ ID NO:22; or xiv) a neural retinal basic leucine zipper factor comprising SEQ ID NO:28, a CMV enhancer comprising SEQ ID NO:29, an Opsin promoter (−500 to +17) comprising SEQ ID NO:22, and an MVM intron comprising SEQ ID NO:23. In some embodiments, the nucleic acid encoding miR-708 is embedded in an intron. In some embodiments, the nucleic acid encoding miR-708 comprises an endogenous miR-708 scaffold or a miR-155 scaffold.

In some embodiments, the invention provides compositions to treat RP and/or ER stress comprising a rAAV particle comprising a rAAV vector comprising nucleic acid encoding miR-708. In some embodiments, the nucleic acid encoding miR-708 comprises the nucleic acid of SEQ ID NO:1. In some embodiments, the nucleic acid encoding miR-708 comprises a nucleic acid having about at least 85%, 90%, 91%, 92%, 93%, 94%, 95%, 96%, 97%, 98%, or 99% identity to SEQ ID NO:1.

In some embodiments, the invention provides compositions to treat RP and/or ER stress comprising a rAAV particle comprising a rAAV vector comprising nucleic acid encoding rhodopsin. In some embodiments, the rhodopsin is mammalian rhodopsin or functional equivalent thereof. In some embodiments, the rhodopsin is human rhodopsin or functional equivalent thereof. In some embodiments, the rhodopsin lacks the 3' untranslated region (UTR) miR-708 target sequence. In some embodiments, the nucleic acid encoding rhodopsin comprises a substitution, insertion or deletion of nucleic acid in the miR-708 target sequence. In some embodiments, the substitution, insertion or deletion reduces or prevents recognition by miR-708. In some embodiments, the nucleic acid encoding rhodopsin comprises a substitution, insertion or deletion of nucleic acid in the miR-708 target sequence wherein the miR-708 target sequence is SEQ ID NO:19. In some embodiments, expression of the rhodopsin is refractory to suppression by miR-708. In some embodiments, the rhodopsin comprises the amino acid sequence of SEQ ID NO:2. In some embodiments, the rhodopsin comprises an amino acid sequence having about at least 85%, 90%, 91%, 92%, 93%, 94%, 95%, 96%, 97%, 98%, or 99% identity to SEQ ID NO:2. In some embodiments, the nucleic acid encoding the rhodopsin comprises nucleic acid of SEQ ID NO:3. In some embodiments, the nucleic acid encoding the rhodopsin comprises a nucleic acid having about 85%, 90%, 91%, 92%, 93%, 94%, 95%, 96%, 97%, 98%, or 99% identity to SEQ ID NO:3.

In some embodiments, the invention provides compositions to treat RP and/or ER stress comprising a rAAV particle comprising a polynucleotide of SEQ ID NO:5, SEQ ID NO:6, SEQ ID NO:7, SEQ ID NO:8 or SEQ ID NO:9. In some embodiments, the AAV viral particle comprises a recombinant viral genome comprises a polynucleotide having about at least t 85%, 90%, 91%, 92%, 93%, 94%, 95%, 96%, 97%, 98%, or 99% identity to SEQ ID NO:5, SEQ ID NO:6, SEQ ID NO:7, SEQ ID NO:8 SEQ ID NO:9, SEQ ID NO:24, SEQ ID NO:25, SEQ ID NO:26, or SEQ ID NO:27.

In some embodiments, the invention provides compositions to treat RP and/or ER stress comprising a rAAV particle wherein the AAV viral particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the rAAV viral particle comprises an AAV serotype 5 capsid. In some embodiments, the rAAV viral particle comprises an AAV serotype 5 tyrosine mutant capsid.

In some embodiments, the invention provides compositions for treating RP and/or ER stress comprising a first rAAV virus particle comprising nucleic acid encoding miR-708 and a second rAAV virus particle encoding rhodopsin. In some embodiments, the first rAAV particle and/or the second rAAV virus particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, or mouse AAV capsid rAAV2/HBoV1 serotype capsid. In some embodiments, the first rAAV viral particle and/or the second rAAV viral particle comprise an AAV serotype 5 capsid. In some embodiments, the first rAAV viral particle and/or the second rAAV viral particle comprise an AAV serotype 5 tyrosine mutant capsid.

In some embodiments, the invention provides compositions to treat RP and/or ER stress comprising a rAAV particle wherein the AAV vector comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITR. In some embodiments, the invention provides compositions for treating RP and/or ER stress comprising a first rAAV virus particle comprising a first rAAV vector comprising nucleic acid encoding miR-708 and a second rAAV virus particle comprising a second rAAV vector encoding rhodopsin. In some embodiments, the first rAAV vector and/or the second rAAV virus vector comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITR.

In some embodiments of the invention, the rAAV vectors of the composition comprise AAV serotype 2 ITRs. In some embodiments, the ITR and the capsid of the rAAV viral particle are derived from the same AAV serotype. In other embodiments, the ITR and the capsid of the rAAV viral particles are derived from different AAV serotypes. In some embodiments, the rAAV viral particle comprises an AAV-5 capsid, and wherein the vector comprises AAV2 ITRs. In some embodiments, the rAAV viral particle comprises an AAV-5 tyrosine mutant capsid, and wherein the vector comprises AAV2 ITRs.

In some embodiments, the invention provides compositions to treat RP and/or ER stress in a mammal, wherein the mammal has a mutation in the endogenous rhodopsin gene. In some embodiments, the mutation in the endogenous rhodopsin gene is an autosomal dominant mutation. In some embodiments, the retinitis pigmentosa is autosomal dominant retinitis pigmentosa. In some embodiments, the mammal is a human. In some embodiments, the human has a P23H mutation in the endogenous rhodopsin gene.

In some embodiments, the invention provides kits to treat RP or to reduce ER stress in a mammal comprising an effective amount of rAAV particles according to the methods described herein. In some embodiments, the kits comprise an effective amount of a composition as described herein. In some embodiments, the kit comprises an effective amount of rAAV particles comprising a rAAV vector comprising nucleic acid encoding miR-708. In some embodiments, the kit comprises an effective amount of rAAV particles comprising a rAAV vector comprising nucleic acid encoding miR-708 and rhodopsin. In some embodiments, the kit comprises an effective amount of first rAAV particles comprising a rAAV vector comprising nucleic acid encoding miR-708 and an effective amount of second rAAV particles comprising a second rAAV vector comprising nucleic acid encoding rhodopsin. In further embodiments, the kit comprising instructions for use of the rAAV particles in the treatment of retinitis pigmentosa and/or reduction of ER stress. In further embodiments, the kit comprising instructions for use in any one of the methods described herein.

In some aspects, the invention provides an article of manufacture comprising an effective amount of rAAV particles according to the methods described herein. In some embodiments, the article of manufacture comprises an effective amount of any of the compositions described herein. In some embodiments, the article of manufacture comprises an effective amount of rAAV particles comprising a rAAV vector comprising nucleic acid encoding miR-708. In some embodiments, the article of manufacture comprises an effective amount of rAAV particles comprising a rAAV vector comprising nucleic acid encoding miR-708 and rhodopsin. In some embodiments, the article of manufacture comprises an effective amount of first rAAV particles comprising a rAAV vector comprising nucleic acid encoding miR-708 and an effective amount of second rAAV particles comprising a second rAAV vector comprising nucleic acid encoding rhodopsin.

Is some aspects, the invention provides a nucleic acid comprising an intron derived from an MVM. In some embodiments, the MVM intron comprises SEQ ID NO:23. In some embodiments, the nucleic acid further comprises a promoter. In some embodiments, the nucleic acid further comprises an enhancer. In some embodiments, the promoter is located 5' to the MVM intron. In some embodiments, the invention provides an expression construct comprising the nucleic acid. In some embodiments, the invention provides a vector comprising the nucleic acid or the expression construct. In some embodiments, the invention provides a cell comprising the nucleic acid, the expression construct, or the vector.

BRIEF DESCRIPTION OF THE DRAWINGS

(FIG. 2A) Western blot of detergent soluble extracts from cells expressing wild-type ("wt") or P23H mutant rhodopsin. (FIG. 2B) Western blot of detergent soluble extracts from cells expressing wild-type ("wt") or P23H mutant rhodopsin. Extracts were treated with Endoglycosidase H ("Endo-H") or left untreated.

(FIG. 3A) Relative expression of C/EBP homologous protein (CHOP; a.k.a. Ddit3), binding immunoglobulin protein (BiP; a.k.a. Hspa5), and rhodopsin genes in cells expressing wild-type ("wt") or P23H mutant rhodopsin. The relative expression of each gene was compared to beta-glucoronidase expression using the $\Delta\Delta C_t$ method. (FIG. 3B) Percentage of apoptotic cells in cells expressing control (pcDNA), wild-type rhodopsin, or P23H mutant rhodopsin, as measured by TUNEL staining.

(FIG. 9A) Expression of miR-708 in WERI or RPE cells upon transfection of a vector encoding miR-708 driven by the RK promoter or a control miRNA ("Scramble"). Expression is depicted relative to expression of miR-16. (FIG. 9B) Expression of P23H rhodopsin mRNA in WERI cells transfected with a pRK-miR-708 plasmid, relative to cells transfected with a control plasmid.

FIGS. 10A-10C show that subretinal delivery of an AAV5 miR-708 vector results in knockdown of mouse rhodopsin. (FIG. 10A) Expression of mRhodopsin in mouse retinas injected with AAV5 miR-708 or AAV5 miR-Control. (FIG. 10B) Expression of RdCVF in mouse retinas injected with AAV5 miR-708 or AAV5 miR-Control. (FIG. 10C) Expression of miR-708 in mouse retinas injected with AAV5 miR-708 or AAV5 miR-Control.

(FIG. 11A) Three representative electroretinograms representing scoptopic responses in eyes receiving AAV5 miR-708 or AAV5 miR-Control ("Scram"). (FIG. 11B) Three representative electroretinograms representing photopic responses in the same eyes as in (FIG. 11A) receiving AAV5 miR-708 or AAV5 miR-Control ("Scram").

DETAILED DESCRIPTION

Figure 1B:
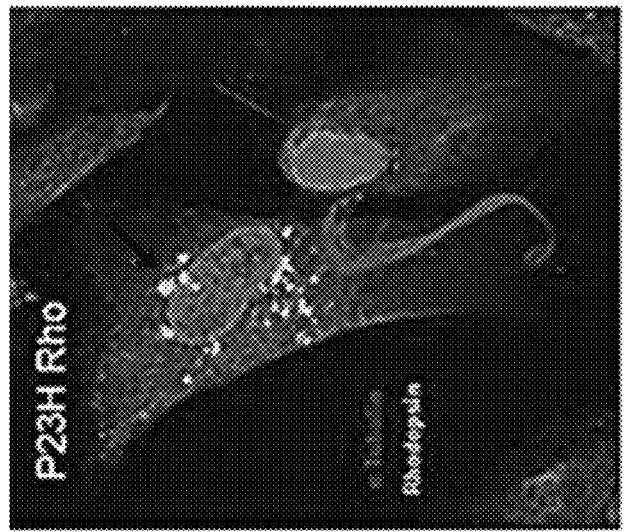
FIGS. 1A & 1B show the localization of wild-type (FIG. 1A) and P23H mutant (FIG. 1B) rhodopsin in human retinal pigmented epithelial cells. Cells are stained for rhodopsin (green), α-tubulin (red), and DNA (blue). The staining pattern of wild-type rhodopsin is characteristic of membrane localization (solid arrow), whereas the staining pattern of P23H mutant rhodopsin is characteristic of perinuclear/reticular localization (dashed arrow).

The present invention provides methods for treating retinitis pigmentosa (RP) in a mammal, comprising administering to the eye of the mammal a recombinant adenoassociated virus (rAAV) viral particle comprising a vector encoding a miR-708. The miR-708 targets a region in the 3' untranslated region of the rhodopsin gene and as such, may suppress activity of a mutant rhodopsin associated with RP. In some aspects, the invention provides methods for treating retinitis pigmentosa in a mammal, comprising administering to the eye of the mammal a recombinant adeno-associated virus (rAAV) viral particle comprising a vector encoding a miR-708 and a wild-type rhodopsin nucleic acid. As such, the vector may suppress the activity of a mutant rhodopsin associated with RP while concurrently replacing the mutant rhodopsin with a wild-type rhodopsin. In some embodiments, the nucleic acid encoding the wild-type rhodopsin does not include the 3' UTR target of miR-708 such that the miR-708 will only target expression of mutant rhodopsin. The invention also provides compositions comprising rAAV particles encoding miR-708 and rAAV particles encoding rhodopsin. In some embodiments, the invention provides compositions comprising rAAV particles encoding both miR-708 and rhodopsin.

I. General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., 4$^{th}$ ed., Cold Spring Harbor Laboratory Press, Cold Spring Harbor, N.Y., 2012); *Current Protocols in Molecular Biology* (F. M. Ausubel, et al. eds., 2003); the series *Methods in Enzymology* (Academic Press, Inc.); *PCR 2: A Practical Approach* (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, 6$^{th}$ ed., J. Wiley and Sons, 2010); *Oligonucleotide Synthesis* (M. J. Gait, ed., 1984); *Methods in Molecular Biology*, Humana Press; *Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty, ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 2011).

II. Definitions

A "vector," as used herein, refers to a recombinant plasmid or virus that comprises a nucleic acid to be delivered into a host cell, either in vitro or in vivo.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate (P—NH$_2$) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

A "recombinant viral vector" refers to a recombinant polynucleotide vector comprising one or more heterologous sequences (i.e., nucleic acid sequence not of viral origin). In the case of recombinant AAV vectors, the recombinant nucleic acid is flanked by at least one, preferably two, inverted terminal repeat sequences (ITRs).

A "recombinant AAV vector (rAAV vector)" refers to a polynucleotide vector comprising one or more heterologous sequences (i.e., nucleic acid sequence not of AAV origin) that are flanked by at least one, preferably two, AAV inverted terminal repeat sequences (ITRs). Such rAAV vectors can be replicated and packaged into infectious viral particles when present in a host cell that has been infected with a suitable helper virus (or that is expressing suitable helper functions) and that is expressing AAV rep and cap gene products (i.e. AAV Rep and Cap proteins). When a rAAV vector is incorporated into a larger polynucleotide (e.g., in a chromosome or in another vector such as a plasmid used for cloning or transfection), then the rAAV vector may be referred to as a "pro-vector" which can be "rescued" by replication and encapsidation in the presence of AAV packaging functions and suitable helper functions. An rAAV vector can be in any of a number of forms, including, but not limited to, plasmids, linear artificial chromosomes, complexed with lipids, encapsulated within liposomes, and, most preferable, encapsidated in a viral particle, particularly an AAV particle. A rAAV vector can be packaged into an AAV virus capsid to generate a "recombinant adeno-associated viral particle (rAAV particle)".

"Heterologous" means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). Similarly, a cellular sequence (e.g., a gene or portion thereof) that is incorporated into a viral vector is a heterologous nucleotide sequence with respect to the vector.

The term "transgene" refers to a polynucleotide that is introduced into a cell and is capable of being transcribed into RNA and optionally, translated and/or expressed under appropriate conditions. In aspects, it confers a desired property to a cell into which it was introduced, or otherwise leads to a desired therapeutic or diagnostic outcome. In another aspect, it may be transcribed into a molecule that mediates RNA interference, such as siRNA.

The terms "genome particles (gp)," "genome equivalents," or "genome copies" as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) *Hum. Gene Ther.,* 10:1031-1039; Veldwijk et al. (2002) *Mol. Ther.,* 6:272-278.

The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) *J. Virol.,* 62:1963-1973.

The term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) *Exp. Neurobiol.,* 144:113-124; or in Fisher et al. (1996) *J. Virol.,* 70:520-532 (LFU assay).

An "inverted terminal repeat" or "ITR" sequence is a term well understood in the art and refers to relatively short sequences found at the termini of viral genomes which are in opposite orientation.

An "AAV inverted terminal repeat (ITR)" sequence, a term well-understood in the art, is an approximately 145-nucleotide sequence that is present at both termini of the native single-stranded AAV genome. The outermost 125 nucleotides of the ITR can be present in either of two alternative orientations, leading to heterogeneity between different AAV genomes and between the two ends of a single AAV genome. The outermost 125 nucleotides also contains several shorter regions of self-complementarity (designated A, A', B, B', C, C' and D regions), allowing intrastrand base-pairing to occur within this portion of the ITR.

A "terminal resolution sequence" or "trs" is a sequence in the D region of the AAV ITR that is cleaved by AAV rep proteins during viral DNA replication. A mutant terminal resolution sequence is refractory to cleavage by AAV rep proteins.

A "helper virus" for AAV refers to a virus that allows AAV (which is a defective parvovirus) to be replicated and packaged by a host cell. A number of such helper viruses have been identified, including adenoviruses, herpesviruses and poxviruses such as vaccinia. The adenoviruses encompass a number of different subgroups, although Adenovirus type 5 of subgroup C (Ad5) is most commonly used. Numerous adenoviruses of human, non-human mammalian and avian origin are known and are available from depositories such as the ATCC. Viruses of the herpes family, which are also available from depositories such as ATCC, include, for example, herpes simplex viruses (HSV), Epstein-Barr viruses (EBV), cytomegaloviruses (CMV) and pseudorabies viruses (PRV).

"Percent (%) sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various ways that are within the skill in the art, for instance, using publicly available computer software programs, for example, those described in Current Protocols in Molecular Biology (Ausubel et al., eds., 1987), Supp. 30, section 7.7.18, Table 7.7.1, and including BLAST, BLAST-2, ALIGN or Megalign (DNASTAR) software. A preferred alignment program is ALIGN Plus (Scientific and Educational Software, Pennsylvania). Those skilled in the art can determine appropriate parameters for measuring alignment, including any algorithms needed to achieve maximal alignment over the full length of the sequences being compared. For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows: 100 times the fraction W/Z, where W is the number of nucleotides scored as identical matches by the sequence alignment program in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

An "isolated" molecule (e.g., nucleic acid or protein) or cell means it has been identified and separated and/or recovered from a component of its natural environment.

An "effective amount" is an amount sufficient to effect beneficial or desired results, including clinical results (e.g., amelioration of symptoms, achievement of clinical endpoints, and the like). An effective amount can be administered in one or more administrations. In terms of a disease state, an effective amount is an amount sufficient to ameliorate, stabilize, or delay development of a disease.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein, "treatment" is an approach for obtaining beneficial or desired clinical results. For purposes of this invention, beneficial or desired clinical results include, but are not limited to, alleviation of symptoms, diminishment of extent of disease, stabilized (e.g., not worsening) state of disease, preventing spread (e.g., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

"Retinitis pigmentosa (RP)" refers to a heterogeneous group of diseases characterized by progressive loss of sight. Symptoms generally stem from degeneration or abnormalities of the retina, which may include the loss of photoreceptor cell function.

"Rhodopsin" refers to a member of the G-protein-coupled receptor family that functions in light perception in the rod photoreceptor cells of the retina. A visual pigment, rhodopsin contains a polypeptide opsin reversibly bound to its cofactor retinal. Light causes isomerization of retinal from an 11-cis to an all-trans form. This in turn causes a conformational change in the polypeptide that leads to G-protein activation. By converting the presence of light into a biochemical response, rhodopsin enables visual perception. Its function is required for scotopic vision (i.e., noncolor vision in dim light), and it is also thought to be required for photoreceptor cell viability.

As used herein, "rhodopsin" may refer to the full visual pigment including retinal or simply the amino acid component or sequence of the molecule. Rhodopsin may also be known as OPN2, Opsin-2, or RP4. Examples of rhodopsin proteins may include without limitation human, mouse, dog, and cat rhodopsin, e.g., NCBI Reference Sequences NP_000530, NP_663358, NP_001008277, and NP_001009242. Examples of rhodopsin genes may include without limitation human, mouse, dog, and cat rhodopsin genes, e.g., GenBank Entrez Gene ID 6010 (RHO, a.k.a. RP4, OPN2, and CSNBAD1), GenBank Entrez Gene ID 212541 (Rho, a.k.a. Ops, RP4, Opn2, and Noerg1), GenBank Entrez Gene ID 493763, and GenBank Entrez Gene ID 493762. The term rhodopsin as used herein also includes functional equivalents of rhodopsin (e.g., rhodopsin variants) including mutations, truncations, deletions, and/or insertions, provided that the functional equivalent maintains at least a portion of the activity of wild-type rhodopsin to ameliorate symptoms of retinitis pigmentosa.

As used herein "refractory" refers to resistance to modulation. For example, a rhodopsin gene that is refractory to suppression by miR-708 is substantially or totally resistant to suppression by miR-708.

"Opsin promoter" refers to a polynucleotide sequence derived from an opsin gene (e.g., mouse opsin) that drives expression specifically in rod photoreceptor cells (e.g., rod photoreceptor cells). As used herein, "opsin promoter" may refer to an entire promoter sequence or a fragment of the promoter sequence sufficient to drive rod-specific expression, such as the sequences described in Quiambao, A. B., et al. (1997) *Vis. Neurosci.* 14(4):617-25 and Le, Y. Z., et al. (2006) *Mol. Vis.* 12:389-98. In some embodiments, the opsin promoter contains a 676 bp fragment encoding a 400 bp CMV enhancer upstream of a portion of the opsin promoter sequence (−500 bp-+15 bp). In addition 65 bp NRL sequence is included; this encodes a neural retinal basic zipper factor (a Rod photoreceptor specific transcription factor).

"Rhodopsin kinase (RK) promoter" refers to a polynucleotide sequence derived from a rhodopsin kinase gene (e.g., human RK, represented by GenBank Entrez Gene ID 6011) that drives expression specifically in rod and cone photoreceptor cells, as well as retinal cell lines such as WERI Rb-1. As used herein, "rhodopsin kinase promoter" may refer to an entire promoter sequence or a fragment of the promoter sequence sufficient to drive photoreceptor-specific expression, such as the sequences described in Khani, S. C., et al. (2007) *Invest. Ophthalmol. Vis. Sci.* 48(9):3954-61 and Young, J. E., et al. (2003) *Invest. Ophthalmol. Vis. Sci.* 44(9):4076-85. In some embodiments, the RK promoter spans from −112 to +180 relative to the transcription start site.

Figure 4:
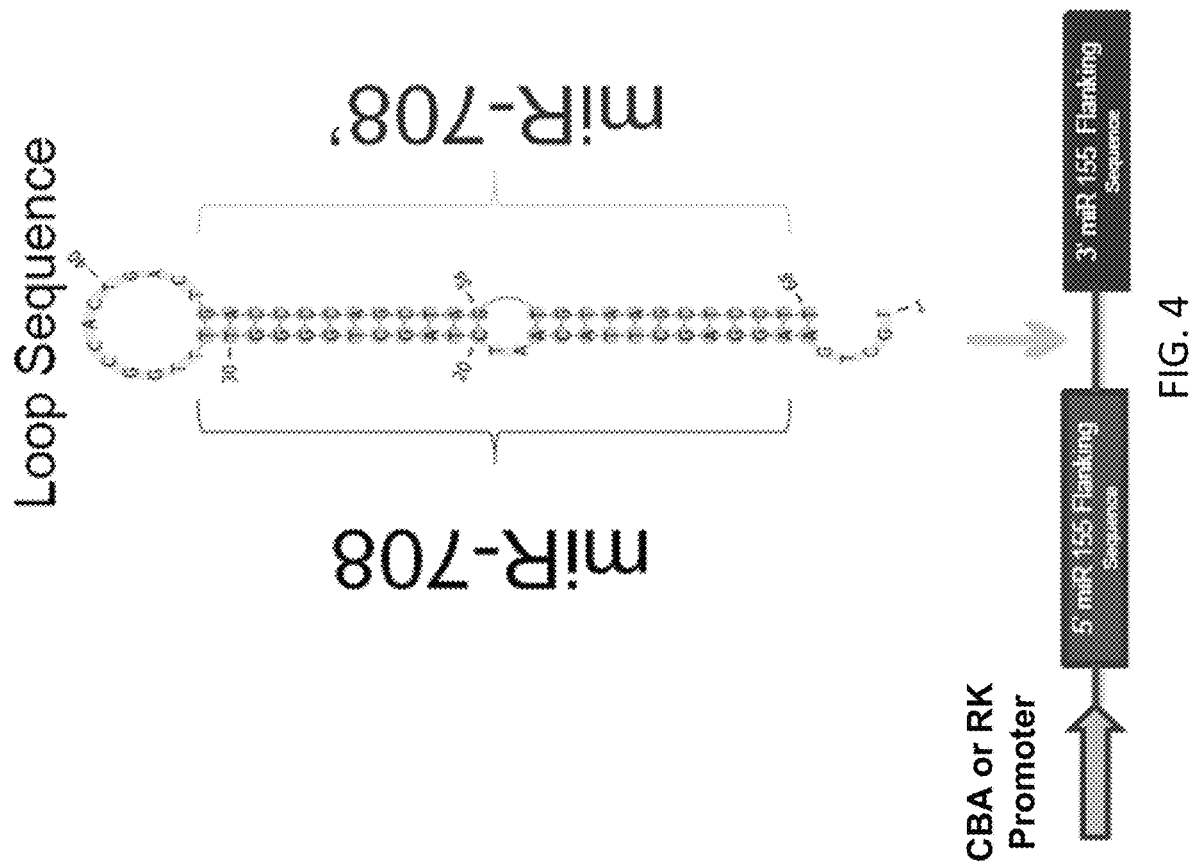
FIG. 4 shows a diagram of the construction of an expression vector for expressing miR-708 under the control of a ubiquitous promoter (chicken β-actin, CBA) or a photoreceptor-specific promoter (rhodopsin kinase, RK). DNA encoding the miR-708 stem and loop sequences was synthesized and cloned between 5' and 3' miR-155 scaffold sequence. This scaffold sequence contains the target sites required for Drosha to process pri-miR-708 into pre-miR-708 in the nucleus, allowing subsequent processing of pre-miR-708 by Dicer in the cytoplasm.

"miR-708" refers to a micro-RNA (miRNA) polynucleotide sequence comprising the stem and loop sequences as shown in FIG. 4. Examples of miR-708 polynucleotides may include without limitation human, mouse, dog, and cat miR-708, e.g., as represented by GenBank Entrez Gene IDs 100126333, 735284, and 100885899. miRNAs are small, non-coding RNA molecules that regulate the expression of genes (e.g., by downregulation of the gene transcript) containing a target site recognized by the miRNA (Bartel, D. P. (2004) *Cell* 116(2):281-97). miR-708 is known to be induced by CHOP and may be involved in the regulating rhodopsin expression (Behrman, S., et al. (2011) *J. Cell Biol.* 192(6):919-27). As used herein, "miR-708" may refer to the processed miR-708 polynucleotide or any intermediate in the processing pathway, e.g., pri-miRNA or pre-miRNA. As used herein, "miR-708" may refer to a DNA sequence that is transcribed to yield miR-708 RNA, or the RNA sequence itself.

Reference to "about" a value or parameter herein includes (and describes) embodiments that are directed to that value or parameter per se. For example, description referring to "about X" includes description of "X."

As used herein, the singular form of the articles "a," "an," and "the" includes plural references unless indicated otherwise.

It is understood that aspects and embodiments of the invention described herein include "comprising," "consisting," and/or "consisting essentially of" aspects and embodiments.

III. Retinitis Pigmentosa and Experimental Models Thereof

As described above, retinitis pigmentosa (RP) refers to a group of degenerative eye diseases that can cause progressive loss of sight, including loss of night vision, loss of peripheral visual fields, and total blindness. In America, the incidence of RP is thought to be approximately 1 in 4,000 people. RP is often inherited, and autosomal dominant, autosomal recessive, and X-linked RP disorders have been described. Mutations in more than 50 different genes have been associated with RP, including components involved in the phototransduction cascade, the retinal cycle, and splicing factors, as well as over 100 distinct mutations in rhodopsin itself. In many cases, mutations associated with RP lead to loss of rod photoreceptor function and/or cell death. This loss results in decreased scotopic vision and may manifest as night blindness or decreased peripheral vision. Rod cell death has also been associated with subsequent cone cell death, causing loss of high acuity vision and, combined with rod cell death, blindness.

A variety of cell- and animal-based models have been established for examining the cellular basis of RP and for testing experimental treatments. One cell-based model for RP is cultured human retinal pigmented epithelial (RPE) cells (Adamowicz, M., et al. (2012) *Adv. Exp. Med. Biol.* 723:573-9). This model may be used to express mutant proteins implicated in RP and test the effect of these mutations on protein function, or the effect of mutant proteins on cellular function and/or viability. For example, human wild-type and mutant rhodopsin may be expressed, using any appropriate promoter (e.g., CMV). Without wishing to be bound by theory, it is thought that misfolding of opsin polypeptides results in ER retention and stress, induction of the unfolded protein response (UPR), and increased cell death. This model may be used to examine the effect of any RP-associated mutation, for example a rhodopsin mutation such as P23H.

Animal-based RP models may include mice harboring mutations known or suspected to cause RP in mice, or mutations orthologous to those found in humans. In some embodiments, mouse models may include mice engineered to express a rhodopsin, for example a mutated human or mouse form, in photoreceptor cells. Examples of mouse models include the rhodopsin P347S mouse (Li, T., et al. (1996) *Proc. Natl. Acad. Sci.* 93(24):14176-81), the Rho$^{-/-}$ mouse (Humphries, M. M., et al. (1997) *Nat. Genet.* 15(2): 216-9), and a mouse expressing P23H mutant rhodopsin ("P23H mouse") (Olsson, J. E., et al. (1992) *Neuron* 9(5): 815-30). In the P23H mouse, mutant human rhodopsin may be inserted into the mouse germline. Any promoter known in the art to express in photoreceptor cells may be used (e.g., the mouse opsin or human RK promoter). In some embodiments, rhodopsin may be expressed using an AAV vector.

Other animal models for RP may also be used. In addition to mouse models, rat, dog, pig, frog (Tam, B. M. and Moritz, O. L. (2006) *Invest. Ophthalmol. Vis. Sci.* 47(8):3234-41), and non-human primate models may also be used.

IV. Methods to Treat Retinitis Pigmentosa

In some aspects, the invention provides methods and compositions for treating retinitis pigmentosa in a mammal comprising administering to the mammal (e.g., to the retina) an effective amount of rAAV viral particles comprising a vector encoding a miR-708. The methods can be used for treating a human with RP, to improve the pathologies and vision impairment associated with RP. In some embodiments, the invention includes administering an effective amount of rAAV viral particles comprising a vector comprising nucleic acid encoding rhodopsin (e.g., a normal or wild-type rhodopsin). In some embodiments, the miR-708 serves to suppress activity of a mutated rhodopsin associated with RP. In some embodiments, the normal or wild-type rhodopsin serves to supplement the eye with a functional rhodopsin. In some embodiments, the viral particle comprises an AAV serotype 5 capsid (AAV5 capsid) and either AAV 2 or AAV 5 inverted terminal repeats. In some embodiments, the viral particle comprises an AAV serotype 5 tyrosine mutant capsid and either AAV 2 or AAV 5 inverted terminal repeats.

In some aspects, the invention provides methods and compositions for ameliorating a symptom of RP, comprising administration to the eye of a mammal an effective amount of rAAV viral particles comprising a vector encoding a miR-708. In other aspects, the invention provides methods and compositions for ameliorating a symptom of RP, comprising administration to the eye of a mammal an effective amount of rAAV viral particles comprising a vector encoding a miR-708 and a rhodopsin. In some embodiments the symptoms of RP include, but is not limited to, blindness, night blindness, decreased peripheral vision, and loss of high acuity vision. In some embodiments, treating retinitis pigmentosa comprises reducing or preventing symptoms associated with the retinitis pigmentosa including but not limited to methods of preventing retinal degeneration, methods for arresting progression of RP, methods for increasing photoreceptor function, and the like. Symptoms and/or pathology of RP include but are not limited to loss of sight, loss of night vision, loss of peripheral visual fields, loss of ERG function; loss of visual acuity and contrast sensitivity; loss of visually guided behavior, reduction in rod photoreceptor function, rod photoreceptor cell death, decreased scotopic vision, reduction in retinal cell changes (loss of photoreceptor structure or function; thinning or thickening of the outer nuclear layer (ONL); thinning or thickening of the outer plexiform layer (OPL); disorganization followed by loss of rod and cone outer segments; shortening of the rod and cone inner segments; retraction of bipolar cell dendrites; thinning or thickening of the inner retinal layers including inner nuclear layer, inner plexiform layer, ganglion cell layer and nerve fiber layer; opsin mislocalization; overexpression of neurofilaments; and the like. In some embodiments, the invention provides methods to prevent deterioration of rod cell function and rod cell death and cone cell function and cone cell death.

In some aspects, the invention provides methods to prevent or delay progression of RP. Autosomal dominant RP is a genetic disease that can be genotyped. Onset and progression of RP may be determined by Optical Coherence Tomography (OCT) which allows examination of outer plexiform layer (OPL) abnormalities.

Means for determining amelioration of the symptoms of RP are known in the art. For example, measurement of visual fields (e.g., Goldmann visual fields), determination of electroretinogram (ERG), fundus photographs, optical coherence tomography, and fluorescein angiography. Improvements in visually-evoked behavior can also be used to determine amelioration of the symptoms of RP; for example, statements such as "I can find things that drop," "I can see faces during a candle-lit dinner," "I can see stripes on my shirt," "I can see stars at night," "I can read regular books and sit in the front of the classroom," "now I can play soccer and don't need someone next to me to help me find the ball," "I can ride my bicycle around my neighborhood by myself," "I achieved my dream: I saw my daughter hit a homerun," and "when can I have my other eye injected?"

In some aspects of the invention, the methods and compositions are used for the treatment of humans with RP. RP can be inherited in an autosomal dominant, autosomal recessive, or X-linked manner. X-linked RP can be either recessive, affecting primarily only males, or dominant, affecting both males and females. RP may be caused by mutations in the rho gene that encodes the rhodopsin protein. In some embodiments of the invention, the methods are used to treat humans with a mutation in the rho gene and/or in the rhodopsin protein. In some embodiments of the invention, the mutation in the rhodopsin protein is a P23H mutation (substitution of histidine for proline at amino acid residue 23 of the rhodopsin protein). In other embodiments, the mutation in the rhodopsin protein is a T58R, P347L, or P347S, or a deletion of residue I255. Mutations associated with retinitis pigmentosa are provided by McWilliam, P, et al., (1989) *Genomics* 5:619-622; Dryja, T P et al., (1990) *Nature* 343:364-266; Farrar, G J et al., (1990) *Genomics* 8:35-40; Farrar, G J et al., (2002) *EMBO J.* 21:857-864; all incorporated herein by reference.

miR-708 is a CHOP regulated micro RNA that regulated rhodopsin expression (Behrman, S., et al. (2011) *J. Cell Biol.* 192(6):919-27). miR-708 is an intronic micro RNA residing within the CHOP inducible gene Odz4 (Tenurin-4). CHOP regulates miR-708 expression during ER stress. There is a putative miR-708 sequence in the 3' UTR of the rhodopsin gene that is highly conserved (see FIG. 4 of Behrman et al., ibid)

In some embodiments, the invention provides methods for treating a human with RP. In some embodiments, the invention provides methods for treating a human with autosomal dominant RP. In some embodiments, the invention provides methods for treating a human with RP associated with a mutation in the rhodopsin gene. In some embodiments, the invention provides a method for treating a human with RP by administering an effective amount of an AAV vector encoding miR-708 to suppress the activity of a mutated rhodopsin. In some embodiments, the invention provides methods for treating a mammal (e.g., a dog or a cat) with RP. In some embodiments, the miR-708 nucleic acid may include without limitation nucleic acid represented by Gen-Bank Entrez Gene IDs 100126333, 735284, or 100885899.

In some embodiments of the invention, the suppression of a mutant rhodopsin is supplemented by the delivery of an effective amount of AAV vector encoding a wild-type rhodopsin or a rhodopsin with activity essentially the same as a wild-type rhodopsin. In some embodiments, the rhodopsin is a human rhodopsin. In some embodiments, the invention provides a method for treating a human with RP by administering an effective amount of an AAV vector encoding miR-708 to suppress the activity of a mutated rhodopsin and an effective amount of an AAV vector encoding a human rhodopsin with wild-type activity. In some embodiments, the AAV vector encoding miR-708 and the AAV vector encoding the human rhodopsin are the same AAV vector. In some embodiments, the AAV vector encoding miR-708 and the AAV vector encoding the human rhodopsin are the different AAV vectors. In some embodiments, nucleic acid encoding rhodopsin may include without limitation nucleic acid provided by identified by NCBI Reference Sequences NP_000530, NP_663358, NP_001008277, and NP_001009242.

In some aspects, the invention provides methods for treating endoplasmic reticulum (ER) stress in a cell comprising administering to the mammal a rAAV viral particle comprising a rAAV vector comprising nucleic acid encoding a miR-708. In some embodiments, the cell is an ocular cell. In further embodiments, the cell is a photoreceptor cell. In yet further embodiments, the cell is a rod photoreceptor cell. In some embodiments, the method comprises reducing one or more cellular markers of ER stress. In further embodiments, the one or more cellular marker of ER stress is spliced XBP-1, CHOP or Grp78. In some embodiments, the rAAV vector comprises nucleic acid encoding a miR-708 further comprises nucleic acid encoding rhodopsin. In other embodiments, the invention provides methods for treating endoplasmic reticulum (ER) stress in a cell comprising administering to the mammal a first rAAV vector comprising nucleic acid encoding a miR-708 and a second rAAV viral particle comprising a second rAAV vector comprising nucleic acid encoding a rhodopsin.

In some aspects, the invention provides methods to deliver miR-708 or miR-708 and rhodopsin to a mammal with RP, the method comprising administering to the retina of the mammal, an effective amount of rAAV viral particles comprising vector encoding the miR-708 and/or rhodopsin. The administration delivers the transgene product to the photoreceptor cells, where the miR-708 and/or rhodopsin mediates a beneficial effect on the photoreceptor cell and surrounding photoreceptor cells. In some embodiments, delivery of AAV viral particles to the retina is by injection of viral particles to the sub-retinal space of the retina. In some embodiments, the delivery of AAV particles to the retina is by intravitreal delivery provided the AAV particle is capable of penetrating to the back of the eye and transduces photoreceptor cells. In some embodiments, the AAV particles are administered in one or more locations in the sub-retinal space of the retina.

In some embodiments, the administration to the retina of an effective amount of rAAV viral particles comprising a vector encoding miR-708 and/or rhodopsin transduces photoreceptor cells at or near the site of administration. In some embodiments, more than about any of 5%, 10%, 15%, 20%, 25%, 30%, 35%, 40%, 45%, 50%, 55%, 60%, 65%, 70%, 75% or 100% of photoreceptor cells are transduced. In some embodiments, about 5% to about 100%, about 10% to about 50%, about 10% to about 30%, about 25% to about 75%, about 25% to about 50%, or about 30% to about 50% of the photoreceptor cells are transduced. Methods to identify photoreceptor cells transduced by AAV expressing miR-708 and/or rhodopsin are known in the art; for example, immunohistochemistry or the use of a marker such as enhanced green fluorescent protein can be used to detect expression of miR-708 and/or rhodopsin.

In some embodiments of the invention, the methods comprise administration to the retina (e.g., the subretinal space) of a mammal an effective amount of AAV viral particles comprising a vector encoding a miR708 and/or rhodopsin for treating a mammal, e.g., a human, with RP. In some embodiments, the composition is injected to one or more subretinal spaces to allow expression of miR-708 and/or rhodopsin in photoreceptor cells. In some embodiments, the composition is injected into any one of one, two, three, four, five, six, seven, eight, nine, ten or more than ten locations in the subretinal space of the retina.

In some embodiments the rAAV viral particles are administered to more than one location simultaneously or sequentially. In some embodiment, multiple injections of rAAV viral particles are no more than one hour, two hours, three hours, four hours, five hours, six hours, nine hours, twelve hours or 24 hours apart.

In some embodiments, first rAAV viral particles encoding miR-708 and second rAAV viral particles encoding rhodopsin are administered to one or more locations simultaneously or sequentially. In some embodiment, multiple injections of rAAV viral particles are no more than one hour, two hours, three hours, four hours, five hours, six hours, nine hours, twelve hours or 24 hours apart. In some embodiments the first rAAV viral particles encoding miR-708 are administered before the second rAAV viral particles encoding rhodopsin are administered. In some embodiments the first rAAV viral particles encoding miR-708 are administered after the second rAAV viral particles encoding rhodopsin are administered.

In some embodiments, the invention provides a method for treating a human with RP by administering an effective amount of a pharmaceutical composition comprising an AAV vector encoding miR-708 to suppress the activity of a mutated rhodopsin. In some embodiments, the invention provides a method for treating a human with RP by administering an effective amount of a pharmaceutical composition comprising an AAV vector encoding miR-708 to suppress the activity of a mutated rhodopsin and an effective amount of a pharmaceutical composition comprising an AAV vector encoding rhodopsin to supplement photoreceptors with wild-type rhodopsin activity. In some embodiments, the pharmaceutical composition comprising an AAV vector encoding miR-708 and the pharmaceutical composition comprising an AAV vector encoding the human rhodopsin are the same pharmaceutical composition. In some embodiments, the pharmaceutical composition comprising an AAV vector encoding miR-708 and the pharmaceutical composition comprising an AAV vector encoding the human rhodopsin are the different pharmaceutical composition. In some embodiments, the pharmaceutical composition comprises one or more pharmaceutically acceptable excipients.

In some embodiments of the invention, the volume of the composition injected to the subretinal space of the retina or intravitreally is more than about any one of 1 µl, 2 µl, 3 µl, 4 µl, 5 µl, 6 µl, 7 µl, 8 µl, 9 µl, 10 µl, 15 µl, 20 µl, 25 µl, 50 µl, 75 µl, 100 µl, 200 µl, 300 µl, 400 µl, 500 µl, 600 µl, 700 µl, 800 µl, 900 µl or 1 mL, or any amount therebetween.

Compositions of the invention (e.g., AAV viral particles comprising a vector encoding miR-708 and/or rhodopsin) can be used either alone or in combination with one or more additional therapeutic agents for treating RP. The interval between sequential administration can be in terms of at least (or, alternatively, less than) minutes, hours, or days.

V. Expression Constructs

In some embodiments, the transgene (e.g., miRNA 708 and/or rhodopsin) is operably linked to a promoter. Exemplary promoters include, but are not limited to, the cytomegalovirus (CMV) immediate early promoter, the RSV LTR, the MoMLV LTR, the phosphoglycerate kinase-1 (PGK) promoter, a simian virus 40 (SV40) promoter and a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), the E2F promoter, the telomerase (hTERT) promoter; the cytomegalovirus enhancer/chicken beta-actin/Rabbit β-globin promoter (CAG promoter; Niwa et al., Gene, 1991, 108(2):193-9) and the elongation factor 1-alpha promoter (EF1-alpha) promoter (Kim et al., Gene, 1990, 91(2):217-23 and Guo et al., Gene Ther., 1996, 3(9):802-10). In some embodiments, the promoter comprises a human β-glucuronidase promoter or a cytomegalovirus enhancer linked to a chicken β-actin (CBA) promoter. The promoter can be a constitutive, inducible or repressible promoter. In some embodiments, the invention provides an AAV vector comprising nucleic acid encoding miR-708 operably linked to a CBA promoter. In some embodiments, the invention provides an AAV vector comprising nucleic acid encoding rhodopsin (e.g., human rhodopsin) operably linked to a CBA promoter. In some embodiments, the invention provides an AAV vector comprising nucleic acid encoding miR-708 and nucleic acid encoding rhodopsin (e.g., human rhodopsin) operably linked to a CBA promoter.

In some embodiments, the promoter is capable of expressing the transgene in photoreceptor cells. In embodiments, the promoter is a rhodopsin kinase (RK) promoter; e.g., a human RK promoter. In some embodiments, the promoter is an opsin promoter; e.g., a human opsin promoter or a mouse opsin promoter.

In some embodiments, the invention provides an AAV vector comprising nucleic acid encoding miR-708 operably linked to an RK promoter. In some embodiments, the invention provides an AAV vector comprising nucleic acid encoding rhodopsin (e.g., human rhodopsin) operably linked to an RK promoter. In some embodiments, the invention provides an AAV vector comprising nucleic acid encoding miR-708 and rhodopsin (e.g., human rhodopsin) operably linked to an RK promoter. In some embodiments, the nucleic acid encoding miR-708 is 5' to nucleic acid encoding rhodopsin. In other embodiments, the nucleic acid encoding miR-708 is 3' to nucleic acid encoding rhodopsin. In some embodiments, the invention provides an AAV vector comprising nucleic acid encoding miR-708 operably linked to a first RK promoter and nucleic acid encoding rhodopsin operably linked to a second RK promoter. In some embodiments, the nucleic acid encoding miR-708 operably linked to a first RK promoter is 5' to nucleic acid encoding rhodopsin operably linked to a second RK promoter. In other embodiments, the nucleic acid encoding miR-708 operably linked to a first RK promoter is 3' to nucleic acid encoding rhodopsin operably linked to a second RK promoter. In some embodiments, the miR-708 comprises the sequence of SEQ ID NO:1. In some embodiments, the miR-708 comprises a nucleotide sequence that is at least about 80%, 85%, 90%, 91%, 92%, 93%, 94%, 95%, 96%, 97%, 98%, or 99% identical to the sequence of SEQ ID NO:1. In some embodiments, the rhodopsin comprises the amino acid sequence of SEQ ID NO:2. In some embodiments, the rhodopsin comprises an amino acid sequence that is at least about 80%, 85%, 90%, 91%, 92%, 93%, 94%, 95%, 96%, 97%, 98%, or 99% identical to the amino acid sequence of SEQ ID NO:2. In some embodiments, the rhodopsin is a functional equivalent of wild-type rhodopsin. In some embodiments, expression of rhodopsin from the AAV vector is refractory to suppression by miR-708. In some embodiments, nucleic acid encoding rhodopsin lacks the miR-708 target site in the 3' UTR of the rhodopsin gene. In some embodiments, nucleic acid encoding rhodopsin comprises a mutation (e.g., a deletion, a substitution, an insertion, etc.) in the miR-708 target site in the 3' UTR of the rhodopsin gene such that it is refractory to suppression by miR-708.

In some embodiments, the invention provides an AAV vector comprising nucleic acid encoding miR-708 operably linked to an opsin promoter. In some embodiments, the invention provides an AAV vector comprising nucleic acid encoding rhodopsin (e.g., human rhodopsin) operably linked to an opsin promoter. In some embodiments, the invention provides an AAV vector comprising nucleic acid encoding miR-708 and nucleic acid encoding rhodopsin (e.g., human rhodopsin) operably linked to an opsin promoter. In some embodiments, the nucleic acid encoding miR-708 is 5' to nucleic acid encoding rhodopsin. In other embodiments, the nucleic acid encoding miR-708 is 3' to nucleic acid encoding rhodopsin. In some embodiments, the invention provides an AAV vector comprising nucleic acid encoding miR-708 operably linked to a first opsin promoter and nucleic acid encoding rhodopsin operably linked to a second opsin promoter. In some embodiments, the nucleic acid encoding miR-708 operably linked to a first opsin promoter is 5' to nucleic acid encoding rhodopsin operably linked to a second opsin promoter. In other embodiments, the nucleic acid encoding miR-708 operably linked to a first opsin promoter is 3' to nucleic acid encoding rhodopsin operably linked to a second opsin promoter. In some embodiments, the miR-708 comprises the sequence of SEQ ID NO:1. In some embodiments, the miR-708 comprises the sequence of SEQ ID NO:1. In some embodiments, the miR-708 comprises a nucleotide sequence that is at least about 80%, 85%, 90%, 91%, 92%, 93%, 94%, 95%, 96%, 97%, 98%, or 99% identical to the sequence of SEQ ID NO:1. In some embodiments, the rhodopsin comprises the amino acid sequence of SEQ ID NO:2. In some embodiments, the rhodopsin comprises an amino acid sequence that is at least about 80%, 85%, 90%, 91%, 92%, 93%, 94%, 95%, 96%, 97%, 98%, or 99% identical to the amino acid sequence of SEQ ID NO:2. In some embodiments, the rhodopsin is a functional equivalent of wild-type rhodopsin. In some embodiments, expression of rhodopsin from the AAV vector is refractory to suppression by miR-708. In some embodiments, nucleic acid encoding rhodopsin lacks the miR-708 target site in the 3' UTR of the rhodopsin gene. In some embodiments, nucleic acid encoding rhodopsin comprises a mutation (e.g., a deletion, a substitution, an insertion, etc.) in the miR-708 target site in the 3' UTR of the rhodopsin gene such that it is refractory to suppression by miR-708.

In some embodiments, the invention provides an AAV vector comprising nucleic acid encoding miR-708 operably linked to an RK promoter and nucleic acid encoding rhodopsin operably linked to an opsin promoter. In some embodiments, the nucleic acid encoding miR-708 operably linked to the RK promoter is 5' to nucleic acid encoding rhodopsin operably linked to an opsin promoter. In some embodiments, the nucleic acid encoding miR-708 operably linked to the RK promoter is 3' to nucleic acid encoding rhodopsin operably linked to an opsin promoter. In some embodiments, the invention provides an AAV vector comprising nucleic acid encoding miR-708 operably linked to an opsin promoter and nucleic acid encoding rhodopsin operably linked to an RK promoter. In some embodiments, the nucleic acid encoding miR-708 operably linked to the opsin promoter is 5' to nucleic acid encoding rhodopsin operably linked to an RK promoter. In some embodiments, the nucleic acid encoding miR-708 operably linked to the opsin promoter is 3' to nucleic acid encoding rhodopsin operably linked to an RK promoter. In some embodiments, the miR-708 comprises the sequence of SEQ ID NO:1. In some embodiments, the miR-708 comprises the sequence of SEQ ID NO:1. In some embodiments, the miR-708 comprises a nucleotide sequence that is at least about 80%, 85%, 90%, 91%, 92%, 93%, 94%, 95%, 96%, 97%, 98%, or 99% identical to the sequence of SEQ ID NO:1. In some embodiments, the rhodopsin comprises the amino acid sequence of SEQ ID NO:2. In some embodiments, the rhodopsin comprises an amino acid sequence that is at least about 80%, 85%, 90%, 91%, 92%, 93%, 94%, 95%, 96%, 97%, 98%, or 99% identical to the amino acid sequence of SEQ ID NO:2. In some embodiments, the rhodopsin is a functional equivalent of wild-type rhodopsin. In some embodiments, expression of rhodopsin from the AAV vector is refractory to suppression by miR-708. In some embodiments, nucleic acid encoding rhodopsin lacks the miR-708 target site in the 3' UTR of the rhodopsin gene. In some embodiments, nucleic acid encoding rhodopsin comprises a mutation (e.g., a deletion, a substitution, an insertion, etc.) in the miR-708 target site in the 3' UTR of the rhodopsin gene such that it is refractory to suppression by miR-708.

In some embodiments, the invention provides an AAV vector comprising nucleic acid encoding miR-708 operably linked to a CBA promoter and nucleic acid encoding rhodopsin operably linked to an RK promoter. In some embodiments, the nucleic acid encoding miR-708 operably linked to the CBA promoter is 5' to nucleic acid encoding rhodopsin operably linked to an RK promoter. In some embodiments, the nucleic acid encoding miR-708 operably linked to the CBA promoter is 3' to nucleic acid encoding rhodopsin operably linked to an RK promoter. In some embodiments, the invention provides an AAV vector comprising nucleic acid encoding miR-708 operably linked to an RK promoter and nucleic acid encoding rhodopsin operably linked to a CBA promoter. In some embodiments, the nucleic acid encoding miR-708 operably linked to the RK promoter is 5' to nucleic acid encoding rhodopsin operably linked to a CBA promoter. In some embodiments, the nucleic acid encoding miR-708 operably linked to the RK promoter is 3' to nucleic acid encoding rhodopsin operably linked to a CBA promoter. In some embodiments, the miR-708 comprises the sequence of SEQ ID NO:1. In some embodiments, the miR-708 comprises the sequence of SEQ ID NO:1. In some embodiments, the miR-708 comprises a nucleotide sequence that is at least about 80%, 85%, 90%, or 95% identical to the sequence of SEQ ID NO:1. In some embodiments, the rhodopsin comprises the amino acid sequence of SEQ ID NO:2. In some embodiments, the rhodopsin comprises an amino acid sequence that is at least about 80%, 85%, 90%, 91%, 92%, 93%, 94%, 95%, 96%, 97%, 98% identical to the amino acid sequence of SEQ ID NO:2. In some embodiments, the rhodopsin is a functional equivalent of wild-type rhodopsin. In some embodiments, expression of rhodopsin from the AAV vector is refractory to suppression by miR-708. In some embodiments, nucleic acid encoding rhodopsin lacks the miR-708 target site in the 3' UTR of the rhodopsin gene. In some embodiments, nucleic acid encoding rhodopsin comprises a mutation (e.g., a deletion, a substitution, an insertion, etc.) in the miR-708 target site in the 3' UTR of the rhodopsin gene such that it is refractory to suppression by miR-708.

In some embodiments, nucleic acid encoding miR-708 comprises an endogenous miR-708 scaffold. In some embodiments, the miR-708 scaffold is provided by SEQ ID NO:14. In some embodiments, nucleic acid encoding miR- 708 comprises a heterologous miRNA scaffold. In some embodiments, use of a heterologous miRNA scaffold is used to modulate miRNA expression; for example, to increase miRNA expression or to decrease miRNA expression. In some embodiments, nucleic acid encoding miR-708 comprises an endogenous miR-155 scaffold. In some embodiments, the miR-155 scaffold is provided by SEQ ID NO:14.

Recombinant Viral Vector

The present invention contemplates the use of a recombinant viral genome for introduction of one or more nucleic acid sequences encoding for a miR-708 miRNA and/or a rhodopsin protein described herein for packaging into an AAV viral particle. The recombinant viral genome may include any element to establish the expression of a miR-708 miRNA and/or a rhodopsin protein, for example, a promoter, a miR-708 miRNA and/or a rhodopsin transgene, an ITR, a ribosome binding element, terminator, enhancer, selection marker, intron, polyA signal, and/or origin of replication.

VI. Viral Particles and Methods of Producing Viral Particles rAAV Viral Particles The invention provides methods of using rAAV particles to treat retinitis pigmentosa and provides compositions comprising rAAV particles. In some embodiments, the viral particle is a recombinant AAV particle comprising a nucleic acid comprising a sequence encoding miR-708 miRNA and/or a rhodopsin protein described herein flanked by one or two ITRs. The nucleic acid is encapsidated in the AAV particle. The AAV particle also comprises capsid proteins. In some embodiments, the nucleic acid comprises the coding sequence(s) of interest (e.g., nucleic acid encoding miR-708 miRNA and/or a rhodopsin protein) operatively linked components in the direction of transcription, control sequences including transcription initiation and termination sequences, thereby forming an expression cassette. In some embodiments, nucleic acid encoding the miR-708 is embedded in an intron. The expression cassette is flanked on the 5' and 3' end by at least one functional AAV ITR sequences. By "functional AAV ITR sequences" it is meant that the ITR sequences function as intended for the rescue, replication and packaging of the AAV virion. See Davidson et al., *PNAS*, 2000, 97(7)3428-32; Passini et al., *J. Virol.*, 2003, 77(12):7034-40; and Pechan et al., *Gene Ther.*, 2009, 16:10-16, all of which are incorporated herein in their entirety by reference. For practicing some aspects of the invention, the recombinant vectors comprise at least all of the sequences of AAV essential for encapsidation and the physical structures for infection by the rAAV. AAV ITRs for use in the vectors of the invention need not have a wild-type nucleotide sequence (e.g., as described in Kotin, *Hum. Gene Ther.*, 1994, 5:793-801), and may be altered by the insertion, deletion or substitution of nucleotides or the AAV ITRs may be derived from any of several AAV serotypes. More than 40 serotypes of AAV are currently known, and new serotypes and variants of existing serotypes continue to be identified. See Gao et al., *PNAS*, 2002, 99(18): 11854-6; Gao et al., *PNAS*, 2003, 100(10):6081-6; and Bossis et al., *J. Virol.*, 2003, 77(12):6799-810. Use of any AAV serotype is considered within the scope of the present invention. In some embodiments, a rAAV vector is a vector derived from an AAV serotype, including without limitation, AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV capsid serotype ITRs or the like. In some embodiments, the nucleic acid in the AAV comprises an ITR of AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV capsid serotype ITRs or the like. In some embodiments, the nucleic acid in the AAV further encodes miR-708, rhodopsin, or miR-708 and rhodopsin as described herein. For example, the nucleic acid in the AAV can comprise at least one ITR of any AAV serotype contemplated herein and can further encode a miR-708 comprising the nucleic acid of SEQ ID NO:1 and/or nucleic acid encoding a human rhodopsin comprising the amino acid sequence of SEQ ID NO:2. In some embodiments, the nucleic acid in the AAV comprises 5' to 3' nucleic acid encoding the following: an AAV ITR, a stuffer fragment (e.g., SEQ ID NO:11), a chimeric intron (e.g., SEQ ID NO:10), a miR-708, a bovine growth hormone polyadenylation sequence, a stuffer fragment, and an AAV ITR. In some embodiments, the nucleic acid in the AAV comprises 5' to 3' nucleic acid encoding the following: an AAV ITR, an RK promoter, a β globin intron, a miR-708 imbedded in the β globin intron, a human rhodopsin, a bovine growth hormone polyadenylation sequence, and an AAV ITR. In some embodiments, the nucleic acid in the AAV comprises 5' to 3' nucleic acid encoding the following: an AAV ITR, a stuffer fragment (e.g., SEQ ID NO:11), an RK promoter, a chimeric intron (e.g., SEQ ID NO:10), a human rhodopsin, a β-globin intron, a miR-708 embedded in a β-globin intron, a bovine growth hormone polyadenylation sequence, a stuffer fragment, and an AAV ITR. In some embodiments, the nucleic acid in the AAV comprises 5' to 3' nucleic acid encoding the following: an AAV ITR, a stuffer fragment (e.g., SEQ ID NO:11), an RK promoter, a chimeric intron (e.g., SEQ ID NO:10), a miR-708, a mouse opsin promoter, a human rhodopsin, a bovine growth hormone polyadenylation sequence, and an AAV ITR. In some embodiments, the nucleic acid in the AAV comprises the nucleic acid of SEQ ID NO:5. In some embodiments, the nucleic acid in the AAV comprises a nucleic acid that is at least about 80%, 85%, 90%, 91%, 92%, 93%, 94%, 95%, 96%, 97%, 98%, or 99% identical to SEQ ID NO:5. In some embodiments, the nucleic acid in the AAV the nucleic acid of SEQ ID NO:6. In some embodiments, the nucleic acid in the AAV comprises a nucleic acid that is at least about 80%, 85%, 90%, 91%, 92%, 93%, 94%, 95%, 96%, 97%, 98%, or 99% identical to SEQ ID NO:6. In some embodiments, the nucleic acid in the AAV comprises the nucleic acid of SEQ ID NO:7. In some embodiments, the nucleic acid in the AAV comprises a nucleic acid that is at least about 80%, 85%, 90%, 91%, 92%, 93%, 94%, 95%, 96%, 97%, 98%, or 99% identical to SEQ ID NO:7. In some embodiments, the nucleic acid in the AAV comprises the nucleic acid of SEQ ID NO:8. In some embodiments, the nucleic acid in the AAV comprises a nucleic acid that is at least about 80%, 85%, 90%, 91%, 92%, 93%, 94%, 95%, 96%, 97%, 98%, or 99% identical to SEQ ID NO:8. In some embodiments, the nucleic acid in the AAV comprises the nucleic acid of SEQ ID NO:9. In some embodiments, the nucleic acid in the AAV comprises a nucleic acid that is at least about 80%, 85%, 90%, 91%, 92%, 93%, 94%, 95%, 96%, 97%, 98%, or 99% identical to SEQ ID NO:9. In some embodiments, the nucleic acid in the AAV comprises the nucleic acid of SEQ ID NO:24. In some embodiments, the nucleic acid in the AAV comprises a nucleic acid that is at least about 80%, 85%, 90%, 91%, 92%, 93%, 94%, 95%, 96%, 97%, 98%, or 99% identical to SEQ ID NO:24. In some embodiments, the nucleic acid in the AAV comprises the nucleic acid of SEQ ID NO:25. In some embodiments, the nucleic acid in the AAV comprises a nucleic acid that is at least about 80%, 85%, 90%, 91%, 92%, 93%, 94%, 95%, 96%, 97%, 98%, or 99% identical to SEQ ID NO:25. In some embodiments, the nucleic acid in the AAV comprises the nucleic acid of SEQ ID NO:26. In some embodiments, the nucleic acid in the AAV comprises a nucleic acid that is at least about 80%, 85%, 90%, 91%, 92%, 93%, 94%, 95%, 96%, 97%, 98%, or 99% identical to SEQ ID NO:26. In some embodiments, the nucleic acid in the AAV comprises the nucleic acid of SEQ ID NO:27. In some embodiments, the nucleic acid in the AAV comprises a nucleic acid that is at least about 80%, 85%, 90%, 91%, 92%, 93%, 94%, 95%, 96%, 97%, 98%, or 99% identical to SEQ ID NO:27. In further embodiments, the rAAV particle comprises capsid proteins of AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV2/2-7m8, AAV DJ, AAV2 N587A, AAV2 E548A, AAV2 N708A, AAV V708K, a goat AAV, AAV1/AAV2 chimeric, bovine AAV, mouse AAV capsid rAAV2/HBoV1 serotype capsid, or mutants of these capsid proteins. In some embodiments, a mutant capsid protein maintains the ability to form an AAV capsid. In some embodiments, the rAAV particle comprises AAV5 tyrosine mutant capsid (Zhong L. et al., (2008) *Proc Natl Acad Sci USA* 105(22):7827-7832. In further embodiments, the rAAV particle comprises capsid proteins of an AAV serotype from Clades A-F (Gao, et al., *J. Virol.* 2004, 78(12):6381). In some embodiments, the nucleic acid in the AAV comprises the nucleic acid sequence selected from the group consisting of SEQ ID NOs:5-8, and is flanked by at least one AAV2 ITR. In some embodiments, the nucleic acid in the AAV comprises the nucleic acid sequence that is at least about 80%, 85%, 90%, 91%, 92%, 93%, 94%, 95%, 96%, 97%, 98%, or 99% identical to the nucleic acid selected from the group consisting of SEQ ID NOs:5-9, and is flanked by at least one AAV2 ITR.

Different AAV serotypes are used to optimize transduction of particular target cells or to target specific cell types within a particular target tissue (e.g., a diseased tissue). A rAAV particle can comprise viral proteins and viral nucleic acids of the same serotype or a mixed serotype. For example, in some embodiments a rAAV particle can comprise AAV5 capsid proteins and at least one AAV2 ITR or it can comprise AAV2 capsid proteins and at least one AAV5 ITR. In other embodiments a rAAV particle can comprise AAV5 tyrosine mutant capsid proteins and at least one AAV2 ITR. In yet another example, a rAAV particle can comprise capsid proteins from both AAV5 and AAV2, and further comprise at least one AAV2 ITR. Any combination of AAV serotypes for production of a rAAV particle is provided herein as if each combination had been expressly stated herein. In some embodiments, the invention provides rAAV particles comprising AAV5 capsid proteins and a nucleic acid encoding miR-708 RNA and/or a rhodopsin transgene, flanked by at least one AAV2 ITR.

Self-Complementary AAV Viral Genomes

In some aspects, the invention provides viral particles comprising a recombinant self-complementing genome. AAV viral particles with self-complementing genomes and methods of use of self-complementing AAV genomes are described in U.S. Pat. Nos. 6,596,535; 7,125,717; 7,765,583; 7,785,888; 7,790,154; 7,846,729; 8,093,054; and 8,361,457; and Wang Z., et al., (2003) *Gene Ther* 10:2105-2111, each of which are incorporated herein by reference in its entirety. A rAAV comprising a self-complementing genome will quickly form a double stranded DNA molecule by virtue of its partially complementing sequences (e.g., complementing coding and non-coding strands of a transgene). In some embodiments, the invention provides an AAV viral particle comprising an AAV genome, wherein the rAAV genome comprises a first heterologous polynucleotide sequence (e.g., miR-708 and/or a rhodopsin coding strand) and a second heterologous polynucleotide sequence (e.g., antisense strand of miR-708 and/or a rhodopsin noncoding or antisense strand) wherein the first heterologous polynucleotide sequence can form intrastrand base pairs with the second polynucleotide sequence along most or all of its length. In some embodiments, the first heterologous polynucleotide sequence and a second heterologous polynucleotide sequence are linked by a sequence that facilitates intrastrand basepairing; e.g., a hairpin DNA structure. Hairpin structures are known in the art, for example in siRNA molecules. In some embodiments, the first heterologous polynucleotide sequence and a second heterologous polynucleotide sequence are linked by a mutated ITR (e.g., the right ITR). In some embodiments, the ITR comprises the polynucleotide sequence 5'-CACTCCCTCTCTGCG-CGCTCGCTCGCTCACTGAGGCCGGGCGACCAAAG-GTCGCCC ACGCCCGGGCTTTGCCCGGGCG-3' (SEQ ID NO:20). The mutated ITR comprises a deletion of the D region comprising the terminal resolution sequence. As a result, on replicating an AAV viral genome, the rep proteins will not cleave the viral genome at the mutated ITR and as such, a recombinant viral genome comprising the following in 5' to 3' order will be packaged in a viral capsid: an AAV ITR, the first heterologous polynucleotide sequence including regulatory sequences, the mutated AAV ITR, the second heterologous polynucleotide in reverse orientation to the first heterologous polynucleotide and a third AAV ITR. In some embodiments, the invention provides AAV viral particles comprising a recombinant viral genome comprising a functional AAV2 ITR, a first polynucleotide sequence encoding miR-708 RNA and/or a rhodopsin transgene, a mutated AAV2 ITR comprising a deletion of the D region and lacking a functional terminal resolution sequence, a second polynucleotide sequence comprising the complementary sequence to the sequence encoding miR-708 RNA and/or a rhodopsin, of the first polynucleotide sequence and a functional AAV2 ITR.

Production of AAV Particles

The rAAV particles can be produced using methods know in the art. See, e.g., U.S. Pat. Nos. 6,566,118; 6,989,264; and 6,995,006. In practicing the invention, host cells for producing rAAV particles include mammalian cells, insect cells, plant cells, microorganisms and yeast. Host cells can also be packaging cells in which the AAV rep and cap genes are stably maintained in the host cell or producer cells in which the AAV vector genome is stably maintained. Exemplary packaging and producer cells are derived from 293, A549 or HeLa cells. AAV vectors are purified and formulated using standard techniques known in the art.

In some aspects, a method is provided for producing any rAAV particle as disclosed herein comprising (a) culturing a host cell under a condition that rAAV particles are produced, wherein the host cell comprises (i) one or more AAV package genes, wherein each said AAV packaging gene encodes an AAV replication and/or encapsidation protein; (ii) an rAAV pro-vector comprising a nucleic acid encoding miR-708 RNA and/or any rhodopsin transgene as described herein flanked by at least one AAV ITR, and (iii) an AAV helper function; and (b) recovering the rAAV particles produced by the host cell. In some embodiments, a nucleic acid encodes miR-708 RNA of SEQ ID NO:1 and/or a transgene encoding a rhodopsin; e.g., a rhodopsin with the amino acid of SEQ ID NO:2. In some embodiments, said at least one AAV ITR is selected from the group consisting of AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, a goat AAV, bovine AAV, or mouse AAV serotype ITR or the like. In some embodiments, said encapsidation protein is selected from the group consisting of AAV1, AAV2, AAV3, AAV4, AAV5, AAV6 (e.g., a wild-type AAV6 capsid, or a variant AAV6 capsid such as ShH10, as described in U.S. PG Pub. 2012/0164106), AAV7, AAV8, AAVrh8, AAVrh8R, AAV9 (e.g., a wild-type AAV9 capsid, or a modified AAV9 capsid as described in U.S. PG Pub. 2013/0323226), AAV10, AAVrh10, AAV11, AAV12, a tyrosine capsid mutant, a heparin binding capsid mutant, an AAV2R471A capsid, an AAVAAV2/2-7m8 capsid, an AAV DJ capsid (e.g., an AAV-DJ/8 capsid, an AAV-DJ/9 capsid, or any other of the capsids described in U.S. PG Pub. 2012/0066783), AAV2 N587A capsid, AAV2 E548A capsid, AAV2 N708A capsid, AAV V708K capsid, goat AAV capsid, AAV1/AAV2 chimeric capsid, bovine AAV capsid, mouse AAV capsid, rAAV2/HBoV1 capsid, an AAV capsid described in U.S. Pat. No. 8,283,151 or International Publication No. WO/2003/042397, or mutants thereof. In some embodiments, the encapsidation protein is an AAV5 tyrosine mutant capsid protein. In further embodiments, the rAAV particle comprises capsid proteins of an AAV serotype from Clades A-F. In some embodiments, the rAAV particles comprise an AAV5 capsid and a recombinant genome comprising AAV2 ITRs, a mutant AAV2 ITR and nucleic acid encoding miR-708 and/or rhodopsin. In some embodiments, the rAAV particles comprise an AAV5 tyrosine mutant capsid and a recombinant genome comprising AAV2 ITRs, a mutant AAV2 ITR and nucleic acid encoding miR-708 and/or rhodopsin. In a further embodiment, the rAAV particles are purified. The term "purified" as used herein includes a preparation of rAAV particles devoid of at least some of the other components that may also be present where the rAAV particles naturally occur or are initially prepared from. Thus, for example, isolated rAAV particles may be prepared using a purification technique to enrich it from a source mixture, such as a culture lysate or production culture supernatant. Enrichment can be measured in a variety of ways, such as, for example, by the proportion of DNase-resistant particles (DRPs) or genome copies (gc) present in a solution, or by infectivity, or it can be measured in relation to a second, potentially interfering substance present in the source mixture, such as contaminants, including production culture contaminants or in-process contaminants, including helper virus, media components, and the like.

Also provided herein are pharmaceutical compositions comprising a rAAV particle comprising a transgene encoding miR-708 and/or a rhodopsin transgene of the invention and a pharmaceutically acceptable carrier. In some embodiments, the composition comprises rAAV particles comprising a transgene encoding miR-708 and rAAV particles comprising a rhodopsin transgene. In some embodiments, the composition comprises rAAV particles comprising a transgene encoding miR-708 and a rhodopsin transgene. The pharmaceutical compositions may be suitable for any mode of administration described herein. A pharmaceutical composition of a rAAV comprising a nucleic acid encoding miR-708 RNA and/or a rhodopsin transgene, described herein can be introduced to the eye; for example, by subretinal administration or intravitreal administration.

In some embodiments, the pharmaceutical compositions comprising a rAAV described herein and a pharmaceutically acceptable carrier is suitable for administration to human. Such carriers are well known in the art (see, e.g., Remington's Pharmaceutical Sciences, 15th Edition, pp. 1035-1038 and 1570-1580). In some embodiments, the pharmaceutical compositions comprising a rAAV described herein and a pharmaceutically acceptable carrier is suitable for ocular injection. Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. The pharmaceutical composition may further comprise additional ingredients, for example preservatives, buffers, tonicity agents, antioxidants and stabilizers, nonionic wetting or clarifying agents, viscosity-increasing agents, and the like. The pharmaceutical compositions described herein can be packaged in single unit dosages or in multidosage forms. The compositions are generally formulated as sterile and substantially isotonic solution.

VII. Articles of Manufacture and Kits

Also provided are kits or articles of manufacture for use in the methods described herein. In aspects, the kits comprise the compositions described herein (e.g., rAAV particles comprising nucleic acid encoding miR-708 RNA and/or a rhodopsin transgene) in suitable packaging. Suitable packaging for compositions (such as ocular compositions) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The present invention also provides kits comprising compositions described herein and may further comprise instruction(s) on methods of using the composition, such as uses described herein. The kits described herein may further include other materials desirable from a commercial and user standpoint, including other buffers, diluents, filters, needles, syringes, and package inserts with instructions for performing any methods described herein. For example, in some embodiments, the kit comprises an rAAV comprising a transgene encoding miR-708 RNA and/or a rhodopsin transgene for intraocular delivery of at least $1 \times 10^9$ genome copies to a primate as described herein, a pharmaceutically acceptable carrier suitable for intraocular injection, and one or more of: a buffer, a diluent, a filter, a needle, a syringe, and a package insert with instructions for performing ocular injections. In some embodiments, the kit comprising instructions for treating retinitis pigmentosa with the rAAV particles described herein. In some embodiments, the kit comprising instructions for reducing ER stress in a cell with the rAAV particles described herein. In some embodiments, the kit comprising instructions for using the rAAV particles described herein according to any one of the methods described herein.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: Development of a Cellular Model of Retinitis Pigmentosa

A therapeutic strategy for RHO-associated autosomal dominant RP would be to knock down both mutant and wild-type rhodopsin and alleviate ER stress. This could be achieved by co-delivering a micro-RNA (miR) that would inhibit the rhodopsin alleles and optionally co-delivering a wild-type rhodopsin sequence refractory to knockdown by the exogenously delivered miR. A CHOP-regulated miR, miR-708, regulates rhodopsin expression (Behrman, S., et al. (2011) *J. Cell Biol.* 192(6):919-27). miR-708 is an intronic miR residing within the CHOP-inducible gene Odz4 (Tenurin-4). CHOP regulates miR-708 expression during ER stress, and there is a putative miR-708 sequence in the 3' UTR of rhodopsin.

Described herein are methods for using an AAV vector to deliver exogenous miR-708 targeting both wild type and mutant rhodopsin through the 3' UTR miR-708 target sequence present in both alleles. In embodiments, a wild-type rhodopsin replacement sequence is also co-delivered. This replacement rhodopsin sequence may be engineered to have decreased binding to miR-708 (e.g., nucleotide substitution, deletion or addition to the 3' UTR) and thus will be refractory to knockdown by the exogenous miR-708. In embodiments, the replacement rhodopsin sequence lacks a 3' UTR miR-708 target sequence. In short, these AAV vectors would knock down expression of the rhodopsin that causes ER stress (and therefore photoreceptor cell death) and optionally supplementing expression of a wild-type, or codon-optimized, rhodopsin gene that is refractory to miR-708-induced knockdown, thereby restoring normal expression and function of rhodopsin.

Methods
Cell Culture

HEK-293 cells were engineered to express human or mouse Rhodopsin P23H using the T-Rex Tetracycline Inducible system from Invitrogen. Confluent cells in 6 well plates were transfected with 4 µg miR-708 (pcDNA) vector or a control miRNA vector using Lipofectamine 2000 (Invitrogen) per the manufacturer's instructions. 48 hours post-transfection the medium was replaced with medium containing 2 µM Tetracycline. The cells were incubated an additional 24 hours and the medium was removed from each well.

Western Blotting

Cells were lysed in 400 µL RIPA buffer (Thermo Scientific) containing 1 mM PMSF, and passed through a 25 g syringe several times. The lysate was centrifuged at 14,000 rpm for 10 min. Cells were kept at 4° C. throughout the process. 30 µL of supernatant was loaded onto a 4-12% Bis/Tris Gel and SDS-PAGE was performed in MOPS buffer (Invitrogen). Proteins were then transferred to a Nitrocellulose membrane using the I-Blot system from Invitrogen. The membrane was blocked for an hour at room temperature in PBS containing 0.05% Tween-20 (PBS-T) and 0.1% I-Block (Invitrogen). The membrane was incubated overnight at 4° C. in PBS-T containing 1 µg/mL anti Rhodopsin mAb 1D4 (Abcam). After washing in PBS-T several times the membrane was incubated in secondary antibody solution containing a 1:1000 dilution of anti-mouse IgG HRP conjugated Ab (R&D Systems) for an hour at room temperature. The membrane was washed in PBS-T several times and developed using ECL Reagent (Thermo Scientific). mRhodopsin protein levels were quantified using the Image-J software. The membrane was stripped of proteins in PBS containing 0.1M Glycine pH 2 and then rinsed several times in PBS-T. The membrane was then probed for hGAPDH in PBS-T containing a 1:20,000 dilution of anti GAPDH pAb (Sigma) for 2 hours at Room Temperature. After washing several times in PBS-T, secondary antibody (Anti-Rabbit IgG-HRP, R&D Systems) was diluted 1:1000 in PBS-T and incubated for 1 hour at room temperature. The membrane was washed several times and developed using ECL reagent (Thermo Scientific). mRhodopsin protein levels were then normalized to hGAPDH protein levels using Image J software.

Endogenous miR-708 Knockdown in HEK-293 Cells

HEK-293 cells expressing mouse or human rhodopsin (described above) were transfected with 100 pmol pre-miR-708, anti-miR-708, or control miRNA (Ambion) using the Lipofectamine 2000 protocol for transfection with siRNA molecules (Invitrogen). At 48 hours post-transfection, the medium was replaced with medium containing 2 uM Tetracycline to induce Rhodopsin expression. 24 hours later each well was split into 2 samples. One was probed for mRhodopsin and hGAPDH using the western blot protocol above, and RNA was extracted from the other for TaqMan® (Life Technologies) analysis of Rhodopsin and miR-708 RNA expression. Total RNA (including small RNAs) was extracted from the cells using the miRNeasy kit from Qiagen, according to the manufacturer's instructions, including DNAse treatment of the samples. cDNA was synthesized from total RNA using the Quantitect Reverse Transcription system from Qiagen. cDNA was added to mRhodopsin, hCHOP (Ddit3), hBiP (Hspa5) or hGAPDH TaqMan® gene expression assays (Life Technologies). Gene expression was normalized relative to hGAPDH using the $\Delta\Delta C_t$ method. miR-708 expression was quantified using the miR-708 TaqMan® expression assay (Life Technologies). miR-708 expression was displayed relative to endogenous miR-16 expression using the $\Delta\Delta C_t$ method.

Rhodopsin Kinase Promoter-Driven Expression of miR-708 in WERI Rb-1 Cells miR-708 sequence was subcloned downstream of the Rhodopsin Kinase (RK) promoter after excision from pcDNA 6.2 GW vector (Block-iT system, Invitrogen) into vector pRK-MVM, which contains the native hRK promoter and MVM intron sequences. WERI Rb-1 cells (ATCC) were transfected with 2 µg pRK-miR-708 or pRK-miR-Control vector using Fugene-HD (Promega), according to the manufacturer's instructions. At 48 hours post-transfection, the cells were collected, and total RNA (including small RNAs) was extracted using the miRNeasy kit protocol (Qiagen). miR-708 was quantified in each sample using the miR-708 TaqMan® gene expression assay as described earlier (Life Technologies). To quantify mRhodopsin knockdown in miR-708 expressing WERI Rb-1 cells, cells were co-transfected with 2 µg each of pRK-miR-708 (or control) and pSport6 mRhodopsin P23H using Fugene-HD according to the manufacturer's instructions (Promega). RNA was extracted as described and mRhodopsin RNA levels were quantified as described above using the $\Delta\Delta Ct$ method relative to hGAPDH RNA levels.

Extraction of RNA from Mouse Retinas Injected with AAV Vectors

RNA was extracted from mouse retinas using the miRNeasy kit according to the manufacturer's instructions (Qiagen). Individual mouse retinas were homogenized in Qiazol Lysis Buffer using 1 mm Zirconia/Silica beads (Biospec) for 10 min. After homogenization RNA was extracted according to the manufacturer's instructions. miR-708 levels in each retina were quantified using the qStar microRNA quantification system (Origene). cDNA was synthesized using the first strand cDNA synthesis kit (Origene), followed by miR-708 specific amplification and quantification using miR-708 specific primers and a miR-708 copy standard (Origene). For quantification of Rhodopsin levels in injected mouse eyes, mRhodopsin was amplified using specific primers (Life Technologies) and quantified against a Rhodopsin cDNA standard. RdCVF levels were qualitatively analyzed against GAPDH expression using the ΔΔCt method.

Rhodopsin Suppression/Replacement Vector hRhodopsin cDNA (with no flanking UTR sequences) was cloned into the pRK vector by excision from the pcDNA vector and performing a blunt ended ligation into pRK-MCS. cDNA was synthesized (Biobasic) containing the hRhodopsin Kinase promoter sequence and the h3-globin Intron with a hmiR-708 sequence insertion (sequence taken from Genbank/NCBI) located between the intron's splice acceptor/donor sites. This sequence was subcloned from pUC57 vector, ligated into pcDNA hRhodopsin vector, and renamed pRK-miR-708 hRho/wt. miRNA-708 and hRhodopsin protein levels were assayed as described above in transfected WERI Rb-1 cells.

Quantification of XBP-1 Splicing in P23H mRhodopsin-Transfected WERI Rb-1 Cells hWERI Rb-1 cells were co-transfected with pcDNA vector encoding a non-glycosylated P23H mutated mRhodopsin and pRK-miR-708 vector. This P23H Rhodopsin cDNA was mutated using site-directed PCR mutagenesis (Agilent Technologies) to change two Asparagine codons (at positions 2 and 5) to Alanine. The cells were transfected as described with 2 μg of each vector and incubated for 72 hrs. Total RNA was collected from the cells as described previously. cDNA was synthesized using the High Capacity cDNA synthesis kit (Invitrogen). XBP-1 spicing was assessed using primers specific for XBP-1 and High Fidelity PCR MasterMix (Roche). Amplified sequences were analyzed on a 2% agarose gel and the relative amounts of spliced (~280 nt) vs. unspliced (~300 nt) XBP-1 transcript was quantified using Image-J software.

Additional Methods

Methods for immunofluorescence, Western blotting with and without Endoglycosidase H treatment, UPR marker expression, and TUNEL staining of cells expressing wild-type or P23H mutant rhodopsin were performed as described in Adamowicz, M., et al. (2012) *Adv. Exp. Med. Biol.* 723:573-9.

Results

Figure 1A:
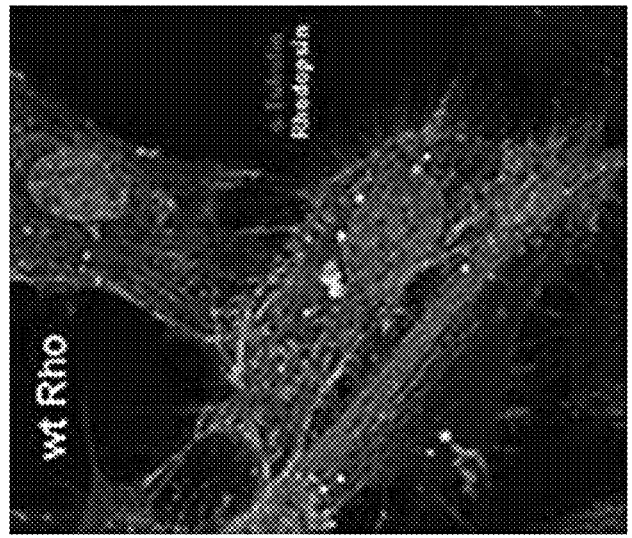

Human retinal pigmented epithelial (RPE) cells were transiently transfected with a gene encoding either human wild-type (WT) or human P23H mutant rhodopsin (a mutation linked to RP). The localization of rhodopsin was investigated by confocal immunofluorescence microscopy using anti-rhodopsin antibody. In the case of the wild type protein, the majority of the protein was processed to the plasma membrane (FIG. 1A), indicating normal biogenesis. By contrast, the mutant P23H showed a perinuclear/reticular distribution characteristic of endoplasmic reticulum (ER) retention, with almost no expression at the cell surface (FIG. 1B). These results demonstrate that P23H mutant rhodopsin fails to be trafficked properly to the plasma membrane and is instead retained in the ER.

Figure 2B:
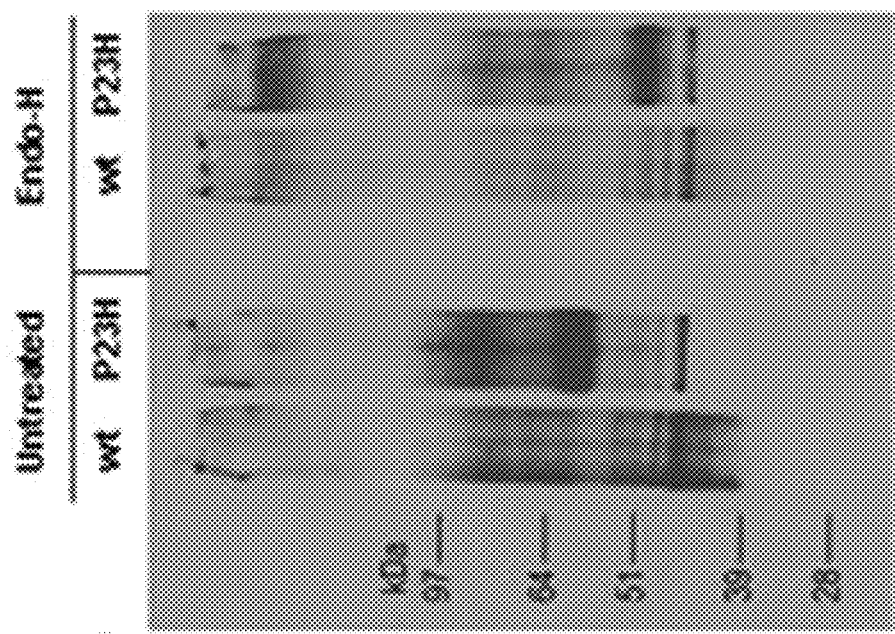
FIGS. 2A & 2B show that P23H mutant rhodopsin forms non-native oligomers and retains ER-specific oligosaccharides.
Figure 2A:
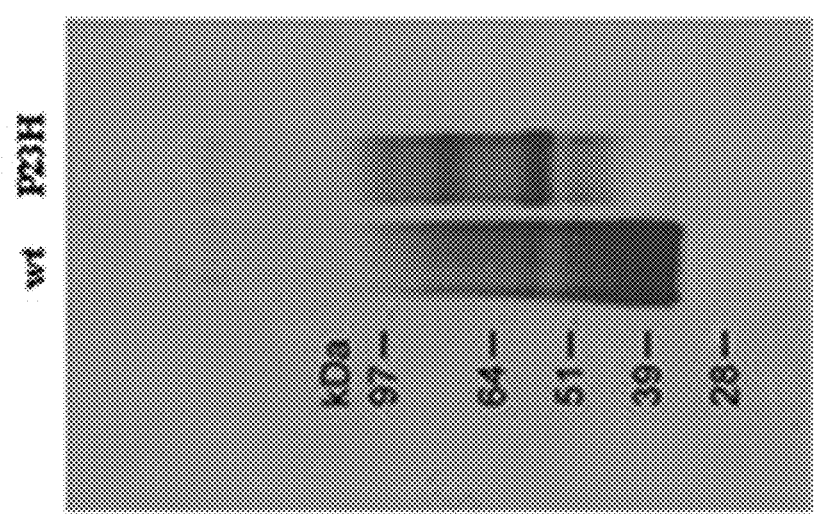

Aggregation of rhodopsin was assessed by SDS-PAGE immunoblot analysis of detergent soluble extracts from RPE cells transiently expressing wild type or P23H mutant protein (FIG. 2A). Wild-type rhodopsin migrated predominantly as a diffuse band at a molecular mass of ~40 kDa. This species corresponds to monomeric, mature rhodopsin containing N-linked glycans. The mobility of P23H mutant rhodopsin differed markedly from wild-type rhodopsin, with the majority of P23H migrating as higher-weight dimers and oligomers (FIG. 2A). P23H was also sensitive to Endoglycosidase H—note that treatment with Endoglycosidase H affects the migration of P23H rhodopsin, but not wild-type, as shown in FIG. 2B. Endoglycosidase H is specific for core glycosylated, high mannose N-linked oligosaccharide structures typical of proteins that have not matured beyond the ER.

Together, these data suggest that in RPE cells wild type rhodopsin is able to fold and mature beyond the ER, whereas the P23H mutant is more prone to forming non-native oligomers and is retained within the ER, perhaps due to an inability to fold productively.

Figure 3A:
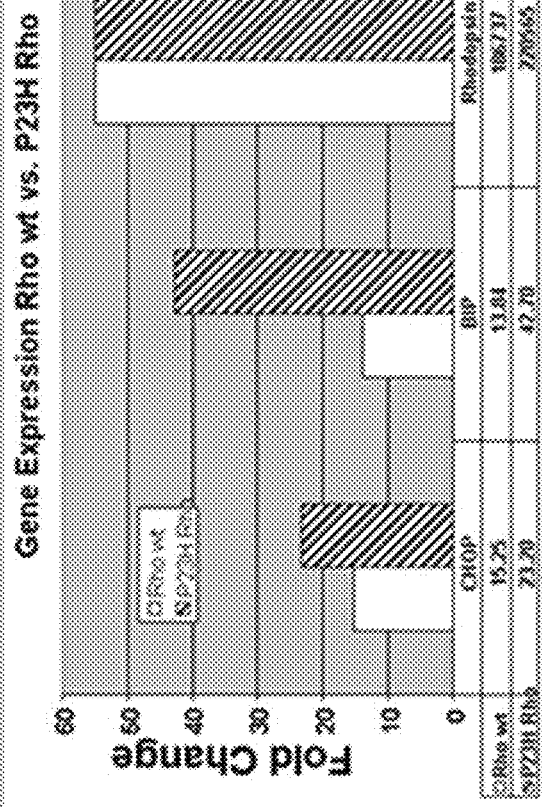
FIGS. 3A & 3B show that cells expressing P23H rhodopsin have higher expression of UPR markers and a higher propensity toward apoptosis.

Next, P23H rhodopsin's ability to induce ER stress in transfected RPE cells was assessed by measuring the levels of two markers of the UPR, BiP and CHOP. Increased BiP mRNA levels were detected in cells transiently expressing both WT and P23H rhodopsin (FIG. 3A), suggesting that increasing the folding load of the ER per se induced the UPR. However, BiP mRNA expression was significantly higher in cells expressing P23H rhodopsin (43-fold over untransfected cells) as compared with cells expressing WT rhodopsin (14-fold over untransfected cells) (FIG. 3A). The rhodopsin mRNA levels were identical in cells expressing WT or mutant forms of the protein (FIG. 3A). Thus, P23H rhodopsin is a more potent inducer of BiP than WT rhodopsin. Without wishing to be bound to theory, this discrepancy may be due to the folding defect of the mutant protein.

Figure 3B:
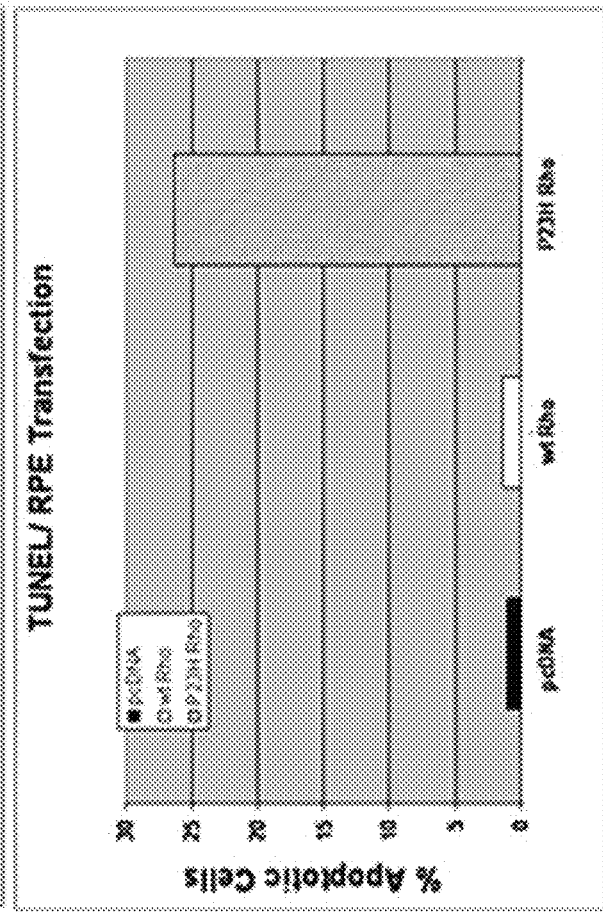

CHOP expression was examined next. Cells expressing the WT rhodopsin protein showed a 15-fold induction of CHOP compared to untransfected cells, while cells expressing P23H mutant showed an even greater 23-fold induction (FIG. 3A). As CHOP is a UPR-induced transcription factor that mediates apoptosis (Lee, E. S., et al. (2007) *FEBS Lett.* 581(22):4325-32), the relative levels of apoptosis between WT and P23H mutant expressing cells was measured. In agreement with the mRNA levels of CHOP, TUNEL assay results further suggested that RPE cells transiently expressing the P23H mutant are more prone to apoptosis than those expressing the wild type rhodopsin (FIG. 3B).

Example 2: Modulation of miR-708 Levels Regulates Rhodopsin Expression and the UPR in HEK-293 Cells A consensus sequence corresponding to a putative miR-708 target site has been found in the 3' UTR of several mammalian rhodopsin genes (Behrman, S., et al. (2011) *J. Cell Biol.* 192(6):919-27). This Example demonstrates that miR-708 regulation of rhodopsin may be used as a tool to modulate rhodopsin expression in cultured cells.

Figure 5:
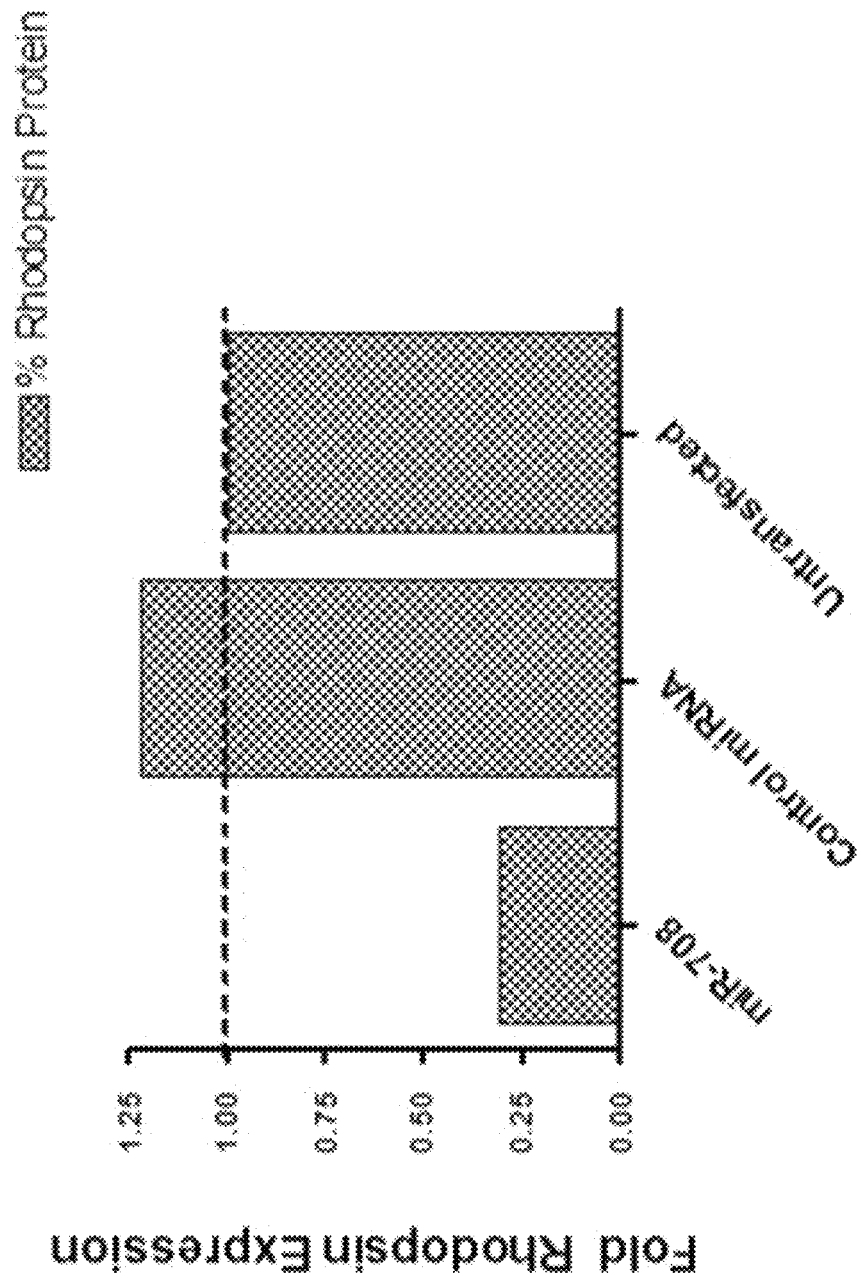
FIG. 5 shows the expression of rhodopsin protein in cells expressing miR-708 or a control miRNA, relative to untransfected cells. All cells are HEK-293 cells expressing mP23H rhodopsin which has a 3'UTR miR708 target sequence. Rhodopsin protein expression is normalized to hGAPDH expression. Rhodopsin protein levels are decreased in the presence of miR708 compared to control miR.

HEK-293 cells expressing a P23H mutant mRhodopsin gene encoding a 3'UTR miR-708 target sequence were transfected with a plasmid expressing miR-708 or miR-Control as depicted in FIG. 4. After 72 hrs, the cells were collected, and mP23H Rhodopsin protein expression was analyzed using a Western blot (FIG. 5). P23H mRhodopsin protein expression was reduced to ~30% in cells transfected with CBA-miR-708, compared to cells transfected with a CBA-miR-Control vector.

Figure 6:
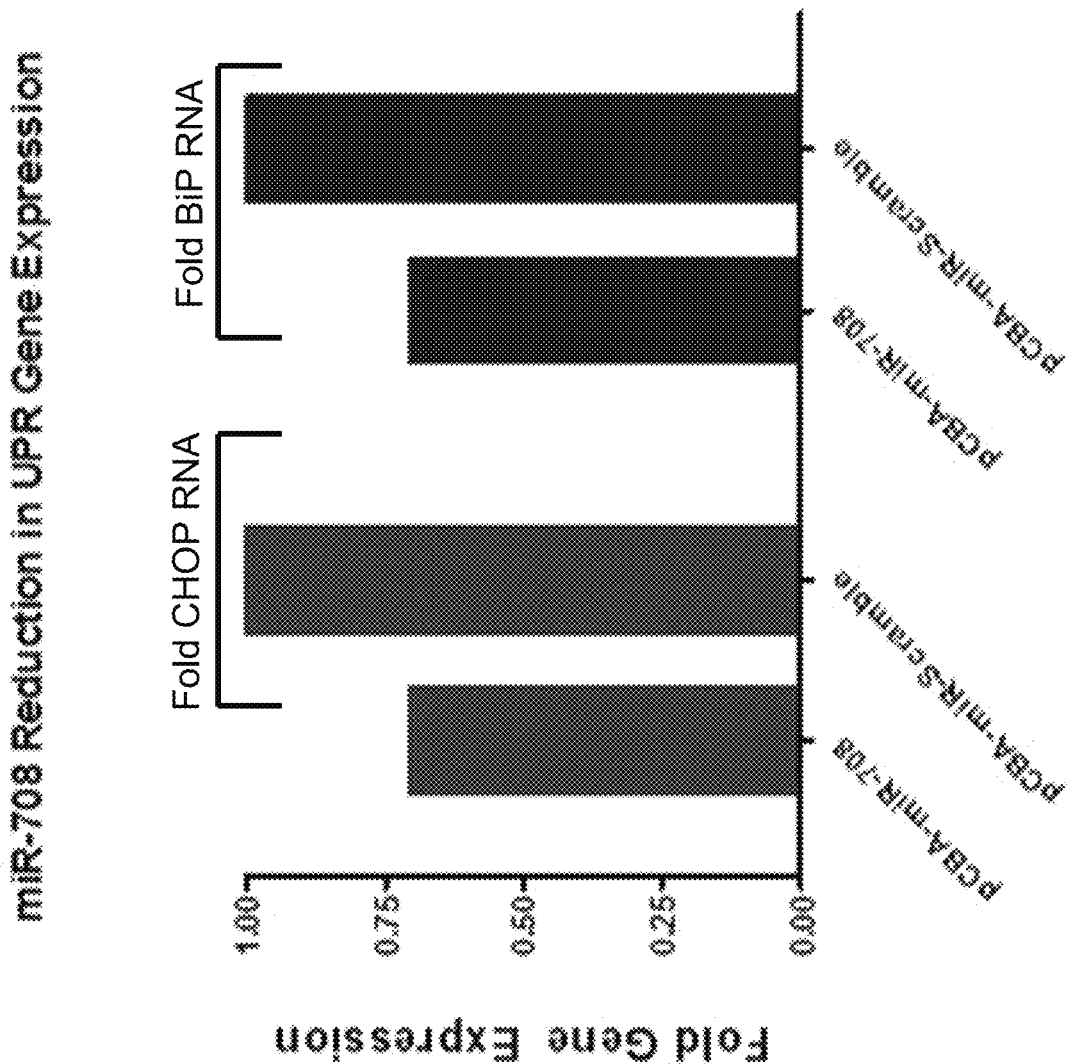
FIG. 6 shows that HEK-293 cells expressing mP23H rhodopsin have reduced RNA levels of the UPR marker genes CHOP and BiP upon expression of miR-708, compared to cells expressing a control miRNA ("Scramble").

Expression of UPR target genes (CHOP/BIP) was also analyzed by TaqMan® gene expression analysis. HEK-293 cells expressing miR-708 also showed reduced expression of CHOP and BiP RNA compared to control cells (FIG. 6). These results suggest that reducing the level of misfolded P23H mRhodopsin results in a concomitant reduction in expression of UPR genes BiP and CHOP.

Figure 7B:
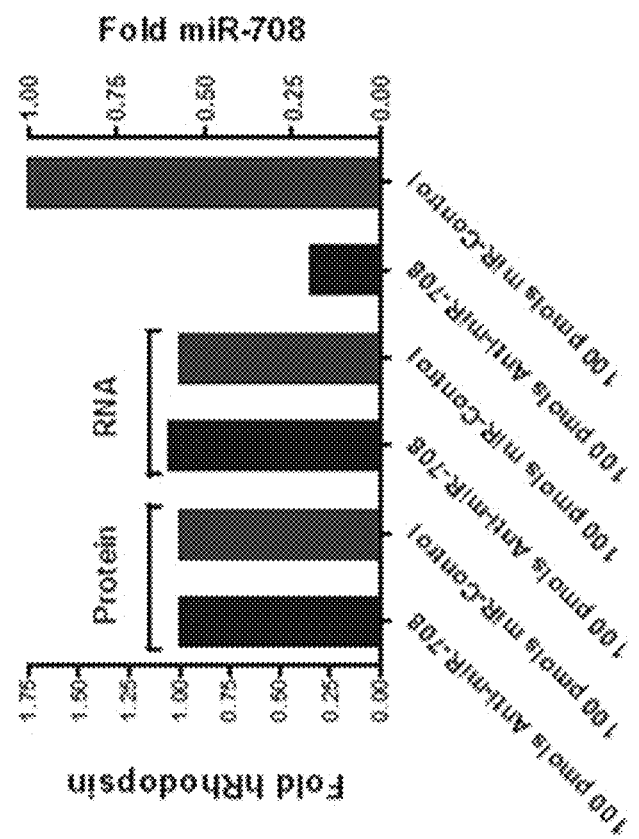
FIGS. 7A & 7B show that down-regulation of rhodopsin by endogenous miR-708 is dependent upon the presence of a miR-708 target sequence in the rhodopsin 3' UTR. HEK-293 cells were transfected with a mouse P23H rhodopsin gene including the miR-708 target sequence (FIG. 7A), or with a human P23H rhodopsin gene lacking the miR-708 target sequence (FIG. 7B). Cells were also transfected with a control pre-miRNA or an anti-miR-708 pre-miRNA to inhibit endogenous miR-708. Rhodopsin protein was measured relative to hGAPDH protein, and rhodopsin mRNA was measured relative to hGAPDH mRNA. Levels of endogenous miR-708 are also shown (right axis and rightmost two columns in FIGS. 7A & 7B).
Figure 7A:
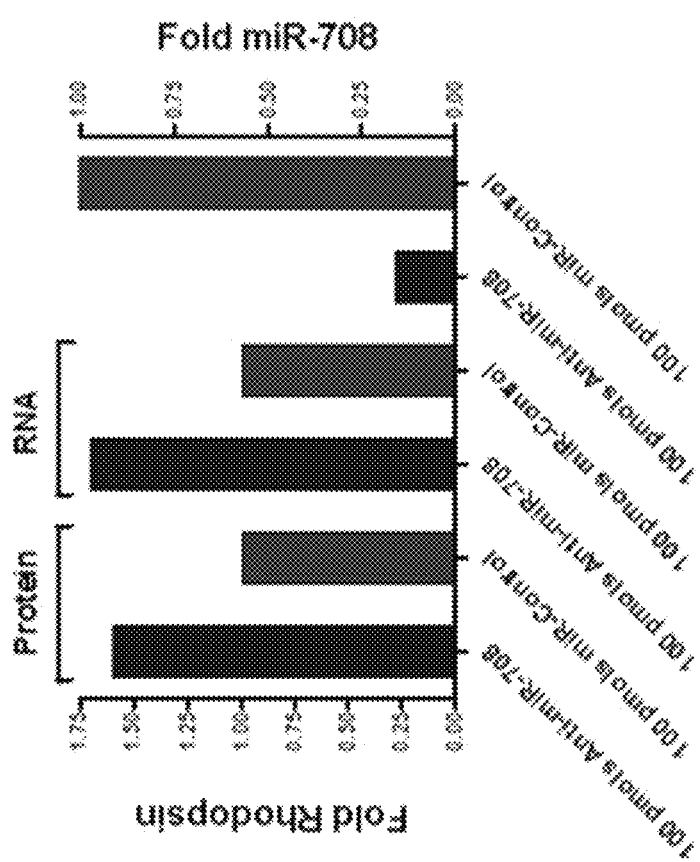

In the converse experiment, HEK-293 cells expressing either mouse P23H Rhodopsin (including a 3' UTR miR-708 target sequence) or human P23H Rhodopsin (lacking the 3' UTR miR-708 target sequence) were transfected with anti-miR-708 pre-miRNA or negative control pre-miRNA (FIG. 7). In this experiment, exogenous anti-miR-708 was used to inhibit endogenous HEK293 miR-708. If endogenous miR-708 regulated rhodopsin expression through the putative miR-708 target sequence, then changes in levels of the P23H rhodopsin would be observed only if there was a miR-708 target sequence in the 3' UTR of the rhodopsin gene. Cells were transfected with 100 pmol of each RNA. Cell lysates were generated, and rhodopsin protein was quantified on a Western blot while mRNA levels were analyzed by TaqMan® analysis (FIG. 7). Inhibition of endogenous miR-708 resulted in an increase of both mouse Rhodopsin mRNA and protein (FIG. 7A), whereas the levels of both human rhodopsin mRNA and protein remained unaffected (FIG. 7B), despite lower levels of endogenous miR-708. These results demonstrate that the regulation of rhodopsin by miR-708 requires the miR-708 target sequence in the rhodopsin 3' UTR.

Together, these results show that rhodopsin is a functional target of miR-708, and that modulation of miR-708 activity may be used as a tool to affect rhodopsin expression.

Example 3: Design of an AAV ITR Plasmid Expressing miR-708 Under the Control of the Photoreceptor-Specific Rhodopsin Kinase Promoter It is thought that buildup of mutant rhodopsin protein in the ER contributes to the ER stress underlying photoreceptor cell death in RP. The previous Example demonstrates that miR-708 expression is able to regulate overall rhodopsin levels. An adeno-associated virus (AAV)-based vector was constructed for specific expression of miR-708 in the photoreceptor cells of the retina to determine if lowering total rhodopsin levels (including wild-type and mutant forms) may alleviate ER stress independent of the rhodopsin mutation.

Figure 8:
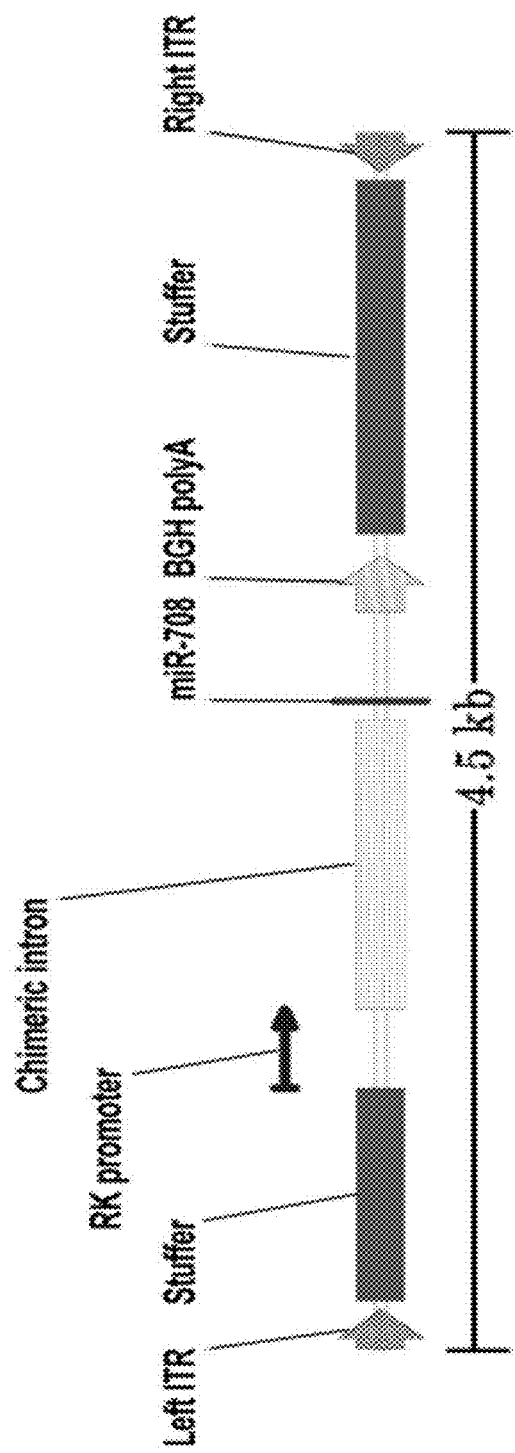
FIG. 8 depicts a diagram of an AAV vector for expressing miR-708 in rod photoreceptors. Relevant vector features are labeled.

FIG. 8 depicts an AAV inverted terminal repeat (ITR) plasmid designed to express miR-708 specifically in retinal photoreceptor cells. miR-708 expression was driven by the rhodopsin kinase promoter (pRK), which is specifically expressed in rod photoreceptor cells. In this vector, miR-708 was expressed from the miR-155 scaffold shown in FIG. 4.

Figure 9A:
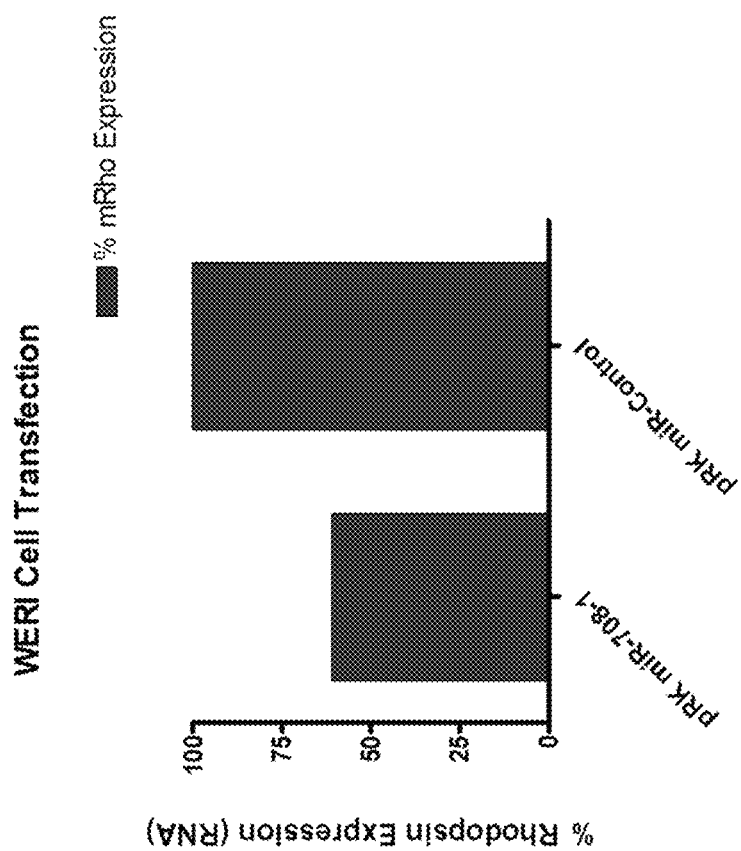
FIGS. 9A & 9B show that expression of miR-708 using an AAV vector down-regulates P23H mutant rhodopsin.

Next, this AAV ITR plasmid was validated in cultured cells. WERI or RPE cells were transfected with the pre-viral plasmid described in FIG. 8, and the levels of miR-708 were quantitated by TaqMan® analysis. FIG. 9A shows that WERI cells transfected with the pRK-driven miR-708 plasmid had over a 2000-fold increase in miR-708 levels compared to WERI cells transfected with a plasmid expressing miR-Scramble (control). In contrast, RPE cells, in which the RK promoter is not significantly expressed, did not show a significant increase in miR-708 levels (FIG. 9A).

Figure 9B:
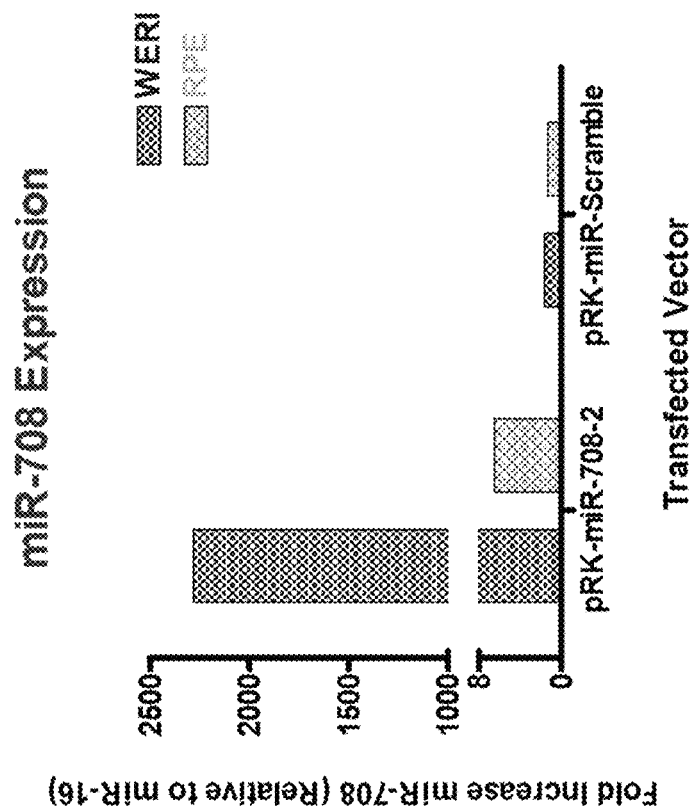

The function of miR-708 in regulating rhodopsin expression was confirmed by co-transfecting the pRK-miR-708 plasmid (or a miR-Control plasmid) and a plasmid with the P23H mouse rhodopsin gene harboring a 3'miR708 target sequence into WERI cells. FIG. 9B shows that the P23H mRhodopsin mRNA was reduced in the presence of the miR-708, compared to a miR-Control. These results demonstrate that expression of miR-708 using an AAV ITR vector is effective in reducing the expression of rhodopsin in photoreceptor cells.

Example 4: Knockdown of Rhodopsin in Mouse Retinas Using a miR-708 AAV5 Vector

To test whether an AAV vector could be used to reduce rhodopsin expression in the retina in vivo, the pRK-miR-708 plasmid described in FIG. 8 was packaged into an AAV5 capsid to generate AAV5-RK miR-708. In addition, an AAV5 miR-Control vector was generated. Wild-type C57bl mice received a subretinal injection of $1 \times 10^8$ vgs of AAV5-RK miR-708 or AAV5 miR-Control in the contralateral eye. At 1 month post-injection, the mice were euthanized, and the neuro retina was extracted and flash-frozen for qPCR analysis of gene expression.

FIG. 10A shows that mouse eyes that had been injected with an AAV5 vector expressing miR-708 had reduced rhodopsin expression, compared to mouse eyes injected with an AAV5 miR-Control vector. In contrast, the expression of another rod-specific gene, Rod Derived Cone Viability Factor (RdCVF), was not affected (FIG. 10B). FIG. 10C confirms that eyes injected with AAV5miR708 vector showed a significant increase in miR-708 copy number, compared to eyes that received AAV5miR control. These results suggest that AAV-based vectors expressing miR-708 in rod photoreceptors are effective in reducing endogenous rhodopsin expression in vivo.

Figure 11A:
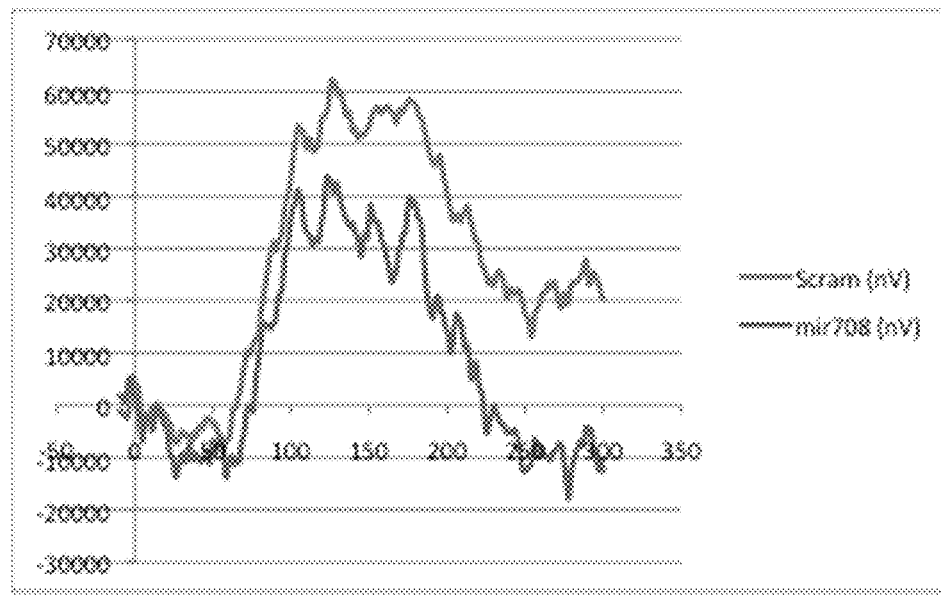
FIGS. 11A & 11B show that treatment of eyes with AAV5 miR-708 reduces rod-mediated, but not cone-mediated, responses.
Figure 11A:
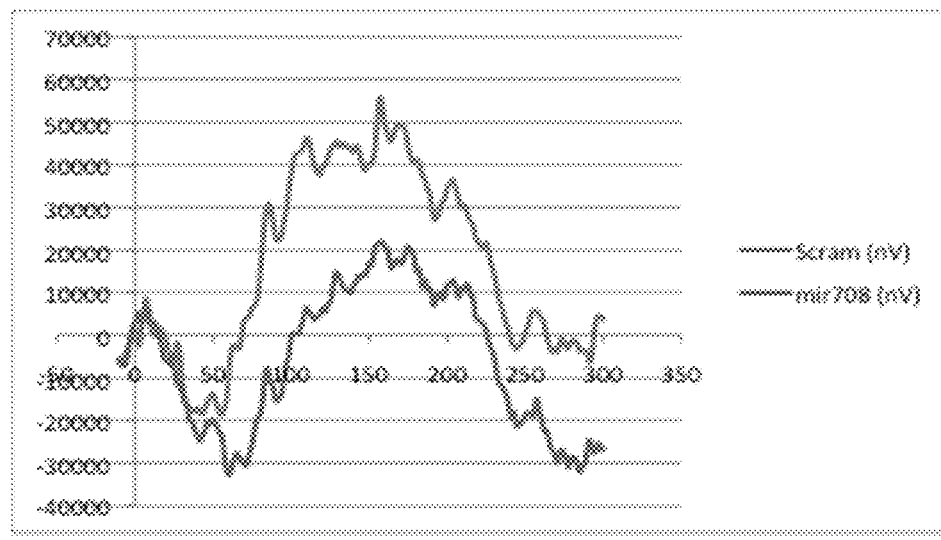
Figure 11A:
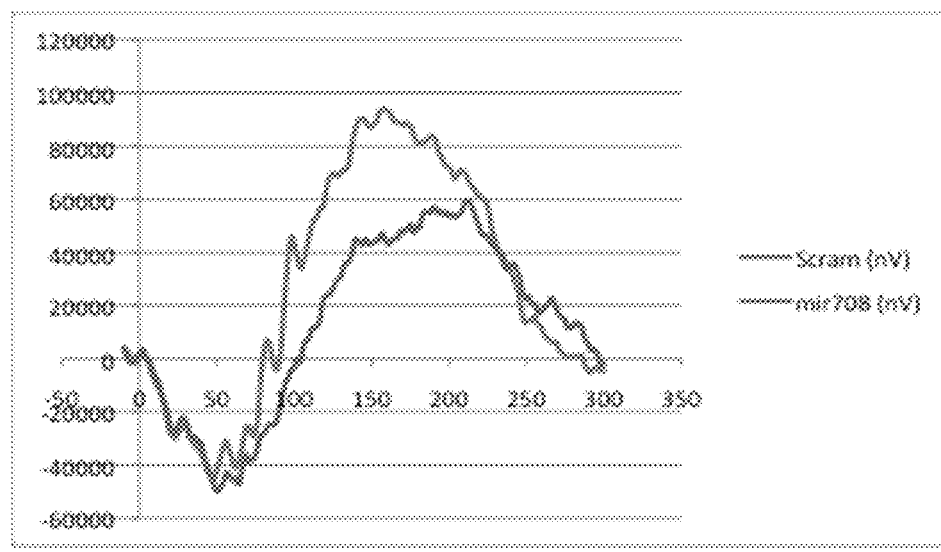
Figure 11B:
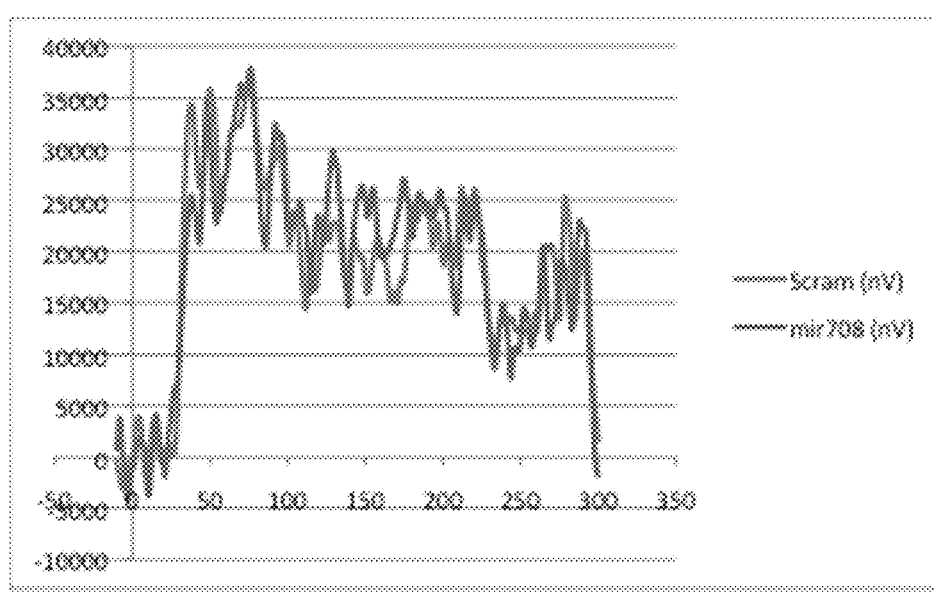
Figure 11B:
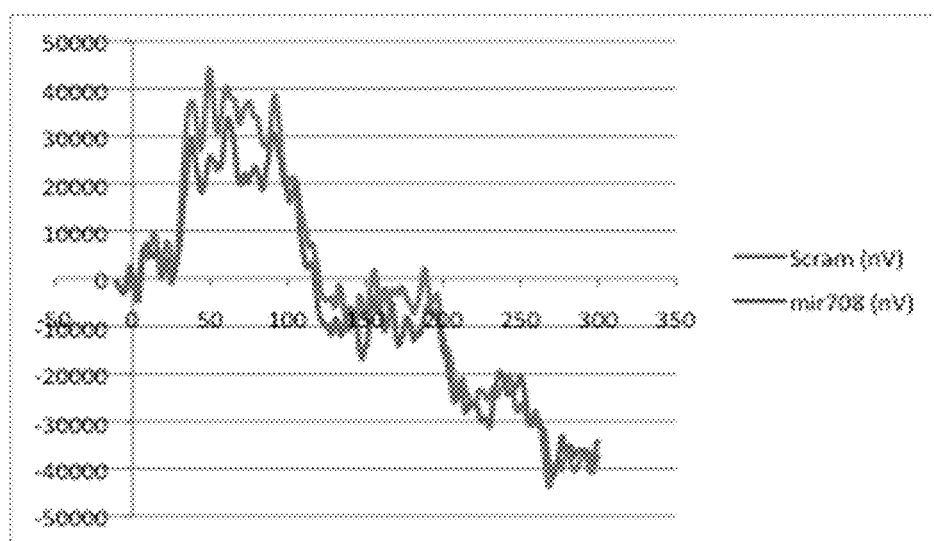
Figure 11B:
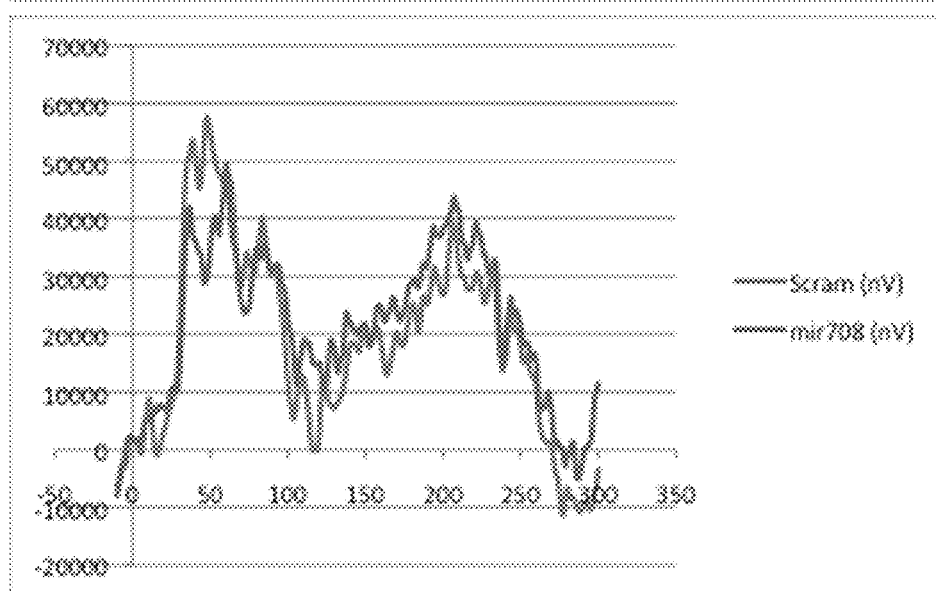

To demonstrate the functional relevance of rhodopsin knockdown, mouse eyes treated with AAV5 miR-708 or AAV5 miR-Control were analyzed by electroretinogram (ERG) to assess retinal function. Eyes that received the AAV5 miR-708 vector showed a decreased scotopic response, as expected if levels of rhodopsin are reduced (FIG. 11A). Scotopic ERG responses are an assessment of rod function, and this measurement can be correlated to rhodopsin levels. However, cone function in the same animals, as assessed by photopic ERG, was unchanged following AAV5 miR-708 delivery (FIG. 11B), confirming that miR-708 had a biological effect on rod photoreceptor cells while sparing the cone cells. These data demonstrate that AAV5 miR-708 delivery results in a biological effect that is restricted to the rod target cell.

Example 5: Construction of a hRhodopsin Suppression/Replacement Vector with an Intron-Embedded miR-708 Expression Cassette miR-708 is normally expressed in vivo from the first intron in the ODZ4 gene. Therefore, a novel construct was designed based on the sequence of miR-708 and its endogenous scaffold/flanking sequence. The miR-708 sequence was embedded into a synthetic intron and cloned downstream of the photoreceptor specific promoter Rhodopsin Kinase (RK), but upstream of the hRhodopsin cDNA. The endogenous miR-708 sequence including its flanking regulatory and processing sequences were cloned into the β-globin intron sequence upstream of the hRhodopsin cDNA sequence but downstream of the RK promoter. As such, the miR-708 sequence is 5' relative to the rhodopsin coding sequence.

Figure 12:
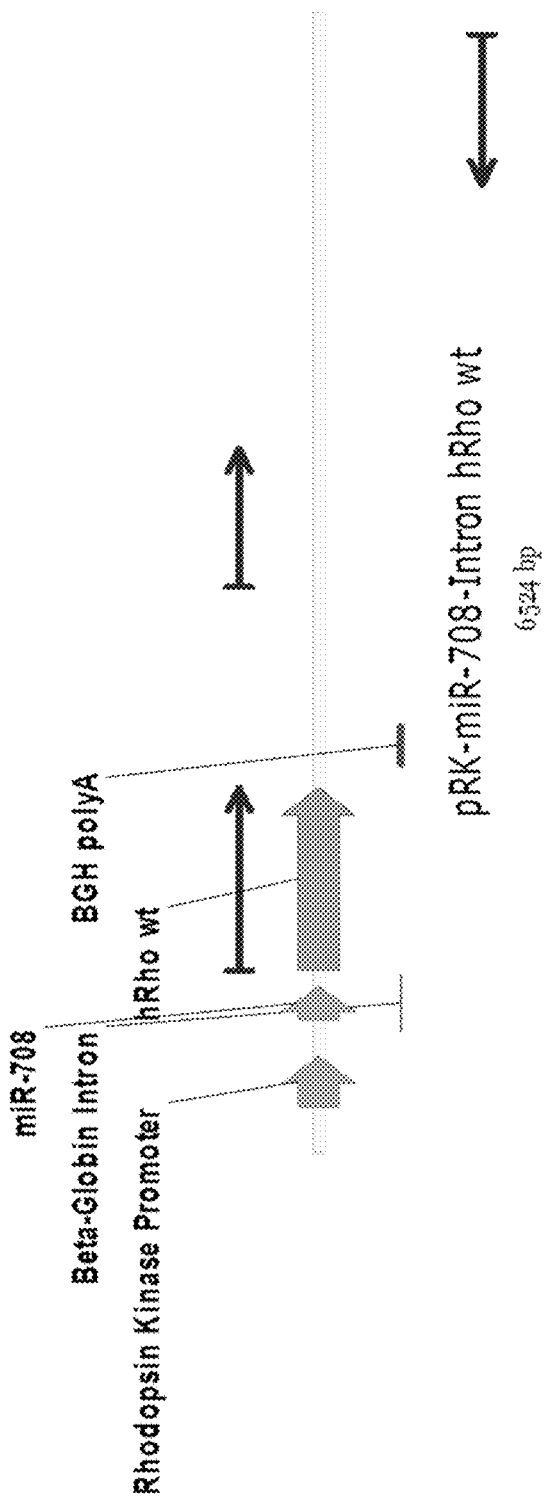
FIG. 12 provides a diagram of the miR-708 intron-embedded hRhodopsin suppression/replacement vector.

FIG. 12 provides a diagram of this 5' suppression/replacement vector. hRhodopsin (lacking a 3' UTR mir708 target sequence) was controlled by the RK promoter. The endogenous miR-708 sequence including endogenous scaffold (e.g., including any Drosha/Dicer recognition motifs) was embedded within the β-globin intron. hRhodopsin cDNA (with no 3' miR-708 UTR target sequence) was included downstream of the splice junction site. miR-708 was embedded within the β-globin, which is located downstream of the RK promoter, and therefore the miR-708 was processed after splicing of the β-globin intronic sequence. In addition vector with a similar structure harboring a control miR was generated.

The vector described in FIG. 12, or a vector with a control miRNA, was used to transfect WERI cells. WERI cells were used because they express little, if any, endogenous miR-708, and they are permissive to the RK promoter. WERI cells were co-transfected with a cDNA encoding P23H mRhodopsin (with a 3'UTR miR-708 sequence). Both rhodopsin knockdown (RNA levels) and levels of the UPR genes CHOP and BIP were examined in transfected cells.

Figure 13:
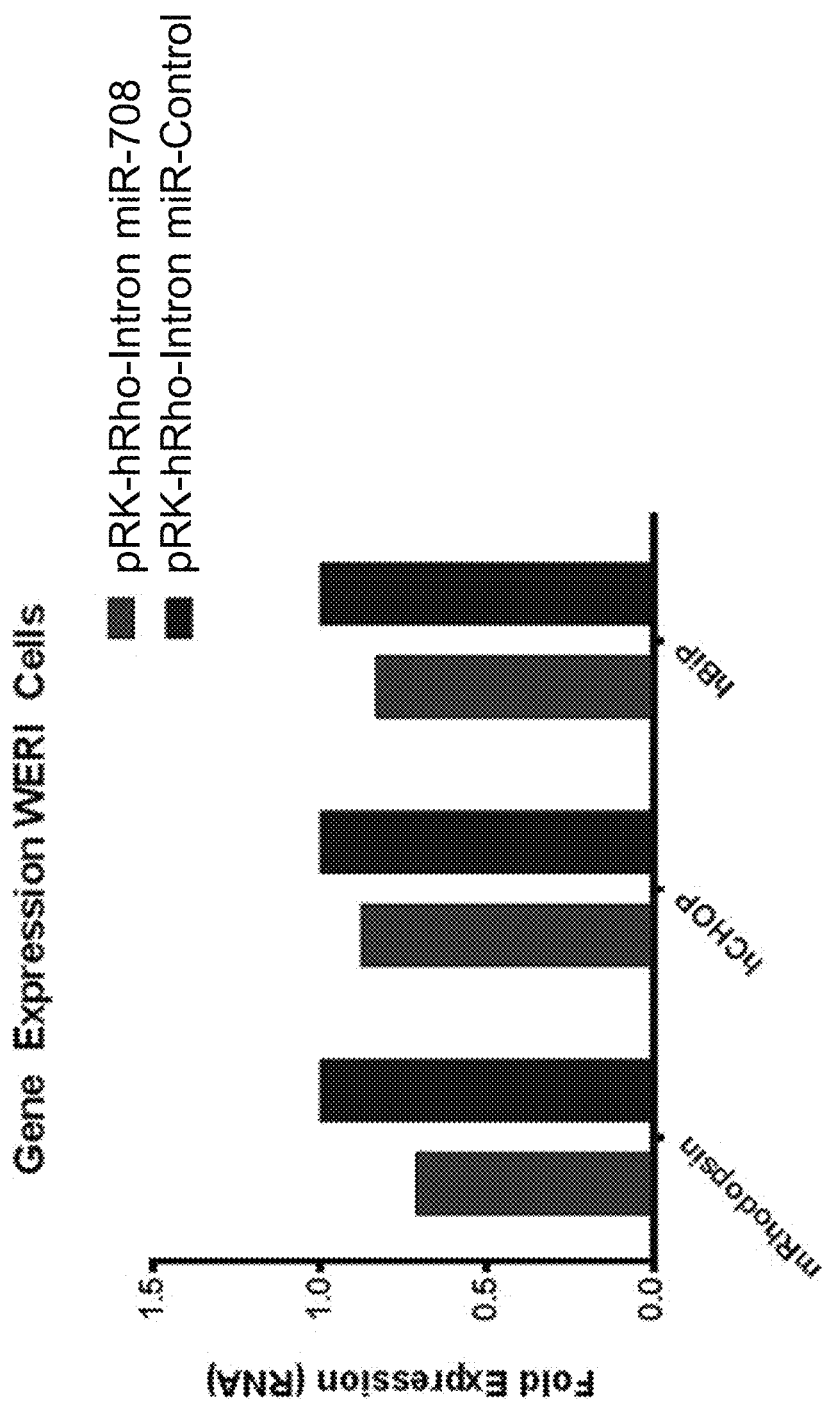
FIG. 13 shows that an intron-embedded miR-708 vector reduces expression of mRhodopsin, hCHOP, and hBiP in WERI cells transfected with P23H mRhodopsin, as compared to a miR-Control vector.

FIG. 13 shows that cells co-transfected with mRhodopsin (P23H) and the miR-708 vector had reduced mRhodopsin levels compared to cells co-transfected with mRhodopsin and control miRNA vector. Additionally, the UPR genes CHOP and BiP were also down regulated in the miR-708 transfected cells compared to control. This data suggests that using the endogenous miR708 scaffold with intronic expression of miR708 provides an alternative scaffold that supports miR708 processing and expression.

Example 6: Comparison of Different miR-708 Scaffolds

Lower levels of miR-708 expression may be beneficial in reducing any potential off-target effects of the miRNA in a clinical setting. Therefore, different miR scaffolds were tested for strength of expression in the WERT human retinoblastoma cell line.

Figure 14:
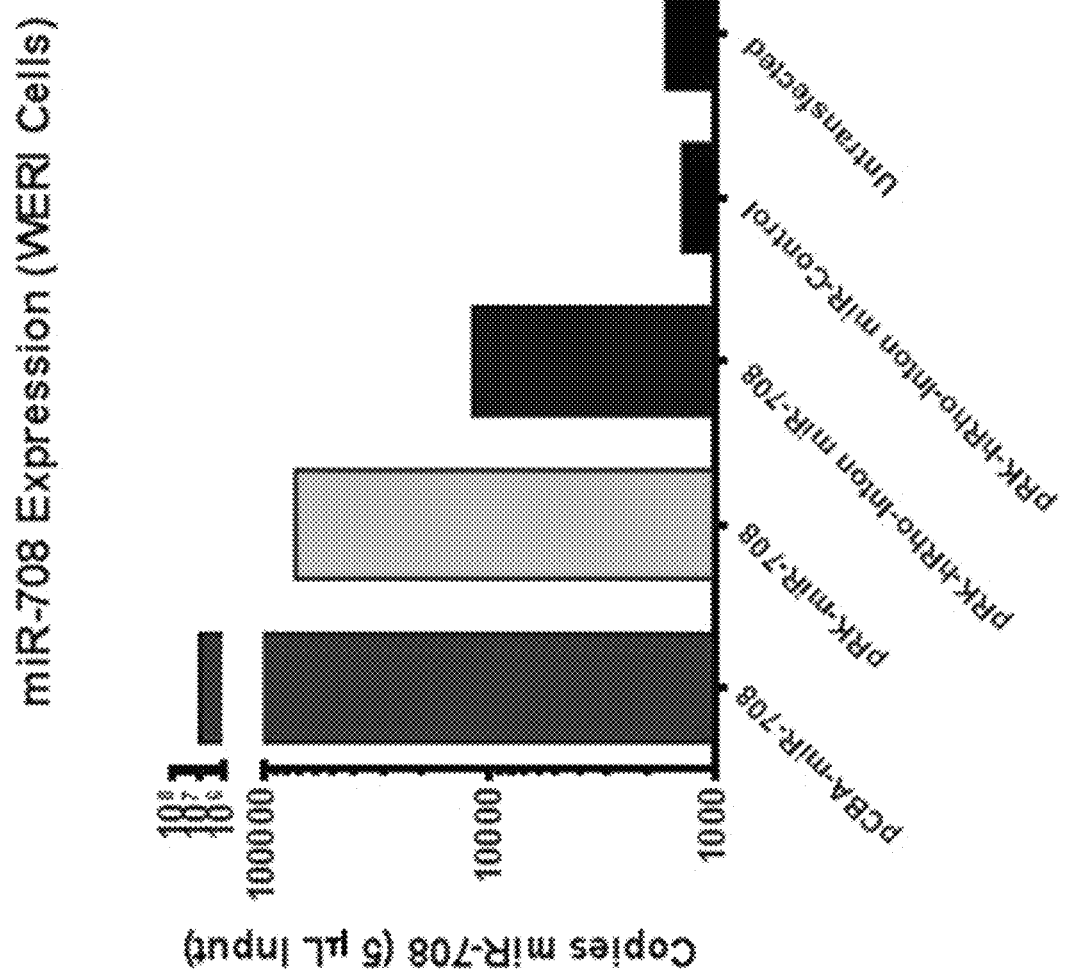
FIG. 14 shows that miR-708 expression from the intron-embedded vector has reduced expression compared to the non-embedded vector in WERI cells, the caveat being that the intron-embedded vector pRK-hRHO-intron miR-708 also co-expresses hRhodopsin. All vectors driving miR-708 expression using the RK promoter had orders of magnitude lower expression than a vector using the CBA promoter.

FIG. 14 depicts quantified miR-708 levels in WERT cells transfected with CBA-driven miR-708, RK-driven miR708 using the miR-155 scaffold shown in FIG. 4, or the RK intron-embedded miR-708 hRhodopsin vector shown in FIG. 12. miR-708 expression in the RK intronic system was not as robust as the CBA driven system. However, miR-708 expression was still well above background and about 5 fold lower than pRKmiR708 using the miR-155 scaffold. Note that hRhodopsin was co-expressed from the intron-embedded vectors, but not in the CBA or RK miR-155 scaffold vectors.

Figure 15:
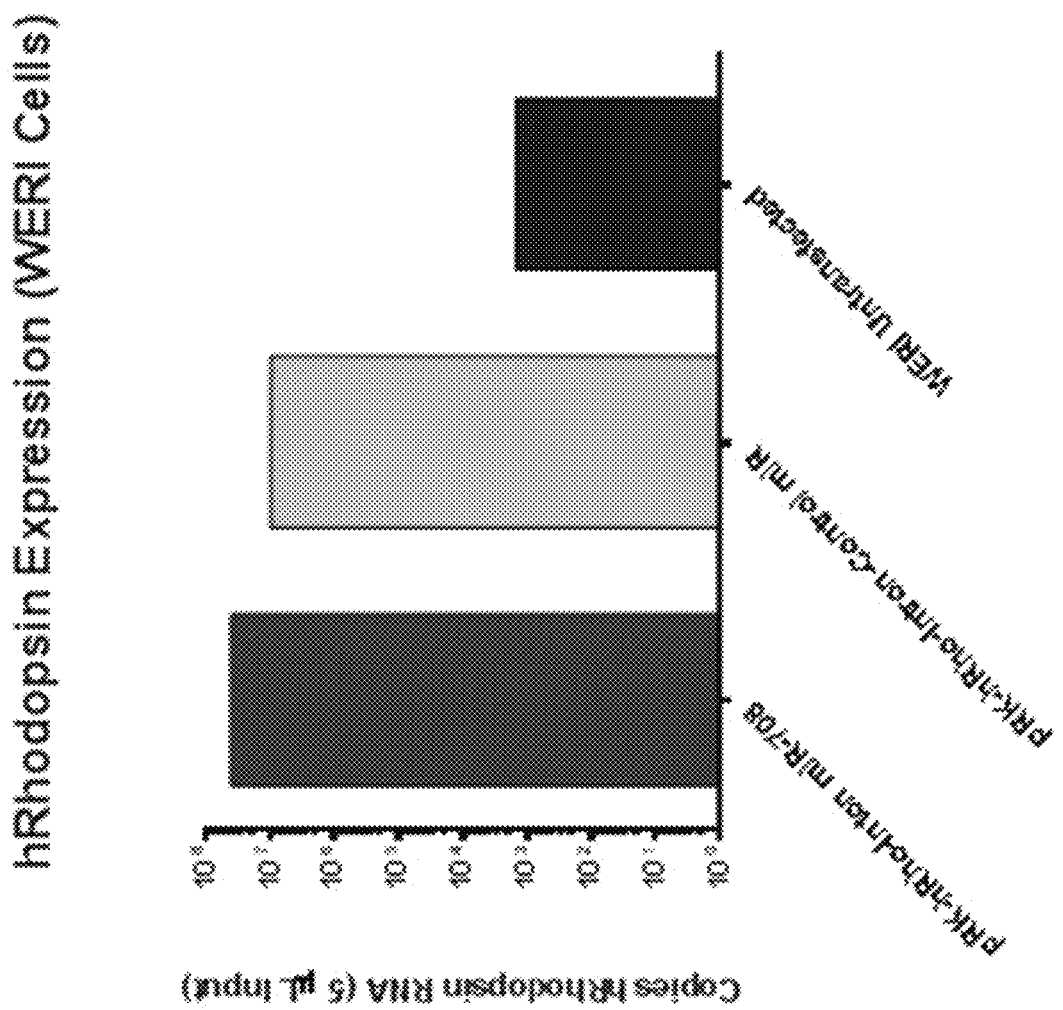
FIG. 15 shows that hRhodopsin expression from the intron-embedded suppression/replacement vector is refractory to knockdown by co-expressed miR-708. The levels of hRhodopsin RNA are the same in cells transfected with vectors expressing miR-708 or miR-Control.

Next, the levels of hRhodopsin mRNA were compared in WERT cells expressing the miR-708 intron-embedded, suppression/replacement vector or a miR-Control vector. FIG. 15 shows that WERT cells transfected with the miR-708 intron-embedded, suppression/replacement vector had a similar level of hRhodopsin compared to cells transfected with the control vector. These results indicate that hRhodopsin expression from the suppression/replacement vector, which lacks the 3' UTR miR-708 target sequence, is refractory to inhibition by miR-708 expression. Both cells showed higher hRhodopsin expression than untransfected WERT cells.

Example 7: Knockdown of Mutant Rhodopsin by the miR-708 Suppression/Replacement Vector Reduces a Marker of ER Stress The ability of the miR-708 suppression/replacement vector to reduce ER stress in cells expressing mutant rhodopsin was examined. WERT cells expressing a non-glycosylated, P23H mutant rhodopsin (N2K/N15K/P23H), with or without a 3'UTR miR708 target sequence, were transfected with the suppression replacement vector described in FIG. 12. Cells were harvested and RNA extracted to measure X-box binding protein 1 (XBP-1) splicing. XBP-1 is a transcription factor important in regulating ER stress genes. Its splicing is a known marker of cellular ER stress/UPR; cells undergoing UPR show increased levels of spliced XBP-1.

Figure 16:
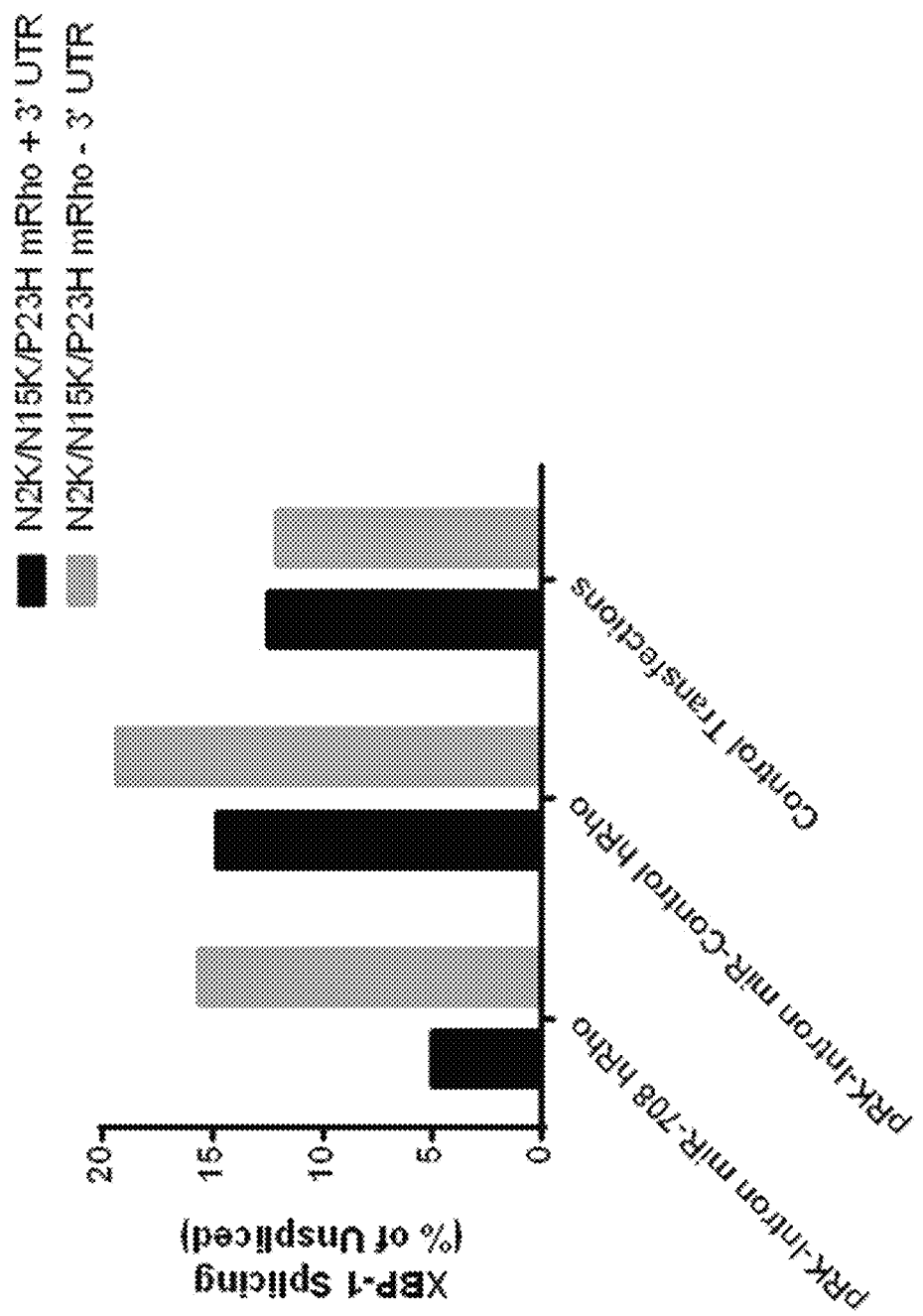
FIG. 16 shows that the miR-708 suppression/replacement vector reduces XBP-1 splicing, a marker of ER stress, in WERI cells expressing mutant rhodopsin. This reduction is observed only if the 3'UTR miR-708 target sequence is present in the rhodopsin transcript.

As shown in FIG. 16, cells expressing mutant Rhodopsin with a 3' UTR target sequence had decreased XBP-1 splicing when transfected with the miR-708 suppression/replacement vector. In contrast, cells expressing the mutant P23H Rhodopsin lacking the 3'UTR miR-708 target sequence had equivalent levels of XBP-1 splicing compared to cells transfected with the miR-Control sequence. These results demonstrate that knockdown of mutant rhodopsin using the miR-708 suppression/replacement vector is effective in reducing ER stress.

Example 8: Expression of miR-708 in the β-Globin Intron Scaffold Placed in the Rhodopsin 3' UTR Increases the Expression of Rhodopsin and miR-708

Figure 17:
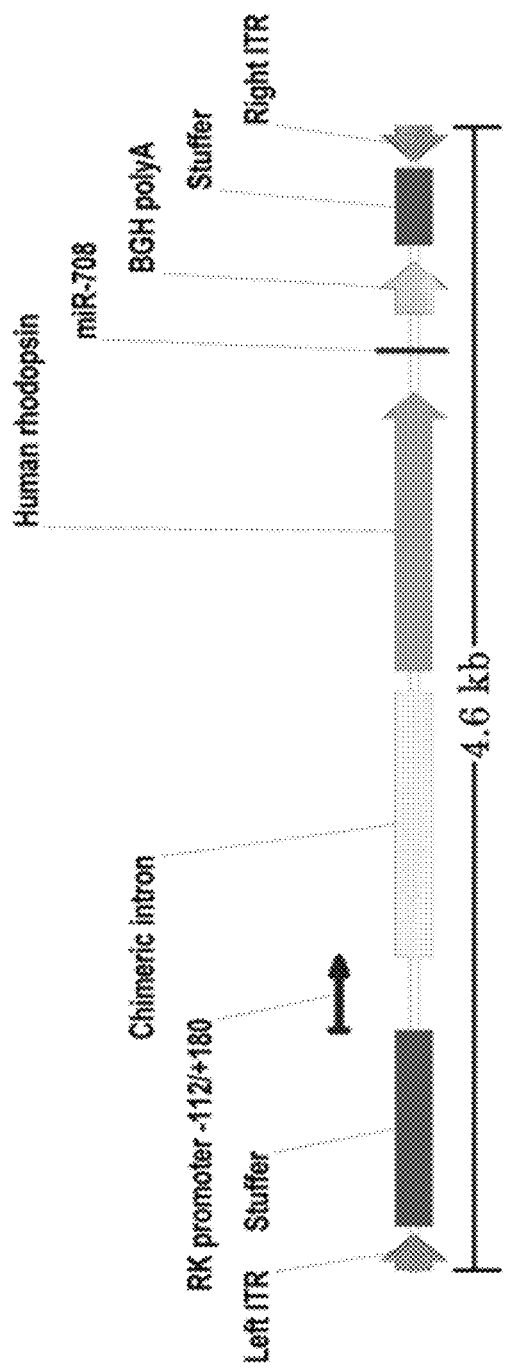
FIG. 17 shows a diagram of a vector with the miR-708 human β-globin intron scaffold in the 3' UTR of the rhodopsin cDNA.

In order to test whether the position of the miR-708 scaffold affects its expression, a vector was constructed where the miR-708 sequence (including its flanking regulatory/processing sequences) was cloned into the β-globin intron sequence downstream of the Rhodopsin cDNA, i.e., within the 3' UTR. FIG. 17 shows a diagram of this 3' suppression/replacement vector, which is similar to that shown in FIG. 12, except that the miR-708 human β-globin intron scaffold is in the 3' UTR of the rhodopsin cDNA, rather than the 5' UTR.

Figure 18:
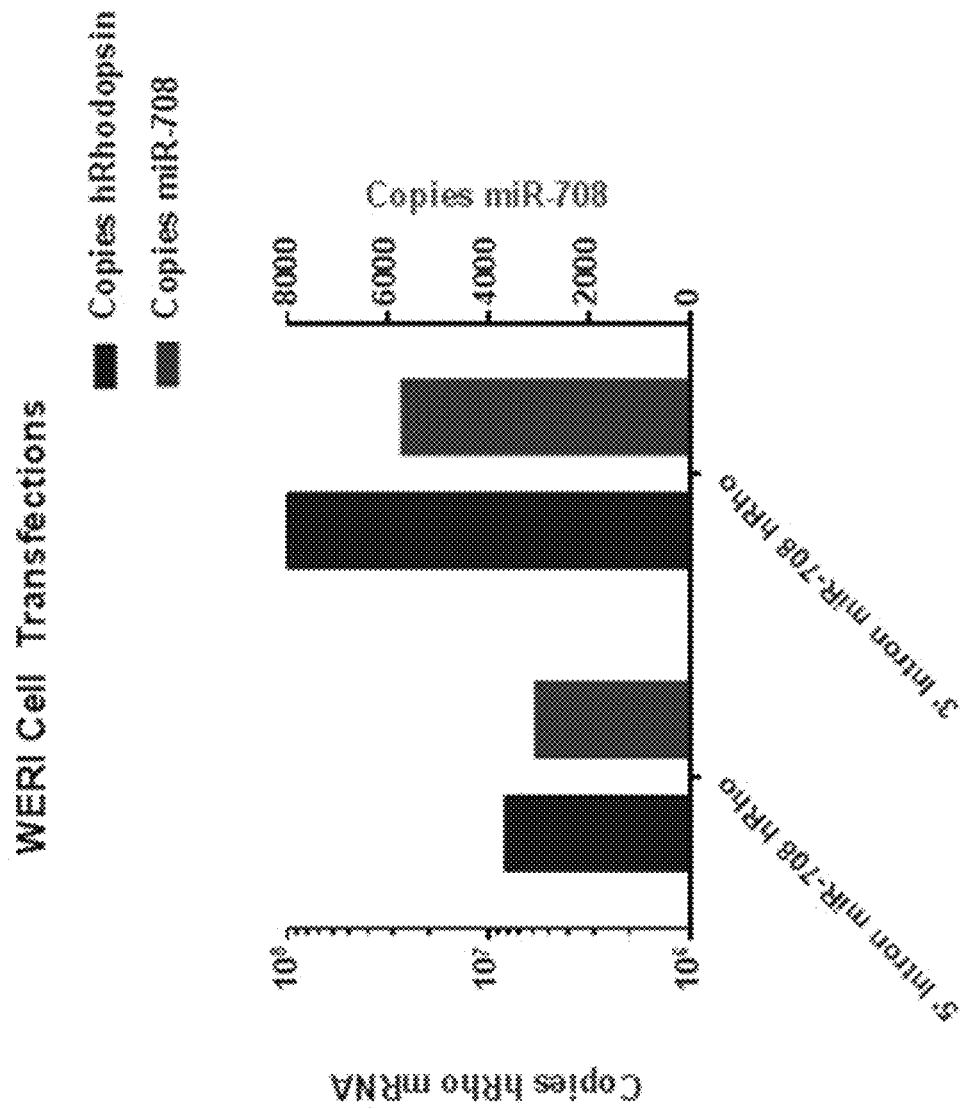
FIG. 18 shows that a vector with the miR-708 human β-globin intron scaffold in the 3' UTR of the rhodopsin cDNA produces higher hRhodopsin and miR-708 expression than a vector with the scaffold in the 5' UTR.

To determine if the position of the miR-708 human β-globin intron scaffold in the vector affected miR-708 or hRhodopsin expression from the vector, WERI cells were transfected with the 5' UTR vector of FIG. 12 or the 3' UTR vector of FIG. 17. FIG. 18 shows the expression of hRhodopsin and miR-708 in these cells. The vector with the miR-708 scaffold in the 3' UTR was found to produce higher levels of both hRhodopsin and miR-708 RNA than the vector using the 5' UTR configuration.

Example 9: Evaluation of the Suppression/Replacement Vector in a P23H Mouse Model of Retinal Degeneration Suppression/replacement constructs are evaluated in a P23H mouse model of retinal degeneration. In this model, the mutant P23H protein expressed in rod photoreceptor cells induces ER stress/UPR, causing apoptosis and ultimate rod cell death (Lee, E. S., et al. (2007) *FEBS Lett.* 581(22): 4325-32). Following rod cell death there is a non-cell-autonomous death of cone cells.

The P23H mouse is treated with a suppression/replacement AAV vector expressing miR-708 and a human rhodopsin gene refractory to knockdown by miR708 (because it lacks a miR-708 target sequence). The suppression/replacement vector results in knockdown of both WT and P23H mouse rhodopsin, but the replacement rhodopsin gene compensates for the reduction in WT levels of rhodopsin. Therefore, the vector provides the necessary rod rhodopsin to maintain rod cell function and integrity.

Figure 19:
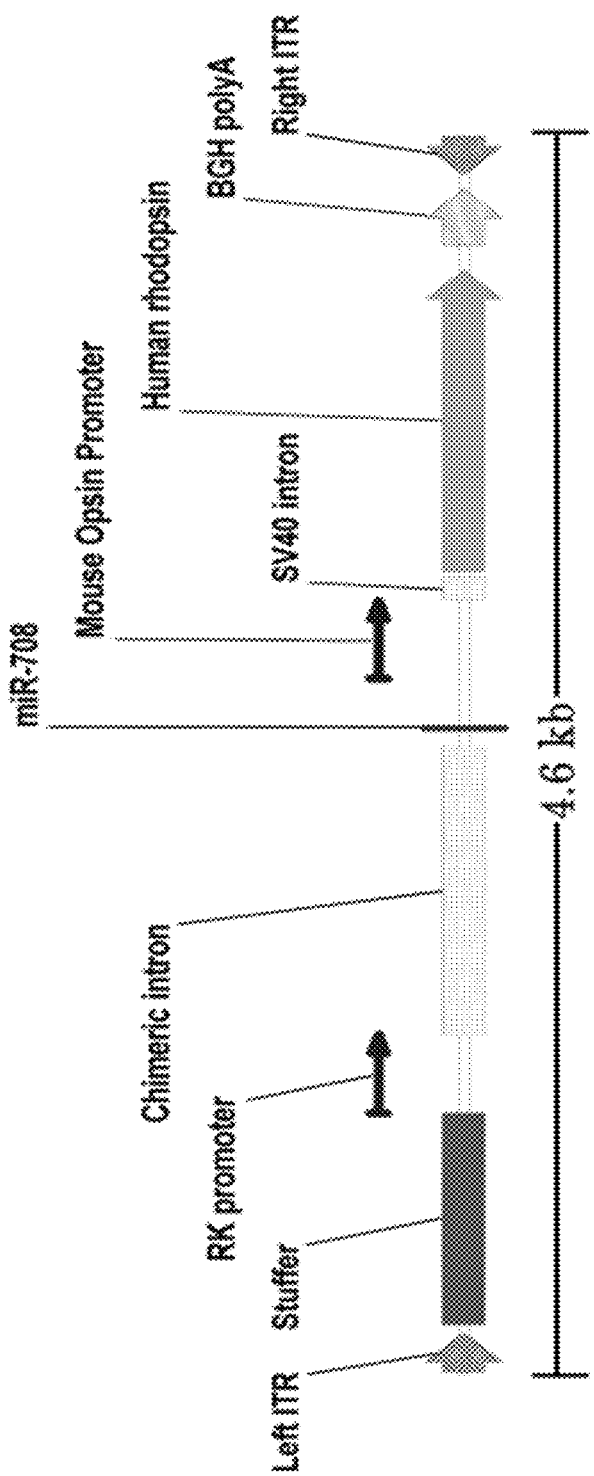
FIG. 19 shows a diagram of an alternate vector design using separate promoters to drive expression of miR-708 (RK promoter) and hRhodopsin (mouse opsin promoter).

An alternate suppression/replacement construct design is also tested. As shown in FIG. 19, this alternate vector drives expression of miR-708 from the RK promoter and co-express hRhodopsin (refractory to miR-708 knockdown) using the mouse opsin promoter.

These suppression/replacement vectors are also tested as described above in a P23H mouse model in which the endogenous mRhodopsin gene harbors a single copy loss-of-function allele (e.g., the mouse is heterozygous with respect to a mRhodopsin knockout allele). This heterozygous mouse model may be constructed using standard mouse genetic techniques from a mRho$^{-/-}$ mouse and the P23H model described above. Without wishing to be bound to theory, it is thought that this mRho$^{+/-}$ P23H mouse model, which contains one copy of the mutant hRhodopsin P23H allele and one copy of the wild-type mouse gene, may resemble a human ADRP genotype in which patients have equal copies of the mutant and wild-type rhodopsin alleles.

Example 10: Evaluation of Additional Suppression/Replacement Vectors

Several vectors were cloned that express both miR-708 (or a control miRNA sequence) and hRhodopsin from a single vector. The vectors differ from each other in that the flanking sequences of the miRNA sequence are derived from either miR-155 (taken from Invitrogen "Block-It" system) or endogenous miR-708 5' and 3' flanking sequences. The miRNA sequences are embedded in the h3-globin intron downstream of the Rhodopsin Kinase promoter and upstream of the hRhodopsin ORF. The goal was to test if expression and miRNA processing are similar from each construct. An additional pair of vectors contained the miRNA sequences (control or miR-708) downstream of the hRhodopsin ORF, also embedded in the β-globin intron. Only the vectors containing the miR-708 endogenous flanking 5' and 3' sequences located downstream of the hRhodopsin ORF were tested in this experiment, both endogenous miR-708 and miR-155 flanking sequences were tested in the vectors where the β-globin intron is located upstream of the hRhodopsin ORF. WERI cells were transfected with each construct and both miR-708 expression and hRhodopsin expression were determined.

Figure 20:
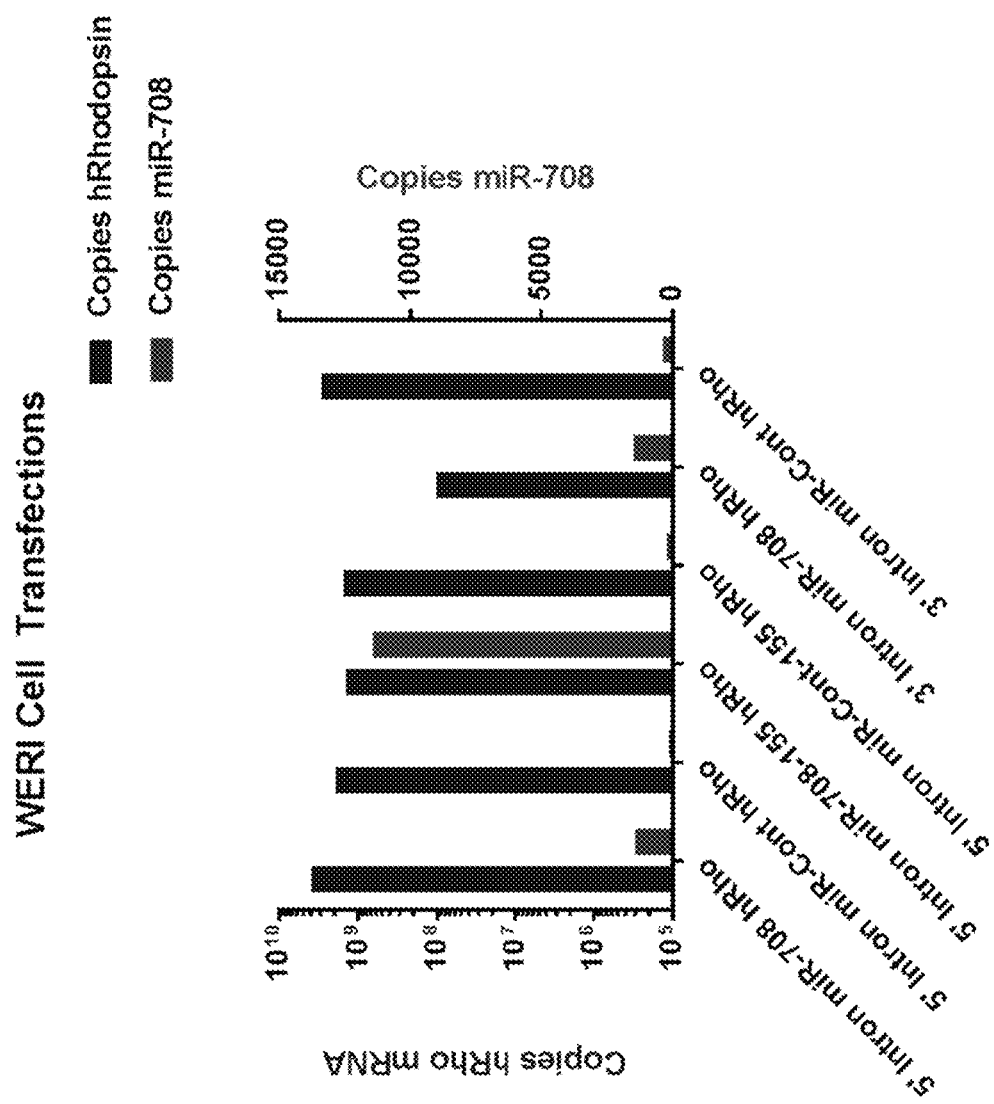
FIG. 20 shows hRhodopsin (left) and miR-708 (right) expression in WERI cells transfected with the specified vector. Expression is expressed as copy number calculated against a DNA standard.

The results in FIG. 20 indicate that the miR-155 flanking sequences generate better expression (or miRNA processing) of miR-708 compared to endogenous miR-708 flanking sequences. miR-708 expression was about 10 fold higher in those cells transfected with vectors containing the miR-155 flanking sequences compared to miR-708 flanking sequences. The vectors containing miR-708 flanking sequences had lower expression of miR-708 regardless of whether the sequences were upstream or downstream relative to the hRhodopsin ORF. hRhodopsin expression was unaffected by miR-708 overexpression, as its expression levels are approximately equal regardless of the miRNA sequence co-expressed in the vector. miR-708 expression was not detected in vectors containing control miRNA sequences, as expected.

Example 11: Evaluation of Additional Suppression/Replacement Vectors with a Mutated miR-708 Target Sequence As described above, a consensus sequence corresponding to a putative miR-708 target site has been found in the 3' UTR of several mammalian rhodopsin genes (Behrman, S., et al. (2011) *J. Cell Biol.* 192(6):919-27). This Example demonstrates that a rhodopsin with a mutated miR-708 target sequence can be used in a suppression/replacement vector.

An rAAV vector is constructed comprising nucleic acid encoding miR-708 and a human rhodopsin gene. The human rhodopsin gene is mutated in the miR-708 target sequence (SEQ ID NO:19) by nucleotide substitution, deletion or insertion to reduce or prevent recognition by miR-708. In some examples, the entire miR-708 target sequence is deleted. In some examples, reduction or prevention by miR-708 is measured in reference to miR-708 recognition of a wild-type rhodopsin 3'UTR comprising the miR-708 target sequence.

To test for suppression of autosomal dominant rhodopsin by miR-708 with concomitant expression of wild-type rhodopsin, HEK-293 cells expressing a P23H mutant mRhodopsin gene encoding a 3'UTR miR-708 target sequence are transfected with a plasmid expressing miR-708 and human rhodopsin with (CBA-miR-708-hRho-3'UTR$^-$) or without (CBA-miR-708-hRho-3'UTR$^+$) a mutated miR-708 target sequence. A miR-Control as described in Example 2 is also used. After 72 hrs, the cells are collected, and mP23H Rhodopsin and human rhodopsin protein expression are analyzed using a Western blot. Reduction of P23H mRhodopsin protein expression in cells transfected with the CBA-miR-708-hRho-3'UTR$^-$ or CBA-miR-708-hRho-3'UTR$^+$ compared to cells transfected with a CBA-miR-Control vector indicates miR-708 activity. Expression of human rhodopsin in cells transfected with CBA-miR-708-hRho-3'UTR$^-$ but not CBA-miR-708-hRho-3'UTR$^+$ indicates that the rhodopsin encoded by CBA-miR-708-hRho-3'UTR$^-$ is refractory to suppression by miR-708.

Example 12: AAV-Mediated Suppression of Endogenous Rhodopsin and Expression of Human Rhodopsin in the Mouse Retina Based on the experiments described above, further experiments were performed to test the rhodopsin suppression/replacement strategy in an intact eye. This Example demonstrates the efficacy of a suppression/replacement AAV vector built using a miR-708 scaffold in the mouse retina.

An AAV5 capsid with a vector bearing the rod-specific opsin promoter, the miR-708 scaffold (e.g., the miR-708 endogenous scaffold/flanking sequences), and a human rhodopsin replacement gene was constructed. In one version of this vector, the miR-708 sequence (e.g., the miR-708 sequence that binds the miR-708 target sequence) was inserted to drive expression of miR-708 in the context of the miR708 scaffold and the human rhodopsin replacement gene (AAV5OPSmiR708$_{708}$hRHO). In another version of this vector, a control vector was generated that harbored a miR control sequence (AAV5OPSmiRcontrol$_{708}$hRHO). In both vectors, the replacement human rhodopsin gene was refractory to miR-708 knockdown because it lacks a miR-708 target sequence. Both vectors were injected subretinally into the retinas of wild type mice. For each mouse, the contralateral naïve eye was uninjected, and expression in each injected retina was normalized as fold expression compared to the contralateral uninjected retina. Three weeks post injection, the retinas were harvested and assayed for miR-708 levels (FIG. 21A), mouse rhodopsin mRNA levels (FIG. 21B), and human rhodopsin (FIG. 21C).

Figure 21A:
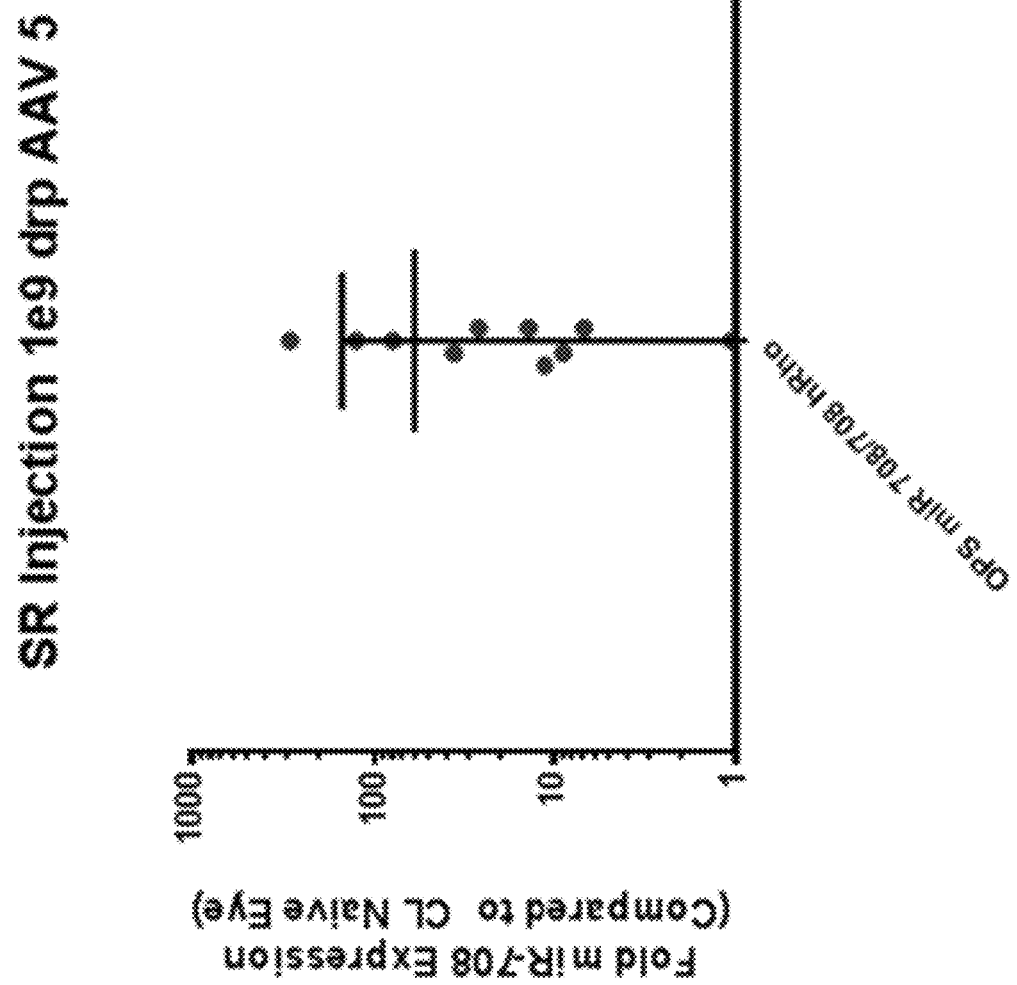
FIGS. 21A-C show the levels of miR-708 (FIG. 21A), mouse rhodopsin (FIG. 21B), and human rhodopsin (FIG. 21C) in mouse retinas three weeks after subretinal injection with an AAV5 capsid vector driving expression of human rhodopsin and miR-708 (miR 708/708), or human rhodopsin and control miRNA (miR-Cont), in a miR-708 scaffold using the opsin promoter. For each experiment, expression is shown as fold expression, as compared to the contralateral, uninjected eye.
Figure 21B:
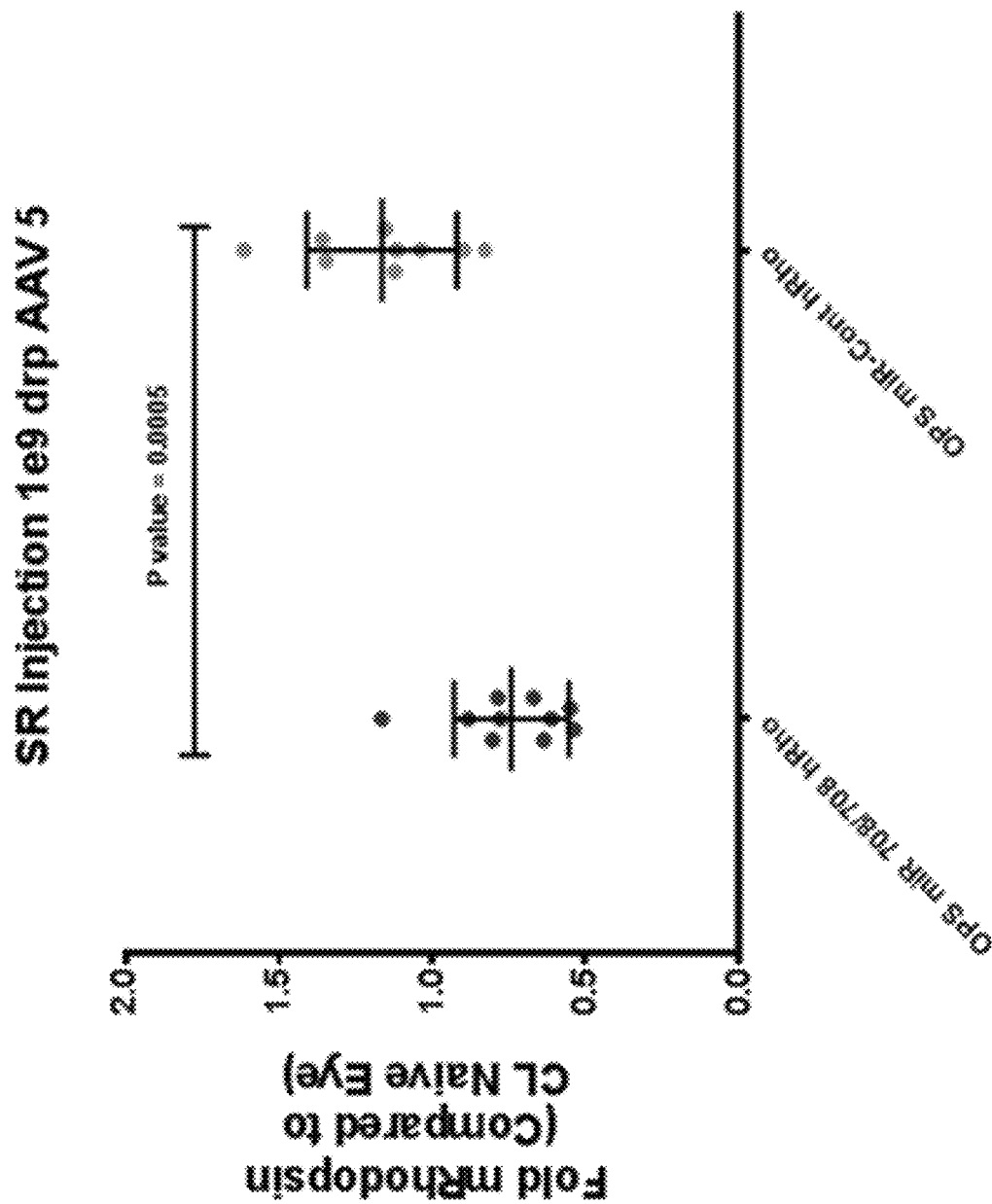
Figure 21C:
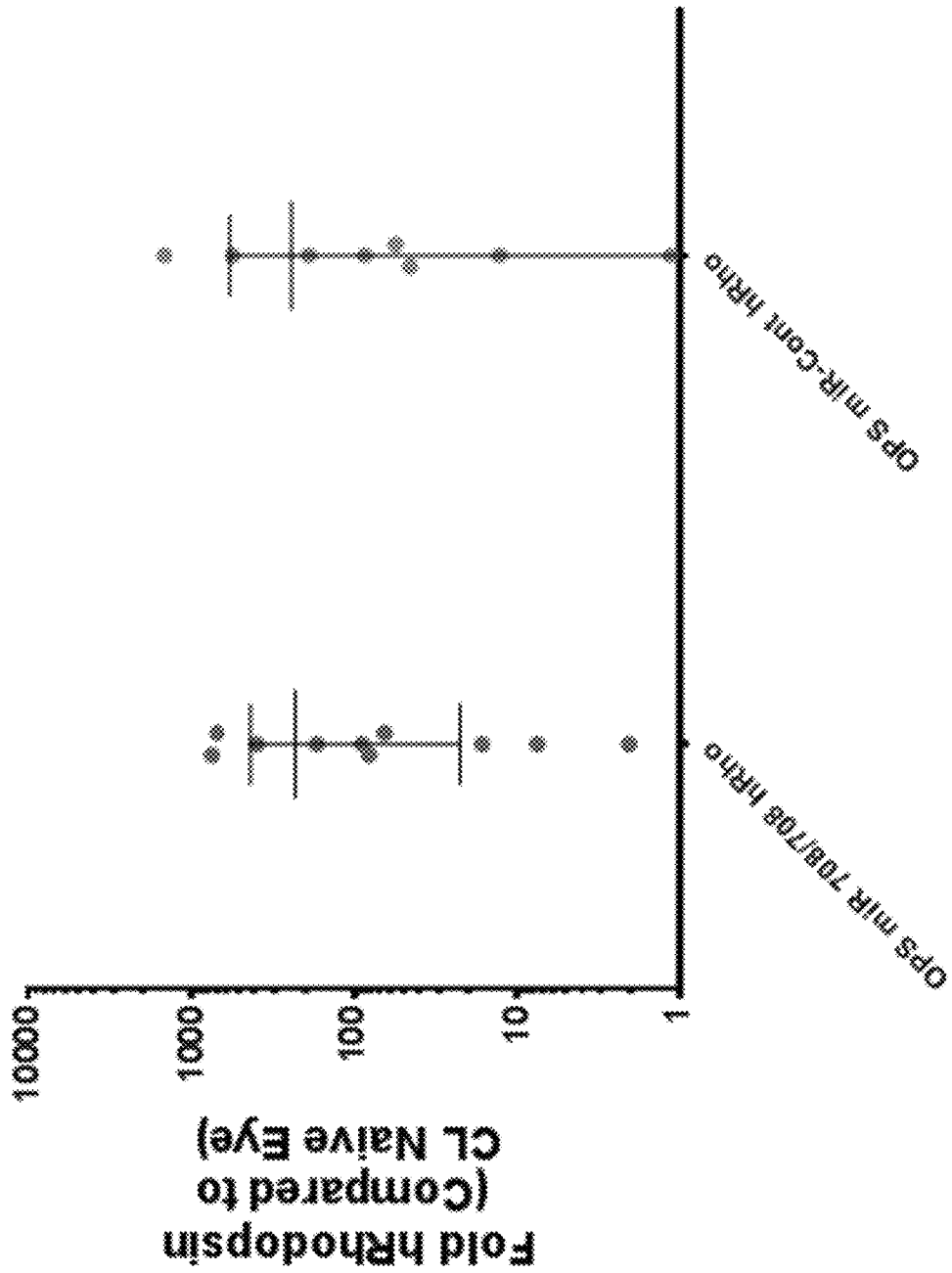

FIG. 21A shows an increase in miR-708 levels in the mouse retina following injection with the AAV5OPSmiR708$_{708}$hRHO vector, as compared to the contralateral naive eye. A significant reduction in mouse rhodopsin was measured in the eye that received AAV5OPSmiR708₇₀₈hRHO, and no reduction in mouse rhodopsin was measured in eyes that received the control vector, AAV5OPSmiRcontrol₇₀₈hRHO (FIG. 21B). In addition, human rhodopsin levels were increased up to 100 fold by both vectors, compared to the contralateral uninjected naïve eye (FIG. 21C). These data demonstrate that the AAV5OPSmiR708₇₀₈hRHO vector was efficacious in vivo.

In summary, the optimized suppression/replacement vector AAV5OPSmiR708₇₀₈hRHO achieved knockdown of mouse rhodopsin by miR-708 (endogenous mouse rhodopsin has a 3'UTR target sequence) with concomitant expression of the replacement human rhodopsin, which was refractory to miR708 knockdown (the human rhodopsin replacement gene lacks a 3'UTR miR708 target sequence). These results show the efficacy of the suppression/replacement strategy in the intact mammalian eye.

Example 13: Validation of Candidate Vectors in Human Cells

Candidate AAV5-based vectors were next assayed for the ability to promote miR-708 and human rhodopsin expression in human cells (HeLa).

Figure 22:
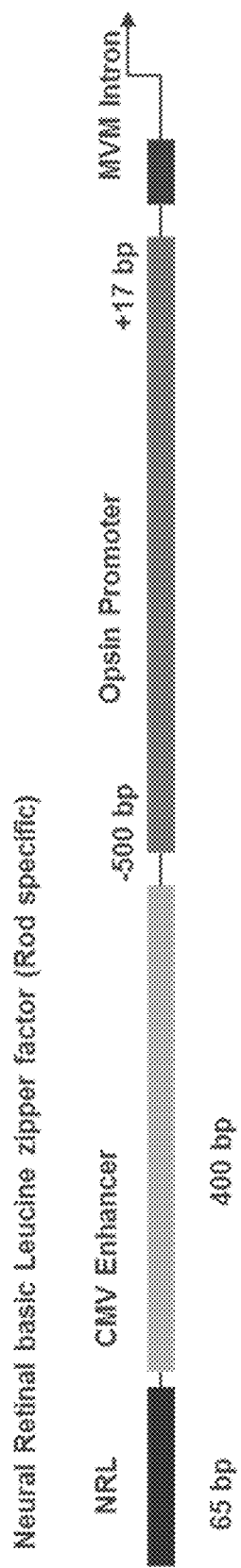
FIG. 22 shows a schematic of the opsin promoter construct, including the neural retinal basic zipper factor sequence (NRL), the CMV enhancer, the opsin promoter, and the MVM intron sequence, which includes a hybrid intron sequence from CBA exon 1 and an intron from the minute virus of mice (MVM).

Two different promoters were tested: rhodopsin kinase (GRK1) and the opsin promoter. The rhodopsin kinase promoter is described above. The opsin promoter (shown in SEQ ID NO:22) contains a 676 bp fragment encoding a 400 bp CMV enhancer upstream of the opsin promoter sequence (−500 bp-+15 bp). In addition 65 bp NRL sequence is included; this encodes a neural retinal basic zipper factor (a Rod photoreceptor specific transcription factor). Downstream of the promoter construct is a hybrid intron sequence from CBA exon1 and minute virus of mouse (MVM)—called MVM intron sequence (shown in SEQ ID NO:23). A diagram of this promoter construct is depicted in FIG. 22.

Figure 23A:
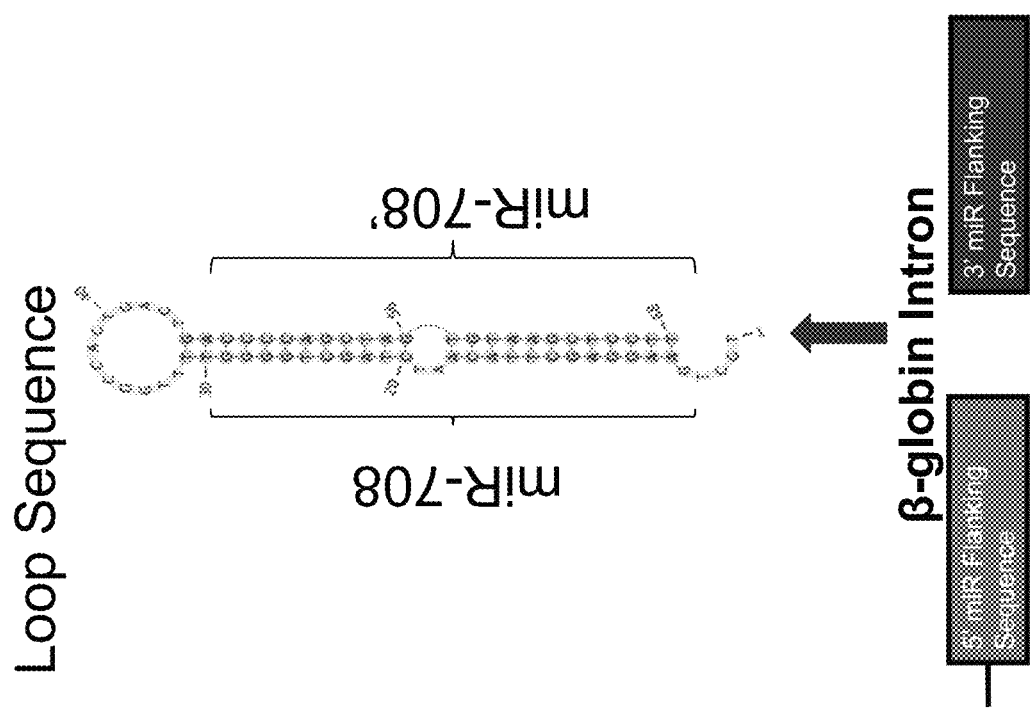
FIG. 23A shows a schematic of the miR-708 sequence embedded in a beta-globin intron.
Figure 23C:
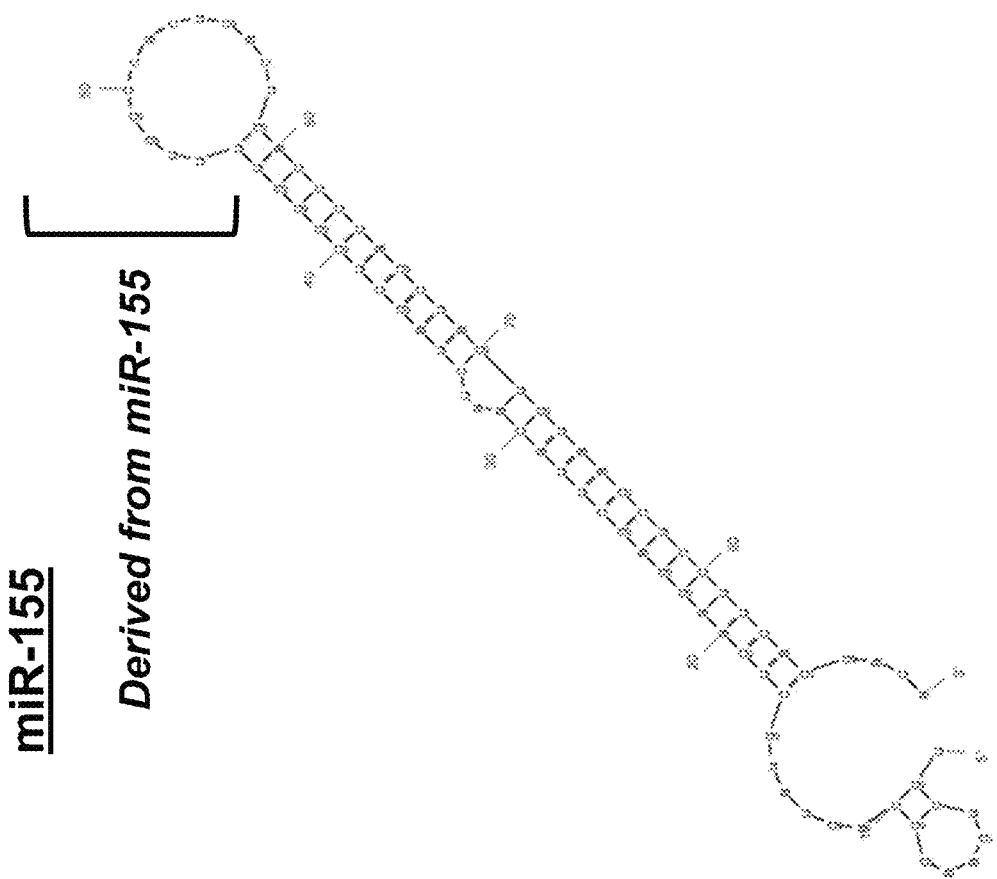
FIGS. 23B & 23C show schematics of the miR-708 sequence in the context of either the miR-708 endogenous scaffold (FIG. 23B) or the miR-155 scaffold (FIG. 23C), embedded in a beta globin intron. The miR-155 "loop sequence" between the 5' and 3' miR flanking sequences is labeled in FIG. 23C.
Figure 23B:
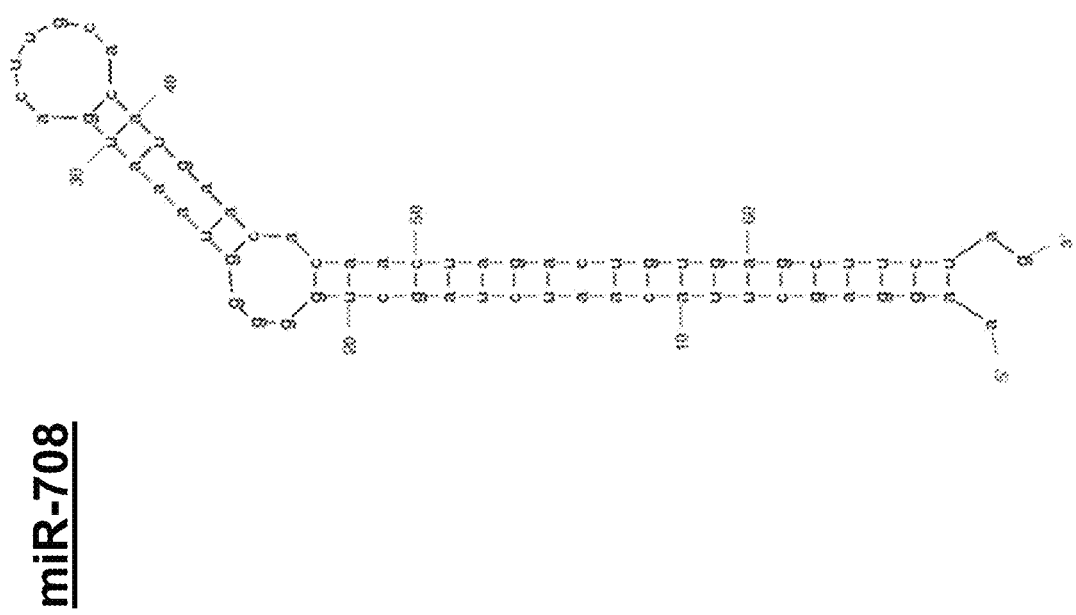

Two different scaffolds were used: the miR-155 scaffold or the miR-708 scaffold. Both were embedded in a beta globin intron. In total, 4 candidate vectors were tested: AAV5GRK1miR708_155hRho (AAV5 vector with rhodopsin kinase promoter driving expression of miR-708 in a miR-155 scaffold and human rhodopsin minus the miR-708 target sequence; SEQ ID NO:24), AAV5GRK1miR708_708hRho (AAV5 vector with rhodopsin kinase promoter driving expression of miR-708 in a miR-708 scaffold and human rhodopsin minus the miR-708 target sequence; SEQ ID NO:25), AAV5OPSmiR708_155hRho (AAV5 vector with opsin promoter driving expression of miR-708 in a miR-155 scaffold and human rhodopsin minus the miR-708 target sequence; SEQ ID NO:26), and AAV5OPSmiR708_708hRho (AAV5 vector with opsin promoter driving expression of miR-708 in a miR-708 scaffold and human rhodopsin minus the miR-708 target sequence; SEQ ID NO:27). FIG. 23A shows the miR-708 sequence embedded in the beta globin intron. The miR-708 and miR-155 scaffolds are shown in FIGS. 23B and 23C, respectively.

Figure 24:
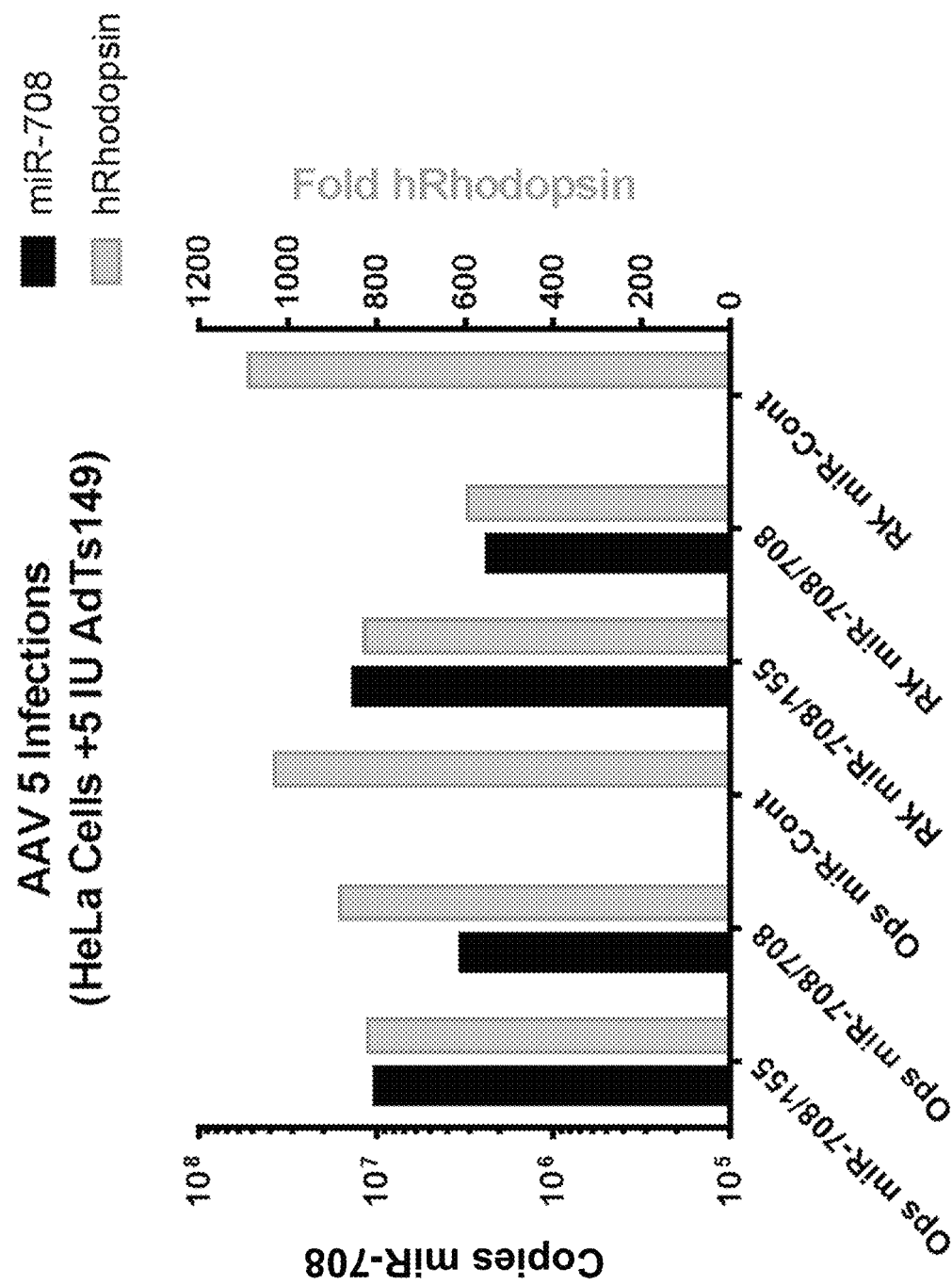
FIG. 24 shows the evaluation of candidate vectors harboring the miR-708 sequence, either in the miR-155 or the miR-708 scaffold (embedded in the beta-globin intron), and the human rhodopsin coding sequence (hRhodopsin; also lacking a 3'UTR miR-708 target sequence) driven by either the rhodopsin kinase (GRK1) promoter or the opsin (Ops) promoter. All four combinations were tested for effects on miR-708 and hRhodopsin expression, as shown.

Each of the 4 candidate AAV5 vectors was used to infect HeLa cells (using the AdTs149 helper virus), and levels of miR-708 and hRhodopsin were measured. As shown in FIG. 24, all four vectors resulted in miR-708 and hRhodopsin expression in human cells in vivo, as compared to vectors driving expression of a control miR from either the opsin or the rhodopsin kinase promoter (Ops miR-Cont and RK miR-Cont, respectively). These results demonstrate the successful validation of several vectors that may be used for suppression/replacement strategies (such as those described above) in human cells.

SEQUENCES miR-708 nucleotide sequence
AACTGCCCTCAAGGAGCTTACAATCTAGCTGGGGGTAAATGACTTGCACATGAACACAACTAGACTGTG
AGCTTCTAGAGGGCAGGGA (SEQ ID NO: 1)

Human rhodopsin amino acid sequence
MNGTEGPNFYVPFSNATGVVRSPFEYPQYYLAEPWQFSMLAAYMFLLIVLGFPINFLTLYVTVQHKKLR
TPLNYILLNLAVADLFMVLGGFTSTLYTSLHGYFVFGPTGCNLEGFFATLGGEIALWSLVVLAIERYVV
VCKPMSNFRFGENHAIMGVAFTWVMALACAAPPLAGWSRYIPEGLQCSCGIDYYTLKPEVNNESFVIYM
FVVHFTIPMIIIFFCYGQLVFTVKEAAAQQQESATTQKAEKEVTRMVIIMVIAFLICWVPYASVAFYIF
THQGSNFGPIFMTIPAFFAKSAAIYNPVIYIMMNKQFRNCMLTTICCGKNPLGDDEASATVSKTETSQV
APA (SEQ ID NO: 2)

Human rhodopsin cDNA-UTR deleted
ATGAATGGCACAGAAGGCCCTAACTTCTACGTGCCCTTCTCCAATGCGACGGGTGTGGTACGCAGCCCC
TTCGAGTACCCACAGTACTACCTGGCTGAGCCATGGCAGTTCTCCATGCTGGCCGCCTACATGTTTCTG
CTGATCGTGCTGGGCTTCCCCATCAACTTCCTCACGCTCTACGTCACCGTCCAGCACAAGAAGCTGCGC
ACGCCTCTCAACTACATCCTGCTCAACCTAGCCGTGGCTGACCTCTTCATGGTCCTAGGTGGCTTCACC
AGCACCCTCTACACCTCTCTGCATGGATACTTCGTCTTCGGGCCCACAGGATGCAATTTGGAGGGCTTC
TTTGCCACCCTGGGCGGTGAAATTGCCCTGTGGTCCTTGGTGGTCCTGGCCATCGAGCGGTACGTGGTG
GTGTGTAAGCCCATGAGCAACTTCCGCTTCGGGGAGAACCATGCCATCATGGGCGTTGCCTTCACCTGG
GTCATGGCGCTGGCCTGCGCCGCACCCCCACTCGCCGGCTGGTCCAGGTACATCCCCGAGGGCCTGCAG
TGCTCGTGTGGAATCGACTACTACACGCTCAAGCCGGAGGTCAACAACGAGTCTTTTGTCATCTACATG
TTCGTGGTCCACTTCACCATCCCCATGATTATCATCTTTTTCTGCTATGGGCAGCTCGTCTTCACCGTC
AAGGAGGCCGCTGCCCAGCAGCAGGAGTCAGCCACCACACAGAAGGCAGAGAAGGAGGTCACCCGCATG
GTCATCATCATGGTCATCGCTTTCCTGATCTGCTGGGTGCCCTACGCCAGCGTGGCATTCTACATCTTC
ACCCACCAGGGCTCCAACTTCGGTCCCATCTTCATGACCATCCCAGCGTTCTTTGCCAAGAGCGCCGCC
ATCTACAACCCTGTCATCTATATCATGATGAACAAGCAGTTCCGGAACTGCATGCTCACCACCATCTGC
TGCGGCAAGAACCCACTGGGTGACGATGAGGCCTCTGCTACCGTGTCCAAGACGGAGACGAGCCAGGTG
GCCCCGGCC (SEQ ID NO: 3)

Human rhodopsin cDNA-includes 3'UTR
AGAGTCATCCAGCTGGAGCCCTGAGTGGCTGAGCTCAGGCCTTCGCAGCATTCTTGGGTGGGAGCAGCC
ACGGGTCAGCCACAAGGGCCACAGCCATGAATGGCACAGAAGGCCCTAACTTCTACGTGCCCTTCTCCA
ATGCGACGGGTGTGGTACGCAGCCCCTTCGAGTACCCACAGTACTACCTGGCTGAGCCATGGCAGTTCT
CCATGCTGGCCGCCTACATGTTTCTGCTGATCGTGCTGGGCTTCCCCATCAACTTCCTCACGCTCTACG
TCACCGTCCAGCACAAGAAGCTGCGCACGCCTCTCAACTACATCCTGCTCAACCTAGCCGTGGCTGACC

| SEQUENCES |
|---|
| TCTTCATGGTCCTAGGTGGCTTCACCAGCACCCTCTACACCTCTCTGCATGGATACTTCGTCTTCGGGC<br>CCACAGGATGCAATTTGGAGGGCTTCTTTGCCACCCTGGGCGGTGAAATTGCCCTGTGGTCCTTGGTGG<br>TCCTGGCCATCGAGCGGTACGTGGTGGTGTGTAAGCCCATGACAACTTCCGCTTCGGGGAGAACCATG<br>CCATCATGGGCGTTGCCTTCACCTGGGTCATGGCGCTGGCCTGCGCCGCACCCCCACTCGCCGGCTGGT<br>CCAGGTACATCCCCGAGGGCCTGCAGTGCTCGTGTGAATCGACTACTACACGCTCAAGCCGGAGGTCA<br>ACAACGAGTCTTTTGTCATCTACATGTTCGTGGTCCACTTCACCATCCCCATGATTATCATCTTTTTCT<br>GCTATGGGCAGCTCGTCTTCACCGTCAAGGAGGCCGCTGCCCAGCAGCAGGAGTCAGCCACCACACAGA<br>AGGCAGAGAAGGAGGTCACCCGCATGGTCATCATCATGGTCATCGCTTTCCTGATCTGCTGGGTGCCCT<br>ACGCCAGCGTGGCATTCTACATCTTCACCCACCAGGGCTCCAACTTCGGTCCCATCTTCATGACCATCC<br>CAGCGTTCTTTGCCAAGAGCGCCGCCATCTACAACCCTGTCATCTATATCATGATGAACAAGCAGTTCC<br>GGAACTGCATGCTCACCACCATCTGCTGCGGCAAGAACCCACTGGGTGACGATGAGGCCTCTGCTACCG<br>TGTCCAAGACGGAGACGAGCCAGGTGGCCCCGGCCTAAGACCTGCCTAGGACTCTGTGGCCGACTATAG<br>GCGTCTCCCATCCCTACACCTTCCCCCAGCCACAGCCATCCCACCAGGAGCAGCGCCTGTGCAGAATG<br>AACGAAGTCACATAGGCTCCTTAATTTTTTTTTTTTTTAAGAAATAATTAATGAGGCTCCTCACTCA<br>CCTGGGACAGCCTGAGAAGGGACATCCACCAAGACCTACTGACTCTGGAGTCCCACGTTCCCCAAGGCCA<br>GCGGGATGTGTGCCCCTCCTCCTCCCAACTCATCTTTCAGGAACACGAGGATTCTTGCTTTCTGGAAAA<br>GTGTCCCAGCTTAGGGATAAGTGTCTAGCACAGAATGGGGCACACAGTAGGTGCTTAATAAATGCTGGA<br>TGGATGCAGGAAGGAATGGAGGAATGAATGGGAAGGGAGAACATATCTATCCTCTCAGACCCTCGCAGC<br>AGCAGCAACTCATACTTGGCTAATGATATGGAGCAGTTGTTTTTCCCTCCCTGGGCCTCACTTTCTTCT<br>CCTATAAAATGGAAATCCCAGATCCCTGGTCCTGCCGACACGCAGCTACTGAGAAGACCAAAAGAGGTG<br>TGTGTGTGTCTATGTGTGTGTTTCAGCACTTTGTAAATAGCAAGAAGCTGTACAGATTCTAGTTAATGT<br>TGTGAATAACATCAATTAATGTAACTAGTTAATTACTATGATTATCACCTCCTGATAGTGAACATTTTG<br>AGATTGGGCATTCAGATGATGGGGTTTCACCCAACCTTGGGGCAGGTTTTTAAAAATTAGCTAGGCATC<br>AAGGCCAGACCAGGGCTGGGGGTTGGGCTGTAGGCAGGGACAGTCACAGGAATGCAGAATGCAGTCATC<br>AGACCTGAAAAAACAACACTGGGGAGGGGGACGGTGAAGGCCAAGTTCCCAATGAGGGTGAGATTGGG<br>CCTGGGGTCTCACCCCTAGTGTGGGGCCCCAGGTCCCGTGCCTCCCCTTCCCAATGTGGCCTATGGAGA<br>GACAGGCCTTTCTCTCAGCCTCTGGAAGCCACCTGCTCTTTTGCTCTAGCACCTGGGTCCCAGCATCTA<br>GAGCATGGAGCCTCTAGAAGCCATGCTCACCCGCCCACATTTAATTAACAGCTGAGTCCCTGATGTCAT<br>CCTTATCTCGAAGAGCTTAGAAACAAAGAGTGGGAAATTCCACTGGGCCTACCTTCCTTGGGGATGTTC<br>ATGGGCCCCAGTTTCCAGTTTCCCTTGCCAGACAAGCCCATCTTCAGCAGTTGCTAGTCCATTCTCCAT<br>TCTGGAGAATCTGCTCCAAAAAGCTGGCCACATCTCTGAGGTGTCAGAATTAAGCTGCCTCAGTAACTG<br>CTCCCCCTTCTCCATATAAGCAAAGCCAGAAGCTCTAGCTTTACCCAGCTCTGCCTGGAGACTAAGGCA<br>AATTGGGCCATTAAAAGCTCAGCTCCTATGTTGGTATTAACGGTGGTGGGTTTTGTTGCTTTCACACTC<br>TATCCACAGGATAGATTGAAACTGCCAGCTTCCACCTGATCCCTGACCCTGGGATGGCTGGATTGAGCA<br>ATGAGCAGAGCCAAGCAGCACAGAGTCCCCTGGGGCTAG<br>AGGTGGAGGAGGCAGTCCTGGGAATGGGAAAAACCCCA (SEQ ID NO: 4) |
| RK-miR708 only<br>GGCCCCAGAAGCCTGGTGGTTGTTTGTCCTTCTCAGGGGAAAAGTGAGGCGGCCCCTTGGAGGAAGGGG<br>CCGGGCAGAATGATCTAATCGGATTCCAAGCAGCTCAGGGGATTGTCTTTTTCTAGCACCTTCTTGCCA<br>CTCCTAAGCGTCCTCCGTGACCCCGGCTGGGATTTAGCCTGGTGCTGTGTCAGCCCCGGTCTCCCAGGG<br>GCTTCCCAGTGGTCCCCAGGAACCCTCGACAGGGCCCGGTCTCTCTCGTCCAGCAAGGGCAGGGACGGG<br>CCACAGGCCAAGGGCGGAGTCGCTGCGACGCTGCCTTCGCCCCGTGCCCGCTCCGCCGCCGCCTCGCG<br>CCGCCCGCCCCGGCTCTGACTGACCGCGTTACTCCCACAGGTGAGCGGGCGGGACGGGCCCTTCTCCTCC<br>GGGCTGTAATTAGCGCTTGGTTTAATGACGGCTTGTTTCTTTTCTGTTGGCTGCGTGAAAGCCTTGAGGG<br>GCTCCGGGAGGGCCCTTTGTGCGGGGGGAGCGGCTCGGGGGGTGCGTGCGTGTGTGTGCGTGGGGAG<br>CGCCGCGTGCGGCTCCGCGCTGCCCGGCGGCTGTGAGCGCTGCGGGCGCGGCGCGGGCTTTGTGCGCT<br>CCGCAGTGTGCGCGAGGGGAGCGCGGCCGGGGCGGTGCCCCGCGGTGCGGGGGGGGCTGCGAGGGGAA<br>CAAAGGCTGCGTGCGGGGTGTGTGCGTGGGGGGGTGAGCAGGGGGTGTGGGCGCGTCGGTCGGGCTGCA<br>ACCCCCCCTGCACCCCCCTCCCCGAGTTGCTGAGCACGGCCCGGCTTCGGGTGCGGGGCTCCGTACGGG<br>GCGTGGCGCGGGCTCGCCGTGCCGGGCGGGGGTGGCGGCAGGTGGGGGTGCCGGGCGGGGCGGGGCC<br>GCCTCGGGCCGGGGAGGGCTCGGGGGAGGGGCGCGGCGGCCCCGGAGCGCCGGCGGCTGTCGAGGCGC<br>GGCGAGCCGCAGCCATTGCCTTTTATGGTAATCGTGCGAGAGGGCACGAGGGACTTCCTTTGTCCAAAT<br>CTGTGCGGAGCCGAAATCTGGGAGGCGCCGCCGCACCCCCTCTAGCGGGCGCGGGGCGAAGCGGTGCGG<br>CGCCGGCAGGAAGGAAATGGGCGGGAGGGCCTTCGTGCGTCGCCGCGCCGCCGTCCCCTTCTCCCTCT<br>CCAGCCTCGGGGCTGTCCGCGGGGGACGGCTGCCTTCGGGGGGGACGGGGCAGGGCGGGGTTCGGCTT<br>CTGGCGTGTGACCGGCGGCTCTAGAGCCTCTGCTAACCATGTTCATGCCTTCTTCTTTTTCCTACAGCT<br>CCTGGGCAACGTGCTGGTTATTGTGCTGTCTCATCATTTTGGCAAAGAATTCTTCGAAAGATCCTGGAG<br>GCTTGCTGAAGGCTGTATGCTGAAGGAGCTTACAATCTAGCTGGGGTTTTGGCCACTGACTGACCCCAG<br>CTAGTGTAAGCTCCTTCAGGACACAAGGCCTGTTACTAGCACTCACATGGAACAAATGGCCCA (SEQ<br>ID NO: 5) |
| RK-miR-708-op-rhodopsin<br>CAATCTCCCAGATGCTGATTCAGCCAGGAACTAGTTATTAATAGTAATCAATTACGGGGTCATTAGTTC<br>ATAGCCCATATATGGAGTTCCGCGTTACATAACTTACGGTAAATGGCCCGCCTGGCTGACCGCCCAACG<br>ACCCCCGCCCATTGACGTCAATAATGACGTATGTTCCCATAGTAACGCCAATAGGGACTTTCCATTGAC<br>GTCAATGGGTGGAGTATTTACGGTAAACTGCCCACTTGGCAGTACATCAAGTGTATCATATGCCAAGTA<br>CGCCCCCTATTGACGTCAATGACGGTAAATGGCCCGCCTGGCATTATGCCCAGTACATGACCTTATGGG<br>ACTTTCCTACTTGGCAGTACATCTACGTATTAGTCATCGCTATTACCACAAATAGTTATCGAGCCGCTG<br>AGCCGGGGGCGGGGGTGTGAGACTGGAGGCGATGGACGGAGCTGACGGCACACACAGCTCAGATCTG<br>TCAAGTGAGCCATTGTCAGGGCTTGGGGACTGGATAAGTCAGGGGTCTCCTGGGAAGAGATGGGATAG<br>GTGAGTTCAGGAGGAGACATTGTCAACTGGAGCCATGTGGAGAAGTGAATTTAGGGCCCAAAGGTTCCA<br>GTCGCAGCCTGAGGCCACCAGACTGACATGGGGAGGAATTCCCAGAGGACTCTGGGCAGACAAGATGA<br>GACACCCTTTCCTTTCTTTACCTAAGGGCCTCCACCCGATGTCACCTTGGCCCCTCTGCAAGCCAATTA<br>GGCCCCGGTGGCAGCAGTGGGATTAGCGTTAGTATGATATCTCGCGGATGCTGAATCAGCCTCTGGCTT<br>AGGGAGAGAAGGTCACTTTATAAGGGTCTGGGGGGGTCAGTGCCTGGAGTTGCGCTGTGGGAGCCGTC<br>AGTGGCTGAGCTCAAGAGGTAAGGGTTTAAGGGATGGTTGGTTGGTGGGGTATTAATGTTTAATTACCT |

| SEQUENCES |
|---|
| GTTTTACAGGCCTGAAATCACTTGGTTTTAGGTTGGTACATCTGCAGAATTCAGCCACCACCGGCACAA |
| TGAATGGCACAGAAGGCCCTAACTTCTACGTGCCCTTCTCCAATGCGACGGGTGTGGTACGCAGCCCCT |
| TCGAGTACCCACAGTACTACCTGGCTGAGCCATGGCAGTTCTCCATGCTGGCCGCCTACATGTTTCTGC |
| TGATCGTGCTGGGCTTCCCCATCAACTTCCTCACGCTCTACGTCACCGTCCAGCACAAGAAGCTGCGCA |
| CGCCTCTCAACTACATCCTGCTCAACCTAGCCGTGGCTGACCTCTTCATGGTCCTAGGTGGCTTCACCA |
| GCACCCTCTACACCTCTCTGCATGGATACTTCGTCTTCGGGCCCACAGGATGCAATTTGGAGGGCTTCT |
| TTGCCACCCTGGGCGGTGAAATTGCCCTGTGGTCCTTGGTGGTCCTGGCCATCGAGCGGTACGTGGTGG |
| TGTGTAAGCCCATGAGCAACTTCCGCTTCGGGGAGAACCATGCCATCATGGGCGTTGCCTTCACCTGGG |
| TCATGGCGCTGGCCTGCGCCGCACCCCCACTCGCCGGCTGGTCCAGGTACATCCCCGAGGGCCTGCAGT |
| GCTCGTGTGGAATCGACTACTACACGCTCAAGCCGGAGGTCAACAACGAGTCTTTTGTCATCTACATGT |
| TCGTGGTCCACTTCACCATCCCCATGATTATCATCTTTTTCTGCTATGGGCAGCTCGTCTTCACCGTCA |
| AGGAGGCCGCTGCCCAGCAGCAGGAGTCAGCCACCACACAGAAGGCAGAGAAGGAGGTCACCCGCATGG |
| TCATCATCATGGTCATCGCTTTCCTGATCTGCTGGGTGCCCTACGCCAGCGTGGCATTCTACATCTTCA |
| CCCACCAGGGCTCCAACTTCGGTCCCATCTTCATGACCATCCCAGCGTTCTTTGCCAAGAGCGCCGCCA |
| TCTACAACCCTGTCATCTATATCATGATGAACAAGCAGTTCCGGAACTGCATGCTCACCACCATCTGCT |
| GCGGCAAGAACCCACTGGGTGACGATGAGGCCTCTGCTACCGTGTCCAAGACGGAGACGAGCCAGGTGG |
| CCCCGGCCTAACCAAGAAAGCTTAAGTTTGTGTCCCGGCTTAGGGCTAAATGTCTAGGACAGAATGGAA |
| CACATAGTAGCTGATTAATAAATGCTAGCTGGATGAAGGGAGGAATGAGTGACTGACTGAGTGGATATA |
| TGAGTGAAGGGATTAATGGAAGGGAACATGGATGTCCTCAGGTGCCCAACCTGGCAGATCCAGTCATGT |
| CTGGCTGGAATCTATAAGCAGTTTTACATACCTGCCCTGAGCTTTATTGCGGTAGTTTATCACAGTTAA |
| ATTGCTAACGCAGTCAGTGCTTCTGACACAACAGTCTCGAACTTAAGCTGCAGTGACTCTCTTAAGGTA |
| GCCTTGCAGAAGTTGGTCGTGAGGCACTGGGCAGGTAAGTATCAAGGTTACAAGACAGGTTTAAGGAGA |
| CCAATAGAAACTGGGCTTGTCGAGACAGAGAAAAACCTAACCCCCATGGTTGGCGAGGGACTGCTGTGT |
| GTGAAATGGTAACTGCCCTCAAGGAGCTTACAATCTAGCTGGGGGTAAATGACTTGCACATGAACACAA |
| CTAGACTGTGAGCTTCTAGAGGGCAGGGACCTTACCCTAGTCATCTCTCTTCTCACCCTGCACACCCTC |
| CCTGAGGGATCTCATGACTCTTGCGTTTCTGATAGGCACCTATTGGTCTTACTGACATCCACTTTGCCT |
| TTCTCTCCACAGGTGTCCACTCCCAGTTCACACCGGCACAATGAATGGCACAGAAGGCCCTAACTTCTA |
| CGTGCCCTTCTCCAATGCGACGGGTGTGGTACGCAGCCCCTTCGAGTACCCACAGTACTACCTGGCTGA |
| CAGTGACAGCAACGTGAGCTGCAGCCCTTAGGACTGAGAAAGCATCGAGACCAGGGGTCTCCGGCAAGG |
| CCTAGGTCCTCCCTTCAGTATGGAAACCTTGCCTCATGTCTCTCAGCCTCCTTGGCCTGTGGAGATCCA |
| GCCCTTCCTCTTGGCTTCTGGATACATTTGCTCTTCTACACCAGCAACCAAGTGGCAACAGTTCCAGGC |
| CAGTATGGAGTTTTAGAAGCCATGCCAATATGCCCACCTTCAGGGAGCAGCTGAGTCCTTGATGCCACC |
| CTTGTTCTGAAGAGTTCAGAAACACAGTGCAAGACATGACCAGGCCTCATCCTTAGGATGCTCATGGAT |
| CCAGTTCTTAGCTCCCTTGTTGGATATGCTGTTTTCCTTGGCCTTTGGTCTTTTCTTTATCCCAGAGGG |
| TTTTGGCTTTAAGGCCAACAGGAACTATGGGGTACCAGAATTGAGCAGCCTCAGTCTGCATCCCTCCTC |
| TATAGAACCACAGCTGGGCCCTCAGCAGGCCCAACTCTGCATGGGGACAGAGGCATTAAAAGC (SEQ ID NO: 6) |

RK-intron-rhodopsin-miR-708.
| |
|---|
| GGGCCCCAGAAGCCTGGTGGTTGTTTGTCCTTCTCAGGGGAAAAGTGAGGCGGCCCCTTGGAGGAAGGGGCCGGGC |
| AGAATGATCTAATCGGATTCCAAGCAGCTCAGGGGATTGTCTTTTTCTAGCACCTTCTTGCCACTCCTAAGCGTCC |
| TCCGTGACCCCGGCTGGGATTTAGCCTGGTGCTGTGTCAGCCCCGGTCTCCCAGGGGCTTCCCAGTGGTCCCCAGG |
| AACCCTCGACAGGGCCCGGTCTCTCTCGTCCAGCAAGGGCAGGGACGGGCCACAGGCCAAGGGCGGAGTCGCTGCG |
| ACGCTGCCTTCGCCCCGTGCCCCGCTCCGCCGCCGCCTCGCGCCGCCCGCCCCGGCTCTGACTGACCGCGTTACTC |
| CCACAGGTGAGCGGGCGGGACGGCCCTTCTCCTCCGGGCTGTAATTAGCAAGAGGTAAGGGTTTAAGGGATGGTTG |
| GTTGGTGGGGTATTAATGTTTAATTACCTGTTTTACAGGCCTGAAATCACTTGGTTTTAGGTTGGGGATCCGGTAC |
| CCAATTGCCATGGGCTAGCATGCATGAGCTCCCTGCAGGGTTTATCTGCAGAATTCAGCCACCACCGGCACAATGA |
| ATGGCACAGAAGGCCCTAACTTCTACGTGCCCTTCTCCAATGCGACGGGTGTGGTACGCAGCCCCTTCGAGTACCC |
| ACAGTACTACCTGGCTGAGCCATGGCAGTTCTCCATGCTGGCCGCCTACATGTTTCTGCTGATCGTGCTGGGCTTC |
| CCCATCAACTTCCTCACGCTCTACGTCACCGTCCAGCACAAGAAGCTGCGCACGCCTCTCAACTACATCCTGCTCA |
| ACCTAGCCGTGGCTGACCTCTTCATGGTCCTAGGTGGCTTCACCAGCACCCTCTACACCTCTCTGCATGGATACTT |
| CGTCTTCGGGCCCACAGGATGCAATTTGGAGGGCTTCTTTGCCACCCTGGGCGGTGAAATTGCCCTGTGGTCCTTG |
| GTGGTCCTGGCCATCGAGCGGTACGTGGTGGTGTGTAAGCCCATGAGCAACTTCCGCTTCGGGGAGAACCATGCCA |
| TCATGGGCGTTGCCTTCACCTGGGTCATGGCGCTGGCCTGCGCCGCACCCCCACTCGCCGGCTGGTCCAGGTACAT |
| CCCCGAGGGCCTGCAGTGCTCGTGTGGAATCGACTACTACACGCTCAAGCCGGAGGTCAACAACGAGTCTTTTGTC |
| ATCTACATGTTCGTGGTCCACTTCACCATCCCCATGATTATCATCTTTTTCTGCTATGGGCAGCTCGTCTTCACCG |
| TCAAGGAGGCCGCTGCCCAGCAGCAGGAGTCAGCCACCACACAGAAGGCAGAGAAGGAGGTCACCCGCATGGTCAT |
| CATCATGGTCATCGCTTTCCTGATCTGCTGGGTGCCCTACGCCAGCGTGGCATTCTACATCTTCACCCACCAGGGC |
| TCCAACTTCGGTCCCATCTTCATGACCATCCCAGCGTTCTTTGCCAAGAGCGCCGCCATCTACAACCCTGTCATCT |
| ATATCATGATGAACAAGCAGTTCCGGAACTGCATGCTCACCACCATCTGCTGCGGCAAGAACCCACTGGGTGACGA |
| TGAGGCCTCTGCTACCGTGTCCAAGACGGAGACGAGCCAGGTGGCCCCGGCCTAACCAAGAAAGCTTAAGTTTGTG |
| TCCCGGCTTAGGGCTAAATGTCTAGGACAGAATGGAACACATAGTAGCTGATTAATAAATGCTAGCTGGATGAAGG |
| GAGGAATGAGTGACTGACTGAGTGGATATATGAGTGAAGGGATTAATGGAAGGGAACATGGATGTCCTCAGGTGCC |
| CAACCTGGCAGATCCAGTCATGTCTGGCTGGAATCTATAAGCAGTTTTACATACCTGCCCTGAGCTTTATTGCGGT |
| AGTTTATCACAGTTAAATTGCTAACGCAGTCAGTGCTTCTGACACAACAGTCTCGAACTTAAGCTGCAGTGACTCT |
| CTTAAGGTAGCCTTGCAGAAGTTGGTCGTGAGGCACTGGGCAGGTAAGTATCAAGGTTACAAGACAGGTTTAAGGA |
| GACCAATAGAAACTGGGCTTGTCGAGACAGAGAAAAACCTAACCCCCATGGTTGGCGAGGGACTGCTGTGTGTGAA |
| ATGGTAACTGCCCTCAAGGAGCTTACAATCTAGCTGGGGGTAAATGACTTGCACATGAACACAACTAGACTGTGAG |
| CTTCTAGAGGGCAGGGACCTTACCCTAGTCATCTCTCTTCTCACCCTGCACACCCTCCCTGAGGGATCTCATGACT |
| CTTGCGTTTCTGATAGGCACCTATTGGTCTTACTGACATCCACTTTGCCTTTCTCTCCACAGGTGTCCACTCCCAG |
| TTCACACCGGCACAATGAATGGCACAGAAGGCCCTAACTTCTACGTGCCCTTCTCCAATGCGACGGGTGTGGTACG |
| CAGCCCCTTCGAGTACCCACAGTCAGAGATAAATGACAGTGACAGCAACGTGAGCTGCAGCCCTTAGGACTGAGAA |
| AGCATCGAGACCAGGGGTCTCCGGCAAGGCCTAGGTCCTCCCTTCAGTATGGAAACCTTGCCTCATGTCTCTCAGC |
| CTCCTTGGCCTGTGGAGATCCAGCCCTTCCTCTTGGCTTCTGGATACATTTGCTCTTCTACACCAGCAACCAAGTG |
| GCAACAGTTCCAGGCCAGTATGGAGTTTTAGAAGCCATGCCAATATGCCCACCTTCAGGGAGCAGCTGAGTCCTTG |
| ATGCCACCCTTGTTCTGAAGAGTTCAGAAACACAGTGCAAGACATGACCAGGCCTCATCCTTAGGATGCTCATGGA |
| TCCAGTTCTTAGCTCCCTTGTTGGATATGCTGTTTTCCTTGGCCTTTGGTCTTTTCTTTATCCCAGAGGGTTTTGG |

| SEQUENCES |
|---|
| CTTTAAGGCCAACAGGAACTATGGGGTACCAGAATTGAGCAGCCTCAGTCTGCATCCCTCCTCTATAGAACCACAG<br>CTGGGCCCTCAGCAGGCCCAACTCTGCATGGGGACAGAGGCATTAAAAGC (SEQ ID NO: 7) |
| RK-miR-708-intron hRho wt<br>GGGCCCCAGAAGCCTGGTGGTTGTTTGTCCTTCTCAGGGGAAAAGTGAGGCGGCCCCTTGGAGGAAGGG<br>GCCGGGCAGAATGATCTAATCGGATTCCAAGCAGCTCAGGGGATTGTCTTTTTCTAGCACCTTCTTGCC<br>ACTCCTAAGCGTCCTCCGTGACCCCGGCTGGGATTTAGCCTGGTGCTGTGTCAGCCCCGGTCTCCCAGG<br>GGCTTCCCAGTGGTCCCCAGGAACCCTCGACAGGGCCCGGTCTCTCTCGTCCAGCAAGGGCAGGGACGG<br>GCCACAGGCCAAGGGCACTAGAAGCTTTATTGCGGTAGTTTATCACAGTTAAATTGCTAACGCAGTCAG<br>TGCTTCTGACACAACAGTCTCGAACTTAAGCTGCAGTGACTCTCTTAAGGTAGCCTTGCAGAAGTTGGT<br>CGTGAGGCACTGGGCAGGTAAGTATCAAGGTTACAAGACAGGTTTAAGGAGACCAATAGAAACTGGGCT<br>TGTCGAGACAGAGAAAAACCTAACCCCCATGGTTGGCGAGGGACTGCTGTGTGTGAAATGGTAACTGCC<br>CTCAAGGAGCTTACAATCTAGCTGGGGGTAAATGACTTGCACATGAACACAACTAGACTGTGAGCTTCT<br>AGAGGGCAGGGACCTTACCCTAGTCATCTCTCTTCTCACCCTGCACACCCTCCCTGAGGGATCTCATGA<br>CTCTTGCGTTTCTGATAGGCACCTATTGGTCTTACTGACATCCACTTTGCCTTTCTCTCCACAGGTGTC<br>CACTCCCAGTTCACACCGGCACAATGAATGGCACAGAAGGCCCTAACTTCTACGTGCCCTTCTCCAATG<br>CGACGGGTGTGGTACGCAGCCCCTTCGAGTACCCACAGTACTACCTGGCTGAGCCATGGCAGTTCTCCA<br>TGCTGGCCGCCTACATGTTTCTGCTGATCGTGCTGGGCTTCCCCATCAACTTCCTCACGCTCTACGTCA<br>CCGTCCAGCACAAGAAGCTGCGCACGCCTCTCAACTACATCCTGCTCAACCTAGCCGTGGCTGACCTCT<br>TCATGGTCCTAGGTGGCTTCACCAGCACCCTCTACACCTCTGCATGGATACTTCGTCTTCGGGCCCA<br>CAGGATGCAATTTGGAGGGCTTCTTTGCCACCCTGGGCGGTGAAATTGCCCTGTGGTCCTTGGTGGTCC<br>TGGCCATCGAGCGGTACGTGGTGGTGTGTAAGCCCATGAGCAACTTCCGCTTCGGGGAGAACCATGCCA<br>TCATGGGCGTTGCCTTCACCTGGGTCATGGCGCTGGCCTGCGCCGCACCCCCACTCGCCGGCTGGTCCA<br>GGTACATCCCCGAGGGCCTGCAGTGCTCGTGTGGAATCGACTACTACACGCTCAAGCCGGAGGTCAACA<br>ACGAGTCTTTTGTCATCTACATGTTCGTGGTCCACTTCACCATCCCCATGATTATCATCTTTTTCTGCT<br>ATGGGCAGCTCGTCTTCACCGTCAAGGAGGCCGCTGCCCAGCAGCAGGAGTCAGCCACCACACAGAAGG<br>CAGAGAAGGAGGTCACCCGCATGGTCATCATCATGGTCATCGCTTTCCTGATCTGCTGGGTGCCCTACG<br>CCAGCGTGGCATTCTACATCTTCACCCACCAGGGCTCCAACTTCGGTCCCATCTTCATGACCATCCCAG<br>CGTTCTTTGCCAAGAGCGCCGCCATCTACAACCCTGTCATCTATATCATGATGAACAAGCAGTTCCGGA<br>ACTGCATGCTCACCACCATCTGCTGCGGCAAGAACCCACTGGGTGACGATGAGGCCTCTGCTACCGTGT<br>CCAAGACGGAGACGAGCCAGGTGGCCCCGGCC (SEQ ID NO: 8) |
| RK-intron-miR-708-op-hRho wt<br>CAATCTCCCAGATGCTGATTCAGCCAGGAACTAGTTATTAATAGTAATCAATTACGGGGTCATTAGTTC<br>ATAGCCCATATATGGAGTTCCGCGTTACATAACTTACGGTAAATGGCCCGCCTGGCTGACCGCCCAACG<br>ACCCCCGCCCATTGACGTCAATAATGACGTATGTTCCCATAGTAACGCCAATAGGGACTTTCCATTGAC<br>GTCAATGGGTGGAGTATTTACGGTAAACTGCCCACTTGGCAGTACATCAAGTGTATCATATGCCAAGTA<br>CGCCCCCTATTGACGTCAATGACGGTAAATGGCCCGCCTGGCATTATGCCCAGTACATGACCTTATGGG<br>ACTTTCCTACTTGGCAGTACATCTACGTATTAGTCATCGCTATTACCACAAATAGTTATCGAGCCGCTG<br>AGCCGGGGGCGGGGGGTGTGAGACTGGAGGCGATGGACGGAGCTGACGGCACACACAGCTCAGATCTG<br>TCAAGTGAGCCATTGTCAGGGCTTGGGGACTGGATAAGTCAGGGGTCTCCTGGGAAGAGATGGGATAG<br>GTGAGTTCAGGAGGAGACATTGTCAACTGGAGCCATGTGGAGAAGTGAATTTAGGGCCCAAAGGTTCCA<br>GTCGCAGCCTGAGGCCACCAGACTGACATGGGGAGGAATTCCCAGAGGACTCTGGGGCAGACAAGATGA<br>GACACCCTTTCCTTTCTTTACCTAAGGGCCTCCACCCGATGTCACCTTGGCCCCTCTGCAAGCCAATTA<br>GGCCCCGGTGGCAGCAGTGGGATTAGCGTTAGTATGATATCTCGCGGATGCTGAATCAGCCTCTGGCTT<br>AGGGAGAGAAGGTCACTTTATAAGGGTCTGGGGGGGTCAGTGCCTGGAGTTGCGCTGTGGGAGCCGTC<br>AGTGGCTGAGCTCAAGAGGTAAGGGTTTAAGGGATGGTTGGTTGGTGGGGTATTAATGTTTAATTACCT<br>GTTTTACAGGCCTGAAATCACTTGGTTTTAGGTTGGTACATCTGCAGAATTCAGCCACCACCGGCACAA<br>TGAATGGCACAGAAGGCCCTAACTTCTACGTGCCCTTCTCCAATGCGACGGGTGTGGTACGCAGCCCCT<br>TCGAGTACCCACAGTACTACCTGGCTGAGCCATGGCAGTTCTCCATGCTGGCCGCCTACATGTTTCTGC<br>TGATCGTGCTGGGCTTCCCCATCAACTTCCTCACGCTCTACGTCACCGTCCAGCACAAGAAGCTGCGCA<br>CGCCTCTCAACTACATCCTGCTCAACCTAGCCGTGGCTGACCTCTTCATGGTCCTAGGTGGCTTCACCA<br>GCACCCTCTACACCTCTCTGCATGGATACTTCGTCTTCGGGCCCACAGGATGCAATTTGGAGGGCTTCT<br>TTGCCACCCTGGGCGGTGAAATTGCCCTGTGGTCCTTGGTGGTCCTGGCCATCGAGCGGTACGTGGTGG<br>TGTGTAAGCCCATGAGCAACTTCCGCTTCGGGGAGAACCATGCCATCATGGGCGTTGCCTTCACCTGGG<br>TCATGGCGCTGGCCTGCGCCGCACCCCCACTCGCCGGCTGGTCCAGGTACATCCCCGAGGGCCTGCAGT<br>GCTCGTGTGGAATCGACTACTACACGCTCAAGCCGGAGGTCAACAACGAGTCTTTTGTCATCTACATGT<br>TCGTGGTCCACTTCACCATCCCCATGATTATCATCTTTTTCTGCTATGGGCAGCTCGTCTTCACCGTCA<br>AGGAGGCCGCTGCCCAGCAGCAGGAGTCAGCCACCACACAGAAGGCAGAGAAGGAGGTCACCCGCATGG<br>TCATCATCATGGTCATCGCTTTCCTGATCTGCTGGGTGCCCTACGCCAGCGTGGCATTCTACATCTTCA<br>CCCACCAGGGCTCCAACTTCGGTCCCATCTTCATGACCATCCCAGCGTTCTTTGCCAAGAGCGCCGCCA<br>TCTACAACCCTGTCATCTATATCATGATGAACAAGCAGTTCCGGAACTGCATGCTCACCACCATCTGCT<br>GCGGCAAGAACCCACTGGGTGACGATGAGGCCTCTGCTACCGTGTCCAAGACGGAGACGAGCCAGGTGG<br>CCCCGGCCTAACCAAGAAAGCTTAAGTTTGTGTCCCGGCTTAGGGCTAAATGTCTAGGACAGAATGGAA<br>CACATAGTAGCTGATTAATAAATGCTAGCTGGATGAAGGGAGGAATGAGTGACTGACTGAGTGGATATA<br>TGAGTGAAGGGATTAATGGAAGGGAACATGGATGTCCTCAGGTGCCAACCTGGCAGATCCAGTCATGT<br>CTGGCTGGAATCTATAAGCAGTTTTACATACCTGCCCTGAGCTTTATTGCGGTAGTTTATCACAGTTAA<br>ATTGCTAACGCAGTCAGTGCTTCTGACACAACAGTCTCGAACTTAAGCTGCAGTGACTCTCTTAAGGTA<br>GCCTTGCAGAAGTTGGTCGTGAGGCACTGGGCAGGTAAGTATCAAGGTTACAAGACAGGTTTAAGGAGA<br>CCAATAGAAACTGGGCTTGTCGAGACAGAGAAAAACCTAACCCCCATGGTTGGCGAGGGACTGCTGTGT<br>GTGAAATGGTAACTGCCCTCAAGGAGCTTACAATCTAGCTGGGGGTAAATGACTTGCACATGAACACAA<br>CTAGACTGTGAGCTTCTAGAGGGCAGGGACCTTACCCTAGTCATCTCTCTTCTCACCCTGCACACCCTC<br>CCTGAGGGATCTCATGACTCTTGCGTTTCTGATAGGCACCTATTGGTCTTACTGACATCCACTTTGCCT<br>TTCTCTCCACAGGTGTCCACTCCCAGTTCACACCGGCACAATGAATGGCACAGAAGGCCCTAACTTCTA<br>CGTGCCCTTCTCCAATGCGACGGGTGTGGTACGCAGCCCCTTCGAGTACCCACAGTCAGAGATAAATGA<br>CAGTGACAGCAACGTGAGCTGCAGCCCTTAGGACTGAGAAAGCATCGAGACCAGGGGTCTCCGGCAAGG<br>CCTAGGTCCTCCCTTCAGTATGGAAACCTTGCCTCATGTCTCTCAGCCTCCTTGGCCTGTGGAGATCCA |

| SEQUENCES |
|---|
| GCCCTTCCTCTTGGCTTCTGGATACATTTGCTCTTCTACACCAGCAACCAAGTGGCAACAGTTCCAGGC<br>CAGTATGGAGTTTTAGAAGCCATGCCAATATGCCCACCTTCAGGGAGCAGCTGAGTCCTTGATGCCACC<br>CTTGTTCTGAAGAGTTCAGAAACACAGTGCAAGACATGACCAGGCCTCATCCTTAGGATGCTCATGGAT<br>CCAGTTCTTAGCTCCCTTGTTGGATATGCTGTTTTCCTTGGCCTTTGGTCTTTTCTTTATCCCAGAGGG<br>TTTTGGCTTTAAGGCCAACAGGAACTATGGGGTACCAGAATTGAGCAGCCTCAGTCTGCATCCCTCCTC<br>TATAGAACCACAGCTGGGCCCTCAGCAGGCCCAACTCTGCATGGGGACAGAGGCATTAAAAGC (SEQ<br>ID NO: 9)<br><br>Chimeric Intron<br>GGAGTCGCTGCGACGCTGCCTTCGCCCCGTGCCCCGCTCCGCCGCCGCCTCGCGCCGCCCGCCCCGGCT<br>CTGACTGACCGCGTTACTCCCACAGGTGAGCGGGCGGGACGGCCCTTCTCCTCCGGGCTGTAATTAGCG<br>CTTGGTTTAATGACGGCTTGTTTCTTTTCTGTGGCTGCGTGAAAGCCTTGAGGGGCTCCGGGAGGGCCC<br>TTTGTGCGGGGGGAGCGGCTCGGGGGGTGCGTGCGTGTGTGTGCGTGGGGAGCGCCGCGTGCGGCTC<br>CGCGCTGCCCGGCGGCTGTGAGCGCTGCGGGCGCGGCGCGGGGCTTTGTGCGCTCCGCAGTGTGCGCGA<br>GGGGAGCGCGGCCGGGGGCGGTGCCCCGCGGTGCGGGGGGGGCTGCGAGGGGAACAAAGGCTGCGTGCG<br>GGGTGTGTGCGTGGGGGGGTGAGCAGGGGGTGTGGGCGCGTCGGTCGGGCGTGCAACCCCCCTGCACCC<br>CCCTCCCCGAGTTGCTGAGCACGGCCCGGCTTCGGGTGCGGGGCTCCGTACGGGGCGTGGCGCGGGGCT<br>CGCCGTGCCGGGCGGGGGTGGCGGCAGGTGGGGGTGCCGGGCGGGGCGGGGCCGCTCGGGCCGGGGA<br>GGGCTCGGGGGAGGGCGCGGCGGCCCCCGGAGCGCCGGCGGCTGTCGAGGCGCGGCGAGCCGCAGCCA<br>TTGCCTTTTATGGTAATCGTGCGAGAGGGCGCAGGGACTTCCTTTGTCCCAAATCTGTGCGGAGCCGAA<br>ATCTGGGAGGCGCCGCCGCACCCCCTCTAGCGGGCGCGGGGCGAAGCGGTGCGGCGCCGGCAGGAAGGA<br>AATGGGCGGGAGGGCCTTCGTGCGTCGCCGCGCCGTCCCCTTCTCCCTCTCCAGCCTCGGGGCTG<br>TCCGCGGGGGACGGCTGCCTTCGGGGGGACGGGGCAGGGCGGGGTTCGGCTTCTGGCGTGTGACCGG<br>CGGCTCTAGAGCCTCTGCTAACCATGTTCATGCCTTCTTCTTTTTCCTACA (SEQ ID NO: 10)<br><br>Stuffer sequence<br>AAGCTTGAAATGCCACCTCCTCTGATATTCTAGGTGTCCTGGAAGCCTGTCTCATCTTGCCCTGTAGTG<br>TTGGGTCACCTGGCCCCCAGCCTGTAACATCCCCAGGGCCTACACCCAGAGAAACACGGGGCTGGTGG<br>CAGTGCCCAGTGACAACCGTTTAGTGGATAAGAGAAGAGTGACCACACCAGGCTGAGTGCTCCTCTCTG<br>GTTTTCCATGGGGAGACAATGCCACCCTGAGCAGGGTCTGGTGTGAGCGGCAGCTGGCTCTGGGCTCTC<br>TGATCCGTTACCCTCTCAGCCTCTTTGTTCTTTCTCAACCCCTGGAGCAGAGACCTCAGGAGGTGCTGG<br>CATGGAACAGAGAAATTCCAGCCTCGATTCCTATTATGAACCCGACACCTTTTGTATTTTCATCTTGGT<br>TTTACAGTGTACAAAACGAACTAGATCAGCAGGGCATGGGCATAATCACGAATGCACACACATACACTA<br>ATGTGTGGCTCATGTTTAAGTATCACTTACTACAGGACACCCAATCTAACAGCACCGATAAAGTGACAG<br>AGAAACGCAAGCCTTCTGCGAACATGGCCTGGCTGTTCCAATTCCGAACCTTGCTTTTCTGGGCCTTGC<br>CACACAGGCTCTTCCCCCGTCCCCCAGGGACATTCTACCCTTGAACTCCACACTCCACTGCTGCCTTT<br>GCCAGGAAGCCCATCTGTTCCTTTTTGGTTCTGCCAGAACGTGTGGTGGTGCTGCTGCCCTGCCTTGG<br>GCACTGGATATTGGGAAGGGACAGTGTCCACACTGGAGTGGGAAGTTCCCAGGGACGAGACCTTTACCT<br>CCTCACCCTGGGTACTGTTCTCCTCATGGAGCATGGACGGCGCTGCCTGAACTCAGTGGTGGCCTCATT<br>CTGGAAGCCAAGTTTATACAGAGTAGCAGTGACCCAGGGATGTGGGGTTCACCCTCCTCAGCCCTCTGG<br>CCAGTCCTGATGGGCCTCAGTCCCAACATGGCTAAGAGGTGTGGGCAGCTTCTTGGTCACCCTCAGGTT<br>GGGGAATCACCTTCTGTCTTCATTTTCCAGGAACTTGGTGATGATATCGTGGGTGAGTTCATTTACCAG<br>GTGCTGTAGTTTCCCCTCATCAGGCAGGAAGAAGATGGCGGTGGCATTGCCCAGGTATTTCATCAGCAG<br>CACCCAGCTGGACAGCTTCTTACAGTGCTGGATGTTAAACATGCCTAAACGCTTCATCATAGGCACCTT<br>CACGGTGGTCACCTGGTCCACGTGGAAGTCCTCTTCCTCGGTGTCCTTGACTTCAAAGGGTCTCTCCCA<br>TTTGCCTGGAGAGAGGGGAAGGTGGGCATCACCAGGGGTGAGTGAAGGTTTGGAAGAGTGTAGCAGAAT<br>AAGAAACCATGAGTCCCCTCCCTGAGAAGCCCTGAGCCCCCTTGACGACACACATCCCTCGAGGCTCAG<br>CTTCATCATCTGTAAAAGGTGCTGAAACTGACCATCCAAGCTGCCGAAAAAGATTGTGTGGGGATAATT<br>CAAAACTAGAGGAAGATGCAGAATTTCTACATCGTGGCGATGTCAGGCTAAGAGATGCCATCGTGGCTG<br>TGCATTTTTATTGGAATCATATGTTTATTTGAGGGTGTCTTGGATATTACAAATAAAATGTTGGAGCAT<br>CAGGCATATTTGGTACCTTCTGTCTAAGGCTCCCTGCCCCTTGTTAATTGGCAGCTCAGTTATTCATCC<br>AGGGCAAACATTCTGCTTACTATTCCTGAGAGCTTTCCTCATCCTCTAGATTGGCAGGGGAAATGCAGA<br>TGCCTGAGCAGCCTCCCCTCTGCCATACCAACAGAGCTTCACCATCGAGGCATGCAGATGGACAGGGG<br>CCTCAGGGACCCCTGATCCCAGCTTTCTCATTGGACAGAAGGAGGAGACTGGGGCTGGAGAGGGACCTG<br>GGCCCCACTAAGGCCACAGCAGAGCCAGGACTTTAGCTGTGCTGACTGCAGCCTGGCTTGCCTCCACT<br>GCCCTCCTTTGCCTCAAGAGCAAGGGAGCCTCAGAGTGGAGGAAGCAGCCCCTGGCCTTGCCTCCCACC<br>TCCCCTCCCCTATGCTGTTTTCCTGGGACAGTGGGAGCTGGCTTAGAATGCCCTGGGGCCCCAGGACC<br>CTGGCATTTTAACCCCTCAGGGGCAGGAAGGCAGCCTGAGATACAGAAGAGTCCATCACCTGCTGTATG<br>CCACACACCATCCCCACAGTTACGTACTAGT (SEQ ID NO: 11)<br><br>pCBA-hRhodopsin-miR708 (miR-155 scaffold)<br>GAATTCGGACCGTCGACATTGATTATTGACTAGTTATTAATAGTAATCAATTACGGGGTCATTAGTTCA<br>TAGCCCATATATGGAGTTCCGCGTTACATAACTTACGGTAAATGGCCCGCCTGGCTGACCGCCCAACGA<br>CCCCCGCCCATTGACGTCAATAATGACGTATGTTCCCATAGTAACGCCAATAGGGACTTTCCATTGACG<br>TCAATGGGTGGAGTATTTACGGTAAACTGCCCACTTGGCAGTACATCAAGTGTATCATATGCCAAGTAC<br>GCCCCCTATTGACGTCAATGACGGTAAATGGCCCGCCTGGCATTATGCCCAGTACATGACCTTATGGGA<br>CTTTCCTACTTGGCAGTACATCTACGTATTAGTCATCGCTATTACCATGGTCGAGGTGAGCCCCACGTT<br>CTGCTTCACTCTCCCCATCTCCCCCCCCTCCCACCCCCAATTTTGTATTTATTTATTTTTTAATTATT<br>TTGTGCAGCGATGGGGGCGGGGGGGGGGGGGGCGCGCGCCAGGCGGGGCGGGGCGGGGCGAGGGGCG<br>GGGCGGGGCGAGGCGGAGAGGTGCGGCGGCAGCCAATCAGAGCGGCGCGCTCCGAAAGTTTCCTTTTAT<br>GGCGAGGCGGCGGCGGCGGCGGCCCTATAAAAAGCGAAGCGCGCGGCGGGCGGGAGTCGCTGCGACGC<br>TGCCTTCGCCCCGTGCCCCGCTCCGCCGCCGCCTCGCGCCGCCCGCCCCGGCTCTGACTGACCGCGTTA<br>CTCCCACAGGTGAGCGGGCGGGACGGCCCTTCTCCTCCGGGCTGTAATTAGCGCTTGGTTTAATGACGG<br>CTTGTTTCTTTTCTGTGGCTGCGTGAAAGCCTTGAGGGGCTCCGGGAGGGCCCTTTGTGCGGGGGGAGC<br>GGCTCGGGGGTGCGTGCGTGTGTGTGCGTGGGGAGCGCCGCGTGCGGCTCCGCGCTGCCCGGCGGC<br>TGTGAGCGCTGCGGGCGCGGCGCGGGGCTTTGTGCGCTCCGCAGTGTGCGCGAGGGGAGCGCGGCCGGG<br>GGCGGTGCCCCGCGGTGCGGGGGGGGCTGCGAGGGGAACAAAGGCTGCGTGCGGGGTGTGTGCGTGGGG |

-continued

| SEQUENCES |
|---|
| GGGTGAGCAGGGGGTGTGGGCGCGTCGGTCGGGCTGCAACCCCCCTGCACCCCCCTCCCCGAGTTGCT |
| GAGCACGGCCCGGCTTCGGGTGCGGGGCTCCGTACGGGGCGTGGCGCGGGGCTCGCCGTGCCGGGCGGG |
| GGGTGGCGGCAGGTGGGGGTGCCGGGCGGGGCGGGCCGCCTCGGGCCGGGAGGGCTCGGGGGAGGGG |
| CGCGGCGGCCCCCGGAGCGCCGGCGGCTGTCGAGGCGCGGCGAGCCGCAGCCATTGCCTTTTATGGTAA |
| TCGTGCGAGAGGGCGCAGGGACTTCCTTTGTCCCAAATCTGTGCGGAGCCGAAATCTGGGAGGCGCCGC |
| CGCACCCCCTCTAGCGGGCGCGGGGCGAAGCGGTGCGGCGCCGGCAGGAAGGAAATGGGCGGGGAGGGC |
| CTTCGTGCGTCGCCGCGCCGTCCCCTTCTCCCTCTCCAGCCTCGGGGCTGTCCGCGGGGGGACGGC |
| TGCCTTCGGGGGGGACGGGGCAGGGCGGGGTTCGGCTTCTGGCGTGTGACCGGCGGCTCTAGAGCCTCT |
| GCTAACCATGTTCATGCCTTCTTCTTTTTCCTACAGCTCCTGGGCAACGTGCTGGTTATTGTGCTGTCT |
| CATCATTTTGGCAAAGAATTCTTCGAAAGATCTGCTAGCTTAATTAACCCAAACGGGCCCTCTAGACTC |
| GAGCGGCCGCCACTGTGCTGGATATCTGCAGAATTCAGCCACCACCGGCACAATGAATGGCACAGAAGG |
| CCCTAACTTCTACGTGCCCTTCTCCAATGCGACGGGTGTGGTACGCAGCCCCTTCGAGTACCCACAGTA |
| CTACCTGGCTGAGCCATGGCAGTTCTCCATGCTGGCCGCCTACATGTTTCTGCTGATCGTGCTGGGCTT |
| CCCCATCAACTTCCTCACGCTCTACGTCACCGTCCAGCACAAGAAGCTGCGCACGCCTCTCAACTACAT |
| CCTGCTCAACCTAGCCGTGGCTGACCTCTTCATGGTCCTAGGTGGCTTCACCAGCACCCTCTACACCTC |
| TCTGCATGGATACTTCGTCTTCGGGCCCACAGGATGCAATTTGGAGGGCTTCTTTGCCACCCTGGGCGG |
| TGAAATTGCCCTGTGGTCCTTGGTGGTCCTGGCCATCGAGCGGTACGTGGTGGTGTGTAAGCCCATGAG |
| CAACTTCCGCTTCGGGGAGAACCATGCCATCATGGGCGTTGCCTTCACCTGGGTCATGGCGCTGGCCTG |
| CGCCGCACCCCCACTCGCCGGCTGGTCCAGGTACATCCCCGAGGGCCTGCAGTGCTCGTGTGGAATCGA |
| CTACTACACGCTCAAGCCGGAGGTCAACAACGAGTCTTTTGTCATCTACATGTTCGTGGTCCACTTCAC |
| CATCCCCATGATTATCATCTTTTTCTGCTATGGGCAGCTCGTCTTCACCGTCAAGGAGGCCGCTGCCCA |
| GCAGCAGGAGTCAGCCACCACACAGAAGGCAGAGAAGGAGGTCACCCGCATGGTCATCATCATGGTCAT |
| CGCTTTCCTGATCTGCTGGGTGCCCTACGCCAGCGTGGCATTCTACATCTTCACCCACCAGGGCTCCAA |
| CTTCGGTCCCATCTTCATGACCATCCCAGCGTTCTTTGCCAAGAGCGCCGCCATCTACAACCCTGTCAT |
| CTATATCATGATGAACAAGCAGTTCCGGAACTGCATGCTCACCACCATCTGCTGCGGCAAGAACCCACT |
| GGGTGACGATGAGGCCTCTGCTACCGTGTCCAAGACGGAGACGAGCCAGGTGGCCCCGGCCTAACCAAG |
| AAAGCTTAAGTTTGGGACTAGTGGCGGCCGCTCGAGCATGCATCTAGAGGGCCCTATTCTATAGTGTCA |
| CCTAAATGCTAGAGCTCGCTGATCAGCCTCGACTGTGCCTTCTAGTTGCCAGCCATCTGTTGTTTGCCC |
| CTCCCCCGTGCCTTCCTTGACCCTGGAAGGTGCCACTCCCACTGTCCTTTCCTAATAAAATGAGGAAAT |
| TGCATCGCATTGTCTGAGTAGGTGTCATTCTATTCTGGGGGGTGGGGTGGGGCAGGACAGCAAGGGGGA |
| GGATTGGGAAGACAATAGCAGGCATGCTGGGGAGCTAGAGTCGACCGGACCGCTGCAGGCATGCAAGCT |
| TGGCGTAATCATGGTCATAGCTGTTTCCTGTGTGAAATTGTTATCCGCTCACAATTCCACACAACATAC |
| GAGCCGGAAGCATAAAGTGTAAAGCCTGGGGTGCCTAATGAGTGAGCTAACTCACATTAATTGCGTTGC |
| GCTCACTGCCCGCTTTCCAGTCGGGAAACCTGTCGTGCCAGCTGCATTAATGAATCGGCCAACGCGCGG |
| GGAGAGGCGGTTTGCGTATTGGGCGCTCTTCCGTATTAGTCATCGCTATTACCATGGTGATGCGGTTTT |
| GGCAGTACATCAATGGGCGTGGATAGCGGTTTGACTCACGGGGATTTCCAAGTCTCCACCCCATTGACG |
| TCAATGGAGTTTGTTTTGGCACCAAAATCAACGGGACTTTCCAAAATGTCGTAACAACTCCGCCCCAT |
| TGACGCAAATGGGCGGTAGGCGTGTACGGTGGGAGGTCTATATAAGCAGAGCTCTCTGGCTAACTAGAG |
| AACCCACTGCTTACTGGCTTATCGAAATTAATACGACTCACTATAGGGAGTCCCAAGCTGGCTAGTTAA |
| GCTATCAACAAGTTTGTACAAAAAAGCAGGCTTTAAAGGGAGGTAGTGAGTCGACCAGTGGATCCTGGA |
| GGCTTGCTGAAGGCTGTATGCTGAAGGAGCTTACAATCTAGCTGGGGTTTTGGCCACTGACTGACCCCA |
| GCTAGTGTAAGCTCCTTCAGGACAAAGGCCTGTTACTAGCACTCACATGGAACAAATGGCCCAGATCT |
| GGCCGCACTCGAGATGCTTCCTCGCTCACTGACTCGCTGCGCTCGGTCGTTCGGCTGCGGCGAGCGGTA |
| TCAGCTCACTCAAAGGCGGTAATACGGTTATCCACAGAATCAGGGGATAACGCAGGAAAGAACATGTGA |
| GCAAAAGGCCAGCAAAAGGCCAGGAACCGTAAAAAGGCCGCGTTGCTGGCGTTTTTCCATAGGCTCCGC |
| CCCCCTGACGAGCATCACAAAAATCGACGCTCAAGTCAGAGGTGGCGAAACCCGACAGGACTATAAAGA |
| TACCAGGCGTTTCCCCCTGGAAGCTCCCTCGTGCGCTCTCCTGTTCCGACCCTGCCGCTTACCGGATAC |
| CTGTCCGCCTTTCTCCCTTCGGGAAGCGTGGCGCTTTCTCATAGCTCACGCTGTAGGTATCTCAGTTCG |
| GTGTAGGTCGTTCGCTCCAAGCTGGGCTGTGTGCACGAACCCCCCGTTCAGCCCGACCGCTGCGCCTTA |
| TCCGGTAACTATCGTCTTGAGTCCAACCCGGTAAGACACGACTTATCGCCACTGGCAGCAGCCACTGGT |
| AACAGGATTAGCAGAGCGAGGTATGTAGGCGGTGCTACAGAGTTCTTGAAGTGGTGGCCTAACTACGGC |
| TACACTAGAAGGACAGTATTTGGTATCTGCGCTCTGCTGAAGCCAGTTACCTTCGGAAAAAGAGTTGGT |
| AGCTCTTGATCCGGCAAACAAACCACCGCTGGTAGCGGTGGTTTTTTTGTTTGCAAGCAGCAGATTACG |
| CGCAGAAAAAAAGGATCTCAAGAAGATCCTTTGATCTTTTCTACGGGGTCTGACGCTCAGTGGAACGAA |
| AACTCACGTTAAGGGATTTTGGTCATGAGATTATCAAAAAGGATCTTCACCTAGATCCTTTTAAATTAA |
| AAATGAAGTTTTAAATCAATCTAAAGTATATATGAGTAAACTTGGTCTGACAGTTACCAATGCTTAATC |
| AGTGAGGCACCTATCTCAGCGATCTGTCTATTTCGTTCATCCATAGTTGCCTGACTCCCCGTCGTGTAG |
| ATAACTACGATACGGGAGGGCTTACCATCTGGCCCCAGTGCTGCAATGATACCGCGAGACCCACGCTCA |
| CCGGCTCCAGATTTATCAGCAATAAACCAGCCAGCCGGAAGGGCCGAGCGCAGAAGTGGTCCTGCAACT |
| TTATCCGCCTCCATCCAGTCTATTAATTGTTGCCGGGAAGCTAGAGTAAGTAGTTCGCCAGTTAATAGT |
| TTGCGCAACGTTGTTGCCATTGCTACAGGCATCGTGGTGTCACGCTCGTCGTTTGGTATGGCTTCATTC |
| AGCTCCGGTTCCCAACGATCAAGGCGAGTTACATGATCCCCCATGTTGTGCAAAAAAGCGGTTAGCTCC |
| TTCGGTCCTCCGATCGTTGTCAGAAGTAAGTTGGCCGCAGTGTTATCACTCATGGTTATGGCAGCACTG |
| CATAATTCTCTTACTGTCATGCCATCCGTAAGATGCTTTTCTGTGACTGGTGAGTACTCAACCAAGTCA |
| TTCTGAGAATAGTGTATGCGGCGACCGAGTTGCTCTTGCCCGGCGTCAATACGGGATAATACCGCGCCA |
| CATAGCAGAACTTTAAAAGTGCTCATCATTGGAAAACGTTCTTCGGGGCGAAAACTCTCAAGGATCTTA |
| CCGCTGTTGAGATCCAGTTCGATGTAACCCACTCGTGCACCCAACTGATCTTCAGCATCTTTTACTTTC |
| ACCAGCGTTTCTGGGTGAGCAAAAACAGGAAGGCAAAATGCCGCAAAAAAGGGAATAAGGGCGACACGG |
| AAATGTTGAATACTCATACTCTTCCTTTTTCAATATTATTGAAGCATTTATCAGGGTTATTGTCTCATG |
| AGCGGATACATATTTGAATGTATTTAGAAAAATAAACAAATAGGGGTTCCGCGCACATTTCCCCGAAAA |
| GTGCCACCTGACGTCTAAGAAACCATTATTATCATGACATTAACCTATAAAAATAGGCGTATCACGAGG |
| CCCTTTCGTCTCGCGCGTTTCGGTGATGACGGTGAAAACCTCTGACACATGCAGCTCCCGGAGACGGTC |
| ACAGCTTGTCTGTAAGCGGATGCCGGGAGCAGACAAGCCCGTCAGGGCGCGTCAGCGGGTGTTGGCGGG |
| TGTCGGGGCTGGCTTAACTATGCGGCATCAGAGCAGATTGTACTGAGAGTGCACCATATGCGGTGTGAA |
| ATACCGCACAGATGCGTAAGGAGAAAATACCGCATCAGGCGCCATTCGCCATTCAGGCTGCGCAACTGT |

| SEQUENCES |
|---|
| TGGGAAGGGCGATCGGTGCGGGCCTCTTCGCTATTACGCCAGCTGGCGAAAGGGGGATGTGCTGCAAGG<br>CGATTAAGTTGGGTAACGCCAGGGTTTTCCCAGTCACGACGTTGTAAAACGACGGCCAGT (SEQ ID<br>NO: 12)<br><br>MIR155 scaffold<br>GATCCTGGAGGCTTGCTGAAGGCTGTATGCTGAAGGAGCTTACAATCTAGCTGGGGTTTTGGCCACTGA<br>CTGACCCCAGCTAGTGTAAGCTCCTTCAGGACACAAGGCCTGTTACTAGCACTCACATGGAACAAATGG<br>CCCAGATCTGGCCGCAC (SEQ ID NO: 13)<br><br>Endogenous MIR708 scaffold<br>AACCTAACCCCCATGGTTGGCGAGGGACTGCTGTGTGTGAAATGGTAACTGCCCTCAAGGAGCTTACAA<br>TCTAGCTGGGGGTAAATGACTTGCACATGAACACAACTAGACTGTGAGCTTCTAGAGGGCAGGGACCTT<br>ACCCTAGTCATCTCTCTTCTCACCCTGCACACCCTCCCTGAGGGATCTCAT (SEQ ID NO: 14)<br><br>pRK-hRhodopsin-miR-708 (mir708 in the miR708 endogenous scaffold, located<br>in the 3'UTR of hRhodopsin)<br>TATGCGGTGTGAAATACCGCACAGATGCGTAAGGAGAAAATACCGCATCAGGCGCCATTCGCCATTCAG<br>GCTGCGCAACTGTTGGGAAGGGCGATCGGTGCGGGCCTCTTCGCTATTACGCCAGCTGGCGAAAGGGGG<br>ATGTGCTGCAAGGCGATTAAGTTGGGTAACGCCAGGGTTTTCCCAGTCACGACGTTGTAAAACGACGGC<br>CAGTGAATTCGGACCGTCGACATTGATTATTGGGCCCCAGAAGCCTGGTGGTTGTTTGTCCTTCTCAGG<br>GGAAAAGTGAGGCGGCCCCTTGGAGGAAGGGGCCGGGCAGAATGATCTAATCGGATTCCAAGCAGCTCA<br>GGGGATTGTCTTTTTCTAGCACCTTCTTGCCACTCCTAAGCGTCCTCCGTGACCCCGGCTGGGATTTAG<br>CCTGGTGCTGTGTCAGCCCCGGTCTCCCAGGGGCTTCCCAGTGGTCCCCAGGAACCCTCGACAGGGCCC<br>GGTCTCTCTCGTCCAGCAAGGGCAGGGACGGGCCACAGGCCAAGGGCGGAGTCGCTGCGACGCTGCCTT<br>CGCCCCGTGCCCCGCTCCGCCGCCGCCTCGCGCCGCCCGCCCCGGCTCTGACTGACCGCGTTACTCCCA<br>CAGGTGAGCGGGCGGGACGGCCCTTCTCCTCGGGCTGTAATTAGCAAGAGGTAAGGGTTTAAGGGATG<br>GTTGGTTGGTGGGGTATTAATGTTTAATTACCTGTTTTACAGGCCTGAAATCACTTGGTTTTAGGTTGG<br>GGATCCGGTACCCAATTGCCATGGGCTAGCATGCATGAGCTCCTGCAGGGTTTATCTGCAGAATTCAG<br>CCACCACCGGCACAATGAATGGCACAGAAGGCCCTAACTTCTACGTGCCCTTCTCCAATGCGACGGGTG<br>TGGTACGCAGCCCCTTCGAGTACCCACAGTACTACCTGGCTGAGCCATGGCAGTTCTCCATGCTGGCCG<br>CCTACATGTTTCTGCTGATCGTGCTGGGCTTCCCCATCAACTTCCTCACGCTCTACGTCACCGTCCAGC<br>ACAAGAAGCTGCGCACGCCTCTCAACTACATCCTGCTCAACCTAGCCGTGGCTGACCTCTTCATGGTCC<br>TAGGTGGCTTCACCAGCACCCTCTACACCTCTCTGCATGGATACTTCGTCTTCGGGCCCACAGGATGCA<br>ATTTGGAGGGCTTCTTTGCCACCCTGGGCGGTGAAATTGCCCTGTGGTCCTTGGTGGTCCTGGCCATCG<br>AGCGGTACGTGGTGGTGTGTAAGCCCATGAGCAACTTCCGCTTCGGGGAGAACCATGCCATCATGGGCG<br>TTGCCTTCACCTGGGTCATGGCGCTGGCCTGCGCCGCACCCCCACTCGCCGGCTGGTCCAGGTACATCC<br>CCGAGGGCTGCAGTGCTCGTGTGGAATGACTACTACACGCTCAAGCCGGAGGTCAACAACGAGTCTT<br>TTGTCATCTACATGTTCGTGGTCCACTTCACCATCCCCATGATTATCATCTTTTTCTGCTATGGGCAGC<br>TCGTCTTCACCGTCAAGGAGGCCGCTGCCCAGCAGCAGGAGTCAGCCACCACACAGAAGGCAGAGAAGG<br>AGGTCACCCGCATGGTCATCATCATGGTCATCGCTTTCCTGATCTGCTGGGTGCCCTACGCCAGCGTGG<br>CATTCTACATCTTCACCCACCAGGGCTCCAACTTCGGTCCCATCTTCATGACCATCCCAGCGTTCTTTG<br>CCAAGAGCGCCGCCATCTACAACCCTGTCATCTATATCATGATGAACAAGCAGTTCCGGAACTGCATGC<br>TCACCACCATCTGCTGCGGCAAGAACCCACTGGGTGACGATGAGGCCTCTGCTACCGTGTCCAAGACGG<br>AGACGAGCCAGGTGGCCCCGGCCTAACCAAGAAAGCTTAAGTTTGTGTCCCGGCTTAGGGCTAAATGTC<br>TAGGACAGAATGGAACACATAGTAGCTGATTAATAAATGCTAGCTGGATGAAGGGAGGAATGAGTGACT<br>GACTGAGTGGATATATGAGTGAAGGGATTAATGGAAGGGAACATGGATGTCCTCAGGTGCCCAACCTGG<br>CAGATCCAGTCATGTCTGGCTGGAATCTATAAGCAGTTTTACATACCTGCCCTGAGCTTTATTGCGGTA<br>GTTTATCACAGTTAAATTGCTAACGCAGTCAGTGCTTCTGACACAACAGTCTCGAACTTAAGCTGCAGT<br>GACTCTCTTAAGGTAGCCTTGCAGAAGTTGGTCGTGAGGCACTGGAGGTAAGTATCAAGGTTACAAG<br>ACAGGTTTAAGGAGACCAATAGAAACTGGGCTTGTCGAGACAGAGAAAAACCTAACCCCCATGGTTGGC<br>GAGGGACTGCTGTGTGTGAAATGGTAACTGCCCTCAAGGAGCTTACAATCTAGCTGGGGTAAATGACT<br>TGCACATGAACACAACTAGACTGTGAGCTTCTAGAGGGCAGGGACCTTACCCTAGTCATCTCTCTTCTC<br>ACCCTGCACACCCTCCCTGAGGGATCTCATGACTCTTGCGTTTCTGATAGGCACCTATTGGTCTTACTG<br>ACATCCACTTTGCCTTTCTCTCCACAGGTGTCCACTCCCAGTTCACACCGGCACAATGAATGGCACAGA<br>AGGCCCTAACTTCTACGTGCCCTTCTCCAATGCGACGGGTGTGGTACGCAGCCCCTTCGAGTACCCACA<br>GTCAGAGATAAATGACAGTGACAGCAACGTGAGCTGCAGCCCTTAGGACTGAGAAAGCATCGAGACCAG<br>GGGTCTTCCGGCAAGGCCTAGGTCCTCCCTTCAGTATGGAAACTTTGCTCTTCTACACCAGCAACCAAGTG<br>GCAACAGTTCCAGGCCAGTATGGAGTTTTAGAAGCCATGCCAATATGCCCACCTTCAGGGAGCAGCTGA<br>GTCCTTGATGCCACCCTTGTTCTGAAGAGTTCAGAAACACAGTGCAAGACATGACCAGGCCTCATCCTT<br>AGGATGCTCATGGATCCAGTTCTTAGCTCCCTTGTTGGATATGCTGTTTTCCTTGGCCTTTGGTCTTTT<br>CTTTATCCCAGAGGGTTTTGGCTTTAAGGCCAACAGGAACTATGGGGTACCAGAATTGAGCAGCCTCAG<br>TCTGCATCCTCCTCTATAGAACCACAGCTGGGCCCTCAGCAGGCCCAACTCTGCATGGGGACAGAGGC<br>ATTAAAAGCCTAGAGTATCCCTCGAGGGGCCCAAGCTTACGCGTACCCAGCTTTCTTGTACAAAGTGGT<br>CCCTATAGTGAGTCGTATTATAAGCTAGGCACTGGCCGTCGTTTTACAACGTCGTGACTGGGAAAACTG<br>CTAGCTTGGGACTCTTTGTGAAGGAACCTTACTTCTGTGGTGTGGACATAATTGGACAAACTACCTACAGA<br>GATTTAAAGCTCTAAGGTAAATATAAAATTTTAAGTGTATAATGTGTTAAACTAGCTGCAAAACCTGT<br>GCCTTCTAGTTGCCAGCCATCTGTTGTTTGCCCCTCCCCGTGCCTTCCTTGACCCTGGAAGGTGCCAC<br>TCCCACTGTCCTTTCCTAATAAAATGAGGAAATTGCATCGCATTGTCTGAGTAGGTGTCATTCTATTCT<br>GGGGGGTGGGGTGGGGCAGGACAGCAAGGGGGAGGATTGGGAAGACAATAGCAGGCATGCTGGGGAACT<br>AGTCGGACCGCTGCAGGCATGCAAGCTTGGCGTAATCATGGTCATAGCTGTTTCCTGTGTGAAATTGTT<br>ATCCGCTCACAATTCCACACAACATACGAGCCGGAAGCATAAAGTGTAAAGCCTGGGGTGCCTAATGAG<br>TGAGCTAACTCACATTAATTGCGTTGCGCTCACTGCCCGCTTTCCAGTCGGGAAACCTGTCGTGCCAGC<br>TGCATTAATGAATCGGCCAACGCGCGGGGAGAGGCGGTTTGCGTATTGGGCGCTCTTCCGCTTCCTCGC<br>TCACTGACTCGCTGCGCTCGGTCGTTCGGCTGCGGCGAGCGGTATCAGCTCACTCAAAGGCGGTAATAC<br>GGTTATCCACAGAATCAGGGGATAACGCAGGAAAGAACATGTGAGCAAAAGGCCAGCAAAAGGCCAGGA<br>ACCGTAAAAAGGCCGCGTTGCTGGCGTTTTTCCATAGGCTCCGCCCCCCTGACGAGCATCACAAAAATC |

| SEQUENCES |
|---|
| GACGCTCAAGTCAGAGGTGGCGAAACCCGACAGGACTATAAAGATACCAGGCGTTTCCCCCTGGAAGCT
CCCTCGTGCGCTCTCCTGTTCCGACCCTGCCGCTTACCGGATACCTGTCCGCCTTTCTCCCTTCGGGAA
GCGTGGCGCTTTCTCATAGCTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGTAACTATCGTCTTGAGTCCA
ACCCGGTAAGACACGACTTATCGCCACTGGCAGCAGCCACTGGTAACAGGATTAGCAGAGCGAGGTATG
TAGGCGGTGCTACAGAGTTCTTGAAGTGGTGGCCTAACTACGGCTACACTAGAAGGACAGTATTTGGTA
TCTGCGCTCTGCTGAAGCCAGTTACCTTCGGAAAAAGAGTTGGTAGCTCTTGATCCGGCAAACAAACCA
CCGCTGGTAGCGGTGGTTTTTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCACGTTAAGGGATTTTGGTCA
TGAGATTATCAAAAAGGATCTTCACCTAGATCCTTTTAAATTAAAAATGAAGTTTTAAATCAATCTAAA
GTATATATGAGTAAACTTGGTCTGACAGTTACCAATGCTTAATCAGTGAGGCACCTATCTCAGCGATCT
GTCTATTTCGTTCATCCATAGTTGCCTGACTCCCCGTCGTGTAGATAACTACGATACGGGAGGGCTTAC
CATCTGGCCCCAGTGCTGCAATGATACCGCGAGACCCACGCTCACCGGCTCCAGATTTATCAGCAATAA
ACCAGCCAGCCGGAAGGGCCGAGCGCAGAAGTGGTCCTGCAACTTTATCCGCCTCCATCCAGTCTATTA
ATTGTTGCCGGGAAGCTAGAGTAAGTAGTTCGCCAGTTAATAGTTTGCGCAACGTTGTTGCCATTGCTA
CAGGCATCGTGGTGTCACGCTCGTCGTTTGGTATGGCTTCATTCAGCTCCGGTTCCCAACGATCAAGGC
GAGTTACATGATCCCCCATGTTGTGCAAAAAAGCGGTTAGCTCCTTCGGTCCTCCGATCGTTGTCAGAA
GTAAGTTGGCCGCAGTGTTATCACTCATGGTTATGGCAGCACTGCATAATTCTCTTACTGTCATGCCAT
CCGTAAGATGCTTTTCTGTGACTGGTGAGTACTCAACCAAGTCATTCTGAGAATAGTGTATGCGGCGAC
CGAGTTGCTCTTGCCCGGCGTCAATACGGGATAATACCGCGCCACATAGCAGAACTTTAAAAGTGCTCA
TCATTGGAAAACGTTCTTCGGGGCGAAAACTCTCAAGGATCTTACCGCTGTTGAGATCCAGTTCGATGT
AACCCACTCGTGCACCCAACTGATCTTCAGCATCTTTTACTTTCACCAGCGTTTCTGGGTGAGCAAAAA
CAGGAAGGCAAAATGCCGCAAAAAAGGGAATAAGGGCGACACGGAAATGTTGAATACTCATACTCTTCC
TTTTTCAATATTATTGAAGCATTTATCAGGGTTATTGTCTCATGAGCGGATACATATTTGAATGTATTT
AGAAAAATAAACAAATAGGGGTTCCGCGCACATTTCCCCGAAAAGTGCCACCTGACGTCTAAGAAACCA
TTATTATCATGACATTAACCTATAAAAATAGGCGTATCACGAGGCCCTTTCGTCTCGCGCGTTTCGGTG
ATGACGGTGAAAACCTCTGACACATGCAGCTCCCGGAGACGGTCACAGCTTGTCTGTAAGCGGATGCCG
GGAGCAGACAAGCCCGTCAGGGCGCGTCAGCGGGTGTTGGCGGGTGTCGGGGCTGGCTTAACTATGCGG
CATCAGAGCAGATTGTACTGAGAGTGCACCA (SEQ ID NO: 15) |

β-globin intron sequence
ACTAGAAGCTTTATTGCGGTAGTTTATCACAGTTAAATTGCTAACGCAGTCAGTGCTTCTGACACAACA
GTCTCGAACTTAAGCTGCAGTGACTCTCTTAAGGTAGCCTTGCAGTAAGTTGGTCGTGAGGCACTGGGCA
GGTAAGTATCAAGGTTACAAGACAGGTTTAAGGAGACCAATAGAAACTGGGCTTGTCGAGACAGAGAAT
GGATCCTGGAGGCTTGCTGAAGGCTGTATGCTGAAGGAGCTTACAATCTAGCTGGGGTTTTGGCCACTG
ACTGACCCCAGCTAGTGTAAGCTCCTTCAGGACACAAGGCCTGTTACTAGCACTCACATGGAACAAATG
GCCCAGATCTGAGACTCTTGCGTTTCTGATAGGCACCTATTGGTCTTACTGACATCCACTTTGCCTTTC
TCTCCACAGGTGTCCACTCCCAGTTCA (SEQ ID NO: 16)

MIR708 sequence in a MIR155 scaffold
TGGATCCTGGAGGCTTGCTGAAGGCTGTATGCTGAAGGAGCTTACAATCTAGCTGGGGTTTTGGCCACT
GACTGACCCCAGCTAGTGTAAGCTCCTTCAGGACACAAGGCCTGTTACTAGCACTCACATGGAACAAAT
GGCCCAGATCTG (SEQ ID NO: 17)

MIR708 sequence in a native scaffold
AAACCTAACCCCCATGGTTGGCGAGGGACTGCTGTGTGTGAAATGGTAACTGCCCTCAAGGAGCTTACA
ATCTAGCTGGGGGTAAATGACTTGCACATGAACACAACTAGACTGTGAGCTTCTAGAGGGCAGGGACCT
TACCCTAGTCATCTCTCTTCTCACCCTGCACACCCTCCCTGAGGGATCTCAT (SEQ ID NO: 18)

Human rhodopsin miR-708 target from 3'UTR
CUCUGCCUGGAGACUAAGGCAAAUUGGGCCAUUAAAAGCUCAGCUCCUAUGUUGGUAUUAACGGUGGUGG
GUUUUGUUG (SEQ ID NO: 19)

Mutated AAV ITR
CCACTCCCTCTCTGCGCGCTCGCTCGCTCACTGAGGCCGGGCGACCAAAGGTCGCCCGACGCCCGGGCTT
TGCCCGGGCGGCCTCAGTGAGCGAGCGAGCGCGCAGAGAGGGA (SEQ ID NO: 20)

Wild Type ITR sequence
GGCCACTCCCTCTCTGCGCGCTCGCTCGCTCACTGAGGCCGGGCGACCAAAGGTCGCCCGACGCCCGGGC
TTTGCCCGGGCGGCCTCAGTGAGCGAGCGAGCGCGCAGAGAGGGAGTGGCCAACTCCATCACTAGGGGTT
CCT (SEQ ID NO: 21)

Opsin promoter
TGCTGATTCAGCCAGGAACTAGTTATTAATAGTAATCAATTACGGGGTCATTAGTTCATAGCCCATATAT
GGAGTTCCGCGTTACATAACTTACGGTAAATGGCCCGCCTGGCTGACCGCCCAACGACCCCCGCCCATTG
ACGTCAATAATGACGTATGTTCCCATAGTAACGCCAATAGGGACTTTCCATTGACGTCAATGGGTGGAGT
ATTTACGGTAAACTGCCCACTTGGCAGTACATCAAGTGTATCATATGCCAAGTACGCCCCCTATTGACGT
CAATGACGGTAAATGGCCCGCCTGGCATTATGCCCAGTACATGACCTTATGGGACTTTCCTACTTGGCAG
TACATCTACGTATTAGTCATCGCTATTACCACAAATGGTTATCGAGCCGCTGAGCCGGGGGGCGGGGGT
GTGAGACTGGAGGCGATGGACGGAGCTGACGGCACACACAGCTCAGATCTGTCAAGTGAGCCATTGTCAG
GGCTTGGGGACTGGATAAGTCAGGGGGTCTCCTGGGAAGAGATGGGATAGGTGAGTTCAGGAGGAGACAT
TGTCAACTGGAGCCATGTGGAGAAGTGAATTTAGGGCCCAAAGGTTCCAGTCGCAGCCTGAGGCCACCAG
ACTGACATGGGGAGGAATTCCCAGAGGACTCTGGGGCAGACAAGATGAGACACCCTTTCCTTTCTTTACC
TAAGGGCCTCCACCCGATGTCACCTTGGCCCCTCTGCAAGCCAATTAGGCCCCGGTGGCAGCAGTGGGAT
TAGCGTTAGTATGATATCTCGCGGA (SEQ ID NO: 22)

-continued

SEQUENCES

MVM intron
GGGAGTCGCTGCGACGCTGCCTTCGCCCCGTGCCCCGCTCCGCCGCCGCCTCGCGCCGCCCGCCCCGGCTC
TGACTGACCGCGTTACTCCCACAGGTGAGCGGGCGGGACGGCCCTTCTCCTCCGGGCTGTAATTAGCAAG
AGGTAAGGGTTTAAGGGATGGTTGGTTGGTGGGGTATTAATGTTTAATTACCTGTTTTACAGGCCTGAAA
TCACTTGGTTTTAGGTTGGGGATCCGGTACCCAATTGCCATGGGCTAGCATGCATGAGCTCCCTGCAGGG
TTTTAATGCCAACTTTGTACAAAAAAGCAGGCACC (SEQ ID NO: 23)

AAV5GRK1miR708_155hRho (AAV5 vector with rhodopsin kinase promoter driving
expression of miR-708 in a miR-155 scaffold and human rhodopsin minus the
miR-708 target sequence)
TGACTAGTTAGGGCCCCAGAAGCCTGGTGGTTGTTTGTCCTTCTCAGGGGAAAAGTGAGGCGGCCCCTTG
GAGGAAGGGGCCGGGCAGAATGATCTAATCGGATTCCAAGCAGCTCAGGGGATTGTCTTTTTCTAGCACC
TTCTTGCCACTCCTAAGCGTCCTCCGTGACCCCGGCTGGGATTTAGCCTGGTGCTGTGTCAGCCCCGGTC
TCCCAGGGGCTTCCCAGTGGTCCCCAGGAACCCTCGACAGGGCCCGGTCTCTCTCGTCCAGCAAGGGCAG
GGACGGGCCACAGGCCAAGGGCACTAGAAGCTTTATTGCGGTAGTTTATCACAGTTAAATTGCTAACGCA
GTCAGTGCTTCTGACACAACAGTCTCGAACTTAAGCTGCAGTGACTCTCTTAAGGTAGCCTTGCAGAAGT
TGGTCGTGAGGCACTGGGCAGGTAAGTATCAAGGTTACAAGACAGGTTTAAGGAGACCAATAGAAACTGG
GCTTGTCGAGACAGAGAATGGATCCTGGAGGCTTGCTGAAGGCTGTATGCTGAAGGAGCTTACAATCTAG
CTGGGGTTTTGGCCACTGACTGACCCCAGCTAGTGTAAGCTCCTTCAGGACACAAGGCCTGTTACTAGCA
CTCACATGGAACAAATGGCCCAGATCTGAGACTCTTGCGTTTCTGATAGGCACCTATTGGTCTTACTGAC
ATCCACTTTGCCTTTCTCTCCACAGGTGTCCACTCCCAGTTCACACCGGCACAATGAATGGCACAGAAGG
CCCTAACTTCTACGTGCCCTTCTCCAATGCGACGGGTGTGGTACGCAGCCCCTTCGAGTACCCACAGTAC
TACCTGGCTGAGCCATGGCAGTTCTCCATGCTGGCCGCCTACATGTTTCTGCTGATCGTGCTGGGCTTCC
CCATCAACTTCCTCACGCTCTACGTCACCGTCCAGCACAAGAAGCTGCGCACGCCTCTCAACTACATCCT
GCTCAACCTAGCCGTGGCTGACCTCTTCATGGTCCTAGGTGGCTTCACCAGCACCCTCTACACCTCTCTG
CATGGATACTTCGTCTTCGGGCCCACAGGATGCAATTTGGAGGGCTTCTTTGCCACCCTGGGCGGTGAAA
TTGCCCTGTGGTCCTTGGTGGTCCTGGCCATCGAGCGGTACGTGGTGGTGTGTAAGCCCATGAGCAACTT
CCGCTTCGGGGAGAACCATGCCATCATGGGCGTTGCCTTCACCTGGGTCATGGCGCTGGCCTGCGCCGCA
CCCCCACTCGCCGGCTGGTCCAGGTACATCCCCGAGGGCCTGCAGTGCTCGTGTGGAATCGACTACTACA
CGCTCAAGCCGGAGGTCAACAACGAGTCTTTTGTCATCTACATGTTCGTGGTCCACTTCACCATCCCCAT
GATTATCATCTTTTTCTGCTATGGGCAGCTCGTCTTCACCGTCAAGGAGGCCGCTGCCCAGCAGCAGGAG
TCAGCCACCACACAGAAGGCAGAGAAGGAGGTCACCCGCATGGTCATCATCATGGTCATCGCTTTCCTGA
TCTGCTGGGTGCCCTACGCCAGCGTGGCATTCTACATCTTCACCCACCAGGGCTCCAACTTCGGTCCCAT
CTTCATGACCATCCCAGCGTTCTTTGCCAAGAGCGCCGCCATCTACAACCCTGTCATCTATATCATGATG
AACAAGCAGTTCCGGAACTGCATGCTCACCACCATCTGCTGCGGCAAGAACCCACTGGGTGACGATGAGG
CCTCTGCTACCGTGTCCAAGACGGAGACGAGCCAGGTGGCCCCGGCCTAACCAAGAAAGCTTAAGTTTAA
ACCGCTGATCAGCCTCGACTGTGCCTTCTAGTTGCCAGCCATCTGTTGTTTGCCCCTCCCCCGTGCCTTC
CTTGACCCTGGAAGGTGCCACTCCCACTGTCCTTTCCTAATAAAATGAGGAAATTGCATCGCATTGTCTG
AGTAGGTGTCATTCTATTCTGGGGGGTGGGGTGGGGCAGGACAGCAAGGGGGAGGATTGGGAAGACAATA
GCAGGCATGCTGGGGATGCGGTGGGCTCTATGGC (SEQ ID NO: 24)

AAV5GRK1miR708_708hRho (AAV5 vector with rhodopsin kinase promoter driving
expression of miR-708 in a miR-708 scaffold and human rhodopsin minus the
miR-708 target sequence)
GGGCCCCAGAAGCCTGGTGGTTGTTTGTCCTTCTCAGGGGAAAAGTGAGGCGGCCCCTTGGAGGAAGGGG
CCGGGCAGAATGATCTAATCGGATTCCAAGCAGCTCAGGGGATTGTCTTTTTCTAGCACCTTCTTGCCAC
TCCTAAGCGTCCTCCGTGACCCCGGCTGGGATTTAGCCTGGTGCTGTGTCAGCCCCGGTCTCCCAGGGGC
TTCCCAGTGGTCCCCAGGAACCCTCGACAGGGCCCGGTCTCTCTCGTCCAGCAAGGGCAGGGACGGGCCA
CAGGCCAAGGGCACTAGAAGCTTTATTGCGGTAGTTTATCACAGTTAAATTGCTAACGCAGTCAGTGCTT
CTGACACAACAGTCTCGAACTTAAGCTGCAGTGACTCTCTTAAGGTAGCCTTGCAGAAGTTGGTCGTGAG
GCACTGGGCAGGTAAGTATCAAGGTTACAAGACAGGTTTAAGGAGACCAATAGAAACTGGGCTTGTCGAG
ACAGAGAAAAACCTAACCCCCATGGTTGGCGAGGGACTGCTGTGTGTGAAATGGTAACTGCCCTCAAGGA
GCTTACAATCTAGCTGGGGGTAAATGACTTGCACATGAACAACTAGACTGTGAGCTTCTAGAGGGCAG
GGACCTTACCCTAGTCATCTCTCTTCTCACCCTGCACACCCTCCCTGAGGGATCTCATGACTCTTGCGTT
TCTGATAGGCACCTATTGGTCTTACTGACATCCACTTTGCCTTTCTCTCCACAGGTGTCCACTCCCAGTT
CACACCGGCACAATGAATGGCACAGAAGGCCCTAACTTCTACGTGCCCTTCTCCAATGCGACGGGTGTGG
TACGCAGCCCCTTCGAGTACCCACAGTACTACCTGGCTGAGCCATGGCAGTTCTCCATGCTGGCCGCCTA
CATGTTTCTGCTGATCGTGCTGGGCTTCCCCATCAACTTCCTCACGCTCTACGTCACCGTCCAGCACAAG
AAGCTGCGCACGCCTCTCAACTACATCCTGCTCAACCTAGCCGTGGCTGACCTCTTCATGGTCCTAGGTG
GCTTCACCAGCACCCTCTACACCTCTCTGCATGGATACTTCGTCTTCGGGCCCACAGGATGCAATTTGGA
GGGCTTCTTTGCCACCCTGGGCGGTGAAATTGCCCTGTGGTCCTTGGTGGTCCTGGCCATCGAGCGGTAC
GTGGTGGTGTGTAAGCCCATGAGCAACTTCCGCTTCGGGGAGAACCATGCCATCATGGGCGTTGCCTTCA
CCTGGGTCATGGCGCTGGCCTGCGCCGCACCCCCACTCGCCGGCTGGTCCAGGTACATCCCCGAGGGCCT
GCAGTGCTCGTGTGGAATCGACTACTACACGCTCAAGCCGGAGGTCAACAACGAGTCTTTTGTCATCTAC
ATGTTCGTGGTCCACTTCACCATCCCCATGATTATCATCTTTTTCTGCTATGGGCAGCTCGTCTTCACCG
TCAAGGAGGCCGCTGCCCAGCAGCAGGAGTCAGCCACCACACAGAAGGCAGAGAAGGAGGTCACCCGCAT
GGTCATCATCATGGTCATCGCTTTCCTGATCTGCTGGGTGCCCTACGCCAGCGTGGCATTCTACATCTTC
ACCCACCAGGGCTCCAACTTCGGTCCCATCTTCATGACCATCCCAGCGTTCTTTGCCAAGAGCGCCGCCA
TCTACAACCCTGTCATCTATATCATGATGAACAAGCAGTTCCGGAACTGCATGCTCACCACCATCTGCTG
CGGCAAGAACCCACTGGGTGACGATGAGGCCTCTGCTACCGTGTCCAAGACGGAGACGAGCCAGGTGGCC
CCGGCCTAACCAAGAAAGCTTAAGTTTAAACCGCTGATCAGCCTCGACTGTGCCTTCTAGTTGCCAGCCA
TCTGTTGTTTGCCCCTCCCCCGTGCCTTCCTTGACCCTGGAAGGTGCCACTCCCACTGTCCTTTCCTAAT
AAAATGAGGAAATTGCATCGCATTGTCTGAGTAGGTGTCATTCTATTCTGGGGGGTGGGGTGGGGCAGGA
CAGCAAGGGGGAGGATTGGGAAGACAATAGCAGGCATGCTGGGGATGCGGTGGGCTCTATGGC (SEQ
ID NO: 25)

SEQUENCES

AAV5OPSmiR708_155hRho (AAV5 vector with opsin promoter driving expression of miR-708 in a miR-155 scaffold and human rhodopsin minus the miR-708 target sequence)
ACGCGTTTTCTGCAGCGGGGATTAATATGATTATGAACACCCCCAATCTCCCAGATGCTGATTCAGCCAG
GAACTAGTTATTAATAGTAATCAATTACGGGGTCATTAGTTCATAGCCCATATATGGAGTTCCGCGTTAC
ATAACTTACGGTAAATGGCCCGCCTGGCTGACCGCCCAACGACCCCCGCCCATTGACGTCAATAATGACG
TATGTTCCCATAGTAACGCCAATAGGGACTTTCCATTGACGTCAATGGGTGGAGTATTTACGGTAAACTG
CCCACTTGGCAGTACATCAAGTGTATCATATGCCAAGTACGCCCCCTATTGACGTCAATGACGGTAAATG
GCCCGCCTGGCATTATGCCCAGTACATGACCTTATGGGACTTTCCTACTTGGCAGTACATCTACGTATTA
GTCATCGCTATTACCACAAATAGTTATCGAGCCGCTGAGCCGGGGGCGGGGGGTGTGAGACTGGAGGCG
ATGGACGGAGCTGACGGCACACACAGCTCAGATCTGTCAAGTGAGCCATTGTCAGGGCTTGGGGACTGGA
TAAGTCAGGGGGTCTCCTGGGAAGAGATGGGATAGGTGAGTTCAGGAGGAGACATTGTCAACTGGAGCCA
TGTGGAGAAGTGAATTTAGGGCCCAAAGGTTCCAGTCGCAGCCTGAGGCCACCAGACTGACATGGGGAGG
AATTCCCAGAGGACTCTGGGGCAGACAAGATGAGACACCCTTTCCTTTCTTTACCTAAGGGCCTCCACCC
GATGTCACCTTGGCCCCTCTGCAAGCCAATTAGGCCCCGGTGGCAGCAGTGGGATTAGCGTTAGTATGAT
ATCTCGCGGATGCTGAATCAGCCTCTGGCTTAGGGAGAGAAGGTCACTTTATAAGGGTCTGGGGGGGTC
AGTGCCTGGAGTTGCGCTGTGGGAGCCGTCAGTGGCTGAGCTCAACTAGAAGCTTTATTGCGGTAGTTTA
TCACAGTTAAATTGCTAACGCAGTCAGTGCTTCTGACACAACAGTCTCGAACTTAAGCTGCAGTGACTCT
CTTAAGGTAGCCTTGCAGAAGTTGGTCGTGAGGCACTGGGCAGGTAAGTATCAAGGTTACAAGACAGGTT
TAAGGAGACCAATAGAAACTGGGCTTGTCGAGACAGAGAATGGATCCTGGAGGCTTGCTGAAGGCTGTAT
GCTGAAGGAGCTTACAATCTAGCTGGGGTTTTGGCCACTGACTGACCCCAGCTAGTGTAAGCTCCTTCAG
GACACAAGGCCTGTTACTAGCACTCACATGGAACAAATGGCCCAGATCTGAGACTCTTGCGTTTCTGATA
GGCACCTATTGGTCTTACTGACATCCACTTTGCCTTTCTCTCCACAGGTGTCCACTCCCAGTTCACACCG
GCACAATGAATGGCACAGAAGGCCCTAACTTCTACGTGCCCTTCTCCAATGCGACGGGTGTGGTACGCAG
CCCCTTCGAGTACCCACAGTACTACCTGGCTGAGCCATGGCAGTTCTCCATGCTGGCCGCCTACATGTTT
CTGCTGATCGTGCTGGGCTTCCCCATCAACTTCCTCACGCTCTACGTCACCGTCCAGCACAAGAAGCTGC
GCACGCCTCTCAACTACATCCTGCTCAACCTAGCCGTGGCTGACCTCTTCATGGTCCTAGGTGGCTTCAC
CAGCACCCTCTACACCTCTCTGCATGGATACTTCGTCTTCGGGCCCACAGGATGCAATTTGGAGGGCTTC
TTTGCCACCCTGGGCGGTGAAATTGCCCTGTGGTCCTTGGTGGTCCTGGCCATCGAGCGGTACGTGGTGG
TGTGTAAGCCCATGAGCAACTTCCGCTTCGGGGAGAACCATGCCATCATGGGCGTTGCCTTCACCTGGGT
CATGGCGCTGGCCTGCGCCGCACCCCCACTCGCCGGCTGGTCCAGGTACATCCCCGAGGGCCTGCAGTGC
TCGTGTGGAATCGACTACTACACGCTCAAGCCGGAGGTCAACAACGAGTCTTTTGTCATCTACATGTTCG
TGGTCCACTTCACCATCCCCATGATTATCATCTTTTTCTGCTATGGGCAGCTCGTCTTCACCGTCAAGGA
GGCCGCTGCCCAGCAGCAGGAGTCAGCCACCACACAGAAGGCAGAGAAGGAGGTCACCCGCATGGTCATC
ATCATGGTCATCGCTTTCCTGATCTGCTGGGTGCCCTACGCCAGCGTGGCATTCTACATCTTCACCCACC
AGGGCTCCAACTTCGGTCCCATCTTCATGACCATCCCAGCGTTCTTTGCCAAGAGCGCCGCCATCTACAA
CCCTGTCATCTATATCATGATGAACAAGCAGTTCCGGAACTGCATGCTCACCACCATCTGCTGCGGCAAG
AACCCACTGGGTGACGATGAGGCCTCTGCTACCGTGTCCAAGACGGAGACGAGCCAGGTGGCCCCGGCCT
AACCAAGAAAGCTTAAGTTTAAACCGCTGATCAGCCTCGACTGTGCCTTCTAGTTGCCAGCCATCTGTTG
TTTGCCCCTCCCCCGTGCCTTCCTTGACCCTGGAAGGTGCCACTCCCACTGTCCTTTCCTAATAAAATGA
GGAAATTGCATCGCATTGTCTGAGTAGGTGTCATTCTATTCTGGGGGGTGGGGTGGGGCAGGACAGCAAG
GGGGAGGATTGGGAAGACAATAGCAGGCATGCTGGGGATGCGGTGGGCTCTATGGC (SEQ ID
NO: 26)

AAV5OPSmiR708_708hRho (AAV5 vector with opsin promoter driving expression of miR-708 in a miR-708 scaffold and human rhodopsin minus the miR-708 target sequence)
ACGCGTTTTCTGCAGCGGGGATTAATATGATTATGAACACCCCCAATCTCCCAGATGCTGATTCAGCCAG
GAACTAGTTATTAATAGTAATCAATTACGGGGTCATTAGTTCATAGCCCATATATGGAGTTCCGCGTTAC
ATAACTTACGGTAAATGGCCCGCCTGGCTGACCGCCCAACGACCCCCGCCCATTGACGTCAATAATGACG
TATGTTCCCATAGTAACGCCAATAGGGACTTTCCATTGACGTCAATGGGTGGAGTATTTACGGTAAACTG
CCCACTTGGCAGTACATCAAGTGTATCATATGCCAAGTACGCCCCCTATTGACGTCAATGACGGTAAATG
GCCCGCCTGGCATTATGCCCAGTACATGACCTTATGGGACTTTCCTACTTGGCAGTACATCTACGTATTA
GTCATCGCTATTACCACAAATAGTTATCGAGCCGCTGAGCCGGGGGCGGGGGGTGTGAGACTGGAGGCG
ATGGACGGAGCTGACGGCACACACAGCTCAGATCTGTCAAGTGAGCCATTGTCAGGGCTTGGGGACTGGA
TAAGTCAGGGGGTCTCCTGGGAAGAGATGGGATAGGTGAGTTCAGGAGGAGACATTGTCAACTGGAGCCA
TGTGGAGAAGTGAATTTAGGGCCCAAAGGTTCCAGTCGCAGCCTGAGGCCACCAGACTGACATGGGGAGG
AATTCCCAGAGGACTCTGGGGCAGACAAGATGAGACACCCTTTCCTTTCTTTACCTAAGGGCCTCCACCC
GATGTCACCTTGGCCCCTCTGCAAGCCAATTAGGCCCCGGTGGCAGCAGTGGGATTAGCGTTAGTATGAT
ATCTCGCGGATGCTGAATCAGCCTCTGGCTTAGGGAGAGAAGGTCACTTTATAAGGGTCTGGGGGGGTC
AGTGCCTGGAGTTGCGCTGTGGGAGCCGTCAGTGGCTGAGCTCAACTAGAAGCTTTATTGCGGTAGTTTA
TCACAGTTAAATTGCTAACGCAGTCAGTGCTTCTGACACAACAGTCTCGAACTTAAGCTGCAGTGACTCT
CTTAAGGTAGCCTTGCAGAAGTTGGTCGTGAGGCACTGGGCAGGTAAGTATCAAGGTTACAAGACAGGTT
TAAGGAGACCAATAGAAACTGGGCTTGTCGAGACAGAGAAAAACCTAACCCCCATGGTTGGCGAGGGACT
GCTGTGTGTGAAATGGTAACTGCCCTCAAGGAGCTTACAATCTAGCTGGGGTAAATGACTTGCACATGA
ACACAACTAGACTGTGAGCTTCTAGAGGGCAGGGACCTTACCCTAGTCATCTCTTCTCACCCTGCACA
CCCTCCCTGAGGGATCTCATGACTCTTGCGTTTCTGATAGGCACCTATTGGTCTTACTGACATCCACTTT
GCCTTTCTCTCCACAGGTGTCCACTCCCAGTTCACACCGGCACAATGAATGGCACAGAAGGCCCTAACTT
CTACGTGCCCTTCTCCAATGCGACGGGTGTGGTACGCAGCCCCTTCGAGTACCCACAGTACTACCTGGCT
GAGCCATGGCAGTTCTCCATGCTGGCCGCCTACATGTTTCTGCTGATCGTGCTGGGCTTCCCCATCAACT
TCCTCACGCTCTACGTCACCGTCCAGCACAAGAAGCTGCGCACGCCTCTCAACTACATCCTGCTCAACCT
AGCCGTGGCTGACCTCTTCATGGTCCTAGGTGGCTTCACCAGCACCCTCTACACCTCTCTGCATGGATAC
TTCGTCTTCGGGCCCACAGGATGCAATTTGGAGGGCTTCTTTGCCACCCTGGGCGGTGAAATTGCCCTGT
GGTCCTTGGTGGTCCTGGCCATCGAGCGGTACGTGGTGGTGTGTAAGCCCATGAGCAACTTCCGCTTCGG
GGAGAACCATGCCATCATGGGCGTTGCCTTCACCTGGGTCATGGCGCTGGCCTGCGCCGCACCCCCACTC
GCCGGCTGGTCCAGGTACATCCCCGAGGGCCTGCAGTGCTCGTGTGGAATCGACTACTACACGCTCAAGC
CGGAGGTCAACAACGAGTCTTTTGTCATCTACATGTTCGTGGTCCACTTCACCATCCCCATGATTATCAT

SEQUENCES

```
CTTTTTCTGCTATGGGCAGCTCGTCTTCACCGTCAPGGAGGCCGCTGCCCAGCAGCAGGAGTCAGCCACC
ACACAGAAGGCAGAGAAGGAGGTCACCCGCATGGTCATCATCATGGTCATCGCTTTCCTGATCTGCTGGG
TGCCCTACGCCAGCGTGGCATTCTACATCTTCACCCACCAGGGCTCCAACTTCGGTCCCATCTTCATGAC
CATCCCAGCGTTCTTTGCCAAGAGCGCCGCCATCTACAACCCTGTCATCTATATCATGATGAACAAGCAG
TTCCGGAACTGCATGCTCACCACCATCTGCTGCGGCAAGAACCCACTGGGTGACGATGAGGCCTCTGCTA
CCGTGTCCAAGACGGAGACGAGCCAGGTGGCCCCGGCCTAACCAAGAAAGCTTAAGTTTAAACCGCTGAT
CAGCCTCGACTGTGCCTTCTAGTTGCCAGCCATCTGTTGTTTGCCCCTCCCCGTGCCTTCCTTGACCCT
GGAAGGTGCCACTCCCACTGTCCTTTCCTAATAAAATGAGGAAATTGCATCGCATTGTCTGAGTAGGTGT
CATTCTATTCTGGGGGGTGGGGTGGGGCAGGACAGCAAGGGGGAGGATTGGGAAGACAATAGCAGGCATG
CTGGGGATGCGGTGGGCTCTATGGC (SEQ ID NO: 27)
```

Cone Rod Homeobox Containing Transcription Factor

```
AGAGGACTAAGCCACAGGTGAGGAGAAAGGGGGGGGGGGTCTGCTGACCCAGCAACACTCTTTCCTTCT
GAGGCTTAAGAGCTATTAGCGTAGGTGACTCAGTCCCTAATCCTCCATTCAATGCCCTGTGACTGCCCCT
GCTTC (SEQ ID NO: 28)
```

CMV Enhancer

```
ACTAGTTATTAATAGTAATCAATTACGGGGTCATTAGTTCATAGCCCATATATGGAGTTCCGCGTTACAT
AACTTACGGTAAATGGCCCGCCTGGCTGACCGCCCAACGACCCCCGCCCATTGACGTCAATAATGACGTA
TGTTCCCATAGTAACGCCAATAGGGACTTTCCATTGACGTCAATGGGTGGAGTATTTACGGTAAACTGCC
CACTTGGCAGTACATCAAGTGTATCATATGCCAAGTACGCCCCCTATTGACGTCAATGACGGTAAATGGC
CCGCCTGGCATTATGCCCAGTACATGACCTTATGGGACTTTCCTACTTGGCAGTACATCTACGTATTAGT
CATCGCTATTACCA (SEQ ID NO: 29)
```

Neural retinal basic leucine zipper factor

```
TTTCTGCAGCGGGGATTAATATGATTATGAACACCCCCAATCTCCCAGATGCTGATTCAGCCAGGA
(SEQ ID NO: 30)
```

What is claimed is:

1. A rAAV particle comprising a rAAV vector comprising a nucleic acid encoding a miR-708 and a nucleic acid encoding rhodopsin, wherein the nucleic acid encoding rhodopsin comprises a substitution, insertion or deletion of nucleic acid in the miR-708 target sequence wherein the miR-708 target sequence is SEQ ID NO:19.

2. The rAAV particle of claim 1, wherein the nucleic acid encoding miR-708 is operably linked to a promoter.

3. The rAAV particle of claim 2, wherein the promoter comprises a RK promoter or an opsin promoter, or a chicken β-actin (CBA) promoter.

4. The rAAV particle of claim 1, wherein the nucleic acid encoding rhodopsin is operably linked to a promoter.

5. The rAAV particle of claim 4, wherein the promoter comprises a RK promoter or an opsin promoter.

6. The rAAV particle of claim 5, wherein i) the nucleic acid encoding miR-708 and the nucleic acid encoding rhodopsin are operably linked to one RK promoter or opsin promoter; or ii) the nucleic acid encoding miR-708 is operably linked to a first RK promoter or a first opsin promoter and the nucleic acid encoding rhodopsin is operably linked to a second RK promoter or a second opsin promoter.

7. The rAAV particle of claim 2, wherein a sequence derived from a minute virus of mouse (MVM) intron is located 3' to the promoter.

8. The rAAV particle of claim 2, wherein the promoter further comprises i) a CMV enhancer;
ii) a sequence derived from a photoreceptor specific transcription factor;
iii) a sequence derived from a rod photoreceptor specific transcription factor;
iv) a sequence derived from a neural retinal basic zipper factor;
v) a sequence derived from a cone rod homeobox-containing transcription factor sequence;
vi) a CMV enhancer and at least one or more of a sequence derived from a photoreceptor specific transcription factor, a sequence derived from a rod photoreceptor specific transcription factor, a sequence derived from a neural retinal basic zipper factor; or a sequence derived from a cone rod homeobox-containing transcription factor sequence;
vii) a neural retinal basic leucine zipper factor, a CMV enhancer and an Opsin promoter (−500 to +17);
viii) a neural retinal basic leucine zipper factor, a CMV enhancer, an Opsin promoter (−500 to +17), and an MVM intron;
ix) a CMV enhancer comprising SEQ ID NO:29;
x) a neural retinal basic leucine zipper factor sequence comprising SEQ ID NO:30;
xi) a sequence derived from a cone rod homeobox-containing transcription factor sequence comprising SEQ ID NO:28;
xii) a CMV enhancer comprising SEQ ID NO:29 and at least one or more of a sequence derived from a photoreceptor specific transcription factor, a sequence derived from a rod photoreceptor specific transcription factor, a sequence derived from a neural retinal basic zipper factor comprising SEQ ID NO:30; a sequence derived from a cone rod homeobox-containing transcription factor sequence comprising SEQ ID NO:28;

xiii) a neural retinal basic leucine zipper factor comprising SEQ ID NO:30, a CMV enhancer comprising SEQ ID NO:29 and an Opsin promoter (−500 to +17) comprising SEQ ID NO:22; or xiv) a neural retinal basic leucine zipper factor comprising SEQ ID NO:30, a CMV enhancer comprising SEQ ID NO:29, an Opsin promoter (−500 to +17) comprising SEQ ID NO:22, and an MVM intron comprising SEQ ID NO:23.

9. The rAAV particle of claim 1, wherein the nucleic acid encoding miR-708 is embedded in an intron.

10. The rAAV particle of claim 1, wherein the nucleic acid encoding miR-708 comprises an endogenous miR-708 scaffold or a miR-155 scaffold.

11. The rAAV particle of claim 1, wherein the rhodopsin is human rhodopsin.

12. The rAAV particle of claim 1, wherein the substitution, insertion or deletion reduces or prevents recognition by miR-708.

13. The rAAV particle of claim 1, wherein the rhodopsin lacks the 3' UTR miR-708 target sequence.

14. The rAAV particle of claim 1, wherein expression of the rhodopsin is refractory to suppression by miR-708.

15. The rAAV particle of claim 1, wherein the nucleic acid encoding miR-708 comprises the nucleic acid of SEQ ID NO:1, or a nucleic acid having about at least 85% identity to SEQ ID NO:1 and the nucleic acid encoding the rhodopsin comprises nucleic acid of SEQ ID NO:3 or a nucleic acid having about 85% identity to SEQ ID NO:3.

16. The rAAV particle of claim 1, wherein the rhodopsin comprises the amino acid sequence of SEQ ID NO:2, or amino acid sequence having about at least 85% identity to SEQ ID NO:2.

17. The rAAV particle of claim 1, wherein the AAV viral particle comprises a recombinant viral genome comprising a polynucleotide of SEQ ID NO:5, or a polynucleotide having about at least 85% identity to SEQ ID NO:5.

18. The rAAV particle of claim 1, wherein the AAV viral particle comprises a recombinant viral genome comprising a polynucleotide of SEQ ID NO:6, SEQ ID NO:7, SEQ ID NO:24, SEQ ID NO:25, SEQ ID NO:26, or SEQ ID NO:27, or a polynucleotide having about at least 85% identity to SEQ ID NO:6 SEQ ID NO:7, SEQ ID NO:24, SEQ ID NO:25, SEQ ID NO:26, or SEQ ID NO:27.

19. The rAAV particle of claim 1, wherein the AAV viral particle comprises an AAV1, AAV2, AAV3, AAV4, AAV5, AAV6, AAV7, AAV8, AAVrh8, AAVrh8R, AAV9, AAV10, AAVrh10, AAV11, AAV12, AAV2_R471A, AAV2/2-7m8, AAV DJ, AAV2 N587A, AAV2 E548A, AAV2 N708A, AAV V708K, goat AAV, AAV1/AAV2 chimeric AAV, bovine AAV, mouse AAV, or rAAV2/HBoV1 serotype capsid.

20. The rAAV particle of claim 1, wherein the rAAV vector comprises AAV1, AAV2, AAV3, AAV4, AAV5, AAV6, AAV7, AAV8, AAVrh8, AAVrh8R, AAV9, AAV10, AAVrh10, AAV11, AAV12, AAV2R471A, AAV DJ, goat AAV, bovine AAV, or mouse AAV serotype inverted terminal repeats (ITRs).

21. The rAAV particle of claim 1, wherein the ITR and the capsid of the rAAV viral particles are derived from different AAV serotypes.

22. The rAAV particle of claim 21, wherein the rAAV viral particle comprises an AAV-5 capsid or an AAV-5 tyrosine mutant capsid, and wherein the vector comprises AAV2 ITRs.

23. A composition comprising the rAAV particle of claim 1.

24. A composition comprising a first rAAV particle comprising a rAAV vector comprising a nucleic acid encoding a miR-708 and a second rAAV particle comprising a rAAV vector comprising nucleic acid encoding rhodopsin, wherein the nucleic acid encoding rhodopsin comprises a substitution, insertion or deletion of nucleic acid in the miR-708 target sequence wherein the miR-708 target sequence is SEQ ID NO:19.

25. A kit comprising an effective amount of the rAAV particle according to claim 1.

26. A kit comprising an effective amount of the composition of claim 24.

27. An article of manufacture comprising an effective amount of the rAAV particle according to claim 1.

28. An article of manufacture comprising an effective amount of the composition of claim 24.

* * * * *

SEQUENCE LISTING

```
<160> NUMBER OF SEQ ID NOS: 30

<210> SEQ ID NO 1
<211> LENGTH: 88
<212> TYPE: DNA
<213> ORGANISM: Homo sapiens

<400> SEQUENCE: 1
aactgccctc aaggagctta caatctagct gggggtaaat gacttgcaca tgaacacaac    60
tagactgtga gcttctagag ggcaggga                                      88

<210> SEQ ID NO 2
<211> LENGTH: 348
<212> TYPE: PRT
<213> ORGANISM: Homo sapiens

<400> SEQUENCE: 2

Met Asn Gly Thr Glu Gly Pro Asn Phe Tyr Val Pro Phe Ser Asn Ala
1               5                   10                  15

Thr Gly Val Val Arg Ser Pro Phe Glu Tyr Pro Gln Tyr Tyr Leu Ala
            20                  25                  30

Glu Pro Trp Gln Phe Ser Met Leu Ala Ala Tyr Met Phe Leu Leu Ile
        35                  40                  45

Val Leu Gly Phe Pro Ile Asn Phe Leu Thr Leu Tyr Val Thr Val Gln
    50                  55                  60

His Lys Lys Leu Arg Thr Pro Leu Asn Tyr Ile Leu Leu Asn Leu Ala
65                  70                  75                  80

Val Ala Asp Leu Phe Met Val Leu Gly Gly Phe Thr Ser Thr Leu Tyr
                85                  90                  95

Thr Ser Leu His Gly Tyr Phe Val Phe Gly Pro Thr Gly Cys Asn Leu
            100                 105                 110

Glu Gly Phe Phe Ala Thr Leu Gly Gly Glu Ile Ala Leu Trp Ser Leu
```

```
                    115                 120                 125
Val Val Leu Ala Ile Glu Arg Tyr Val Val Cys Lys Pro Met Ser
    130                 135                 140

Asn Phe Arg Phe Gly Glu Asn His Ala Ile Met Gly Val Ala Phe Thr
145                 150                 155                 160

Trp Val Met Ala Leu Ala Cys Ala Ala Pro Pro Leu Ala Gly Trp Ser
                165                 170                 175

Arg Tyr Ile Pro Glu Gly Leu Gln Cys Ser Cys Gly Ile Asp Tyr Tyr
                180                 185                 190

Thr Leu Lys Pro Glu Val Asn Asn Glu Ser Phe Val Ile Tyr Met Phe
                195                 200                 205

Val Val His Phe Thr Ile Pro Met Ile Ile Ile Phe Phe Cys Tyr Gly
    210                 215                 220

Gln Leu Val Phe Thr Val Lys Glu Ala Ala Ala Gln Gln Gln Glu Ser
225                 230                 235                 240

Ala Thr Thr Gln Lys Ala Glu Lys Glu Val Thr Arg Met Val Ile Ile
                245                 250                 255

Met Val Ile Ala Phe Leu Ile Cys Trp Val Pro Tyr Ala Ser Val Ala
                260                 265                 270

Phe Tyr Ile Phe Thr His Gln Gly Ser Asn Phe Gly Pro Ile Phe Met
                275                 280                 285

Thr Ile Pro Ala Phe Phe Ala Lys Ser Ala Ala Ile Tyr Asn Pro Val
                290                 295                 300

Ile Tyr Ile Met Met Asn Lys Gln Phe Arg Asn Cys Met Leu Thr Thr
305                 310                 315                 320

Ile Cys Cys Gly Lys Asn Pro Leu Gly Asp Asp Glu Ala Ser Ala Thr
                325                 330                 335

Val Ser Lys Thr Glu Thr Ser Gln Val Ala Pro Ala
                340                 345
```

<210> SEQ ID NO 3
<211> LENGTH: 1044
<212> TYPE: DNA
<213> ORGANISM: Homo sapiens

<400> SEQUENCE: 3

```
atgaatggca cagaaggccc taacttctac gtgcccttct ccaatgcgac gggtgtggta    60
cgcagcccct tcgagtaccc acagtactac ctggctgagc catggcagtt ctccatgctg   120
gccgcctaca tgtttctgct gatcgtgctg gcttccccca tcaacttcct cacgctctac   180
gtcaccgtcc agcacaagaa gctgcgcacg cctctcaact acatcctgct caacctagcc   240
gtggctgacc tcttcatggt cctaggtggc ttcaccagca ccctctacac ctctctgcat   300
ggatacttcg tcttcgggcc cacaggatgc aatttggagg cttctttgc cacccctgggc   360
ggtgaaattg ccctgtggtc cttggtggtc ctggccatcg agcggtacgt ggtggtgtgt   420
aagcccatga gcaacttccg cttcggggag aaccatgcca tcatgggcgt tgccttcacc   480
tgggtcatgg cgctggcctg cgccgcaccc ccactcgccg gctggtccag gtacatcccc   540
gagggcctgc agtgctcgtg tggaatcgac tactacacgc tcaagccgga ggtcaacaac   600
gagtcttttg tcatctacat gttcgtggtc cacttcacca tccccatgat tatcatcttt   660
ttctgctatg gcagctcgtc ttcaccgtc aaggaggccg ctgcccagca gcaggagtca   720
gccaccacac agaaggcaga gaaggaggtc acccgcatgg tcatcatcat ggtcatcgct   780
ttcctgatct gctgggtgcc ctacgccagc gtggcattct acatcttcac ccaccagggc   840
```

-continued

| | |
|---|---|
| tccaacttcg gtcccatctt catgaccatc ccagcgttct ttgccaagag cgccgccatc | 900 |
| tacaaccctg tcatctatat catgatgaac aagcagttcc ggaactgcat gctcaccacc | 960 |
| atctgctgcg gcaagaaccc actgggtgac gatgaggcct ctgctaccgt gtccaagacg | 1020 |
| gagacgagcc aggtggcccc ggcc | 1044 |

<210> SEQ ID NO 4
<211> LENGTH: 2768
<212> TYPE: DNA
<213> ORGANISM: Homo sapiens

<400> SEQUENCE: 4

| | |
|---|---|
| agagtcatcc agctggagcc ctgagtggct gagctcaggc cttcgcagca ttcttgggtg | 60 |
| ggagcagcca cgggtcagcc acaagggcca cagccatgaa tggcacagaa ggccctaact | 120 |
| tctacgtgcc cttctccaat gcgacgggtg tggtacgcag ccccttcgag tacccacagt | 180 |
| actacctggc tgagccatgg cagttctcca tgctggccgc ctacatgttt ctgctgatcg | 240 |
| tgctgggctt ccccatcaac ttcctcacgc tctacgtcac cgtccagcac aagaagctgc | 300 |
| gcacgcctct caactacatc ctgctcaacc tagccgtggc tgacctcttc atggtcctag | 360 |
| gtggcttcac cagcacccctc tacacctctc tgcatggata cttcgtcttc gggcccacag | 420 |
| gatgcaattt ggagggcttc tttgccaccc tgggcggtga aattgccctg tggtccttgg | 480 |
| tggtcctggc catcgagcgg tacgtggtgg tgtgtaagcc catgagcaac ttccgcttcg | 540 |
| gggagaacca tgccatcatg ggcgttgcct tcacctgggt catggcgctg gcctgcgccg | 600 |
| cacccccact cgccggctgg tccaggtaca tcccgagggg cctgcagtgc tcgtgtggaa | 660 |
| tcgactacta cacgctcaag ccggaggtca caacgagtc ttttgtcatc tacatgttcg | 720 |
| tggtccactt caccatcccc atgattatca tcttttttctg ctatgggcag ctcgtcttca | 780 |
| ccgtcaagga ggccgctgcc cagcagcagg agtcagccac cacacagaag cagagaagg | 840 |
| aggtcacccg catggtcatc atcatggtca tcgctttcct gatctgctgg gtgccctacg | 900 |
| ccagcgtggc attctacatc ttcacccacc agggctccaa cttcggtccc atcttcatga | 960 |
| ccatcccagc gttctttgcc aagagcgccg ccatctacaa ccctgtcatc tatatcatga | 1020 |
| tgaacaagca gttccggaac tgcatgctca ccaccatctg ctgcggcaag aaccccactgg | 1080 |
| gtgacgatga ggcctctgct accgtgtcca agacggagac gagccaggtg gccccggcct | 1140 |
| aagacctgcc taggactctg tggccgacta taggcgtctc ccatccccta caccttcccc | 1200 |
| cagccacagc catcccacca ggagcagcgc ctgtgcagaa tgaacgaagt cacataggct | 1260 |
| ccttaattttt tttttttttt ttaagaaata attaatgagg ctcctcactc acctgggaca | 1320 |
| gcctgagaag ggacatccac caagacctac tgatctggag tcccacgttc cccaaggcca | 1380 |
| gcgggatgtg tgcccctcct cctcccaact catctttcag gaacacgagg attcttgctt | 1440 |
| tctggaaaag tgtcccagct tagggataag tgtctagcac agaatggggc acacagtagg | 1500 |
| tgcttaataa atgctggatg gatgcaggaa ggaatggagg aatgaatggg aagggagaac | 1560 |
| atatctatcc tctcagaccc tcgcagcagc agcaactcat acttggctaa tgatatggag | 1620 |
| cagttgtttt tccctcctg ggcctcactt tcttctccta taaatgaa atcccagatc | 1680 |
| cctggtcctg ccgacacgca gctactgaga agaccaaaag aggtgtgtgt gtgtctatgt | 1740 |
| gtgtgtttca gcactttgta aatagcaaga agctgtacag attctagtta atgttgtgaa | 1800 |
| taacatcaat taatgtaact agttaattac tatgattatc acctcctgat agtgaacatt | 1860 |

```
ttgagattgg gcattcagat gatggggttt cacccaacct tggggcaggt ttttaaaaat    1920
tagctaggca tcaaggccag accagggctg ggggttgggc tgtaggcagg gacagtcaca    1980
ggaatgcaga atgcagtcat cagacctgaa aaaacaacac tgggggaggg ggacggtgaa    2040
ggccaagttc ccaatgaggg tgagattggg cctggggtct caccectagt gtggggcccc    2100 aggtcccgtg cctcccette ccaatgtggc ctatggagag acaggccttt ctctcagcct    2160
ctggaagcca cctgctcttt tgctctagca cctgggtccc agcatctaga gcatggagcc    2220
tctagaagcc atgctcaccc gcccacattt aattaacagc tgagtccctg atgtcatcct    2280
tatctcgaag agcttagaaa caaagagtgg gaaattccac tgggcctacc ttccttgggg    2340
atgttcatgg gccccagttt ccagtttccc ttgccagaca gcccatctt cagcagttgc     2400 tagtccattc tccattctgg agaatctgct ccaaaaagct ggccacatct ctgaggtgtc    2460
agaattaagc tgcctcagta actgctcccc cttctccata taagcaaagc cagaagctct    2520
agctttaccc agctctgcct ggagactaag gcaaattggg ccattaaaag ctcagctcct    2580
atgttggtat taacggtggt gggttttgtt gctttcacac tctatccaca ggatagattg    2640
aaactgccag cttccacctg atccctgacc ctgggatggc tggattgagc aatgagcaga    2700
gccaagcagc acagagtccc ctggggctag aggtggagga ggcagtcctg ggaatgggaa    2760
aaaccccca                                                            2768
```

<210> SEQ ID NO 5
<211> LENGTH: 1512
<212> TYPE: DNA
<213> ORGANISM: Artificial Sequence
<220> FEATURE:
<223> OTHER INFORMATION: Synthetic Construct

<400> SEQUENCE: 5

```
ggccccagaa gcctggtggt tgtttgtcct tctcagggga aaagtgaggc ggcccccttgg     60 aggaaggggc cgggcagaat gatctaatcg gattccaagc agctcagggg attgtctttt    120
tctagcacct tcttgccact cctaagcgtc ctccgtgacc ccggctggga tttagcctgg    180
tgctgtgtca gccccggtct cccaggggct cccagtggt ccccaggaac cctcgacagg     240
gcccggtctc tctcgtccag caagggcagg gacgggccac aggccaaggg cggagtcgct    300
gcgacgctgc cttcgccccg tgccccgctc cgccgccgcc tcgcgccgcc cgccccggct    360
ctgactgacc gcgttactcc cacaggtgag cgggcgggac ggcccttctc ctccgggctg    420
taattagcgc ttggtttaat gacggcttgt ttcttttctg tggctgcgtg aaagccttga    480
ggggctccgg gagggcccct tgtgcggggg gagcggctcg ggggtgcgt gcgtgtgtgt     540 gtgcgtgggg agcgccgcgt gcggctccgc gctgccgc ggctgtgagc gctgcgggcg      600
cggcgcgggg ctttgtgcgc tccgcagtgt gcgcgagggg agcgcggccg ggggcggtgc    660
cccgcggtgc ggggggggct gcgagggaa caaaggctgc gtgcggggtg tgtgcgtggg     720
ggggtgagca gggggtgtgg gcgcgtcggt cgggctgcaa ccccccctgc accccctcc    780 ccgagttgct gagcacggcc cggcttcggg tgcgggctc cgtacggggc gtggcgcggg     840
gctcgccgtg ccgggcgggg ggtggcggca ggtgggggtg ccggcgggg cggggccgcc    900 tcgggccggg gagggctcgg gggagggggcg cggcggcccc cggagcgccg cggctgtcg    960 aggcgcggcg agccgcagcc attgccttt atggtaatcg tgcgagaggg cgcagggact   1020
tcctttgtcc caaatctgtg cggagccgaa atctgggagg cgccgccgca ccccctctag   1080
cgggcgcggg gcgaagcggt gcggcgccgg caggaaggaa atgggcgggg agggccttcg   1140
```

```
tgcgtcgccg cgccgccgtc cccttctccc tctccagcct cggggctgtc cgcgggggga    1200
cggctgcctt cgggggggac ggggcagggc ggggttcggc ttctggcgtg tgaccggcgg    1260
ctctagagcc tctgctaacc atgttcatgc cttcttcttt ttcctacagc tcctgggcaa    1320
cgtgctggtt attgtgctgt ctcatcattt tggcaaagaa ttcttcgaaa gatcctggag    1380
gcttgctgaa ggctgtatgc tgaaggagct tacaatctag ctggggtttt ggccactgac    1440
tgaccccagc tagtgtaagc tccttcagga cacaaggcct gttactagca ctcacatgga    1500
acaaatggcc ca                                                        1512
```

<210> SEQ ID NO 6
<211> LENGTH: 3444
<212> TYPE: DNA
<213> ORGANISM: Artificial Sequence
<220> FEATURE:
<223> OTHER INFORMATION: Synthetic Construct

<400> SEQUENCE: 6

```
caatctccca gatgctgatt cagccaggaa ctagttatta atagtaatca attacgggt      60 cattagttca tagcccatat atggagttcc gcgttacata acttacggta aatggcccgc    120
ctggctgacc gcccaacgac ccccgcccat tgacgtcaat aatgacgtat gttcccatag    180
taacgccaat agggactttc cattgacgtc aatgggtgga gtatttacgg taaactgccc    240
acttggcagt acatcaagtg tatcatatgc caagtacgcc ccctattgac gtcaatgacg    300
gtaaatggcc cgcctggcat tatgcccagt acatgacctt atgggacttt cctacttggc    360
agtacatcta cgtattagtc atcgctatta ccacaaatag ttatcgagcc gctgagccgg    420
ggggcggggg gtgtgagact ggaggcgatg gacggagctg acggcacaca cagctcagat    480
ctgtcaagtg agccattgtc agggcttggg gactggataa gtcaggggt ctcctgggaa     540 gagatgggat aggtgagttc aggaggagac attgtcaact ggagccatgt ggagaagtga    600
atttagggcc caaaggttcc agtcgcagcc tgaggccacc agactgacat ggggaggaat    660
tcccagagga ctctggggca gacaagatga gacacccttt cctttcttta cctaagggcc    720
tccacccgat gtcaccttgg cccctctgca agccaattag gccccggtgg cagcagtggg    780
attagcgtta gtatgatatc tcgcggatgc tgaatcagcc tctggcttag ggagagaagg    840
tcactttata agggtctggg gggggtcagt gcctggagtt gcgctgtggg agccgtcagt    900
ggctgagctc aagaggtaag ggtttaaggg atggttggtt ggtggggtat taatgtttaa    960
ttacctgttt tacaggcctg aaatcacttg gttttaggtt ggtacatctg cagaattcag   1020
ccaccaccgg cacaatgaat ggcacagaag gccctaactt ctacgtgccc ttctccaatg   1080
cgacgggtgt ggtacgcagc cccttcgagt acccacagta ctacctggct gagccatggc   1140
agttctccat gctggccgcc tacatgtttc tgctgatcgt gctgggcttc cccatcaact   1200
tcctcacgct ctacgtcacc gtccagcaca agaagctgcg cacgcctctc aactacatcc   1260
tgctcaacct agccgtggct gacctcttca tggtcctagg tggcttcacc agcaccctct   1320
acacctctct gcatggatac ttcgtcttcg ggcccacagg atgcaatttg gagggcttct   1380
ttgccaccct gggcggtgaa attgcccgtg gtccttggt ggtcctggcc atcgagcggt    1440
acgtggtggt gtgtaagccc atgagcaact tccgcttcgg ggagaaccat gccatcatgg   1500
gcgttgcctt cacctgggtc atggcgctgg cctgcgccgc acccccactc gccgctggt    1560 ccaggtacat ccccgagggc ctgcagtgct cgtgtggaat cgactactac acgctcaagc   1620
```

-continued

```
cggaggtcaa caacgagtct tttgtcatct acatgttcgt ggtccacttc accatcccca    1680
tgattatcat cttttctgc tatgggcagc tcgtcttcac cgtcaaggag gccgctgccc     1740
agcagcagga gtcagccacc acacagaagg cagagaagga ggtcacccgc atggtcatca   1800
tcatggtcat cgctttcctg atctgctggg tgccctacgc cagcgtggca ttctacatct   1860
tcacccacca gggctccaac ttcggtccca tcttcatgac catcccagcg ttctttgcca   1920
agagcgccgc catctacaac cctgtcatct atatcatgat gaacaagcag ttccggaact   1980
gcatgctcac caccatctgc tgcggcaaga acccactggg tgacgatgag gcctctgcta   2040
ccgtgtccaa gacggagacg agccaggtgg ccccggccta accaagaaag cttaagtttg   2100
tgtcccggct tagggctaaa tgtctaggac agaatggaac acatagtagc tgattaataa   2160
atgctagctg gatgaaggga ggaatgagtg actgactgag tggatatatg agtgaaggga   2220
ttaatggaag ggaacatgga tgtcctcagg tgcccaacct ggcagatcca gtcatgtctg   2280
gctggaatct ataagcagtt ttacatacct gccctgagct ttattgcggt agtttatcac   2340
agttaaattg ctaacgcagt cagtgcttct gacacaacag tctcgaactt aagctgcagt   2400
gactctctta aggtagcctt gcagaagttg gtcgtgaggc actgggcagg taagtatcaa   2460
ggttacaaga caggtttaag gagaccaata gaaactgggc ttgtcgagac agagaaaaac   2520
ctaaccccca tggttggcga gggactgctg tgtgtgaaat ggtaactgcc ctcaaggagc   2580
ttacaatcta gctgggggta aatgacttgc acatgaacac aactagactg tgagcttcta   2640
gagggcaggg accttaccct agtcatctct cttctcaccc tgcacaccct ccctgaggga   2700
tctcatgact cttgcgtttc tgataggcac ctattggtct tactgacatc cactttgcct   2760
ttctctccac aggtgtccac tcccagttca caccggcaca atgaatggca cagaaggccc   2820
taacttctac gtgcccttct ccaatgcgac gggtgtggta cgcagcccct tcgagtaccc   2880
acagtcagag ataaatgaca gtgacagcaa cgtgagctgc agcccttagg actgagaaag   2940
catcgagacc aggggtctcc ggcaaggcct aggtcctccc ttcagtatgg aaaccttgcc   3000
tcatgtctct cagcctcctt ggcctgtgga gatccagccc ttcctcttgg cttctggata   3060
catttgctct tctacaccag caaccaagtg gcaacagttc caggccagta tggagtttta   3120
gaagccatgc caatatgccc accttcaggg agcagctgag tccttgatgc caccettgtt   3180 ctgaagagtt cagaaacaca gtgcaagaca tgaccaggcc tcatccttag gatgctcatg   3240
gatccagttc ttagctccct tgttggatat gctgttttcc ttggcctttg gtcttttctt   3300
tatcccagag ggttttggct ttaaggccaa caggaactat ggggtaccag aattgagcag   3360
cctcagtctg catccctcct ctatagaacc acagctgggc cctcagcagg cccaactctg   3420
catggggaca gaggcattaa aagc                                          3444
```

<210> SEQ ID NO 7
<211> LENGTH: 3014
<212> TYPE: DNA
<213> ORGANISM: Artificial Sequence
<220> FEATURE:
<223> OTHER INFORMATION: Synthetic Construct
<400> SEQUENCE: 7

```
gggccccaga agcctggtgg ttgtttgtcc ttctcagggg aaaagtgagg cggcccttg      60 gaggaagggg ccgggcagaa tgatctaatc ggattccaag cagctcaggg gattgtcttt    120
ttctagcacc ttcttgccac tcctaagcgt cctccgtgac cccggctggg atttagcctg    180
gtgctgtgtc agccccggtc tcccaggggc ttcccagtgg tccccaggaa ccctcgacag    240
```

```
ggcccggtct ctctcgtcca gcaagggcag ggacgggcca caggccaagg gcggagtcgc    300
tgcgacgctg ccttcgcccc gtgccccgct ccgccgccgc ctcgcgccgc ccgcccccgg    360
tctgactgac cgcgttactc ccacaggtga gcgggcggga cggccttct cctccgggct     420 gtaattagca agaggtaagg gtttaaggga tggttggttg gtggggtatt aatgtttaat    480
tacctgtttt acaggcctga aatcacttgg ttttaggttg gggatccggt acccaattgc    540
catgggctag catgcatgag ctccctgcag ggtttatctg cagaattcag ccaccaccgg    600
cacaatgaat ggcacagaag gccctaactt ctacgtgccc ttctccaatg cgacgggtgt    660
ggtacgcagc cccttcgagt acccacagta ctacctggct gagccatggc agttctccat    720
gctggccgcc tacatgtttc tgctgatcgt gctgggcttc cccatcaact tcctcacgct    780
ctacgtcacc gtccagcaca gaagctgcg cacgcctctc aactacatcc tgctcaacct     840
agccgtggct gacctcttca tggtcctagg tggcttcacc agcaccctct acacctctct    900
gcatggatac ttcgtcttcg ggcccacagg atgcaatttg gagggcttct ttgccaccct    960
gggcggtgaa attgccctgt ggtccttggt ggtcctggcc atcgagcggt acgtggtggt    1020
gtgtaagccc atgagcaact tccgcttcgg ggagaaccat gccatcatgg gcgttgcctt    1080
cacctgggtc atggcgctgg cctgcgccgc accccactc gccggctggt ccaggtacat      1140
ccccgagggc ctgcagtgct cgtgtggaat cgactactac acgctcaagc cggaggtcaa    1200
caacgagtct tttgtcatct acatgttcgt ggtccacttc accatcccca tgattatcat    1260 cttttctgc tatgggcagc tcgtcttcac cgtcaaggag gccgctgccc agcagcagga     1320
gtcagccacc acacagaagg cagagaagga ggtcacccgc atggtcatca tcatggtcat    1380
cgctttcctg atctgctggg tgccctacgc cagcgtggca ttctacatct tcacccacca    1440
gggctccaac ttcggtccca tcttcatgac catcccagcg ttctttgcca agagcgccgc    1500
catctacaac cctgtcatct atatcatgat gaacaagcag ttccggaact gcatgctcac    1560
caccatctgc tgcggcaaga acccactggg tgacgatgag gcctctgcta ccgtgtccaa    1620
gacggagacg agccaggtgg ccccggccta accaagaaag cttaagtttg tgtcccggct    1680
tagggctaaa tgtctaggac agaatggaac acatagtagc tgattaataa atgctagctg    1740
gatgaaggga ggaatgagtg actgactgag tggatatatg agtgaaggga ttaatggaag    1800
ggaacatgga tgtcctcagg tgcccaacct ggcagatcca gtcatgtctg gctgaatct     1860 ataagcagtt ttacatacct gccctgagct ttattgcggt agtttatcac agttaaattg    1920
ctaacgcagt cagtgcttct gacacaacag tctcgaactt aagctgcagt gactctctta    1980
aggtagcctt gcagaagttg gtcgtgaggc actgggcagg taagtatcaa ggttacaaga    2040
caggtttaag gagaccaata gaaactgggc ttgtcgagac agagaaaaac ctaaccccca    2100
tggttggcga gggactgctg tgtgtgaaat ggtaactgcc ctcaaggagc ttacaatcta    2160
gctgggggta aatgacttgc acatgaacac aactagactg tgagcttcta gagggcaggg    2220
accttaccct agtcatctct cttctcaccc tgcacaccct ccctgaggga tctcatgact    2280
cttgcgtttc tgataggcac ctattggtct tactgacatc cactttgcct ttctctccac    2340
aggtgtccac tcccagttca caccggcaca atgaatggca cagaaggccc taacttctac    2400
gtgcccttct ccaatgcgac gggtgtggta cgcagcccct tcgagtaccc acagtcagag    2460
ataaatgaca gtgacagcaa cgtgagctgc agccctagg actgagaaag catcgagacc     2520
aggggtctcc ggcaaggcct aggtcctccc ttcagtatgg aaaccttgcc tcatgtctct    2580
```

| | |
|---|---:|
| cagcctcctt ggcctgtgga gatccagccc ttcctcttgg cttctggata catttgctct | 2640 |
| tctacaccag caaccaagtg gcaacagttc caggccagta tggagtttta gaagccatgc | 2700 |
| caatatgccc accttcaggg agcagctgag tccttgatgc cacccttgtt ctgaagagtt | 2760 |
| cagaaacaca gtgcaagaca tgaccaggcc tcatccttag gatgctcatg gatccagttc | 2820 |
| ttagctccct tgttggatat gctgttttcc ttggcctttg gtcttttctt tatcccagag | 2880 |
| ggttttggct ttaaggccaa caggaactat ggggtaccag aattgagcag cctcagtctg | 2940 |
| catccctcct ctatagaacc acagctgggc cctcagcagg cccaactctg catggggaca | 3000 |
| gaggcattaa aagc | 3014 |

<210> SEQ ID NO 8
<211> LENGTH: 1826
<212> TYPE: DNA
<213> ORGANISM: Artificial Sequence
<220> FEATURE:
<223> OTHER INFORMATION: Synthetic Construct

<400> SEQUENCE: 8

| | |
|---|---:|
| gggccccaga agcctggtgg ttgtttgtcc ttctcagggg aaaagtgagg cggcccttg | 60 |
| gaggaagggg ccgggcagaa tgatctaatc ggattccaag cagctcaggg gattgtcttt | 120 |
| ttctagcacc ttcttgccac tcctaagcgt cctccgtgac cccggctggg atttagcctg | 180 |
| gtgctgtgtc agccccggtc tcccaggggc ttcccagtgg tccccaggaa ccctcgacag | 240 |
| ggcccggtct ctctcgtcca gcaagggcag ggacgggcca caggccaagg gcactagaag | 300 |
| ctttattgcg gtagtttatc acagttaaat tgctaacgca gtcagtgctt ctgacacaac | 360 |
| agtctcgaac ttaagctgca gtgactctct taaggtagcc ttgcagaagt tggtcgtgag | 420 |
| gcactgggca ggtaagtatc aaggttacaa gacaggttta aggagaccaa tagaaactgg | 480 |
| gcttgtcgag acagagaaaa acctaacccc catggttggc gagggactgc tgtgtgtgaa | 540 |
| atggtaactg ccctcaagga gcttacaatc tagctggggg taaatgactt gcacatgaac | 600 |
| acaactagac tgtgagcttc tagagggcag ggaccttacc ctagtcatct ctcttctcac | 660 |
| cctgcacacc ctccctgagg gatctcatga ctccttgcgtt tctgataggc acctattggt | 720 |
| cttactgaca tccactttgc cttttctctcc acaggtgtcc actcccagtt cacaccggca | 780 |
| caatgaatgg cacagaaggc cctaacttct acgtgccctt ctccaatgcg acgggtgtgg | 840 |
| tacgcagccc cttcgagtac ccacagtact acctggctga gccatggcag ttctccatgc | 900 |
| tggccgccta catgtttctg ctgatcgtgc tgggcttccc catcaacttc ctcacgctct | 960 |
| acgtcaccgt ccagcacaag aagctgcgca cgcctctcaa ctacatcctg ctcaacctag | 1020 |
| ccgtggctga cctcttcatg gtcctaggtg gcttcaccag caccctctac acctctctgc | 1080 |
| atggatactt cgtcttcggg cccacaggat gcaatttgga gggcttcttt gccaccctgg | 1140 |
| gcggtgaaat tgccctgtgg tccttggtgg tcctggccat cgagcggtac gtggtggtgt | 1200 |
| gtaagccat gagcaacttc cgcttcgggg agaaccatgc catcatgggc gttgccttca | 1260 |
| cctgggtcat ggcgctggcc tgcgccgcac ccccactcgc cggctggtcc aggtacatcc | 1320 |
| ccgagggcct gcagtgctcg tgtggaatcg actactacac gctcaagccg gaggtcaaca | 1380 |
| acgagtcttt tgtcatctac atgttcgtgg tccacttcac catccccatg attatcatct | 1440 |
| ttttctgcta tgggcagctc gtcttcaccg tcaaggaggc cgctgcccag cagcaggagt | 1500 |
| cagccaccac acagaaggca gagaaggagg tcacccgcat ggtcatcatc atggtcatcg | 1560 |
| cttttcctga tctgctgggtg ccctacgcca gcgtggcatt ctacatcttc acccaccagg | 1620 |

```
gctccaactt cggtcccatc ttcatgacca tcccagcgtt ctttgccaag agcgccgcca    1680
tctacaaccc tgtcatctat atcatgatga acaagcagtt ccggaactgc atgctcacca    1740
ccatctgctg cggcaagaac ccactgggtg acgatgaggc ctctgctacc gtgtccaaga    1800
cggagacgag ccaggtggcc ccggcc                                        1826

<210> SEQ ID NO 9
<211> LENGTH: 3444
<212> TYPE: DNA
<213> ORGANISM: Artificial Sequence
<220> FEATURE:
<223> OTHER INFORMATION: Synthetic Construct

<400> SEQUENCE: 9
caatctccca gatgctgatt cagccaggaa ctagttatta atagtaatca attacggggt      60
cattagttca tagcccatat atggagttcc gcgttacata acttacggta aatggcccgc     120
ctggctgacc gcccaacgac ccccgcccat tgacgtcaat aatgacgtat gttcccatag     180
taacgccaat agggactttc cattgacgtc aatgggtgga gtatttacgg taaactgccc     240
acttggcagt acatcaagtg tatcatatgc caagtacgcc ccctattgac gtcaatgacg     300
gtaaatggcc cgcctggcat tatgcccagt acatgacctt atgggacttt cctacttggc     360
agtacatcta cgtattagtc atcgctatta ccacaaatag ttatcgagcc gctgagccgg     420
ggggcggggg gtgtgagact ggaggcgatg gacggagctg acggcacaca cagctcagat     480
ctgtcaagtg agccattgtc agggcttggg gactggataa gtcagggggt ctcctgggaa     540
gagatgggat aggtgagttc aggaggagac attgtcaact ggagccatgt ggagaagtga     600
atttagggcc caaaggttcc agtcgcagcc tgaggccacc agactgacat ggggaggaat     660
tcccagagga ctctggggca gacaagatga gacaccctt cctttcttta cctaagggcc     720
tccacccgat gtcaccttgg cccctctgca agccaattag gccccggtgg cagcagtggg     780
attagcgtta gtatgatatc tcgcggatgc tgaatcagcc tctggcttag ggagagaagg     840
tcactttata agggtctggg gggggtcagt gcctggagtt gcgctgtggg agccgtcagt     900
ggctgagctc aagaggtaag ggtttaaggg atggttggtg gtgggggtat taatgtttaa     960
ttacctgttt tacaggcctg aaatcacttg gttttaggtt ggtacatctg cagaattcag    1020
ccaccaccgg cacaatgaat ggcacagaag gccctaactt ctacgtgccc ttctccaatg    1080
cgacgggtgt ggtacgcagc cccttcgagt acccacagta ctacctggct gagccatggc    1140
agttctccat gctggccgcc tacatgtttc tgctgatcgt gctgggcttc cccatcaact    1200
tcctcacgct ctacgtcacc gtccagcaca gaagctgcg cacgcctctc aactacatcc    1260
tgctcaacct agccgtggct gacctcttca tggtcctagg tggcttcacc agcacctct    1320 acacctctct gcatggatac ttcgtcttcg ggcccacagg atgcaatttg gagggcttct    1380
ttgccaccct gggcggtgaa attgcccgtg gtccttggt ggtcctggcc atcgagcggt    1440
acgtggtggt gtgtaagccc atgagcaact tccgcttcgg ggagaaccat gccatcatgg    1500
gcgttgcctt cacctgggtc atggcgctgg cctgcgccgc accccactc gccggctggt    1560 ccaggtacat ccccgagggc ctgcagtgct cgtgtggaat cgactactac acgctcaagc    1620
cggaggtcaa caacgagtct tttgtcatct acatgttcgt ggtccacttc accatcccca    1680
tgattatcat cttttttctgc tatgggcagc tcgtcttcac cgtcaaggag gccgctgccc    1740
agcagcagga gtcagccacc acacagaagg cagagaagga ggtcacccgc atggtcatca    1800
```

```
tcatggtcat cgctttcctg atctgctggg tgccctacgc cagcgtggca ttctacatct    1860
tcacccacca gggctccaac ttcggtccca tcttcatgac catcccagcg ttctttgcca    1920
agagcgccgc catctacaac cctgtcatct atatcatgat gaacaagcag ttccggaact    1980
gcatgctcac caccatctgc tgcggcaaga acccactggg tgacgatgag gcctctgcta    2040
ccgtgtccaa gacggagacg agccaggtgg ccccggccta accagaaaag cttaagtttg    2100
tgtcccggct tagggctaaa tgtctaggac agaatggaac acatagtagc tgattaataa    2160
atgctagctg gatgaaggga ggaatgagtg actgactgag tggatatatg agtgaaggga    2220
ttaatggaag ggaacatgga tgtcctcagg tgcccaacct ggcagatcca gtcatgtctg    2280
gctggaatct ataagcagtt ttacatacct gccctgagct ttattgcggt agtttatcac    2340
agttaaattg ctaacgcagt cagtgcttct gacacaacag tctcgaactt aagctgcagt    2400
gactctctta aggtagcctt gcagaagttg gtcgtgaggc actgggcagg taagtatcaa    2460
ggttacaaga caggtttaag gagaccaata gaaactgggc ttgtcgagac agagaaaaac    2520
ctaaccccca tggttggcga gggactgctg tgtgtgaaat ggtaactgcc tcaaggagc    2580 ttacaatcta gctgggggta aatgacttgc acatgaacac aactagactg tgagcttcta    2640
gagggcaggg accttaccct agtcatctct cttctcaccc tgcacaccct ccctgaggga    2700
tctcatgact cttgcgtttc tgataggcac ctattggtct tactgacatc cactttgcct    2760
ttctctccac agtgtccac tcccagttca caccggcaca atgaatggca cagaaggccc    2820
taacttctac gtgcccttct ccaatgcgac gggtgtggta cgcagcccct tcgagtaccc    2880
acagtcagag ataaatgaca gtgacagcaa cgtgagctgc agcccttagg actgagaaag    2940
catcgagacc aggggtctcc ggcaaggcct aggtcctccc ttcagtatgg aaaccttgcc    3000
tcatgtctct cagcctcctt ggctgtggtga gatccagccc ttcctcttgg cttctggata    3060
catttgctct tctacaccag caaccaagtg gcaacagttc caggccagta tggagtttta    3120
gaagccatgc caatatgccc accttcaggg agcagctgag tccttgatgc caccccttgtt    3180 ctgaagagtt cagaaacaca gtgcaagaca tgaccaggcc tcatccttag gatgctcatg    3240
gatccagttc ttagctccct tgttggatat gctgttttcc ttggcctttg gtcttttctt    3300
tatcccagag ggttttggct ttaaggccaa caggaactat ggggtaccag aattgagcag    3360
cctcagtctg catccctcct ctatagaacc acagctgggc cctcagcagg cccaactctg    3420
catggggaca gaggcattaa aagc                                            3444

<210> SEQ ID NO 10
<211> LENGTH: 1017
<212> TYPE: DNA
<213> ORGANISM: Artificial Sequence
<220> FEATURE:
<223> OTHER INFORMATION: Synthetic Construct

<400> SEQUENCE: 10
ggagtcgctg cgacgctgcc ttcgccccgt gccccgctcc gccgccgcct cgcgccgccc      60
gccccggctc tgactgaccg cgttactccc acaggtgagc gggcgggacg gcccttctcc    120
tccgggctgt aattagcgct tggtttaatg acggcttgtt tcttttctgt ggctgcgtga    180
aagccttgag gggctccggg agggcccttt gtgcgggggg agcggctcgg ggggtgcgtg    240
cgtgtgtgtg tgcgtgggga gcgccgcgtg cggctccgcg ctgcccggcg gctgtgagcg    300
ctgcgggcgc ggcgcggggc tttgtgcgct ccgcagtgtg cgcgagggga gcgcggccgg    360
gggcggtgcc ccgcggtgcg ggggggggctg cgaggggaac aaaggctgcg tgcggggtgt    420
```

```
gtgcgtgggg gggtgagcag ggggtgtggg cgcgtcggtc gggctgcaac ccccctgca      480 cccccctccc cgagttgctg agcacggccc ggcttcgggt gcggggctcc gtacggggcg      540
tggcgcgggg ctcgccgtgc cgggcggggg gtggcggcag gtgggggtgc cgggcggggc      600
ggggccgcct cgggccgggg agggctcggg ggaggggcgc ggcggccccc ggagcgccgg      660
cggctgtcga ggcgcggcga gccgcagcca ttgcctttta tggtaatcgt gcgagagggc      720
gcagggactt cctttgtccc aaatctgtgc ggagccgaaa tctgggaggc gccgccgcac      780
cccctctagc gggcgcgggg cgaagcggtg cggcgccggc aggaaggaaa tgggcgggga      840
gggccttcgt gcgtcgccgc gccgccgtcc ccttctccct ctccagcctc ggggctgtcc      900 gcgggggggac ggctgccttc ggggggggacg gggcagggcg gggttcggct tctggcgtgt     960
gaccggcggc tctagagcct ctgctaacca tgttcatgcc ttcttctttt tcctaca        1017

<210> SEQ ID NO 11
<211> LENGTH: 2239
<212> TYPE: DNA
<213> ORGANISM: Artificial Sequence
<220> FEATURE:
<223> OTHER INFORMATION: Synthetic Construct

<400> SEQUENCE: 11
aagcttgaaa tgccacctcc tctgatattc taggtgtcct ggaagcctgt ctcatcttgc       60
cctgtagtgt tgggtcacct ggcccccagc ctgtaacatc cccagggccc tacacccaga      120
gaaacacggg gctggtggca gtgcccagtg acaaccgttt agtggataag agaagagtga      180
ccacaccagg ctgagtgctc ctctctggtt ttccatgggg agacaatgcc accctgagca      240
gggtctggtg tgagcggcag ctggctctgg gctctctgat ccgttaccct ctcagcctct      300
ttgttctttc tcaacccctg gagcagagac ctcaggaggt gctggcatgg aacagagaaa      360
ttccagcctc gattcctatt atgaacccga cacctttttgt attttcatct tggttttaca      420
gtgtacaaaa cgaactagat cagcagggca tgggcataat cacgaatgca cacacataca      480
ctaatgtgtg gctcatgttt aagtatcact tactacagga cacccaatct aacagcaccg      540
ataaagtgac agagaaacgc aagccttctg cgaacatggc ctggctgttc caattccgaa      600
ccttgctttt ctgggccttg ccacacaggc tcttcccccg tccccccagg gacattctac      660
ccttgaactc cacactccac tgctgccttt gccaggaagc ccatctgttc cttttttggtt      720 ctgccagaac gtgtggtggt gctgctgtcc ctgccttggg cactggatat tgggaaggga      780
cagtgtccac actggagtgg gaagttccca gggacgagac ctttacctcc tcaccctggg      840
tactgttctc ctcatggagc atggacggcg ctgcctgaac tcagtggtgg cctcattctg      900
gaagccaagt ttatacagag tagcagtgac ccagggatgt ggggttcacc ctcctcagcc      960
ctctggccag tcctgatggg cctcagtccc aacatggcta agaggtgtgg gcagcttctt     1020
ggtcaccctc aggtttggga atcaccttct gtcttcattt tccaggaact tggtgatgat     1080
atcgtgggtg agttcattta ccaggtgctg tagtttcccc tcatcaggca ggaagaagat     1140
ggcggtggca ttgcccaggt atttcatcag cagcacccag ctggacagct tcttacagtg     1200
ctggatgtta aacatgccta aacgcttcat cataggcacc ttcacggtgg tcacctggtc     1260
cacgtggaag tcctcttcct cggtgtcctt gacttcaaag ggtctctccc atttgcctgg     1320
agagagggga aggtgggcat caccaggggt gagtgaaggt ttggaagagt gtagcagaat     1380
aagaaaccat gagtcccctc cctgagaagc cctgagcccc cttgacgaca cacatccctc     1440
```

```
gaggctcagc ttcatcatct gtaaaaggtg ctgaaactga ccatccaagc tgccgaaaaa    1500
gattgtgtgg ggataattca aaactagagg aagatgcaga atttctacat cgtggcgatg    1560
tcaggctaag agatgccatc gtggctgtgc attttttattg gaatcatatg tttatttgag   1620
ggtgtcttgg atattacaaa taaaatgttg gagcatcagg catatttggt accttctgtc    1680
taaggctccc tgccccttgt taattggcag ctcagttatt catccagggc aaacattctg    1740
cttactattc ctgagagctt tcctcatcct ctagattggc aggggaaatg cagatgcctg    1800
agcagcctcc cctctgccat accaacagag cttcaccatc gaggcatgca gagtggacag    1860
gggcctcagg gaccctgat cccagctttc tcattggaca aaggaggag actgggctg       1920 gagagggacc tgggccccca ctaaggccac agcagagcca ggactttagc tgtgctgact    1980
gcagcctggc ttgcctccac tgccctcctt tgcctcaaga gcaagggagc ctcagagtgg    2040
aggaagcagc ccctggcctt gcctcccacc tcccctcccc tatgctgttt tcctgggaca    2100
gtgggagctg gcttagaatg ccctggggcc cccaggaccc tggcatttta acccctcagg    2160
ggcaggaagg cagcctgaga tacagaagag tccatcacct gctgtatgcc acacaccatc    2220
cccacagtta cgtactagt                                                 2239
```

<210> SEQ ID NO 12
<211> LENGTH: 6408
<212> TYPE: DNA
<213> ORGANISM: Artificial Sequence
<220> FEATURE:
<223> OTHER INFORMATION: Synthetic Construct

<400> SEQUENCE: 12

```
gaattcggac cgtcgacatt gattattgac tagttattaa tagtaatcaa ttacggggtc      60
attagttcat agcccatata tggagttccg cgttacataa cttacggtaa atggcccgcc     120
tggctgaccg cccaacgacc cccgcccatt gacgtcaata atgacgtatg ttcccatagt     180
aacgccaata gggactttcc attgacgtca atgggtggag tatttacggt aaactgccca    240
cttggcagta catcaagtgt atcatatgcc aagtacgccc cctattgacg tcaatgacgg    300
taaatggccc gcctggcatt atgcccagta catgacctta tgggactttc ctacttggca    360
gtacatctac gtattagtca tcgctattac catggtcgag gtgagcccca cgttctgctt    420
cactctcccc atctcccccc cctccccacc cccaattttg tatttattta ttttttaatt   480
attttgtgca gcgatggggg cggggggggg gggggggcgc gcgccaggcg gggcggggcg   540
gggcgagggg cggggcgggg cgaggcggag aggtgcggcg gcagccaatc agagcggcgc   600
gctccgaaag tttcctttta tggcgaggcg gcggcggcgg cggccctata aaaagcgaag   660
cgcgcggcgg gcggggagtc gctgcgacgc tgccttcgcc ccgtgccccg ctccgccgcc   720
gcctcgcgcc gcccgccccg gctctgactg accgcgttac tcccacaggt gagcgggcgg   780
gacggccctt ctcctccggg ctgtaattag cgcttggttt aatgacggct tgtttctttt    840
ctgtggctgc gtgaaagcct tgaggggctc cgggagggcc ctttgtgcgg gggagcggc    900 tcggggggtg cgtgcgtgtg tgtgtgcgtg gggagcgccg cgtgcggctc cgcgctgccc   960
ggcggctgtg agcgctgcgg gcgcggcgcg ggctttgtg cgctccgcag tgtgcgcgag   1020
gggagcgcgg ccggggcgg tgccccgcgg tgcgggggg gctgcgaggg gaacaaaggc   1080
tgcgtgcggg gtgtgtgcgt ggggggtga gcaggggtg tgggcgcgtc ggtcgggctg    1140 caacccccc tgcacccccc tcccgagtt gctgagcacg gccgcttc gggtgcgggg    1200 ctccgtacgg ggcgtggcgc ggggctcgcc gtgccgggcg gggggtggcg gcaggtgggg   1260
```

```
gtgccgggcg gggcgggcc gcctcgggcc ggggagggct cggggagggg gcgcggcggc    1320
ccccggagcg ccggcggctg tcgaggcgcg gcgagccgca gccattgcct tttatggtaa    1380
tcgtgcgaga gggcgcaggg acttcctttg tcccaaatct gtgcggagcc gaaatctggg    1440
aggcgccgcc gcaccccctc tagcgggcgc ggggcgaagc ggtgcggcgc cggcaggaag    1500
gaaatgggcg gggagggcct tcgtgcgtcg ccgcgccgcc gtccccttct ccctctccag    1560
cctcggggct gtccgcgggg ggacggctgc cttcggggggg acggggcag ggcgggttc     1620 ggcttctggc gtgtgaccgg cggctctaga gcctctgcta accatgttca tgccttcttc    1680 ttttttcctac agctcctggg caacgtgctg gttattgtgc tgtctcatca ttttggcaaa    1740
gaattcttcg aaagatctgc tagcttaatt aacccaaacg ggccctctag actcgagcgg    1800
ccgccactgt gctggatatc tgcagaattc agccaccacc ggcacaatga atggcacaga    1860
aggccctaac ttctacgtgc ccttctccaa tgcgacgggt gtggtacgca gcccttcga    1920 gtacccacag tactacctgg ctgagccatg gcagttctcc atgctggccg cctacatgtt    1980
tctgctgatc gtgctgggct tccccatcaa cttcctcacg ctctacgtca ccgtccagca    2040
caagaagctg cgcacgcctc tcaactacat cctgctcaac ctagccgtgg ctgacctctt    2100
catggtccta ggtggcttca ccagcaccct ctacacctct ctgcatggat acttcgtctt    2160
cgggcccaca ggatgcaatt tggagggctt ctttgccacc ctgggcggtg aaattgccct    2220
gtggtccttg gtggtcctgg ccatcgagcg gtacgtggtg gtgtgtaagc ccatgagcaa    2280
cttccgcttc ggggagaacc atgccatcat gggcgttgcc ttcacctggg tcatggcgct    2340
ggcctgcgcc gcaccccac tcgccggctg gtccaggtac atccccgagg cctgcagtg     2400 ctcgtgtgga atcgactact acacgctcaa gccggaggtc aacaacgagt cttttgtcat    2460
ctacatgttc gtggtccact tcaccatccc catgattatc atcttttcct gctatgggca    2520
gctcgtcttc accgtcaagg aggccgctgc ccagcagcag gagtcagcca ccacacagaa    2580
ggcagagaag gaggtcaccc gcatggtcat catcatggtc atcgctttcc tgatctgctg    2640
ggtgccctac gccagcgtgg cattctacat cttcacccac cagggctcca acttcggtcc    2700
catcttcatg accatcccag cgttctttgc caagagcgcc gccatctaca accctgtcat    2760
ctatatcatg atgaacaagc agttccggaa ctgcatgctc accaccatct gctgcgggcaa    2820 gaacccactg ggtgacgatg aggcctctgc taccgtgtcc aagacggaga cgagccaggt    2880
ggccccggcc taaccaagaa agcttaagtt tgggactagt ggcggccgct cgagcatgca    2940
tctagagggc cctattctat agtgtcacct aaatgctaga gctcgctgat cagcctcgac    3000
tgtgccttct agttgccagc catctgttgt ttgcccctcc ccgtgcctt cctgaccct      3060 ggaaggtgcc actcccactg tccttttccta ataaaatgag gaaattgcat cgcattgtct    3120
gagtaggtgt cattctattc tggggggtgg ggtggggcag gacagcaagg gggaggattg    3180
ggaagacaat agcaggcatg ctggggagct agagtcgacc ggaccgctgc aggcatgcaa    3240
gcttggcgta atcatggtca tagctgtttc ctgtgtgaaa ttgttatccg ctcacaattc    3300
cacacaacat acgagccgga agcataaagt gtaaagcctg gggtgcctaa tgagtgagct    3360
aactcacatt aattgcgttg cgctcactgc ccgctttcca gtcgggaaac ctgtcgtgcc    3420
agctgcatta atgaatcggc caacgcgcgg ggagaggcgg tttgcgtatt gggcgctctt    3480
ccgtattagt catcgctatt accatggtga tgcggttttg gcagtacatc aatgggcgtg    3540
gatagcggtt tgactcacgg ggatttccaa gtctccaccc cattgacgtc aatgggagtt    3600
```

-continued

```
tgttttggca ccaaaatcaa cgggactttc caaaatgtcg taacaactcc gccccattga  3660
cgcaaatggg cggtaggcgt gtacggtggg aggtctatat aagcagagct ctctggctaa  3720
ctagagaacc cactgcttac tggcttatcg aaattaatac gactcactat agggagtccc  3780
aagctggcta gttaagctat caacaagttt gtacaaaaaa gcaggcttta aagggaggta  3840
gtgagtcgac cagtggatcc tggaggcttg ctgaaggctg tatgctgaag gagcttacaa  3900
tctagctggg gttttggcca ctgactgacc ccagctagtg taagctcctt caggacacaa  3960
ggcctgttac tagcactcac atggaacaaa tgggcccagat ctggccgcac tcgagatgct  4020
tcctcgctca ctgactcgct gcgctcggtc gttcggctgc ggcgagcggt atcagctcac  4080
tcaaaggcgg taatacggtt atccacagaa tcaggggata acgcaggaaa gaacatgtga  4140
gcaaaaggcc agcaaaaggc caggaaccgt aaaaaggccg cgttgctggc gtttttccat  4200
aggctccgcc cccctgacga gcatcacaaa aatcgacgct caagtcagag gtggcgaaac  4260
ccgacaggac tataaagata ccaggcgttt cccctggaa gctccctcgt gcgctctcct  4320
gttccgaccc tgccgcttac cggatacctg tccgcctttc tcccttcggg aagcgtggcg  4380
ctttctcata gctcacgctg taggtatctc agttcggtgt aggtcgttcg ctccaagctg  4440
ggctgtgtgc acgaaccccc cgttcagccc gaccgctgcg ccttatccgg taactatcgt  4500
cttgagtcca acccggtaag acacgactta tcgccactgg cagcagccac tggtaacagg  4560
attagcagag cgaggtatgt aggcggtgct acagagttct tgaagtggtg gcctaactac  4620
ggctacacta aaggacagt atttggtatc tgcgctctgc tgaagccagt taccttcgga  4680
aaaagagttg gtagctcttg atccggcaaa caaaccaccg ctggtagcgg tggttttttt  4740
gtttgcaagc agcagattac gcgcagaaaa aaggatctc aagaagatcc tttgatcttt  4800
tctacggggt ctgacgctca gtggaacgaa aactcacgtt aagggatttt ggtcatgaga  4860
ttatcaaaaa ggatcttcac ctagatcctt ttaaattaaa aatgaagttt taaatcaatc  4920
taaagtatat atgagtaaac ttggtctgac agttaccaat gcttaatcag tgaggcacct  4980
atctcagcga tctgtctatt tcgttcatcc atagttgcct gactccccgt cgtgtagata  5040
actacgatac gggagggctt accatctggc cccagtgctg caatgatacc gcgagaccca  5100
cgctcaccgg ctccagattt atcagcaata aaccagccag ccggaagggc cgagcgcaga  5160
agtggtcctg caactttatc cgcctccatc cagtctatta attgttgccg ggaagctaga  5220
gtaagtagtt cgccagttaa tagtttgcgc aacgttgttg ccattgctac aggcatcgtg  5280
gtgtcacgct cgtcgtttgg tatggcttca ttcagctccg gttcccaacg atcaaggcga  5340
gttacatgat cccccatgtt gtgcaaaaaa gcggttagct ccttcggtcc tccgatcgtt  5400
gtcagaagta agttggccgc agtgttatca ctcatggtta tggcagcact gcataattct  5460
cttactgtca tgccatccgt aagatgcttt tctgtgactg gtgagtactc aaccaagtca  5520
ttctgagaat agtgtatgcg gcgaccgagt tgctcttgcc cggcgtcaat acgggataat  5580
accgcgccac atagcagaac tttaaaagtg ctcatcattg gaaaacgttc ttcggggcga  5640
aaactctcaa ggatcttacc gctgttgaga tccagttcga tgtaacccac tcgtgcaccc  5700
aactgatctt cagcatcttt tactttcacc agcgtttctg ggtgagcaaa aacaggaagg  5760
caaaatgccg caaaaaaggg aataagggcg acacggaaat gttgaatact catactcttc  5820
ctttttcaat attattgaag catttatcag ggttattgtc tcatgagcgg atacatattt  5880
gaatgtattt agaaaaataa acaaataggg gttccgcgca catttccccg aaaagtgcca  5940
cctgacgtct aagaaaccat tattatcatg acattaacct ataaaaatag gcgtatcacg  6000
```

```
aggcccttc  gtctcgcgcg  tttcggtgat  gacggtgaaa  acctctgaca  catgcagctc     6060
ccggagacgg  tcacagcttg  tctgtaagcg  gatgccggga  gcagacaagc  ccgtcagggc     6120
gcgtcagcgg  gtgttggcgg  gtgtcggggc  tggcttaact  atgcggcatc  agagcagatt     6180
gtactgagag  tgcaccatat  gcggtgtgaa  ataccgcaca  gatgcgtaag  gagaaaatac     6240
cgcatcaggc  gccattcgcc  attcaggctg  cgcaactgtt  gggaagggcg  atcggtgcgg     6300
gcctcttcgc  tattacgcca  gctggcgaaa  gggggatgtg  ctgcaaggcg  attaagttgg     6360
gtaacgccag  ggttttccca  gtcacgacgt  tgtaaaacga  cggccagt                   6408

<210> SEQ ID NO 13
<211> LENGTH: 155
<212> TYPE: DNA
<213> ORGANISM: Artificial Sequence
<220> FEATURE:
<223> OTHER INFORMATION: Synthetic Construct

<400> SEQUENCE: 13
gatcctggag  gcttgctgaa  ggctgtatgc  tgaaggagct  tacaatctag  ctggggtttt       60
ggccactgac  tgaccccagc  tagtgtaagc  tccttcagga  cacaaggcct  gttactagca      120
ctcacatgga  acaaatggcc  cagatctggc  cgcac                                   155

<210> SEQ ID NO 14
<211> LENGTH: 189
<212> TYPE: DNA
<213> ORGANISM: Homo sapiens

<400> SEQUENCE: 14
aacctaaccc  ccatggttgg  cgagggactg  ctgtgtgtga  aatggtaact  gccctcaagg       60
agcttacaat  ctagctgggg  gtaaatgact  tgcacatgaa  cacaactaga  ctgtgagctt      120
ctagagggca  gggaccttac  cctagtcatc  tctcttctca  ccctgcacac  cctccctgag      180
ggatctcat                                                                   189

<210> SEQ ID NO 15
<211> LENGTH: 6172
<212> TYPE: DNA
<213> ORGANISM: Artificial Sequence
<220> FEATURE:
<223> OTHER INFORMATION: Synthetic Construct

<400> SEQUENCE: 15
tatgcggtgt  gaaataccgc  acagatgcgt  aaggagaaaa  taccgcatca  ggcgccattc       60
gccattcagg  ctgcgcaact  gttgggaagg  gcgatcggtg  cgggcctctt  cgctattacg      120
ccagctggcg  aaaggggggat  gtgctgcaag  gcgattaagt  tgggtaacgc  cagggttttc      180
ccagtcacga  cgttgtaaaa  cgacggccag  tgaattcgga  ccgtcgacat  tgattattgg      240
gccccagaag  cctggtggtt  gtttgtcctt  tcaggggaa  aagtgaggcg  gcccccttgga      300 ggaaggggcc  gggcagaatg  atctaatcgg  attccaagca  gctcagggga  ttgtcttttt      360
ctagcacctt  cttgccactc  ctaagcgtcc  tccgtgaccc  cggctgggat  ttagcctggt      420
gctgtgtcag  ccccggtctc  ccaggggctt  cccagtggtc  cccaggaacc  ctcgacaggg      480
cccggtctct  ctcgtccagc  aagggcaggg  acgggccaca  ggccaagggc  ggagtcgctg      540
cgacgctgcc  ttcgccccgt  gccccgctcc  gccgccgcct  cgcgccgccc  gccccggctc      600
tgactgaccg  cgttactccc  acaggtgagc  gggcgggacg  gcccttctcc  tccgggctgt      660
```

-continued

```
aattagcaag aggtaagggt ttaagggatg gttggttggt ggggtattaa tgtttaatta    720
cctgttttac aggcctgaaa tcacttggtt ttaggttggg gatccggtac ccaattgcca    780
tgggctagca tgcatgagct ccctgcaggg tttatctgca gaattcagcc accaccggca    840
caatgaatgg cacagaaggc cctaacttct acgtgccctt ctccaatgcg acgggtgtgg    900
tacgcagccc cttcgagtac ccacagtact acctggctga gccatggcag ttctccatgc    960
tggccgccta catgtttctg ctgatcgtgc tgggcttccc catcaacttc ctcacgctct   1020
acgtcaccgt ccagcacaag aagctgcgca cgcctctcaa ctacatcctg ctcaacctag   1080
ccgtggctga cctcttcatg gtcctaggtg gcttcaccag caccctctac acctctctgc   1140
atggatactt cgtcttcggg cccacaggat gcaatttgga gggcttcttt gccaccctgg   1200
gcggtgaaat tgccctgtgg tccttggtgg tcctggccat cgagcggtac gtggtggtgt   1260
gtaagcccat gagcaacttc cgcttcgggg agaaccatgc catcatgggc gttgccttca   1320
cctgggtcat ggcgctggcc tgcgccgcac ccccactcgc cggctggtcc aggtacatcc   1380
ccgagggcct gcagtgctcg tgtggaatcg actactacac gctcaagccg gaggtcaaca   1440
acgagtcttt tgtcatctac atgttcgtgg tccacttcac catccccatg attatcatct   1500
tttctgcta tgggcagctc gtcttcaccg tcaaggaggc cgctgcccag cagcaggagt   1560
cagccaccac acagaaggca gagaaggagg tcacccgcat ggtcatcatc atggtcatcg   1620
cttcctgat ctgctgggtg ccctacgcca gcgtggcatt ctacatcttc acccaccagg   1680
gctccaactt cggtcccatc ttcatgacca tcccagcgtt ctttgccaag agcgccgcca   1740
tctacaaccc tgtcatctat atcatgatga acaagcagtt ccggaactgc atgctcacca   1800
ccatctgctg cggcaagaac ccactgggtg acgatgaggc ctctgctacc gtgtccaaga   1860
cggagacgag ccaggtggcc ccggcctaac caagaaagct taagtttgtg tcccggctta   1920
gggctaaatg tctaggacag aatggaacac atagtagctg attaataaat gctagctgga   1980
tgaagggagg aatgagtgac tgactgagtg gatatatgag tgaagggatt aatggaaggg   2040
aacatggatg tcctcaggtg cccaacctgg cagatccagt catgtctggc tggaatctat   2100
aagcagtttt acatacctgc cctgagcttt attgcggtag tttatcacag ttaaattgct   2160
aacgcagtca gtgcttctga cacaacagtc tcgaacttaa gctgcagtga ctctcttaag   2220
gtagccttgc agaagttggt cgtgaggcac tgggcaggta agtatcaagg ttacaagaca   2280
ggtttaagga gaccaataga aactgggctt gtcgagacag agaaaaacct aacccccatg   2340
gttggcgagg gactgctgtg tgtgaaatgg taactgccct caaggagctt acaatctagc   2400
tgggggtaaa tgacttgcac atgaacacaa ctagactgtg agcttctaga gggcagggac   2460
cttaccctag tcatctctct tctcaccctg cacaccctcc ctgagggatc tcatgactct   2520
tgcgtttctg ataggcacct attggtctta ctgacatcca ctttgccttt ctctccacag   2580
gtgtccactc ccagttcaca ccggcacaat gaatggcaca gaaggcccta acttctacgt   2640
gcccttctcc aatgcgacgg tgtggtacg cagccccttc gagtacccac agtcagagat   2700
aaatgacagt gacagcaacg tgagctgcag cccttaggac tgagaaagca tcgagaccag   2760
gggtctccgg caaggcctag gtcctcccct cagtatggaa accttgcctc atgtctctca   2820
gcctccttgg cctgtggaga tccagccctt cctcttggct tctggataca tttgctcttc   2880
tacaccagca accaagtggc aacagttcca ggccagtatg gagttttaga agccatgcca   2940
atatgcccac cttcagggag cagctgagtc cttgatgcca cccttgttct gaagagttca   3000
gaaacacagt gcaagacatg accaggcctc atccttagga tgctcatgga tccagttctt   3060
```

```
agctcccttg ttggatatgc tgttttcctt ggcctttggt cttttcttta tcccagaggg    3120
ttttggcttt aaggccaaca ggaactatgg ggtaccagaa ttgagcagcc tcagtctgca    3180
tccctcctct atagaaccac agctgggccc tcagcaggcc caactctgca tggggacaga    3240
ggcattaaaa gcctagagta tccctcgagg ggcccaagct tacgcgtacc cagctttctt    3300
gtacaaagtg gtccctatag tgagtcgtat tataagctag gcactggccg tcgttttaca    3360
acgtcgtgac tgggaaaact gctagcttgg gatctttgtg aaggaacctt acttctgtgg    3420
tgtgacataa ttggacaaac tacctacaga gatttaaagc tctaaggtaa atataaaatt    3480
tttaagtgta taatgtgtta aactagctgc aaaacctgtg ccttctagtt gccagccatc    3540
tgttgtttgc ccctcccccg tgccttcctt gaccctggaa ggtgccactc ccactgtcct    3600
ttcctaataa aatgaggaaa ttgcatcgca ttgtctgagt aggtgtcatt ctattctggg    3660
gggtggggtg gggcaggaca gcaaggggga ggattgggaa gacaatagca ggcatgctgg    3720
ggaactagtc ggaccgctgc aggcatgcaa gcttggcgta atcatggtca tagctgtttc    3780
ctgtgtgaaa ttgttatccg ctcacaattc cacacaacat acgagccgga agcataaagt    3840
gtaaagcctg gggtgcctaa tgagtgagct aactcacatt aattgcgttg cgctcactgc    3900
ccgctttcca gtcgggaaac ctgtcgtgcc agctgcatta atgaatcggc caacgcgcgg    3960
ggagaggcgg tttgcgtatt gggcgctctt ccgcttcctc gctcactgac tcgctgcgct    4020
cggtcgttcg gctgcggcga gcggtatcag ctcactcaaa ggcggtaata cggttatcca    4080
cagaatcagg ggataacgca ggaaagaaca tgtgagcaaa aggccagcaa aaggccagga    4140
accgtaaaaa ggccgcgttg ctggcgtttt tccataggct ccgcccccct gacgagcatc    4200
acaaaaatcg acgctcaagt cagaggtggc gaaacccgac aggactataa agataccagg    4260
cgtttccccc tggaagctcc ctcgtgcgct ctcctgttcc gaccctgccg cttaccggat    4320
acctgtccgc ctttctccct tcgggaagcg tggcgctttc tcatagctca cgctgtaggt    4380
atctcagttc ggtgtaggtc gttcgctcca agctgggctg tgtgcacgaa ccccccgttc    4440
agcccgaccg ctgcgcctta tccggtaact atcgtcttga gtccaacccg gtaagacacg    4500
acttatcgcc actggcagca gccactggta acaggattag cagagcgagg tatgtaggcg    4560
gtgctacaga gttcttgaag tggtggccta actacggcta cactagaagg acagtatttg    4620
gtatctgcgc tctgctgaag ccagttacct tcggaaaaag agttggtagc tcttgatccg    4680
gcaaacaaac caccgctggt agcggtggtt tttttgtttg caagcagcag attacgcgca    4740
gaaaaaaagg atctcaagaa gatcctttga tcttttctac ggggtctgac gctcagtgga    4800
acgaaaactc acgttaaggg attttggtca tgagattatc aaaaaggatc ttcacctaga    4860
tccttttaaa ttaaaaatga agttttaaat caatctaaag tatatatgag taaacttggt    4920
ctgacagtta ccaatgctta atcagtgagg cacctatctc agcgatctgt ctatttcgtt    4980
catccatagt tgcctgactc cccgtcgtgt agataactac gatacgggag ggcttaccat    5040
ctggccccag tgctgcaatg ataccgcgag acccacgctc accggctcca gatttatcag    5100
caataaacca gccagccgga agggccgagc gcagaagtgg tcctgcaact ttatccgcct    5160
ccatccagtc tattaattgt tgccgggaag ctagagtaag tagttcgcca gttaatagtt    5220
tgcgcaacgt tgttgccatt gctacaggca tcgtggtgtc acgctcgtcg tttggtatgg    5280
cttcattcag ctccggttcc caacgatcaa ggcgagttac atgatccccc atgttgtgca    5340
aaaaagcggt tagctccttc ggtcctccga tcgttgtcag aagtaagttg gccgcagtgt    5400
```

| | |
|---|---|
| tatcactcat ggttatggca gcactgcata attctcttac tgtcatgcca tccgtaagat | 5460 |
| gcttttctgt gactggtgag tactcaacca agtcattctg agaatagtgt atgcggcgac | 5520 |
| cgagttgctc ttgcccggcg tcaatacggg ataataccgc gccacatagc agaactttaa | 5580 |
| aagtgctcat cattggaaaa cgttcttcgg ggcgaaaact ctcaaggatc ttaccgctgt | 5640 |
| tgagatccag ttcgatgtaa cccactcgtg cacccaactg atcttcagca tcttttactt | 5700 |
| tcaccagcgt ttctgggtga gcaaaaacag gaaggcaaaa tgccgcaaaa aagggaataa | 5760 |
| gggcgacacg gaaatgttga atactcatac tcttcctttt tcaatattat tgaagcattt | 5820 |
| atcaggggtta ttgtctcatg agcggataca tatttgaatg tatttagaaa aataaacaaa | 5880 |
| taggggttcc gcgcacattt ccccgaaaag tgccacctga cgtctaagaa accattatta | 5940 |
| tcatgacatt aacctataaa aataggcgta tcacgaggcc ctttcgtctc gcgcgtttcg | 6000 |
| gtgatgacgg tgaaaacctc tgacacatgc agctcccgga gacggtcaca gcttgtctgt | 6060 |
| aagcggatgc cgggagcaga caagcccgtc agggcgcgtc agcgggtgtt ggcgggtgtc | 6120 |
| ggggctggct taactatgcg gcatcagagc agattgtact gagagtgcac ca | 6172 |

<210> SEQ ID NO 16
<211> LENGTH: 441
<212> TYPE: DNA
<213> ORGANISM: Homo sapiens

<400> SEQUENCE: 16

| | |
|---|---|
| actagaagct ttattgcggt agtttatcac agttaaattg ctaacgcagt cagtgcttct | 60 |
| gacacaacag tctcgaactt aagctgcagt gactctctta aggtagcctt gcagaagttg | 120 |
| gtcgtgaggc actgggcagg taagtatcaa ggttacaaga caggtttaag gagaccaata | 180 |
| gaaactgggc ttgtcgagac agagaatgga tcctggaggc ttgctgaagg ctgtatgctg | 240 |
| aaggagctta caatctagct ggggttttgg ccactgactg accccagcta gtgtaagctc | 300 |
| cttcaggaca caaggcctgt tactagcact cacatggaac aaatggccca gatctgagac | 360 |
| tcttgcgttt ctgataggca cctattggtc ttactgacat ccactttgcc tttctctcca | 420 |
| caggtgtcca ctcccagttc a | 441 |

<210> SEQ ID NO 17
<211> LENGTH: 150
<212> TYPE: DNA
<213> ORGANISM: Artificial Sequence
<220> FEATURE:
<223> OTHER INFORMATION: Synthetic Construct

<400> SEQUENCE: 17

| | |
|---|---|
| tggatcctgg aggcttgctg aaggctgtat gctgaaggag cttacaatct agctggggtt | 60 |
| ttggccactg actgacccca gctagtgtaa gctccttcag gacacaaggc ctgttactag | 120 |
| cactcacatg gaacaaatgg cccagatctg | 150 |

<210> SEQ ID NO 18
<211> LENGTH: 190
<212> TYPE: DNA
<213> ORGANISM: Homo sapiens

<400> SEQUENCE: 18

| | |
|---|---|
| aaacctaacc cccatggttg gcgagggact gctgtgtgtg aaatggtaac tgccctcaag | 60 |
| gagcttacaa tctagctggg ggtaaatgac ttgcacatga acacaactag actgtgagct | 120 |
| tctagagggc agggacctta ccctagtcat ctctcttctc accctgcaca ccctccctga | 180 |

```
gggatctcat                                                                    190

<210> SEQ ID NO 19
<211> LENGTH: 79
<212> TYPE: RNA
<213> ORGANISM: Homo sapiens

<400> SEQUENCE: 19
cucugccugg agacuaaggc aaauugggcc auuaaaagcu cagcuccuau guugguauua              60
acgguggugg guuuuguug                                                          79

<210> SEQ ID NO 20
<211> LENGTH: 113
<212> TYPE: DNA
<213> ORGANISM: Artificial Sequence
<220> FEATURE:
<223> OTHER INFORMATION: Synthetic Construct

<400> SEQUENCE: 20
ccactccctc tctgcgcgct cgctcgctca ctgaggccgg gcgaccaaag gtcgcccgac              60
gcccgggctt tgcccgggcg gcctcagtga gcgagcgagc gcgcagagag gga                   113

<210> SEQ ID NO 21
<211> LENGTH: 143
<212> TYPE: DNA
<213> ORGANISM: Artificial Sequence
<220> FEATURE:
<223> OTHER INFORMATION: Synthetic Construct

<400> SEQUENCE: 21
ggccactccc tctctgcgcg ctcgctcgct cactgaggcc gggcgaccaa aggtcgcccg              60
acgcccgggc tttgcccggg cggcctcagt gagcgagcga gcgcgcagag agggagtggc             120
caactccatc actaggggtt cct                                                    143

<210> SEQ ID NO 22
<211> LENGTH: 795
<212> TYPE: DNA
<213> ORGANISM: Mus musculus

<400> SEQUENCE: 22
tgctgattca gccaggaact agttattaat agtaatcaat tacggggtca ttagttcata              60
gcccatatat ggagttccgc gttacataac ttacggtaaa tggcccgcct ggctgaccgc             120
ccaacgaccc ccgcccattg acgtcaataa tgacgtatgt tcccatagta acgccaatag             180
ggactttcca ttgacgtcaa tgggtggagt atttacggta aactgcccac ttggcagtac             240
atcaagtgta tcatatgcca agtacgcccc ctattgacgt caatgacggt aaatggcccg             300
cctggcatta tgcccagtac atgaccttat gggactttcc tacttggcag tacatctacg             360
tattagtcat cgctattacc acaaatagtt atcgagccgc tgagccgggg ggcgggggt              420 gtgagactgg aggcgatgga cggagctgac ggcacacaca gctcagatct gtcaagtgag             480
ccattgtcag ggcttgggga ctggataagt caggggtct cctggaaga gatgggatag               540 gtgagttcag gaggagacat tgtcaactgg agccatgtgg agaagtgaat ttagggccca             600
aaggttccag tcgcagcctg aggccaccag actgacatgg ggaggaattc ccagaggact             660
ctggggcaga caagatgaga caccctttcc tttcttacc taagggcctc cacccgatgt              720
caccttggcc cctctgcaag ccaattaggc cccggtggca gcagtgggat tagcgttagt             780
```
atgatatctc gcgga 795

<210> SEQ ID NO 23
<211> LENGTH: 315
<212> TYPE: DNA
<213> ORGANISM: Artificial Sequence
<220> FEATURE:
<223> OTHER INFORMATION: Synthetic Construct

<400> SEQUENCE: 23
ggagtcgctg cgacgctgcc ttcgcccgt gccccgctcc gccgccgcct cgcgccgccc 60
gccccggctc tgactgaccg cgttactccc acaggtgagc gggcgggacg gcccttctcc 120
tccgggctgt aattagcaag aggtaagggt ttaagggatg gttggttggt ggggtattaa 180
tgtttaatta cctgttttac aggcctgaaa tcacttggtt ttaggttggg gatccggtac 240
ccaattgcca tgggctagca tgcatgagct ccctgcaggg ttttaatgcc aactttgtac 300
aaaaaagcag gcacc 315

<210> SEQ ID NO 24
<211> LENGTH: 2064
<212> TYPE: DNA
<213> ORGANISM: Artificial Sequence
<220> FEATURE:
<223> OTHER INFORMATION: Synthetic Construct

<400> SEQUENCE: 24
tgactagtta gggccccaga agcctggtgg ttgtttgtcc ttctcagggg aaaagtgagg 60
cggccccttg gaggaagggg ccgggcagaa tgatctaatc ggattccaag cagctcaggg 120
gattgtcttt ttctagcacc ttcttgccac tcctaagcgt cctccgtgac cccggctggg 180
atttagcctg gtgctgtgtc agcccggtc tcccaggggc ttcccagtgg tcccaggaa 240
ccctcgacag ggcccggtct ctctcgtcca gcaagggcag ggacgggcca caggccaagg 300
gcactagaag ctttattgcg gtagtttatc acagttaaat tgctaacgca gtcagtgctt 360
ctgacacaac agtctcgaac ttaagctgca gtgactctct taaggtagcc ttgcagaagt 420
tggtcgtgag gcactgggca ggtaagtatc aaggttacaa dacaggttta aggagaccaa 480
tagaaactgg gcttgtcgag acagagaatg gatcctggag gcttgctgaa ggctgtatgc 540
tgaaggagct acaatctag ctggggtttt ggccactgac tgaccccagc tagtgtaagc 600
tccttcagga cacaaggcct gttactagca ctcacatgga acaaatggcc cagatctgag 660
actcttgcgt ttctgatagg cacctattgg tcttactgac atccactttg cctttctctc 720
cacaggtgtc cactcccagt tcacaccggc acaatgaatg gcacagaagg ccctaacttc 780
tacgtgccct tctccaatgc gacgggtgtg gtacgcagcc ccttcgagta cccacagtac 840
tacctggctg agccatggca gttctccatg ctggccgcct acatgtttct gctgatcgtg 900
ctgggcttcc ccatcaactt cctcacgctc tacgtcaccg tccagcacaa gaagctgcgc 960
acgcctctca actacatcct gctcaaccta gccgtggctg acctcttcat ggtcctaggt 1020
ggcttcacca gcaccctcta cacctctctg catggatact tcgtcttcgg gcccacagga 1080
tgcaattggg agggcttctt tgccaccctg ggcggtgaaa ttgccctgtg gtccttggtg 1140
gtcctggcca tcgagcggta cgtggtggtg tgtaagccca tgagcaactt ccgcttcggg 1200
gagaaccatg ccatcatggg cgttgccttc acctgggtca tggcgctggc ctgcgccgca 1260
cccccactcg ccggctggtc caggtacatc cccgagggcc tgcagtgctc gtgtggaatc 1320
gactactaca cgctcaagcc ggaggtcaac aacgagtctt ttgtcatcta catgttcgtg 1380

```
gtccacttca ccatccccat gattatcatc ttttctgct atgggcagct cgtcttcacc    1440
gtcaaggagg ccgctgccca gcagcaggag tcagccacca cacagaaggc agagaaggag    1500
gtcacccgca tggtcatcat catggtcatc gctttcctga tctgctgggt ccctacgcc    1560 agcgtggcat tctacatctt cacccaccag ggctccaact tcggtcccat cttcatgacc    1620
atcccagcgt tctttgccaa gagcgccgcc atctacaacc ctgtcatcta tcatgatg     1680 aacaagcagt tccggaactg catgctcacc accatctgct gcggcaagaa cccactgggt    1740
gacgatgagg cctctgctac cgtgtccaag acggagacga gccaggtggc cccggcctaa    1800
ccaagaaagc ttaagtttaa accgctgatc agcctcgact gtgccttcta gttgccagcc    1860
atctgttgtt tgcccctccc ccgtgccttc cttgaccctg gaaggtgcca ctcccactgt    1920
cctttcctaa taaaatgagg aaattgcatc gcattgtctg agtaggtgtc attctattct    1980 gggggtggg gtggggcagg acagcaaggg ggaggattgg gaagacaata gcaggcatgc    2040 tgggatgcg gtgggctcta tggc                                           2064

<210> SEQ ID NO 25
<211> LENGTH: 2093
<212> TYPE: DNA
<213> ORGANISM: Artificial Sequence
<220> FEATURE:
<223> OTHER INFORMATION: Synthetic Construct

<400> SEQUENCE: 25
gggccccaga agcctggtgg ttgtttgtcc ttctcagggg aaaagtgagg cggccccttg      60
gaggaagggg ccgggcagaa tgatctaatc ggattccaag cagctcaggg gattgtcttt    120
ttctagcacc ttcttgccac tcctaagcgt cctccgtgac cccggctggg atttagcctg    180
gtgctgtgtc agccccggtc tcccaggggc ttcccagtgg tccccaggaa ccctcgacag    240
ggcccggtct ctctcgtcca gcaagggcag ggacgggcca caggccaagg gcactagaag    300
ctttattgcg gtagtttatc acagttaaat tgctaacgca gtcagtgctt ctgacacaac    360
agtctcgaac ttaagctgca gtgactctct taaggtagcc ttgcagaagt tggtcgtgag    420
gcactgggca ggtaagtatc aaggttacaa gacaggttta aggagaccaa tagaaactgg    480
gcttgtcgag acagagaaaa acctaacccc catggttggc gagggactgc tgtgtgtgaa    540
atggtaactg ccctcaagga gcttacaatc tagctggggg taaatgactt gcacatgaac    600
acaactagac tgtgagcttc tagagggcag ggaccttacc ctagtcatct ctcttctcac    660
cctgcacacc ctccctgagg gatctcatga ctcttgcgtt tctgataggc acctattggt    720
cttactgaca tccactttgc ctttctctcc acaggtgtcc actcccagtt cacaccggca    780
caatgaatgg cacagaaggc cctaacttct acgtgccctt ctccaatgcg acgggtgtgg    840
tacgcagccc cttcgagtac ccacagtact acctggctga gccatggcag ttctccatgc    900
tggccgccta catgtttctg ctgatcgtgc tgggcttccc catcaacttc ctcacgctct    960
acgtcaccgt ccagcacaag aagctgcgca cgcctctcaa ctacatcctg ctcaacctag   1020
ccgtggctga cctcttcatg gtcctaggtg gcttcaccag caccctctac acctctctgc   1080
atggatactt cgtcttcggg cccacaggat gcaatttgga gggcttcttt gccaccctgg   1140
gcggtgaaat tgccctgtgg tccttggtgg tcctggccat cgagcggtac gtggtggtgt   1200
gtaagcccat gagcaacttc cgcttcgggg agaaccatgc catcatgggc gttgccttca   1260
cctgggtcat ggcgctggcc tgcgccgcac ccccactcgc cggctggtcc aggtacatcc   1320
```

| | | | | |
|---|---|---|---|---|
| ccgagggcct | gcagtgctcg | tgtggaatcg | actactacac | gctcaagccg gaggtcaaca | 1380 |
| acgagtcttt | tgtcatctac | atgttcgtgg | tccacttcac | catccccatg attatcatct | 1440 |
| ttttctgcta | tgggcagctc | gtcttcaccg | tcaaggaggc | cgctgcccag cagcaggagt | 1500 |
| cagccaccac | acagaaggca | gagaaggagg | tcacccgcat | ggtcatcatc atggtcatcg | 1560 |
| ctttcctgat | ctgctgggtg | ccctacgcca | gcgtggcatt | ctacatcttc acccaccagg | 1620 |
| gctccaactt | cggtcccatc | ttcatgacca | tcccagcgtt | ctttgccaag agcgccgcca | 1680 |
| tctacaaccc | tgtcatctat | atcatgatga | caagcagtt | ccggaactgc atgctcacca | 1740 |
| ccatctgctg | cggcaagaac | ccactgggtg | acgatgaggc | ctctgctacc gtgtccaaga | 1800 |
| cggagacgag | ccaggtggcc | ccggcctaac | caagaaagct | taagtttaaa ccgctgatca | 1860 |
| gcctcgactg | tgccttctag | ttgccagcca | tctgttgttt | gcccctcccc cgtgccttcc | 1920 |
| ttgaccctgg | aaggtgccac | tcccactgtc | ctttcctaat | aaaatgagga aattgcatcg | 1980 |
| cattgtctga | gtaggtgtca | ttctattctg | ggggtgggg | tggggcagga cagcaagggg | 2040 |
| gaggattggg | aagacaatag | caggcatgct | ggggatgcgg | tgggctctat ggc | 2093 |

<210> SEQ ID NO 26
<211> LENGTH: 2716
<212> TYPE: DNA
<213> ORGANISM: Artificial Sequence
<220> FEATURE:
<223> OTHER INFORMATION: Synthetic Construct

<400> SEQUENCE: 26

| | | | | |
|---|---|---|---|---|
| acgcgttttc | tgcagcgggg | attaatatga | ttatgaacac | ccccaatctc ccagatgctg | 60 |
| attcagccag | gaactagtta | ttaatagtaa | tcaattacgg | ggtcattagt tcatagccca | 120 |
| tatatggagt | tccgcgttac | ataacttacg | gtaaatggcc | cgcctggctg accgcccaac | 180 |
| gacccccgcc | cattgacgtc | aataatgacg | tatgttccca | tagtaacgcc aatagggact | 240 |
| ttccattgac | gtcaatgggt | ggagtattta | cggtaaactg | cccacttggc agtacatcaa | 300 |
| gtgtatcata | tgccaagtac | gcccctatt | gacgtcaatg | acggtaaatg gcccgcctgg | 360 |
| cattatgccc | agtacatgac | cttatgggac | tttcctactt | ggcagtacat ctacgtatta | 420 |
| gtcatcgcta | ttaccacaaa | tagttatcga | gccgctgagc | cgggggggcgg ggggtgtgag | 480 |
| actggaggcg | atggacggag | ctgacggcac | acacagctca | gatctgtcaa gtgagccatt | 540 |
| gtcagggctt | ggggactgga | taagtcaggg | ggtctcctgg | gaagagatgg gataggtgag | 600 |
| ttcaggagga | gacattgtca | actggagcca | tgtggagaag | tgaatttagg gcccaaaggt | 660 |
| tccagtcgca | gcctgaggcc | accagactga | catggggagg | aattcccaga ggactctggg | 720 |
| gcagacaaga | tgagacaccc | tttcctttct | ttacctaagg | gcctccaccc gatgtcacct | 780 |
| tggcccctct | gcaagccaat | taggccccgg | tggcagcagt | gggattagcg ttagtatgat | 840 |
| atctcgcgga | tgctgaatca | gcctctggct | tagggagaga | aggtcacttt ataagggtct | 900 |
| gggggggtc | agtgcctgga | gttgcgctgt | gggagccgtc | agtggctgag ctcaactaga | 960 |
| agctttattg | cggtagttta | tcacagttaa | attgctaacg | cagtcagtgc ttctgacaca | 1020 |
| acagtctcga | acttaagctg | cagtgactct | cttaaggtag | ccttgcagaa gttggtcgtg | 1080 |
| aggcactggg | caggtaagta | tcaaggttac | aagacaggtt | taaggagacc aatagaaact | 1140 |
| gggcttgtcg | agacagagaa | tggatcctgg | aggcttgctg | aaggctgtat gctgaaggag | 1200 |
| cttacaatct | agctggggtt | ttggccactg | actgaccccca | gctagtgtaa gctccttcag | 1260 |
| gacacaaggc | ctgttactag | cactcacatg | gaacaaatgg | cccagatctg agactcttgc | 1320 |

```
gtttctgata ggcacctatt ggtcttactg acatccactt tgcctttctc tccacaggtg      1380
tccactccca gttcacaccg gcacaatgaa tggcacagaa ggccctaact tctacgtgcc      1440
cttctccaat gcgacgggtg tggtacgcag ccccttcgag tacccacagt actacctggc      1500
tgagccatgg cagttctcca tgctggccgc ctacatgttt ctgctgatcg tgctgggctt      1560
ccccatcaac ttcctcacgc tctacgtcac cgtccagcac aagaagctgc gcacgcctct      1620
caactacatc ctgctcaacc tagccgtggc tgacctcttc atggtcctag gtggcttcac      1680
cagcaccctc tacacctctc tgcatggata cttcgtcttc gggcccacag gatgcaattt      1740
ggagggcttc tttgccaccc tgggcggtga aattgccctg tggtccttgg tggtcctggc      1800
catcgagcgg tacgtggtgg tgtgtaagcc catgagcaac ttccgcttcg gggagaacca      1860
tgccatcatg ggcgttgcct tcacctgggt catggcgctg gcctgcgccg cacccccact      1920
cgccggctgg tccaggtaca tccccgaggg cctgcagtgc tcgtgtggaa tcgactacta      1980
cacgctcaag ccggaggtca caacgagtc ttttgtcatc tacatgttcg tggtccactt      2040
caccatcccc atgattatca tcttttttctg ctatgggcag ctcgtcttca ccgtcaagga      2100
ggccgctgcc cagcagcagg agtcagccac cacacagaag gcagagaagg aggtcacccg      2160
catggtcatc atcatggtca tcgctttcct gatctgctgg gtgccctacg ccagcgtggc      2220
attctacatc ttcacccacc agggctccaa cttcggtccc atcttcatga ccatcccagc      2280
gttctttgcc aagagcgccg ccatctacaa ccctgtcatc tatatcatga tgaacaagca      2340
gttccggaac tgcatgctca ccaccatctg ctgcggcaag aacccactgg gtgacgatga      2400
ggcctctgct accgtgtcca agacggagac gagccaggtg gccccggcct aaccaagaaa      2460
gcttaagttt aaaccgctga tcagcctcga ctgtgccttc tagttgccag ccatctgttg      2520
tttgcccctc cccgtgcct tccttgaccc tggaaggtgc cactcccact gtcctttcct      2580
aataaaatga ggaaattgca tcgcattgtc tgagtaggtg tcattctatt ctggggggtg      2640
gggtggggca ggacagcaag ggggaggatt gggaagacaa tagcaggcat gctggggatg      2700
cggtgggctc tatggc                                                      2716
```

<210> SEQ ID NO 27
<211> LENGTH: 2755
<212> TYPE: DNA
<213> ORGANISM: Artificial Sequence
<220> FEATURE:
<223> OTHER INFORMATION: Synthetic Construct

<400> SEQUENCE: 27

```
acgcgttttc tgcagcgggg attaatatga ttatgaacac ccccaatctc ccagatgctg       60
attcagccag gaactagtta ttaatagtaa tcaattacgg ggtcattagt tcatagccca      120
tatatggagt tccgcgttac ataacttacg gtaaatggcc cgcctggctg accgcccaac      180
gacccccgcc cattgacgtc aataatgacg tatgttccca tagtaacgcc aatagggact      240
ttccattgac gtcaatgggt ggagtattta cggtaaactg cccacttggc agtacatcaa      300
gtgtatcata tgccaagtac gccccctatt gacgtcaatg acggtaaatg gcccgcctgg      360
cattatgccc agtacatgac cttatgggac tttcctactt ggcagtacat ctacgtatta      420
gtcatcgcta ttaccacaaa tagttatcga gccgctgagc cggggggcgg ggggtgtgag      480
actggaggcg atggacggag ctgacggcac acacagctca gatctgtcaa gtgagccatt      540
gtcagggctt ggggactgga taagtcaggg ggtctcctgg gaagagatgg gataggtgag      600
```

| | | | | |
|---|---|---|---|---|
| ttcaggagga | gacattgtca | actggagcca | tgtggagaag | tgaatttagg gcccaaaggt | 660 |
| tccagtcgca | gcctgaggcc | accagactga | catgggagg | aattcccaga ggactctggg | 720 |
| gcagacaaga | tgagacaccc | tttcctttct | tacctaagg | gcctccaccc gatgtcacct | 780 |
| tggcccctct | gcaagccaat | taggcccgg | tggcagcagt | gggattagcg ttagtatgat | 840 |
| atctcgcgga | tgctgaatca | gcctctggct | tagggagaga | aggtcacttt ataagggtct | 900 |
| gggggggggtc | agtgcctgga | gttgcgctgt | gggagccgtc | agtggctgag ctcaactaga | 960 |
| agctttattg | cggtagttta | tcacagttaa | attgctaacg | cagtcagtgc ttctgacaca | 1020 |
| acagtctcga | acttaagctg | cagtgactct | cttaaggtag | ccttgcagaa gttggtcgtg | 1080 |
| aggcactggg | caggtaagta | tcaaggttac | aagacaggtt | taaggagacc aatagaaact | 1140 |
| gggcttgtcg | agacagagaa | aaacctaacc | cccatggttg | gcgagggact gctgtgtgtg | 1200 |
| aaatggtaac | tgccctcaag | gagcttacaa | tctagctggg | ggtaaatgac ttgcacatga | 1260 |
| acacaactag | actgtgagct | tctagagggc | agggacctta | ccctagtcat ctctcttctc | 1320 |
| accctgcaca | ccctccctga | gggatctcat | gactcttgcg | tttctgatag gcacctattg | 1380 |
| gtcttactga | catccacttt | gcctttctct | ccacaggtgt | ccactcccag ttcacaccgg | 1440 |
| cacaatgaat | ggcacagaag | gccctaactt | ctacgtgccc | ttctccaatg cgacgggtgt | 1500 |
| ggtacgcagc | cccttcgagt | acccacagta | ctacctggct | gagccatggc agttctccat | 1560 |
| gctggccgcc | tacatgtttc | tgctgatcgt | gctgggcttc | cccatcaact tcctcacgct | 1620 |
| ctacgtcacc | gtccagcaca | agaagctgcg | cacgcctctc | aactacatcc tgctcaacct | 1680 |
| agccgtggct | gacctcttca | tggtcctagg | tggcttcacc | agcaccctct acacctctct | 1740 |
| gcatggatac | ttcgtcttcg | ggcccacagg | atgcaatttg | gagggcttct ttgccaccct | 1800 |
| gggcggtgaa | attgccctgt | ggtccttggt | ggtcctggcc | atcgagcggt acgtggtggt | 1860 |
| gtgtaagccc | atgagcaact | tccgcttcgg | ggagaaccat | gccatcatgg gcgttgcctt | 1920 |
| cacctgggtc | atgcgctggg | cctgcgccgc | accccactc | gccggctggt ccaggtacat | 1980 |
| ccccgagggc | ctgcagtgct | cgtgtggaat | cgactactac | acgctcaagc cggaggtcaa | 2040 |
| caacgagtct | tttgtcatct | acatgttcgt | ggtccacttc | accatcccca tgattatcat | 2100 |
| cttttttctgc | tatgggcagc | tcgtcttcac | cgtcaaggag | gccgctgccc agcagcagga | 2160 |
| gtcagccacc | acacagaagg | cagagaagga | ggtcacccgc | atggtcatca tcatggtcat | 2220 |
| cgctttcctg | atctgctggg | tgccctacgc | cagcgtggca | ttctacatct tcacccacca | 2280 |
| gggctccaac | ttcggtccca | tcttcatgac | catcccagcg | ttctttgcca agagcgccgc | 2340 |
| catctacaac | cctgtcatct | atatcatgat | gaacaagcag | ttccggaact gcatgctcac | 2400 |
| caccatctgc | tgcggcaaga | acccactggg | tgacgatgag | gcctctgcta ccgtgtccaa | 2460 |
| gacggagacg | agccaggtgg | ccccggccta | accaagaaag | cttaagttta aaccgctgat | 2520 |
| cagcctcgac | tgtgccttct | agttgccagc | catctgttgt | ttgcccctcc cccgtgcctt | 2580 |
| ccttgaccct | ggaaggtgcc | actcccactg | tcctttccta | ataaaatgag gaaattgcat | 2640 |
| cgcattgtct | gagtaggtgt | cattctattc | tggggggtgg | ggtggggcag gacagcaagg | 2700 |
| gggaggattg | ggaagacaat | agcaggcatg | ctggggatgc | ggtgggctct atggc | 2755 |

<210> SEQ ID NO 28
<211> LENGTH: 145
<212> TYPE: DNA
<213> ORGANISM: Mus musculus

<400> SEQUENCE: 28

```
agaggactaa gccacaggtg aggagaaagg ggggggggggg tctgctgacc cagcaacact    60
ctttccttct gaggcttaag agctattagc gtaggtgact cagtccctaa tcctccattc   120
aatgccctgt gactgcccct gcttc                                         145

<210> SEQ ID NO 29
<211> LENGTH: 364
<212> TYPE: DNA
<213> ORGANISM: Cytomegalovirus

<400> SEQUENCE: 29
actagttatt aatagtaatc aattacgggg tcattagttc atagcccata tatggagttc    60
cgcgttacat aacttacggt aaatggcccg cctggctgac cgcccaacga cccccgccca   120
ttgacgtcaa taatgacgta tgttcccata gtaacgccaa tagggacttt ccattgacgt   180
caatgggtgg agtatttacg gtaaactgcc cacttggcag tacatcaagt gtatcatatg   240
ccaagtacgc cccctattga cgtcaatgac ggtaaatggc ccgcctggca ttatgcccag   300
tacatgacct tatgggactt tcctacttgg cagtacatct acgtattagt catcgctatt   360
acca                                                                364

<210> SEQ ID NO 30
<211> LENGTH: 66
<212> TYPE: DNA
<213> ORGANISM: Artificial Sequence
<220> FEATURE:
<223> OTHER INFORMATION: Synthetic Construct

<400> SEQUENCE: 30
tttctgcagc ggggattaat atgattatga acacccccaa tctcccagat gctgattcag    60
ccagga                                                               66
```